US012539309B2

(12) United States Patent
Kahvejian et al.

(10) Patent No.: US 12,539,309 B2
(45) **Date of Patent: *Feb. 3, 2026**

(54) COMPOSITIONS COMPRISING CIRCULAR POLYRIBONUCLEOTIDES AND USES THEREOF

(71) Applicant: FLAGSHIP PIONEERING INNOVATIONS VI, LLC, Cambridge, MA (US)

(72) Inventors: Avak Kahvejian, Lexington, MA (US); Nicholas McCartney Plugis, Duxbury, MA (US); Alexandra Sophie De Boer, Somerville, MA (US)

(73) Assignee: Flagship Pioneering Innovations VI, LLC, Cambridge, MA (US)

( * ) Notice: Subject to any disclaimer, the term of this patent is extended or adjusted under 35 U.S.C. 154(b) by 548 days.

This patent is subject to a terminal disclaimer.

(21) Appl. No.: 17/898,947

(22) Filed: Aug. 30, 2022

(65) Prior Publication Data

US 2023/0070937 A1 Mar. 9, 2023

Related U.S. Application Data

(63) Continuation of application No. 17/482,346, filed on Sep. 22, 2021, now Pat. No. 11,458,156, which is a continuation of application No. 17/313,963, filed on May 6, 2021, now Pat. No. 11,160,822, which is a continuation of application No. 17/173,991, filed on Feb. 11, 2021, now Pat. No. 11,058,706, which is a continuation of application No. 16/438,073, filed on Jun. 11, 2019, now Pat. No. 10,953,033, which is a continuation of application No. PCT/US2018/065836, filed on Dec. 14, 2018.

(60) Provisional application No. 62/676,688, filed on May 25, 2018, provisional application No. 62/599,547, filed on Dec. 15, 2017.

(51) Int. Cl.

| | |
|---|---|
| ***A61K 31/7088*** | (2006.01) |
| ***C07K 7/00*** | (2006.01) |
| ***C07K 7/06*** | (2006.01) |
| ***C12N 15/67*** | (2006.01) |
| ***C12P 21/00*** | (2006.01) |

(52) U.S. Cl.

CPC ............ *A61K 31/7088* (2013.01); *C07K 7/00* (2013.01); *C07K 7/06* (2013.01); *C12N 15/67* (2013.01); *C12P 21/00* (2013.01)

(58) Field of Classification Search

CPC ........ A61K 31/7088; C07K 7/00; C07K 7/06; C12N 15/67; C12N 15/88; C12N 15/85; C12P 21/00; Y02A 50/30

See application file for complete search history.

(56) References Cited

U.S. PATENT DOCUMENTS

| | | | | |
|---|---|---|---|---|
| 5,223,409 | A | 6/1993 | Ladner et al. | |
| 5,426,180 | A | 6/1995 | Kool | |
| 5,438,119 | A | 8/1995 | Rutter et al. | |
| 5,440,016 | A | 8/1995 | Blondelle et al. | |
| 5,463,564 | A | 10/1995 | Agrafiotis et al. | |
| 5,523,735 | A | 6/1996 | Goseberg et al. | |
| 5,525,735 | A | 6/1996 | Gallop et al. | |
| 5,541,061 | A | 7/1996 | Fodor et al. | |
| 5,545,568 | A | 8/1996 | Ellman | |
| 5,549,974 | A | 8/1996 | Holmes | |
| 5,565,324 | A | 10/1996 | Still et al. | |
| 5,571,698 | A | 11/1996 | Ladner et al. | |
| 5,574,656 | A | 11/1996 | Agrafiotis et al. | |
| 5,593,853 | A | 1/1997 | Chen et al. | |
| 5,639,603 | A | 6/1997 | Dower et al. | |
| 5,641,862 | A | 6/1997 | Rutter et al. | |
| 5,684,711 | A | 11/1997 | Agrafiotis et al. | |
| 5,688,696 | A | 11/1997 | Lebl | |
| 5,688,997 | A | 11/1997 | Baldwin et al. | |
| 5,697,673 | A | 12/1997 | Favaretto | |
| 5,698,673 | A | 12/1997 | Blondelle et al. | |
| 5,708,153 | A | 1/1998 | Dower et al. | |
| 5,712,128 | A | 1/1998 | Been et al. | |
| 5,721,099 | A | 2/1998 | Still et al. | |
| 5,731,423 | A | 3/1998 | Kakarla et al. | |
| 5,734,018 | A | 3/1998 | Rutter et al. | |
| 5,741,713 | A | 4/1998 | Brown et al. | |
| 5,766,903 | A * | 6/1998 | Sarnow | C12N 15/67 435/6.12 |
| 5,773,244 | A | 6/1998 | Ares, Jr. et al. | |
| 5,877,160 | A | 3/1999 | Harper et al. | |
| 6,210,931 | B1 | 4/2001 | Feldstein et al. | |
| 8,084,599 | B2 | 12/2011 | Rossi et al. | |
| 8,349,809 | B2 | 1/2013 | Brown | |
| 8,513,207 | B2 | 8/2013 | Brown | |
| 9,822,378 | B2 * | 11/2017 | Kruse | C12Q 1/6865 |

(Continued)

FOREIGN PATENT DOCUMENTS

| | | | |
|---|---|---|---|
| CN | 105664239 | A | 6/2016 |
| CN | 106222174 | A | 12/2016 |

(Continued)

OTHER PUBLICATIONS

Abe, et al., Rolling circle translation of circular RNA in living human cells. Scientific Reports, 2015; 5: 16435.

Abouhaidar, et al., Novel coding, translation, and gene expression of a replicating covalently closed circular RNA of 220 nt. PNAS, Aug. 30, 2016; 113(35):E5253, 14542-14547.

Agresti et al.: Selection of Ribozymes that Catalyse Multiple-Turnover Diels-Alder Cycloadditions by Using in Vitro Compartmentalization. Proc Natl Acad Sci US A. 102(45): 16170-16175 (2005).

(Continued)

*Primary Examiner* — Kimberly Chong

(74) *Attorney, Agent, or Firm* — Clark & Elbing LLP

(57) ABSTRACT

This invention relates generally to pharmaceutical compositions and preparations of circular polyribonucleotides and uses thereof.

14 Claims, 61 Drawing Sheets

Specification includes a Sequence Listing.

(56) References Cited

U.S. PATENT DOCUMENTS

| | | | | |
|---|---|---|---|---|
| 10,407,683 | B2 | 9/2019 | Nelson et al. | |
| 10,953,033 | B2 | 3/2021 | Stewart et al. | |
| 11,000,547 | B2 | 5/2021 | Goldberg et al. | |
| 11,058,706 | B2 | 7/2021 | Stewart et al. | |
| 11,160,822 | B2 | 11/2021 | De Boer et al. | |
| 11,458,156 | B2 | 10/2022 | De Boer et al. | |
| 11,844,759 | B2 | 12/2023 | Kahvejian et al. | |
| 12,357,653 | B2 | 7/2025 | Kahvejian et al. | |
| 2003/0082768 | A1 | 5/2003 | Baskerville et al. | |
| 2005/0015829 | A1 | 1/2005 | Koop et al. | |
| 2005/0059005 | A1 | 3/2005 | Tuschl et al. | |
| 2005/0112639 | A1 | 5/2005 | Wang et al. | |
| 2005/0176940 | A1 | 8/2005 | King | |
| 2005/0261218 | A1 | 11/2005 | Esau et al. | |
| 2006/0292611 | A1 | 12/2006 | Berka et al. | |
| 2010/0129877 | A1 | 5/2010 | Sahin et al. | |
| 2010/0137407 | A1 | 6/2010 | Abe et al. | |
| 2014/0068797 | A1 | 3/2014 | Doudna et al. | |
| 2014/0134636 | A1 | 5/2014 | Kim et al. | |
| 2015/0064236 | A1 | 3/2015 | Bancel et al. | |
| 2015/0079630 | A1 | 3/2015 | Abe et al. | |
| 2015/0299702 | A1 | 10/2015 | Kjems et al. | |
| 2016/0194368 | A1 | 7/2016 | Hoge et al. | |
| 2017/0042782 | A1 | 2/2017 | Wendel et al. | |
| 2018/0023079 | A1 | 1/2018 | Dimmeler et al. | |
| 2018/0037894 | A1 | 2/2018 | Bovell et al. | |
| 2019/0345503 | A1* | 11/2019 | Chang .................... | A61K 39/39 |
| 2020/0131498 | A1 | 4/2020 | Martini et al. | |
| 2020/0306286 | A1 | 10/2020 | Stewart et al. | |
| 2021/0292761 | A1 | 9/2021 | Kahvejian et al. | |
| 2021/0371494 | A1 | 12/2021 | Wesselhoeft et al. | |
| 2022/0088049 | A1 | 3/2022 | Kahvejian et al. | |
| 2022/0142896 | A1 | 5/2022 | Kahvejian et al. | |
| 2022/0143062 | A1 | 5/2022 | Kahvejian et al. | |
| 2022/0296729 | A1 | 9/2022 | Kahvejian et al. | |

FOREIGN PATENT DOCUMENTS

| | | | |
|---|---|---|---|
| DE | 102005001784 | A1 | 10/2006 |
| EP | 1598421 | A2 | 11/2005 |
| EP | 1723958 | A2 | 11/2006 |
| EP | 2996697 | B1 | 6/2019 |
| JP | 2008-278784 | A | 11/2008 |
| WO | 199201813 | A1 | 2/1992 |
| WO | WO-2007/016507 | A2 | 2/2007 |
| WO | 2010084371 | A1 | 7/2010 |
| WO | WO-2013/053481 | A1 | 4/2013 |
| WO | WO-2013151663 | A1 | 10/2013 |
| WO | WO-2013151664 | A1 | 10/2013 |
| WO | WO-2013151665 | A2 | 10/2013 |
| WO | WO-2013151666 | A2 | 10/2013 |
| WO | WO-2013151668 | A2 | 10/2013 |
| WO | WO-2013151669 | A1 | 10/2013 |
| WO | WO-2013151670 | A2 | 10/2013 |
| WO | WO-2013151671 | A1 | 10/2013 |
| WO | WO-2013151672 | A2 | 10/2013 |
| WO | WO-2013151736 | A2 | 10/2013 |
| WO | WO-2014/039523 | A1 | 3/2014 |
| WO | 2014164253 | A1 | 10/2014 |
| WO | 2014186334 | A1 | 11/2014 |
| WO | 2015023975 | A1 | 2/2015 |
| WO | 2015034925 | A1 | 3/2015 |
| WO | WO-2015058069 | A1 | 4/2015 |
| WO | 2015164674 | A1 | 10/2015 |
| WO | 2016011222 | A2 | 1/2016 |
| WO | 2016197121 | A1 | 12/2016 |
| WO | 2017001570 | A2 | 1/2017 |
| WO | WO-2017/040815 | A1 | 3/2017 |
| WO | 2017222911 | A1 | 12/2017 |
| WO | 2018191722 | A1 | 10/2018 |
| WO | 2018237372 | A1 | 12/2018 |
| WO | WO-2019/118919 | A1 | 6/2019 |
| WO | WO-2019/236673 | A1 | 12/2019 |
| WO | WO-2020/023655 | A1 | 1/2020 |
| WO | 2020173171 | A1 | 9/2020 |
| WO | WO-2020/180751 | A1 | 9/2020 |
| WO | WO-2020/180752 | A1 | 9/2020 |
| WO | WO-2020/181013 | A1 | 9/2020 |
| WO | WO-2020/198403 | A2 | 10/2020 |
| WO | 2020/257727 | A1 | 12/2020 |
| WO | WO-2020/252436 | A1 | 12/2020 |
| WO | WO-2020/257730 | A1 | 12/2020 |
| WO | WO-2021/155171 | A1 | 8/2021 |
| WO | WO-2021/155175 | A1 | 8/2021 |
| WO | WO-2021/155177 | A1 | 8/2021 |
| WO | WO-2021/236930 | A1 | 11/2021 |
| WO | WO-2021/236952 | A1 | 11/2021 |
| WO | WO-2021/236980 | A1 | 11/2021 |

OTHER PUBLICATIONS

Alhasan, et al., Circular RNA enrichment in platelets is a signature of transcriptome degradation. Blood, Mar. 3, 2016; 127(9):e1-e11.

Anand et al.: MicroRNA-Mediated Regulation of the Angiogenic Switch. Curr Opin Hematol. 18(3): 171-176 (2011).

Auslander et al.: A Ligand-Dependent Hammerhead Ribozyme Switch for Controlling Mammalian Gene Expression. Mal Biosyst. 6(5): 807-814 (2010).

Bartel, "MicroRNAs: Genomics, Biogenesis, Mechanism, and Function", Cell, vol. 116, pp. 281-297, Jan. 23, 2004.

Bartel. MicroRNAs: target recognition and regulatory functions. Cell 136:215-233 (2009).

Beaudry, et al., An efficient strategy for the synthesis of circular RNA molecules. Nucleic Acids Research, 1995; 23 (15):3064-3066.

Bee Harry et al.: Conserved Features of an RNA Promoter for RNA Polymerase II Determined from Sequence Heterogeneity of a Hepatitis Delta Virus Population. Virology 450-451: 165-173 (2014).

Birmingham et al., "3 UTR Seed Matches, but Not Overall Identity are Associated with RNAi Off-Targets"; Nature Methods, 3(3): 199-204 (2006); Addendum: Nature Methods, 3(6): 487 (2006).

Bonauer et al.: Vascular MicroRNAs. Curr Drug Targets. 11(8): 943-949 (2010).

Carmona, "Circular RNA: Design Criteria for Optimal Therapeutic Utility," Dissertation, Harvard Librarym, Office for Scholarly Communication, Jan. 19, 2019, 129 pages.

Chen et al. Fusion protein linkers: Property, design and functionality. Advanced Drug Delivery Reviews 65:1357-1369 (2013).

Chen et al.: Sensing Self and Foreign Circular RNAs by Intron Identity. Molecular Cell. 67:228-238.e1-e5. (2017).

Chesnoy et al. Structure and function of lipid-DNA complexes for gene delivery. Annu Rev Biophys Biomol Struct. 29:27-47 (2000).

Claire Roulston (PhD Dissertation. University of St. Andrews. 2015 "Occurrence & Function of Cellular 2A Sequences" http:/hdl.handle.net/10023/7062). (Year: 2015) 282 pages.

Cong et al. Multiplex genome engineering using CRISPR/Cas systems. Science 339:819-823 (2013).

Contreras et al.: MicroRNAs in Inflammation and Immune Responses. Leukemia. 26(3): 404-413 (2012) oi:0.1038/leu.2011.356. Epub Dec. 20, 2011.

Defenbaugh et al.: Hepatitis Delta Antigen Requires a Minimum Length of the Hepatitis Delta Virus Unbranched Rod RNA Structure for Binding. Journal of Virology 83(9): 4548-4556 (2009).

Ding et al.: Three-Dimensional RNA Structure Refinement by Hydroxyl Radical Probing. Nat Methods. 9(6): 603-608. doi:10.1038/nmeth.1976. (2012) 20 pages.

Doench et al., "siRNAs can function as miRNAs," Genes & Dev, 17:438-442, 2003.

Dudekula, et al., Circinteractome: A web tool for exploring circular RNAs and their interacting proteins and microRNAs. RNA Biology, 2016; 13(1 ): 34-42.

Elabd et al.: DNA Methyltransferase-3-Dependent Nonrandom Template Segregation in Differentiating Embryonic Stem Cells. J. Cell Biol. 203(1): 73-85 (2013).

Gentner et al.: Exploiting MicroRNA Regulation for Genetic Engineering. Tissue Antigens 80(5): 393-403 (2012).

Gori et al.: Delivery and Specificity of CRISPR-Cas9 Genome Editing Technologies for Human Gene Therapy. Hum Gene Ther. 26(7): 443-451 doi: 10.1089/hum.2015.074 (2015).

(56) References Cited

OTHER PUBLICATIONS

Griffin et al.: Hepatitis Delta Antigen Requires a Flexible Quasi-Double-Stranded RNA Structure to Bind and Condense Hepatitis Delta Virus RNA in a Ribonucleoprotein Complex. J Viral. 88(13): 7402-7411 doi: 10.1128/JVI.00443-14 (2014).
Grimson et al.: MicroRNA Targeting Specificity in Mammals:Determinants Beyond Seed Pairing. Molecular Cell 27 (1 ): 91-105 (2007).
Guedj, et al., Understanding early serum hepatitis D virus and HBsAg kinetics during pegylated interferon-alfa therapy via mathematical modeling. Hepatology, Dec. 2014; 60(6): 1902-1910.
Hendel, et al. Chemically modified guide RNAs enhance CRISPR-Cas genome editing in human primary cells. Nat Biotechnol. Sep. 2015;33(9):985-9. doi: 10.1038/nbt.3290. Epub Jun. 29, 2015.
International search report with written opinion dated Mar. 28, 2019 for PCT/US2018/065836.
International Search Report, Int'l Application No. PCT/US2020/038835, mailed Oct. 10, 2020, 5 pages.
Iwasaki et al.: Rocaglates Convert DEAD-Box Protein elF4A into a Sequence-Selective Translational Repressor. Nature 534: 558-561 http://www.nature.com/articles/nature 17978(2016).
Izuogu, et al., Analysis of human ES cell differentiation establishes that the dominant isoforms of the IncRNAs RMST and FIRRE are circular. BMC Genomics, 2018; 19: 276, 1-18.
Kash et al.: Selective Translation of Eukaryotic mRNAs: Functional Molecular Analysis of GRSF-1, a Positive Regulator of Influenza Virus Protein Synthesis. Journal of Virology. 76(20): 10417-10426 DOI: 10.1128/JVI.76.20.10417-10426.2002 http://jvi.asm.org/content/76/20/10417 .full(2002).
Kimoto et al.: Genetic Alphabet Expansion Transcription Generating Functional RNA Molecules Containing a Five-Letter Alphabet Including Modified Unnatural and Natural Base Nucleotides by Thermostable T7 RNA Polymerase Variants. Chem Commun (Camb). 53(91 ): 12309-12312 doi:10.1039/c7cc06661a (2017).
Kolonko et al.: Transcription of Potato Spindle Tuber Viroid by RNA Polymerase II Starts in the Left Terminal Loop. Virology 347: 392-404 (2006).
Kramer et al., "Combinatorial Controlof Drosophila Circular RNA Expression by Intronic Repeats, hnRNPs, and SR Proteins," Genes & Development 29:2168-2182, 2015.
Kuznetsova, et al., Efficient Synthesis of DNA Dumbbells Using Template-Induced Chemical Ligation in Double-Stranded Polynucleotides Closed by Minihairpin Fragments. Antisense & Nucleic acid drug development. 1999; 9: 95-100.
Lagana et al.: Computational Design of Artificial RNA Molecules for Gene Regulation. Methods Mal Biol. 1269: 393-412 (2015).
Landgraf et al.: A Mammalian MicroRNA Expression Atlas Based on Small RNA Library Sequencing. Cell 129(7): 1401-1414 (2007).
Legnini et al.: Circ-ZNF609 Is a Circular RNA that Can Be Translated and Functions in Myogenesis. Mal Cell. 66(1): 22-37.e9 (2017) .
Leonti Eva et al.: Contact Inhibition and High Cell Density Deactivate the Mammalian target of Rapamycin Pathway, thus Suppressing the Senescence Program. PNAS 111 (24 ): 8832-8837 (2014) .
Lewis et al.: RNA Modifications and Structures Cooperate to Guide RNA-Protein Interactions. Nat Rev Mol Cell Biol. 18(3): 202-210 (2017).
Li, et al., Discovering the interactions between circular RNAs and RNA-binding proteins from CLIP-seq Data using circScan. Mar. 11, 2017. 1-19.
Lim et al., Microarray analysis shows that some microRNAs downregulate large numbers of target mRNAs, Nature, 433(7027):769-773, 2005.
Lingor et al.: Transfection of "Naked" siRNA Results in Endosomal Uptake and Metabolic Impairment in Cultured Neurons. Biochemical and Biophysical Research Communications 315(4): 1126-1133 (2004).
Liu et al.: VSV-G Viral Envelope Glycoprotein Prepared from Pichia Pastoris Enhances Transfection of DNA into Animal Cells. J. Microbial. Biotechnol. 27(6): 1098-1105 (2017).
Mair et al.: Size-Uniform 200 nm Particles: Fabrication and Application to Magnetofection. J Biomed Nanotechnol. 5(2): 182 (2009) 20 pages.
Marchanka et al.: RNA Structure Determination by Solid-State NMR Spectroscopy. Nature Communications 6:7024 DOI: 10.1038/ncomms8024 (2015) 7 pages.
Wesselhoeft et al., "Engineering circular RNA for potent and stable translation in eukaryotic cells," Nat Comm. 9(1):2629 (Jul. 2018) (10 pages).
Micura, "Cyclic Oligoriboneucleotides (RNA) by Solid-Phase Synthesis," Chem Eur J. 5(7):2077-82 (1999).
Angenendt et al., "Cell-Free Protein Expression and Functional Assay in Nanowell Chip Format," Anal Chem. 76(7):1844-9 (2004).
Angenendt et al., "Generation of High Density Protein Microarrays by Cell-free in Situ Expression of Unpurified PCR Products," Mol Cell Proteomics. 5(9):1658-66 (2006).
Bird et al., "Single-chain antigen-binding proteins," Science. 242(4877):423-6 (1988) (5 pages).
Chatterjee et al., "Protein technologies," Curr Opin Biotechnology. 17:334-6 (2006).
Costello et al., "Reinventing the Wheel: Synthetic Circular RNAs for Mammalian Cell Engineering," Trends Biotechnol. 38(2):217-30 (2020) (15 pages).
Goldstein, "Effect of Alcohol on Cellular Membranes," Ann Emerg Med. 15(9):1013-8 (1986).
He et al., "Arraying proteins by cell-free synthesis," Biomol Eng. 24(4):375-80 (2007).
He et al., "DiscernArray™ technology: a cell-free method for the generation of protein arrays from PCR DNA," J Immunol Methods. 274(1-2):265-70 (2003).
He et al., "In situ synthesis of protein arrays," Curr Opin Biotechnol. 19(1):4-9 (2008).
He et al., "Printing protein arrays from DNA arrays," Nat Methods. 5(2):175-7 (2008).
He et al., "Single step generation of protein arrays from DNA by cell-free expression and in situ immobilisation (PISA method)," Nucleic Acids Res. 29(15):E73-3 (2001) (6 pages).
Huston et al., "Protein engineering of antibody binding sites: recovery of specific activity in an anti-digoxin single-chain Fv analogue produced in *Escherichia coli*," Proc Natl Acad Sci U S A. 85(16):5879-83 (1988).
Ingólfsson et al., "Alcohol's Effects on Lipid Bilayer Properties," Biophys J. 101(4):847-55 (2011).
Katzen et al., "The past, present and future of cell-free protein synthesis," Trends Biotechnol. 23(3):150-6 (2005).
Kilb et al., "Protein microarray generation by in situ protein expression from template DNA," Eng Life Sci. 14:352-64 (2014).
Kinpara et al., "A Picoliter Chamber Array for Cell-Free Protein Synthesis," J Biochem 136(2):149-54 (2004).
Marchanka et al., "RNA structure determination by solid-state NMR spectroscopy," Nat Commun. 6:7024 (2015) (7 pages).
Qin et al., "Structure, Regulation, and Function of Linear and Circular Long Non-Coding RNAs," Front Genet. 11:150 (Mar. 3, 2020) (15 pages).
Ramachandran et al., "Self-Assembling Protein Microarrays," Science. 305(5680):86-90 (2004) (6 pages).
Stadel et al., "Orphan G protein-coupled receptors: a neglected opportunity for pioneer drug discovery," Trends Pharmacol Sci. 18(11):430-7 (1997).
Stevens, "Design of high-throughput methods of protein production for structural biology," Structure. 8(9):R177-85 (2000).
Takulapalli et al., "High Density Diffusion-Free Nanowell Arrays," J Proteome Res. 11(8):4382-91 (2012).
Tao et al., "Protein chip fabrication by capture of nascent polypeptides," Nat Biotechnol. 24(10):1253-4 (2006) (3 pages).
Ward et al., "Binding activities of a repertoire of single immunoglobulin variable domains secreted from *Escherichia coli*," Nature. 341(6242):544-6 (1989).
Liang et al., "Short intronic repeat sequences facilitate circular RNA production," Genes Dev. 28(20):2233-47 (Oct. 2014) (16 pages).
Chen et al., "Initiation of Protein Synthesis by the Eukaryotic Translational Apparatus on Circular RNAs" Science. 268(5209):415-417 (1995) (5 pages).

(56) References Cited

OTHER PUBLICATIONS

Klein et al., "Structural Basis of glmS ribozyme activation by glucosamine-6-phosphate". Science. 313(5794): 1752-1756 (2006).
Newick et al., "CAR T Cell Therapy for Solid Tumors," Annu Rev Med. 68:139-152 (Jan. 2017).
Matsuda et al.: Determinants of initiation codon selection during translation in mammalian cells. PLoS One. 5(11): e15057 (2010) .
Mignone et al. Untranslated regions of mRNAs. Genome Biol. 2002;3(3):Reviews0004. Epub Feb. 28, 2002.
Miller et al.: Non-Viral CRISPR/Cas Gene Editing In Vitro and In Vivo Enabled by Synthetic Nanoparticle Co-Delivery of Cas9 mRNA and sgRNA. Angew Chem Int Ed Engl. 56(4 ): 1059-1063 (2017.
Muller et al.: An Efficient Method for Electroporation of Small Interfering RNAs into ENCODE Project Tier 1 GM12878 and K562 Cell Lines. Journal of Biomolecular Techniques 26(4):142-149 (2015).
Muller, et al., In vitro circularization of RNA. RNA Biology, 2017; 14(8): 1018-1027.
Neuhaus et al.: Nanoparticles as Transfection Agents: A Comprehensive Study with Ten Different Cell Lines. RSC Adv. 6: 18102-18112 (2016).
Ogawa, A.: Rational Design of Artificial Riboswitches Based on Ligand-Dependent Modulation of Internal Ribosome Entry in Wheat Germ Extract and their Applications as Label-Free Biosensors. RNA 17(3): 478-488 doi: 10.1261/rna.2433111 (2011).
Olton et al.: Nanostructured Calcium Phosphates (NanoCaPs) for Non-Viral Gene Delivery: Influence of the Synthesis Parameters on Transfection Efficiency. Biomaterials 28(6): 1267-1279 (2007) Epub Nov. 21, 2006.
Petkovic, et al., RNA circularization strategies in vivo and in vitro. Nucleic Acids Research, 2015; 43(4): 2454-2465.
Rajewsky, N., MicroRNA target predictions in animals, Nature Genetics Supplement, 2006; 38:S8-13.
Ran et al. Genome engineering using the CRISPR-Cas9 system. Nature Protocols 8:2281-2308 (2013).
Rozenski et al.: The RNA Modification Database: 1999 Update. Nucleic Acids Res. 27(1 ): 196-197 (1999).
Schlake et al., "Developing mRNA-Vaccine Technologies," RNA Biology, 9:11, Nov. 12, 2012, pp. 1319-1330.
Sooter et al.: Toward Automated Nucleic Acid Enzyme Selection. Biol Chem. 382(9): 1327-1334 (2001).
Steeland et al.: Nanobodies as Therapeutics: Big Opportunities for Small Antibodies. Drug Discov Today. 21 (7): 1076-1113 (2016).
Tannous, B.A .: Gaussia Luciferase Reporter Assay for Monitoring Biological Processes in Culture and in Vivo. Nat Protec. 4(4): 582-591 (2009).
Tijerina et al.: OMS Footprinting of Structured RNAs and RNA-Protein Complexes. Nat Protec. 2(10): 2608-2623 (2007) doi:10.1038/nprot.2007.380.
Tonges et al.: Stearylated Octaarginine and Artificial Virus-Like Particles for Transfection of siRNA into Primary Rat Neurons. RNA 12: 1431-1438 (2006).
Touriol et al.: Generation of Protein Isoform Diversity by Alternative Initiation of Translation at Non-AUG Codons. Biology Cell 95(3-4): 169-178 (2003).
Tucker et al.: Riboswitches as Versatile Gene Control Elements. Curr Opin Struct Biol. 15(3): 342-348 (2005).
U.S. Appl. No. 16/438,073 Final Office Action dated Apr. 27, 2020.
U.S. Appl. No. 16/438,073 non-final Office Action dated Aug. 24, 2020.
U.S. Appl. No. 16/438,073 non-final Office Action dated Jan. 13, 2020.
Wang et al., "Efficient Backsplicing Produces Translatable Circular mRNAs," RNA 21, 2015, pp. 172-179.
Wesselhoeft et al., "RNA Circularization Diminishes Immunogenicity and Can Extend Translation Duration In Vivo," Molecular Cell, 74, May 2, 2019, pp. 508-520.
Wesselhoeft, et al., Engineering circular RNA for potent and stable translation in eukaryotic cells. Nature Communications, 2018: 9;2629, 10 pages.
Winkler et al.: Control of Gene Expression by a Natural Metabolite-Responsive Ribozyme. Nature 428(6980): 281-286 (2004).
Written Opinion of the International Searching Authority, Int'l Application No. PCT/US2020/038835, mailed Oct. 10, 2020, 9 pagse.
Wu et al. MicroRNAs direct rapid deadenylation of mRNA. PNAS USA 103(11 ):4034-4039 (2006).
Yu et al.: RNA Editing by ADAR1 Marks dsRNA as Self. Cell Res. 25(12): 1283-1284 (2015).
Zeng et al. Both natural and designed micro RNAs can inhibit the expression of cognate mRNAs when expressed in human cells. Mal. Cell. 9; 1327-33 (2002).
Zhang et al.: Cell-Penetrating Peptides as Noninvasive Transmembrane Vectors for the Development of Novel Multifunctional Drug-Delivery Systems. Journal of Controlled Release 229: 130-139 (2016).
Ziehler et al.: Probing RNA Structure with Chemical Reagents and Enzymes. Curr Protec Nucleic Acid Chem. 0 6: Unit-6.1. doi:10.1002/0471142700.nc0601s00. (2001) 24 pages.
Zuris et al.: Cationic Lipid-Mediated Delivery of Proteins Enables Efficient Protein-Based Genome Editing in Vitro and in Vivo. Nat Biotechnol. 33(1 ): 73-80 (2015).
Vora et al., "Next stop for the CRISPR revolution: RNA-guided epigenetic regulators," FEBS J. 283(17):3181-93 (Sep. 2016).
Zheng et al., "Circular RNA profiling reveals an abundant circHIPK3 that regulates cell growth by sponging multiple miRNAs," Nat Commun. 7:11215 (Apr. 2016) (13 pages).
Petrov et al., "RNA Purification by Preparative Polyacrylamide Gel Electrophoresis," Methods in Enzymology. 530:315-330 (Jan. 2013) (16 pages).
Walleshauser et al., "A Simple Approach for Evaluating Total MicroRNA Extraction from Mouse Brain Tissues," JASMI. 2(1):5-12 (Jan. 2012) (8 pages).
Zheng et al., "Protein L: a novel reagent for the detection of chimeric antigen receptor (CAR) expression by flow cytometry," J Transl Med. 10:29 (Feb. 2012) (6 pages).
Thess et al., "Sequence-engineered mRNA without chemical nucleoside modifications enables an effective protein therapy in large animals," Mol Ther. 23(9):1456-64 (2015).
Jones & Gowans et al., "Long-Term Storage of DNA-Free RNA for use in Vaccine Studies." Bio Techniques, 43(5), 675-681. (Nov. 2007)(14 pages).
Schmid et al., "Considerations for Producing mRNA Vaccines for Clinical Trials". In: Kramps, T., Elbers, K. (eds) RNA Vaccines. Methods in Molecular Biology, vol. 1499. Humana Press, New York, NY. (2007)(Abstract Only).

* cited by examiner

Example of helical part of construct

Query: 163-179 mmu-miR-692: 1-17

```
UserSeq        163  gaggugcucaaagagau  179 SEQ ID NO: 112
                    |||| ||||||||||||
mmu-miR-692     17  gaggcgcucaaagagau  1   SEQ ID NO: 129
```

COMPOSITIONS COMPRISING CIRCULAR POLYRIBONUCLEOTIDES AND USES THEREOF

CROSS-REFERENCE

This application is a continuation of U.S. application Ser. No. 17/482,346, filed Sep. 22, 2021, which is a continuation of U.S. application Ser. No. 17/313,963, filed May 6, 2021, which is a continuation of U.S. patent application Ser. No. 17/173,991, filed Feb. 11, 2021, which is a continuation of Ser. No. 16/438,073, filed on Jun. 11, 2019, which is a continuation of International Application No. PCT/US2018/065836, filed on Dec. 14, 2018, which claims the benefit of U.S. Provisional Application No. 62/599,547, filed on Dec. 15, 2017, and U.S. Provisional Application No. 62/676,688, filed on May 25, 2018, each of which are incorporated herein by reference in their entirety.

SEQUENCE LISTING

The instant application contains a Sequence Listing which has been submitted electronically in XML format and is hereby incorporated by reference in its entirety. Said XML copy, created on Oct. 24, 2022, is named FLG-100C5-VL-50001-US-05_SL.xml and is 181,569 bytes in size.

BACKGROUND

Certain circular polyribonucleotides are ubiquitously present in human tissues and cells, including tissues and cells of healthy individuals.

SUMMARY

In one aspect, the invention includes a pharmaceutical composition comprising a circular polyribonucleotide that comprises at least one structural element selected from a) an encryptogen; b) a stagger element; c) a regulatory element; d) a replication element; f) quasi-double-stranded secondary structure; and g) expression sequence; and at least one functional characteristic selected from: a) greater translation efficiency than a linear counterpart; b) a stoichiometric translation efficiency of multiple translation products; c) less immunogenicity than a counterpart lacking an encryptogen; d) increased half-life over a linear counterpart; and e) persistence during cell division.

In some embodiments, the circular polyribonucleotide is translation competent. In one such embodiment, the quasi-helical structure comprises at least one double-stranded RNA segment with at least one non-double-stranded segment. In another such embodiment, the quasi-helical structure comprises a first sequence and a second sequence linked with a repetitive sequence, e.g., an A-rich sequence.

In some embodiments, the circular polyribonucleotide comprises an encryptogen. In some embodiments, the encryptogen comprises at least one modified ribonucleotide, e.g., pseudo-uridine, N(6)methyladenosine (m6A). In some embodiments, the encryptogen comprises a protein binding site, e.g., ribonucleotide binding protein. In some embodiments, the encryptogen comprises an immunoprotein binding site, e.g., to evade immune responses, e.g., CTL responses.

In some embodiments, the circular polyribonucleotide comprises at least one modified ribonucleotide.

In some embodiments, the circular polyribonucleotide has at least 2× less immunogenicity than a counterpart lacking the encryptogen, e.g., as assessed by expression or signaling or activation of at least one of RIG-I, TLR-3, TLR-7, TLR-8, MDA-5, LGP-2, OAS, OASL, PKR, IFN-beta.

In some embodiments, the circular polyribonucleotide further comprises a riboswitch.

In some embodiments, the circular polyribonucleotide further comprises an aptazyme.

In some embodiments, the circular polyribonucleotide comprises a translation initiation sequence, e.g., GUG, CUG start codon, e.g., expression under stress conditions.

In some embodiments, the circular polyribonucleotide comprises at least one expression sequence, e.g., encoding a polypeptide. In one such embodiments, the expression sequence encodes a peptide or polynucleotide. In some embodiments, the circular polyribonucleotide comprises a plurality of expression sequences, either the same or different.

In some embodiments, the circular polyribonucleotide comprises a stagger element, e.g., 2A.

In some embodiments, the circular polyribonucleotide comprises a regulatory nucleic acid, e.g., a non-coding RNA. In some embodiments, the circular polyribonucleotide comprises a regulatory element, e.g., that alters expression of an expression sequence.

In some embodiments, the circular polyribonucleotide has a size in the range of about 20 bases to about 20 kb.

In some embodiments, the circular polyribonucleotide is synthesized through circularization of a linear polynucleotide.

In some embodiments, the circular polyribonucleotide is substantially resistant to degradation, e.g., exonuclease.

In some embodiments, the circular polyribonucleotide lacks at least one of: a) a 5'-UTR; b) a 3'-UTR; c) a poly-A sequence; d) a 5'-cap; e) a termination element; f) an internal ribosomal entry site; g) degradation susceptibility by exonucleases and h) binding to a cap-binding protein.

In one aspect, the invention includes a method of producing the composition comprising a circular polyribonucleotide described herein.

In one aspect, the invention includes a pharmaceutical composition comprising a pharmaceutically acceptable carrier or excipient and a circular polyribonucleotide that comprises one or more expression sequences, wherein the circular polyribonucleotide is competent for rolling circle translation.

In some embodiments, each of the one or more expression sequences is separated from a succeeding expression sequence by a stagger element in the circular polyribonucleotide, wherein rolling circle translation of the one or more expression sequences generates at least two polypeptide molecules, e.g., the stagger elements stalls or halts the ribosome such that the elongating polypeptide falls off the ribosome. In some embodiments, the stagger element prevents generation of a single polypeptide (a) from two rounds of translation of a single expression sequence or (b) from one or more rounds of translation of two or more expression sequences. For example, the stagger element can prevent generation of a single polypeptide from two or more rounds of translation of two or more expression sequences, e.g., the stagger element halts the ribosome and/or allows the elongating polypeptide to fall off the ribosome after one circuit around the circular polyribonucleotide.

In some embodiments, the stagger element is a sequence separate from the one or more expression sequences.

In some embodiments, the stagger element comprises a portion of an expression sequence of the one or more expression sequences.

In one aspect, the invention includes a pharmaceutical composition comprising a pharmaceutically acceptable carrier or excipient and a circular polyribonucleotide that comprises one or more expression sequences and is competent for rolling circle translation, wherein the circular polyribonucleotide is configured such that at least 10%, 20%, 30%, 40%, 50%, at least 60%, at least 70%, at least 80%, at least 90%, at least 95%, at least 96%, at least 97%, at least 98%, at least 99%, or 100% of total polypeptides (molar/molar) generated during the rolling circle translation of the circular polyribonucleotide are discrete polypeptides, and wherein each of the discrete polypeptides is generated from a single round of translation or less than a single round of translation of the one or more expression sequences.

In some embodiments, the circular polyribonucleotide is configured such that at least 10%, 20%, 30%, 40%, 50%, at least 60%, at least 70%, at least 80%, at least 90%, at least 95%, at least 96%, at least 97%, at least 98%, at least 99%, or 100% of total polypeptides (molar/molar) generated during the rolling circle translation of the circular polyribonucleotide are the discrete polypeptides, and wherein amount ratio of the discrete products over the total polypeptides is tested in an in vitro translation system.

In some embodiments, the in vitro translation system comprises rabbit reticulocyte lysate.

In some embodiments, the stagger element is downstream of or 3' to at least one of the one or more expression sequences, wherein the stagger element is configured to stall a ribosome during rolling circle translation of the circular polyribonucleotide.

In one aspect, the invention provides a pharmaceutical composition comprising a pharmaceutically acceptable carrier or excipient and a circular polyribonucleotide that comprises one or more expression sequences and a stagger element downstream of or 3' to at least one of the one or more expression sequences. In some embodiments, the stagger element is configured to stall a ribosome during rolling circle translation of the circular polyribonucleotide.

In some embodiments, the stagger element encodes a peptide sequence selected from the group consisting of a 2A sequence and a 2A-like sequence.

In some embodiments, the stagger element encodes a sequence with a C-terminal sequence that is GP.

In some embodiments, the stagger element encodes a sequence with a C-terminal consensus sequence that is D(V/I)ExNPG P (SEQ ID NO: 61), where x=any amino acid.

In some embodiments, the stagger element encodes at least one of of GDVESNPGP (SEQ ID NO: 62), GDIEENPGP (SEQ ID NO: 63), VEPNPGP (SEQ ID NO: 64), IETNPGP (SEQ ID NO: 65), GDIESNPGP (SEQ ID NO: 66), GDVELNPGP (SEQ ID NO: 67), GDIETNPGP (SEQ ID NO: 68), GDVENPGP (SEQ ID NO: 69), GDVEENPGP (SEQ ID NO: 70), GDVEQNPGP (SEQ ID NO: 71), IESNPGP (SEQ ID NO: 72), GDIELNPGP (SEQ ID NO: 73), HDIETNPGP (SEQ ID NO: 74), HDVETNPGP (SEQ ID NO: 75), HDVEMNPGP (SEQ ID NO: 76), GDMESNPGP (SEQ ID NO: 77), GDVETNPGP (SEQ ID NO: 78), GDIEQNPGP (SEQ ID NO: 79), and DSEFNPGP (SEQ ID NO: 80).

In some embodiments, the stagger element is downstream of or 3' to each of the one or more expression sequences.

In some embodiments, the stagger element of a first expression sequence in the circular polyribonucleotide is upstream of (5' to) a first translation initiation sequence of an expression sequence succeeding the first expression sequence in the circular polyribonucleotide, and wherein a distance between the stagger element and the first translation initiation sequence enables continuous translation of the first expression sequence and the succeeding expression sequence. In some embodiments, the stagger element comprises a termination element of a first expression sequence on the circular polyribonucleotide that has a distance upstream from (5' to) a translation initiation sequence of an expression sequence succeeding the first expression sequence on the circular polyribonucleotide, and wherein the distance enables continuous translation of the first expression sequence and its succeeding expression sequence.

In some embodiments, a first stagger element is upstream of (5' to) a first translation initiation sequence of a first expression sequence in the circular polyribonucleotide, wherein the circular polyribonucleotide is continuously translated, wherein a corresponding circular polyribonucleotide comprises a second stagger element upstream of a second translation initiation sequence of a second expression sequence in the corresponding circular polyribonucleotide that is not continuously translated, and wherein the second stagger element in the corresponding circular polyribonucleotide is at a greater distance from the second translation initiation sequence, e.g., at least 2×, 3×, 4×, 5×, 6×, 7×, 8×, 9×, 10×, than a distance between the first stagger element and the first translation initiation in the circular polyribonucleotide. In some embodiments, the stagger element comprises a first termination element upstream of (5' to) a first translation initiation sequence of a first expression sequence in the circular polyribonucleotide, wherein the circular polyribonucleotide is continuously translated and a corresponding circular polyribonucleotide comprises a stagger element comprising a second termination element upstream from a second translation initiation sequence of a second expression sequence in the corresponding circular polyribonucleotide that is not continuously translated, and where the second termination element in the corresponding circular polyribonucleotide is at a greater distance from the second translation initiation sequence, e.g., at least 2×, 3×, 4×, 5×, 6×, 7×, 8×, 9×, 10×, than a distance between the first termination element and the first translation initiation in the circular polyribonucleotide.

In some embodiments, the distance between the first stagger element and the first translation initiation is at least 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, 40 nt, 45 nt, 50 nt, 55 nt, 60 nt, 65 nt, 70 nt, 75 nt, or greater. In some embodiments, the distance between the second stagger element and the second translation initiation is at least 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, 40 nt, 45 nt, 50 nt, 55 nt, 60 nt, 65 nt, 70 nt, 75 nt, or greater than the distance between the first stagger element and the first translation initiation.

In some embodiments, the circular polyribonucleotide comprises more than one expression sequence.

In some embodiments, the circular polyribonucleotide has a translation efficiency at least 5%, at least 10%, at least 15%, at least 20%, at least 30%, at least 40%, at least 50%, at least 60%, at least 70%, at least 80%, at least 90%, at least 100%, at least 150%, at least 2 fold, at least 3 fold, at least 4 fold, at least 5 fold, at least 6 fold, at least 7 fold, at least 8 fold, at least 9 fold, at least 10 fold, at least 20 fold, at least 50 fold, or at least 100 fold greater than a linear counterpart.

In some embodiments, the circular polyribonucleotide has a translation efficiency at least 5 fold greater than a linear counterpart.

In some embodiments, the circular polyribonucleotide lacks an internal ribosomal entry site.

In some embodiments, the one or more expression sequences comprise a Kozak initiation sequence.

In some embodiments, the one or more expression sequences encodes a peptide.

In some embodiments, the circular polyribonucleotide comprises a regulatory nucleic acid, e.g., a non-coding RNA. In some embodiments, the circular polyribonucleotide comprises a regulatory element, e.g., that alters expression of an expression sequence.

In one aspect, the invention provides a circular polyribonucleotide of any of the pharmaceutical composition provided herein.

In one aspect, the invention includes a method of producing the pharmaceutical composition provided herein, comprising combining the circular polyribonucleotide described herein and the pharmaceutically acceptable carrier or excipient described herein.

In one aspect, the invention includes a method of administering the composition comprising a circular polyribonucleotide described herein.

In one aspect, the invention includes a method for protein expression, comprising translating at least a region of the circular polyribonucleotide provided herein.

In some embodiments, the translation of at least a region of the circular polyribonucleotide takes place in vitro. In some embodiments, the translation of the at least a region of the circular polyribonucleotide takes place in vivo.

In one aspect, the invention includes a polynucleotide, e.g., a DNA vector, encoding the circular polyribonucleotide provided herein.

In one aspect, the invention includes a method of producing the circular polyribonucleotide as provided herein.

In some embodiments, the method comprises splint ligation-mediated circularization of a linear polyribonucleotide.

In some embodiments, the circularization, e.g., splint ligation-mediated circularization, has an efficiency of at least 2%, at least 5%, at least 10%, at least 15%, at least 20%, at least 25%, at least 30%, at least 32%, at least 34%, at least 36%, at least 38%, at least 40%, at least 42%, at least 44%, at least 46%, at least 48%, or at least 50%. In some embodiments, the splint ligation-mediated circularization has an efficiency of about 40% to about 50% or more than 50%.

Definitions

The present invention will be described with respect to particular embodiments and with reference to certain figures but the invention is not limited thereto but only by the claims. Terms as set forth hereinafter are generally to be understood in their common sense unless indicated otherwise.

The terms "obtainable by", "producable by" or the like are used to indicate that a claim or embodiment refers to compound, composition, product, etc. per se, i. e. that the compound, composition, product, etc. can be obtained or produced by a method which is described for manufacture of the compound, composition, product, etc., but that the compound, composition, product, etc. may be obtained or produced by other methods than the described one as well. The terms "obtained by", "produced by" or the like indicate that the compound, composition, product, is obtained or produced by a recited specific method. It is to be understood that the terms "obtainable by", "producable by" and the like also disclose the terms "obtained by", "produced by" and the like as a preferred embodiment of "obtainable by", "producible by" and the like.

The wording "compound, composition, product, etc. for treating, modulating, etc." is to be understood to refer a compound, composition, product, etc. per se which is suitable for the indicated purposes of treating, modulating, etc. The wording "compound, composition, product, etc. for treating, modulating, etc." additionally discloses that, as a preferred embodiment, such compound, composition, product, etc. is for use in treating, modulating, etc.

The wording "compound, composition, product, etc. for use in . . . " or "use of a compound, composition, product, etc in the manufacture of a medicament, pharmaceutical composition, veterinary composition, diagnostic composition, etc. for . . . " indicates that such compounds, compositions, products, etc. are to be used in therapeutic methods which may be practiced on the human or animal body. They are considered as an equivalent disclosure of embodiments and claims pertaining to methods of treatment, etc. If an embodiment or a claim thus refers to "a compound for use in treating a human or animal being suspected to suffer from a disease", this is considered to be also a disclosure of a "use of a compound in the manufacture of a medicament for treating a human or animal being suspected to suffer from a disease" or a "method of treatment by administering a compound to a human or animal being suspected to suffer from a disease". The wording "compound, composition, product, etc. for treating, modulating, etc." is to be understood to refer a compound, composition, product, etc. per se which is suitable for the indicated purposes of treating, modulating, etc.

The term "pharmaceutical composition" is intended to also disclose that the circular polyribonucleotide comprised within a pharmaceutical composition can be used for the treatment of the human or animal body by therapy. It is thus meant to be equivalent to the "a circular polyribonucleotide for use in therapy".

The circular polyribonucleotides, compositions comprising such circular polyribonucleotides, methods using such circular polyribonucleotides, etc. as described herein are based in part on the examples which illustrate how circular polyribonucleotides effectors comprising different elements, for example a replication element, an expression sequence, a stagger element and an encryptogen (see e.g., example 1) or for example an expression sequences, a stagger element and a regulatory element (see e.g., examples 30 and 38) can be used to achieve different technical effects (e.g. increased translation efficiency than a linear counterpart in examples 1 and 38 and increased half-life over a linear counterpart in example 38). It is on the basis of inter alia these examples that the description hereinafter contemplates various variations of the specific findings and combinations considered in the examples.

As used herein, the terms "circRNA" or "circular polyribonucleotide" or "circular RNA" are used interchangeably and can refer to a polyribonucleotide that forms a circular structure through covalent or non-covalent bonds.

As used herein, the term "encryptogen" can refer to a nucleic acid sequence or structure of the circular polyribonucleotide that aids in reducing, evading, and/or avoiding detection by an immune cell and/or reduces induction of an immune response against the circular polyribonucleotide.

As used herein, the term "expression sequence" can refer to a nucleic acid sequence that encodes a product, e.g., a peptide or polypeptide, or a regulatory nucleic acid. An exemplary expression sequence that codes for a peptide or polypeptide can comprise a plurality of nucleotide triads, each of which can code for an amino acid and is termed as a "codon".

As used herein, the term "immunoprotein binding site" can refer to a nucleotide sequence that binds to an immunoprotein. In some embodiments, the immunoprotein binding site aids in masking the circular polyribonucleotide as exogenous, for example, the immunoprotein binding site can be bound by a protein (e.g., a competitive inhibitor) that prevents the circular polyribonucleotide from being recognized and bound by an immunoprotein, thereby reducing or avoiding an immune response against the circular polyribonucleotide. As used herein, the term "immunoprotein" can refer to any protein or peptide that is associated with an immune response, e.g., such as against an immunogen, e.g., the circular polyribonucleotide. Non-limiting examples of immunoprotein include T cell receptors (TCRs), antibodies (immunoglobulins), major histocompatibility complex (MHC) proteins, complement proteins, and RNA binding proteins.

As used herein, the term "modified ribonucleotide" can refer to a nucleotide with at least one modification to the sugar, the nucleobase, or the internucleoside linkage.

As used herein, the phrase "quasi-helical structure" can refer to a higher order structure of the circular polyribonucleotide, wherein at least a portion of the circular polyribonucleotide folds into a helical structure.

As used herein, the phrase "quasi-double-stranded secondary structure" can refer to a higher order structure of the circular polyribonucleotide, wherein at least a portion of the circular polyribonucleotide creates an internal double strand.

As used herein, the term "regulatory element" can refer to a moiety, such as a nucleic acid sequence, that modifies expression of an expression sequence within the circular polyribonucleotide.

As used herein, the term "repetitive nucleotide sequence" can refer to a repetitive nucleic acid sequence within a stretch of DNA or RNA or throughout a genome. In some embodiments, the repetitive nucleotide sequence includes poly CA or poly TG (UG) sequences. In some embodiments, the repetitive nucleotide sequence includes repeated sequences in the Alu family of introns.

As used herein, the term "replication element" can refer to a sequence and/or motifs useful for replication or that initiate transcription of the circular polyribonucleotide.

As used herein, the term "stagger element" can refer to a moiety, such as a nucleotide sequence, that induces ribosomal pausing during translation. In some embodiments, the stagger element is a non-conserved sequence of amino-acids with a strong alpha-helical propensity followed by the consensus sequence—D(V/I)ExNPG P (SEQ ID NO: 61), where x=any amino acid. In some embodiments, the stagger element may include a chemical moiety, such as glycerol, a non nucleic acid linking moiety, a chemical modification, a modified nucleic acid, or any combination thereof.

As used herein, the term "substantially resistant" can refer to one that has at least 50%, 55%, 60%, 65%, 70%, 75%, 80%, 85%, 90%, 95%, 96%, 97%, 98% or 99% resistance as compared to a reference.

As used herein, the term "stoichiometric translation" can refer to a substantially equivalent production of expression products translated from the circular polyribonucleotide. For example, for a circular polyribonucleotide having two expression sequences, stoichiometric translation of the circular polyribonucleotide can mean that the expression products of the two expression sequences can have substantially equivalent amounts, e.g., amount difference between the two expression sequences (e.g., molar difference) can be about 0, or less than 1%, 2%, 3%, 4%, 5%, 6%, 7%, 8%, 9%, 10%, 15%, or 20%.

As used herein, the term "translation initiation sequence" can refer to a nucleic acid sequence that initiates translation of an expression sequence in the circular polyribonucleotide.

As used herein, the term "termination element" can refer to a moiety, such as a nucleic acid sequence, that terminates translation of the expression sequence in the circular polyribonucleotide.

As used herein, the term "translation efficiency" can refer to a rate or amount of protein or peptide production from a ribonucleotide transcript. In some embodiments, translation efficiency can be expressed as amount of protein or peptide produced per given amount of transcript that codes for the protein or peptide, e.g., in a given period of time, e.g., in a given translation system, e.g., an in vitro translation system like rabbit reticulocyte lysate, or an in vivo translation system like a eukaryotic cell or a prokaryotic cell.

As used herein, the term "circularization efficiency" can refer to a measurement of resultant circular polyribonucleotide versus its starting material.

As used herein, the term "immunogenic" can refer to a potential to induce an immune response to a substance. In some embodiments, an immune response may be induced when an immune system of an organism or a certain type of immune cells is exposed to an immunogenic substance. The term "non-immunogenic" can refer to a lack of or absence of an immune response above a detectable threshold to a substance. In some embodiments, no immune response is detected when an immune system of an organism or a certain type of immune cells is exposed to a non-immunogenic substance. In some embodiments, a non-immunogenic circular polyribonucleotide as provided herein, does not induce an immune response above a pre-determined threshold when measured by an immunogenicity assay. For example, when an immunogenicity assay is used to measure antibodies raised against a circular polyribonucleotide or inflammatory markers, a non-immunogenic polyribonucleotide as provided herein can lead to production of antibodies or markers at a level lower than a predetermined threshold. The predetermined threshold can be, for instance, at most 1.5 times, 2 times, 3 times, 4 times, or 5 times the level of antibodies or markers raised by a control reference.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The following detailed description of the embodiments of the invention will be better understood when read in conjunction with the appended drawings. For the purpose of illustrating the invention, there are shown in the drawings embodiments, which are presently exemplified. It should be understood, however, that the invention is not limited to the precise arrangement and instrumentalities of the embodiments shown in the drawings.

DETAILED DESCRIPTION

Figure 1:
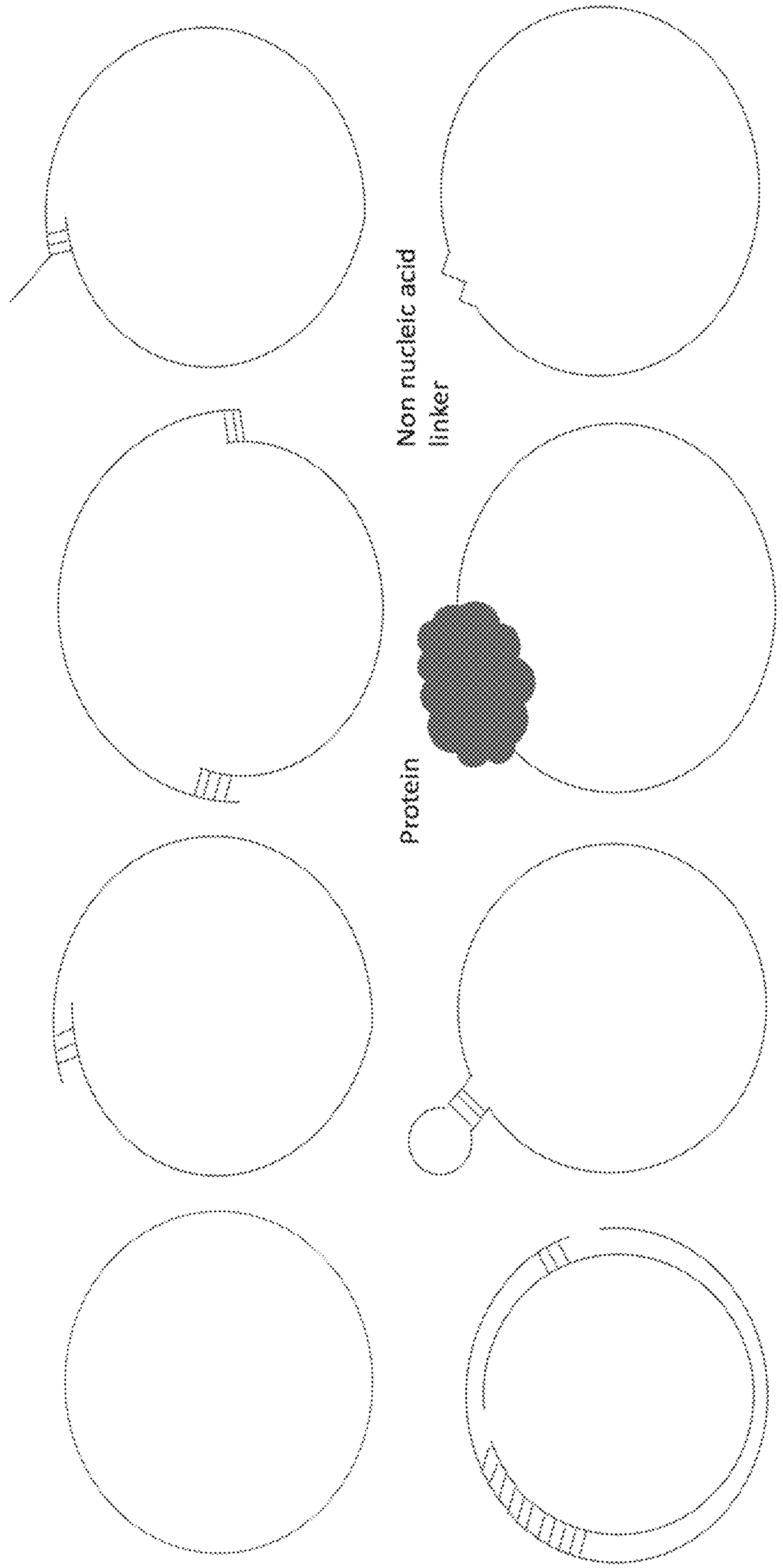
FIG. 1 shows different exemplary circularization methods.

This invention relates generally to pharmaceutical compositions and preparations of circular polyribonucleotides and uses thereof.

Circular Polyribonucleotides

In some aspects, the invention described herein comprises compositions and methods of using and making circular polyribonucleotides, and delivery of circular polyribonucleotides. In some embodiments, the circular polyribonucleotide is non-immunogenic in a mammal, e.g., a human. In some embodiments, the circular polyribonucleotide is capable of replicating or replicates in a cell from an aquaculture animal (fish, crabs, shrimp, oysters etc.), a mammalian cell, e.g., a cell from a pet or zoo animal (cats, dogs, lizards, birds, lions, tigers and bears etc.), a cell from a farm or working animal (horses, cows, pigs, chickens etc.), a human cell, cultured cells, primary cells or cell lines, stem cells, progenitor cells, differentiated cells, germ cells, cancer cells (e.g., tumorigenic, metastic), non-tumorigenic cells (normal cells), fetal cells, embryonic cells, adult cells, mitotic cells, non-mitotic cells, or any combination thereof. In some embodiments, the invention includes a cell comprising the circular polyribonucleotide described herein, wherein the cell is a cell from an aquaculture animal (fish, crabs, shrimp, oysters etc.), a mammalian cell, e.g., a cell from a pet or zoo animal (cats, dogs, lizards, birds, lions, tigers and bears etc.), a cell from a farm or working animal (horses, cows, pigs, chickens etc.), a human cell, a cultured cell, a primary cell or a cell line, a stem cell, a progenitor cell, a differentiated cell, a germ cell, a cancer cell (e.g., tumorigenic, metastic), a non-tumorigenic cell (normal cells), a fetal cell, an embryonic cell, an adult cell, a mitotic cell, a non-mitotic cell, or any combination thereof. In some embodiments, the cell is modified to comprise the circular polyribonucleotide.

In some embodiments, the circular polyribonucleotide includes sequences or expression products.

In some embodiments, the circular polyribonucleotide has a half-life of at least that of a linear counterpart, e.g., linear expression sequence, or linear circular polyribonucleotide. In some embodiments, the circular polyribonucleotide has a half-life that is increased over that of a linear counterpart. In some embodiments, the half-life is increased by about 5%, 10%, 15%, 20%, 25%, 30%, 35%, 40%, 45%, 50%, or greater. In some embodiments, the circular polyribonucleotide has a half-life or persistence in a cell for at least about 1 hr to about 30 days, or at least about 2 hrs, 6 hrs, 12 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or longer or any time therebetween. In certain embodiments, the circular polyribonucleotide has a half-life or persistence in a cell for no more than about 10 mins to about 7 days, or no more than about 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 24 hrs, 36 hrs, 48 hrs, 60 hrs, 72 hrs, 4 days, 5 days, 6 days, 7 days, or any time therebetween. In some embodiments, the circular polyribonucleotide has a half-life or persistence in a cell while the cell is dividing. In some embodiments, the circular polyribonucleotide has a half-life or persistence in a cell post division. In certain embodiments, the circular polyribonucleotide has a half-life or persistence in a dividing cell for greater than about about 10 minutes to about 30 days, or at least about 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or longer or any time therebetween.

In some embodiments, the circular polyribonucleotide modulates a cellular function, e.g., transiently or long term. In certain embodiments, the cellular function is stably altered, such as a modulation that persists for at least about 1 hr to about 30 days, or at least about 2 hrs, 6 hrs, 12 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or longer or any time therebetween. In certain embodiments, the cellular function is transiently altered, e.g., such as a modulation that persists for no more than about 30 mins to about 7 days, or no more than about 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 24 hrs, 36 hrs, 48 hrs, 60 hrs, 72 hrs, 4 days, 5 days, 6 days, 7 days, or any time therebetween.

In some embodiments, the circular polyribonucleotide is at least about 20 nucleotides, at least about 30 nucleotides, at least about 40 nucleotides, at least about 50 nucleotides, at least about 75 nucleotides, at least about 100 nucleotides, at least about 200 nucleotides, at least about 300 nucleotides, at least about 400 nucleotides, at least about 500 nucleotides, at least about 1,000 nucleotides, at least about 2,000 nucleotides, at least about 5,000 nucleotides, at least about 6,000 nucleotides, at least about 7,000 nucleotides, at least about 8,000 nucleotides, at least about 9,000 nucleotides, at least about 10,000 nucleotides, at least about 12,000 nucleotides, at least about 14,000 nucleotides, at least about 15,000 nucleotides, at least about 16,000 nucleotides, at least about 17,000 nucleotides, at least about 18,000 nucleotides, at least about 19,000 nucleotides, or at least about 20,000 nucleotides. In some embodiments, the circular polyribonucleotide may be of a sufficient size to accommodate a binding site for a ribosome. One of skill in the art can appreciate that the maximum size of a circular polyribonucleotide can be as large as is within the technical constraints of producing a circular polyribonucleotide, and/or using the circular polyribonucleotide. While not being bound by theory, it is possible that multiple segments of RNA may be produced from DNA and their 5' and 3' free ends annealed to produce a "string" of RNA, which ultimately may be circularized when only one 5' and one 3' free end remains. In some embodiments, the maximum size of a circular polyribonucleotide may be limited by the ability of packaging and delivering the RNA to a target. In some embodiments, the size of a circular polyribonucleotide is a length sufficient to encode useful polypeptides, and thus, lengths of at least 20,000 nucleotides, at least 15,000 nucleotides, at least 10,000 nucleotides, at least 7,500 nucleotides, or at least 5,000 nucleotides, at least 4,000 nucleotides, at least 3,000 nucleotides, at least 2,000 nucleotides, at least 1,000 nucleotides, at least 500 nucleotides, at least t 400 nucleotides, at least 300 nucleotides, at least 200 nucleotides, at least 100 nucleotides may be useful.

In some embodiments, the circular polyribonucleotide comprises one or more elements described elsewhere herein. In some embodiments, the elements may be separated from one another by a spacer sequence or linker. In some embodiments, the elements may be separated from one another by 1 ribonucleotide, 2 nucleotides, about 5 nucleotides, about 10 nucleotides, about 15 nucleotides, about 20 nucleotides, about 30 nucleotides, about 40 nucleotides, about 50 nucleotides, about 60 nucleotides, about 80 nucleotides, about 100 nucleotides, about 150 nucleotides, about 200 nucleotides, about 250 nucleotides, about 300 nucleotides, about 400 nucleotides, about 500 nucleotides, about 600 nucleotides, about 700 nucleotides, about 800 nucleotides, about 900 nucleotides, about 1000 nucleotides, up to about 1 kb, at least about 1000 nucleotides, any amount of nucleotides therebetween. In some embodiments, one or more elements are contiguous with one another, e.g., lacking a spacer element. In some embodiments, one or more elements in the circular polyribonucleotide is conformationally flexible. In some embodiments, the conformational flexibility is due to the sequence being substantially free of a secondary structure. In some embodiments, the circular polyribonucleotide comprises a secondary or tertiary structure that accommodates one or more desired functions or characteristics described herein, e.g., accommodate a binding site for a ribosome, e.g., translation, e.g., rolling circle translation.

In some embodiments, the circular polyribonucleotide comprises particular sequence characteristics. For example, the circular polyribonucleotide may comprise a particular nucleotide composition. In some such embodiments, the circular polyribonucleotide may include one or more purine rich regions (adenine or guanosine). In some such embodiments, the circular polyribonucleotide may include one or more purine rich regions (adenine or guanosine). In some embodiments, the circular polyribonucleotide may include one or more AU rich regions or elements (AREs). In some embodiments, the circular polyribonucleotide may include one or more adenine rich regions.

In some embodiments, the circular polyribonucleotide may include one or more repetitive elements described elsewhere herein.

In some embodiments, the circular polyribonucleotide comprises one or more modifications described elsewhere herein.

In some embodiments, the circular polyribonucleotide comprises one or more expression sequences and is configured for persistent expression in a cell of a subject in vivo. In some embodiments, the circular polyribonucleotide is configured such that expression of the one or more expression sequences in the cell at a later time point is equal to or higher than an earlier time point. In such embodiments, the expression of the one or more expression sequences can be either maintained at a relatively stable level or can increase over time. The expression of the expression sequences can be relatively stable for an extended period of time. For instance, in some cases, the expression of the one or more expression sequences in the cell over a time period of at least 7, 8, 9, 10, 12, 14, 16, 18, 20, 22, 23 or more days does not decrease by 50%, 45%, 40%, 35%, 30%, 25%, 20%, 15%, 10%, or 5%. In some cases, in some cases, the expression of the one or more expression sequences in the cell is maintained at a level that does not vary by more than 50%, 45%, 40%, 35%, 30%, 25%, 20%, 15%, 10%, or 5% for at least 7, 8, 9, 10, 12, 14, 16, 18, 20, 22, 23 or more days.

Expression Sequences

Peptides or Polypeptides

In some embodiments, the circular polyribonucleotide comprises at least one expression sequence that encodes a peptide or polypeptide. Such peptide may include, but is not limited to, small peptide, peptidomimetic (e.g., peptoid), amino acids, and amino acid analogs. The peptide may be linear or branched. Such peptide may have a molecular weight less than about 5,000 grams per mole, a molecular weight less than about 2,000 grams per mole, a molecular weight less than about 1,000 grams per mole, a molecular weight less than about 500 grams per mole, and salts, esters, and other pharmaceutically acceptable forms of such compounds. Such peptide may include, but is not limited to, a neurotransmitter, a hormone, a drug, a toxin, a viral or microbial particle, a synthetic molecule, and agonists or antagonists thereof.

The polypeptide may be linear or branched. The polypeptide may have a length from about 5 to about 40,000 amino acids, about 15 to about 35,000 amino acids, about 20 to about 30,000 amino acids, about 25 to about 25,000 amino acids, about 50 to about 20,000 amino acids, about 100 to about 15,000 amino acids, about 200 to about 10,000 amino acids, about 500 to about 5,000 amino acids, about 1,000 to about 2,500 amino acids, or any range therebetween. In some embodiments, the polypeptide has a length of less than about 40,000 amino acids, less than about 35,000 amino acids, less than about 30,000 amino acids, less than about 25,000 amino acids, less than about 20,000 amino acids, less than about 15,000 amino acids, less than about 10,000 amino acids, less than about 9,000 amino acids, less than about 8,000 amino acids, less than about 7,000 amino acids, less than about 6,000 amino acids, less than about 5,000 amino acids, less than about 4,000 amino acids, less than about 3,000 amino acids, less than about 2,500 amino acids, less than about 2,000 amino acids, less than about 1,500 amino acids, less than about 1,000 amino acids, less than about 900 amino acids, less than about 800 amino acids, less than about 700 amino acids, less than about 600 amino acids, less than about 500 amino acids, less than about 400 amino acids, less than about 300 amino acids, or less may be useful.

Some examples of a peptide or polypeptide include, but are not limited to, fluorescent tag or marker, antigen, peptide therapeutic, synthetic or analog peptide from naturally-bioactive peptide, agonist or antagonist peptide, anti-microbial peptide, pore-forming peptide, a bicyclic peptide, a targeting or cytotoxic peptide, a degradation or self-destruction peptide, and degradation or self-destruction peptides. Peptides useful in the invention described herein also include antigen-binding peptides, e.g., antigen binding antibody or antibody-like fragments, such as single chain antibodies, nanobodies (see, e.g., Steeland et al. 2016. Nanobodies as therapeutics: big opportunities for small antibodies. Drug Discov Today: 21(7):1076-113). Such antigen binding peptides may bind a cytosolic antigen, a nuclear antigen, an intra-organellar antigen.

In some embodiments, the circular polyribonucleotide comprises one or more RNA expression sequences, each of which may encode a polypeptide. The polypeptide may be produced in substantial amounts. As such, the polypeptide may be any proteinaceous molecule that can be produced. A polypeptide can be a polypeptide that can be secreted from a cell, or localized to the cytoplasm, nucleus or membrane compartment of a cell. Some polypeptides include, but are not limited to, at least a portion of a viral envelope protein, metabolic regulatory enzymes (e.g., that regulate lipid or steroid production), an antigen, a tolerogen, a cytokine, a toxin, enzymes whose absence is associated with a disease, and polypeptides that are not active in an animal until cleaved (e.g., in the gut of an animal), and a hormone.

In some embodiments, the circular polyribonucleotide includes an expression sequence encoding a protein e.g., a therapeutic protein. In some embodiments, therapeutic proteins that can be expressed from the circular polyribonucleotide disclosed herein have antioxidant activity, binding, cargo receptor activity, catalytic activity, molecular carrier activity, molecular function regulator, molecular transducer activity, nutrient reservoir activity, protein tag, structural molecule activity, toxin activity, transcription regulator activity, translation regulator activity, or transporter activity. Some examples of therapeutic proteins may include, but are not limited to, an enzyme replacement protein, a protein for supplementation, a protein vaccination, antigens (e.g. tumor antigens, viral, bacterial), hormones, cytokines, antibodies, immunotherapy (e.g. cancer), cellular reprogramming/transdifferentiation factor, transcription factors, chimeric antigen receptor, transposase or nuclease, immune effector (e.g., influences susceptibility to an immune response/signal), a regulated death effector protein (e.g., an inducer of apoptosis or necrosis), a non-lytic inhibitor of a tumor (e.g., an inhibitor of an oncoprotein), an epigenetic modifying agent, epigenetic enzyme, a transcription factor, a DNA or protein modification enzyme, a DNA-intercalating agent, an efflux pump inhibitor, a nuclear receptor activator or inhibitor, a proteasome inhibitor, a competitive inhibitor for an enzyme, a protein synthesis effector or inhibitor, a nuclease, a protein fragment or domain, a ligand or a receptor, and a CRISPR system or component thereof.

In some embodiments, exemplary proteins that can be expressed from the circular polyribonucleotide disclosed herein include human proteins, for instance, receptor binding protein, hormone, growth factor, growth factor receptor modulator, and regenerative protein (e.g., proteins implicated in proliferation and differentiation, e.g., therapeutic protein, for wound healing). In some embodiments, exemplary proteins that can be expressed from the circular polyribonucleotide disclosed herein include EGF (epithelial growth factor). In some embodiments, exemplary proteins that can be expressed from the circular polyribonucleotide disclosed herein include enzymes, for instance, oxidoreductase enzymes, metabolic enzymes, mitochondrial enzymes, oxygenases, dehydrogenases, ATP-independent enzyme, and desaturases. In some embodiments, exemplary proteins that can be expressed from the circular polyribonucleotide disclosed herein include an intracellular protein or cytosolic protein. In some embodiments, the circular polyribonucleotide expresses a NanoLuc® luciferase (nLuc). In some embodiments, exemplary proteins that can be expressed from the circular polyribonucleotide disclosed herein include a secretary protein, for instance, a secretary enzyme. In some cases, the circular polyribonucleotide expresses a secretary protein that can have a short half-life therapeutic in the blood, or can be a protein with a subcellular localization signal, or protein with secretory signal peptide. In some embodiments, the circular polyribonucleotide expresses a *Gaussia* Luciferase (gLuc). In some cases, the circular polyribonucleotide expresses a non-human protein, for instance, a fluorescent protein, an energy-transfer acceptor, or a protein-tag like Flag, Myc, or His. In some embodiments, exemplary proteins that can be expressed from the circular polyribonucleotide include a GFP. In some embodiments, the circular polyribonucleotide expresses tagged proteins, e.g., fusion proteins or engineered proteins containing a protein tage, e.g., chitin binding protein (CBP), maltose binding protein (MBP), Fc tag, glutathione-S-transferase (GST), AviTag (GLNDIFEAQKIEWHE (SEQ ID NO: 81)), Calmodulin-tag (KRRWKKNFIAVSAANRFK-KISSSGAL (SEQ ID NO: 82)); polyglutamate tag (EE-EEEE (SEQ ID NO: 83)); E-tag (GAPVPYPDPLEPR (SEQ ID NO: 84)); FLAG-tag (DYKDDDDK (SEQ ID NO: 85)), HA-tag (YPYDVPDYA (SEQ ID NO: 86)); His-tag (HHHHHH (SEQ ID NO: 87)); Myc-tag (EQKLISEEDL (SEQ ID NO: 88)); NE-tag (TKENPRSNQEESYDDNES (SEQ ID NO: 89)); S-tag (KETAAAKFERQHMDS (SEQ ID NO: 90)); SBP-tag (MDEKTTGWRGGHVVEG-LAGELEQLRARLEHHPQGQREP (SEQ ID NO: 91)); Softag 1 (SLAELLNAGLGGS (SEQ ID NO: 92)); Softag 3 (TQDPSRVG (SEQ ID NO: 93)); Spot-tag (PDRVRAVSH-WSS (SEQ ID NO: 94)); Strep-tag (Strep-tag II: WSHPQFEK (SEQ ID NO: 95)); TC tag (CCPGCC (SEQ ID NO: 96)); Ty tag (EVHTNQDPLD (SEQ ID NO: 97)); V5 tag (GKPIPNPLLGLDST (SEQ ID NO: 98)); VSV-tag (YTDIEMNRLGK (SEQ ID NO: 99)); or Xpress tag (DLYDDDDK (SEQ ID NO: 100)).

In some embodiments, the circular polyribonucleotide expresses an antibody, e.g., an antibody fragment, or a portion thereof. In some embodiments, the antibody expressed by the circular polyribonucleotide can be of any isotype, such as IgA, IgD, IgE, IgG, IgM. In some embodiments, the circular polyribonucleotide expresses a portion of an antibody, such as a light chain, a heavy chain, a Fc fragment, a CDR (complementary determining region), a Fv fragment, or a Fab fragment, a further portion thereof. In some embodiments, the circular polyribonucleotide expresses one or more portions of an antibody. For instance, the circular polyribonucleotide can comprise more than one expression sequence, each of which expresses a portion of an antibody, and the sum of which can constitute the antibody. In some cases, the circular polyribonucleotide comprises one expression sequence coding for the heavy chain of an antibody, and another expression sequence coding for the light chain of the antibody. In some cases, when the circular polyribonucleotide is expressed in a cell or a a cell-free environment, the light chain and heavy chain can be subject to appropriate modification, folding, or other post-translation modification to form a functional antibody.

Regulatory Elements

In some embodiments, the circular polyribonucleotide comprises a regulatory element, e.g., a sequence that modifies expression of an expression sequence within the circular polyribonucleotide.

A regulatory element may include a sequence that is located adjacent to an expression sequence that encodes an expression product. A regulatory element may be linked operatively to the adjacent sequence. A regulatory element may increase an amount of product expressed as compared to an amount of the expressed product when no regulatory element exists. In addition, one regulatory element can increase an amount of products expressed for multiple expression sequences attached in tandem. Hence, one regulatory element can enhance the expression of one or more expression sequences. Multiple regulatory element are well-known to persons of ordinary skill in the art.

A regulatory element as provided herein can include a selective translation sequence. As used herein, the term "selective translation sequence" can refer to a nucleic acid sequence that selectively initiates or activates translation of an expression sequence in the circular polyribonucleotide, for instance, certain riboswtich aptazymes. A regulatory element can also include a selective degradation sequence. As used herein, the term "selective degradation sequence" can refer to a nucleic acid sequence that initiates degradation of the circular polyribonucleotide, or an expression product of the circular polyribonucleotide. Exemplary selective degradation sequence can include riboswitch aptazymes and miRNA binding sites.

In some embodiments, the regulatory element is a translation modulator. A translation modulator can modulate translation of the expression sequence in the circular polyribonucleotide. A translation modulator can be a translation enhancer or suppressor. In some embodiments, the circular polyribonucleotide includes at least one translation modulator adjacent to at least one expression sequence. In some embodiments, the circular polyribonucleotide includes a translation modulator adjacent each expression sequence. In some embodiments, the translation modulator is present on one or both sides of each expression sequence, leading to separation of the expression products, e.g., peptide(s) and or polypeptide(s).

In some embodiments, a translation initiation sequence can function as a regulatory element. In some embodiments, a translation initiation sequence comprises an AUG codon. In some embodiments, a translation initiation sequence comprises any eukaryotic start codon such as AUG, CUG, GUG, UUG, ACG, AUC, AUU, AAG, AUA, or AGG. In some embodiments, a translation initiation sequence comprises a Kozak sequence. In some embodiments, translation begins at an alternative translation initiation sequence, e.g., translation initiation sequence other than AUG codon, under selective conditions, e.g., stress induced conditions. As a non-limiting example, the translation of the circular polyribonucleotide may begin at alternative translation initiation sequence, such as ACG. As another non-limiting example, the circular polyribonucleotide translation may begin at alternative translation initiation sequence, CTG/CUG. As yet another non-limiting example, the circular polyribonucleotide translation may begin at alternative translation initiation sequence, GTG/GUG. As yet another non-limiting example, the circular polyribonucleotide may begin translation at a repeat-associated non-AUG (RAN) sequence, such as an alternative translation initiation sequence that includes short stretches of repetitive RNA e.g. CGG, GGGGCC, CAG, CTG.

Nucleotides flanking a codon that initiates translation, such as, but not limited to, a start codon or an alternative start codon, are known to affect the translation efficiency, the length and/or the structure of the circular polyribonucleotide. (See e.g., Matsuda and Mauro PLoS ONE, 2010 5: 11; the contents of which are herein incorporated by reference in its entirety). Masking any of the nucleotides flanking a codon that initiates translation may be used to alter the position of translation initiation, translation efficiency, length and/or structure of the circular polyribonucleotide.

In one embodiment, a masking agent may be used near the start codon or alternative start codon in order to mask or hide the codon to reduce the probability of translation initiation at the masked start codon or alternative start codon. Non-limiting examples of masking agents include antisense locked nucleic acids (LNA) oligonucleotides and exon junction complexes (EJCs). (See e.g., Matsuda and Mauro describing masking agents LNA oligonucleotides and EJCs (PLoS ONE, 2010 5: 11); the contents of which are herein incorporated by reference in its entirety). In another embodiment, a masking agent may be used to mask a start codon of the circular polyribonucleotide in order to increase the likelihood that translation will initiate at an alternative start codon.

In some embodiments, translation is initiated under selective conditions, such as but not limited to viral induced selection in the presence of GRSF-1 and the circular polyribonucleotide includes GRSF-1 binding sites, see for example http://jvi.asm.org/content/76/20/10417.full.

Translation Initiation Sequence

In some embodiments, the circular polyribonucleotide encodes a polypeptide and may comprise a translation initiation sequence, e.g, a start codon. In some embodiments, the translation initiation sequence includes a Kozak or Shine-Dalgarno sequence. In some embodiments, the circular polyribonucleotide includes the translation initiation sequence, e.g., Kozak sequence, adjacent to an expression sequence. In some embodiments, the translation initiation sequence is a non-coding start codon. In some embodiments, the translation initiation sequence, e.g., Kozak sequence, is present on one or both sides of each expression sequence, leading to separation of the expression products. In some embodiments, the circular polyribonucleotide includes at least one translation initiation sequence adjacent to an expression sequence. In some embodiments, the translation initiation sequence provides conformational flexibility to the circular polyribonucleotide. In some embodiments, the translation initiation sequence is within a substantially single stranded region of the circular polyribonucleotide.

The circular polyribonucleotide may include more than 1 start codon such as, but not limited to, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 50, at least 60 or more than 60 start codons. Translation may initiate on the first start codon or may initiate downstream of the first start codon.

In some embodiments, the circular polyribonucleotide may initiate at a codon which is not the first start codon, e.g., AUG. Translation of the circular polyribonucleotide may initiate at an alternative translation initiation sequence, such as, but not limited to, ACG, AGG, AAG, CTG/CUG, GTG/

GUG, ATA/AUA, ATT/AUU, TTG/UUG (see Touriol et al. Biology of the Cell 95 (2003) 169-178 and Matsuda and Mauro PLoS ONE, 2010 5: 11; the contents of each of which are herein incorporated by reference in their entireties). In some embodiments, translation begins at an alternative translation initiation sequence under selective conditions, e.g., stress induced conditions. As a non-limiting example, the translation of the circular polyribonucleotide may begin at alternative translation initiation sequence, such as ACG. As another non-limiting example, the circular polyribonucleotide translation may begin at alternative translation initiation sequence, CTG/CUG. As yet another non-limiting example, the circular polyribonucleotide translation may begin at alternative translation initiation sequence, GTG/GUG. As yet another non-limiting example, the circular polyribonucleotide may begin translation at a repeat-associated non-AUG (RAN) sequence, such as an alternative translation initiation sequence that includes short stretches of repetitive RNA e.g. CGG, GGGGCC, CAG, CTG.

In some embodiments, translation is initiated by eukaryotic initiation factor 4A (eIF4A) treatment with Rocaglates (translation is repressed by blocking 43S scanning, leading to premature, upstream translation initiation and reduced protein expression from transcripts bearing the RocA-eIF4A target sequence, see for example, www.nature.com/articles/nature17978).

IRES

In some embodiments, the circular polyribonucleotide described herein comprises an internal ribosome entry site (IRES) element. A suitable IRES element to include in a circular polyribonucleotide comprises an RNA sequence capable of engaging an eukaryotic ribosome. In some embodiments, the IRES element is at least about 5 nt, at least about 8 nt, at least about 9 nt, at least about 10 nt, at least about 15 nt, at least about 20 nt, at least about 25 nt, at least about 30 nt, at least about 40 nt, at least about 50 nt, at least about 100 nt, at least about 200 nt, at least about 250 nt, at least about 350 nt, or at least about 500 nt. In one embodiment, the IRES element is derived from the DNA of an organism including, but not limited to, a virus, a mammal, and a *Drosophila*. Such viral DNA may be derived from, but is not limited to, picornavirus complementary DNA (cDNA), with encephalomyocarditis virus (EMCV) cDNA and poliovirus cDNA. In one embodiment, *Drosophila* DNA from which an IRES element is derived includes, but is not limited to, an Antennapedia gene from *Drosophila melanogaster.*

In some embodiments, the IRES element is at least partially derived from a virus, for instance, it can be derived from a viral IRES element, such as ABPV_IGRpred, AEV, ALPV_IGRpred, BQCV_IGRpred, BVDV1_1-385, BVDV1_29-391, CrPV_5 NCR, CrPV_IGR, crTMV_IREScp, crTMV_IRESmp75, crTMV_IRESmp228, crTMV_IREScp, crTMV_IREScp, CSFV, CVB3, DCV IGR, EMCV-R, EoPV_5NTR, ERAV_245-961, ERBV_162-920, EV71_1-748, FeLV-Notch2, FMDV_type_C, GBV-A, GBV-B, GBV-C, gypsy_env, gypsyD5, gypsyD2, HAV_HM175, HCV_type_1a, HiPV_IGRpred, HIV-1, HoCV1_IGRpred, HRV-2, IAPV_IGRpred, idefix, KBV_IGRpred, LINE-1_ORF1_-101_to_-1, LINE-1_ORF1_-302_to_-202, LINE-1_ORF2_-138_to_-86, LINE-1_ORF1_-44_to_-1, PSIV_IGR, PV_type1_Mahoney, PV_type3_Leon, REV-A, RhPV_5NCR, RhPV_IGR, SINV1_IGRpred, SV40_661-830, TMEV, TMV_UI_IRESmp228, TRV_5NTR, TrV_IGR, or TSV_IGR. In some embodiments, the IRES element is at least partially derived from a cellular IRES, such as AML1/RUNX1, Antp-D, Antp-DE, Antp-CDE, Apaf-1, Apaf-1, AQP4, AT1R_var1, AT1R_var2, AT1R_var3, AT1R_var4, BAG1_p36delta236 nt, BAG1_p36, BCL2, BiP_-222_-3, c-IAP1_285-1399, c-IAP1_1313-1462, c-jun, c-myc, Cat-1_224, CCND1, DAP5, eIF4G, eIF4GI-ext, eIF4GII, eIF4GII-long, ELG1, ELH, FGF1A, FMR1, Gtx-133-141, Gtx-1-166, Gtx-1-120, Gtx-1-196, hairless, HAP4, HIF1a, hSNM1, Hsp101, hsp70, hsp70, Hsp90, IGF2_leader2, Kv1.4_1.2, L-myc, LamB1_-335_-1, LEF1, MNT_75-267, MNT_36-160, MTG8a, MYB, MYT2_997-1152, n-MYC, NDST1, NDST2, NDST3, NDST4L, NDST4S, NRF_-653_-17, NtHSF1, ODC1, p27kip1, p53_128-269, PDGF2/c-sis, Pim-1, PITSLRE_p58, Rbm3, reaper, Scamper, TFIID, TIF4631, Ubx_1-966, Ubx_373-961, UNR, Ure2, UtrA, VEGF-A_-133_-1, XIAP_5-464, XIAP_305-466, or YAP1. In some embodiments, the IRES element comprises a synthetic IRES, for instance, (GAAA)16 (SEQ ID NO: 130), (PPT19)4, KMI1, KMI1, KMI2, KMI2, KMIX, X1, or X2.

In some embodiments, the circular polyribonucleotide includes at least one IRES flanking at least one (e.g., 2, 3, 4, 5 or more) expression sequence. In some embodiments, the IRES flanks both sides of at least one (e.g., 2, 3, 4, 5 or more) expression sequence. In some embodiments, the circular polyribonucleotide includes one or more IRES sequences on one or both sides of each expression sequence, leading to separation of the resulting peptide(s) and or polypeptide(s).

Termination Element

In some embodiments, the circular polyribonucleotide includes one or more expression sequences and each expression sequence may or may not have a termination element. In some embodiments, the circular polyribonucleotide includes one or more expression sequences and the expression sequences lack a termination element, such that the circular polyribonucleotide is continuously translated. Exclusion of a termination element may result in rolling circle translation or continuous expression of expression product, e.g., peptides or polypeptides, due to lack of ribosome stalling or fall-off. In such an embodiment, rolling circle translation expresses a continuous expression product through each expression sequence. In some other embodiments, a termination element of an expression sequence can be part of a stagger element. In some embodiments, one or more expression sequences in the circular polyribonucleotide comprises a termination element. However, rolling circle translation or expression of a succeeding (e.g., second, third, fourth, fifth, etc.) expression sequence in the circular polyribonucleotide is performed. In such instances, the expression product may fall off the ribosome when the ribosome encounters the termination element, e.g., a stop codon, and terminates translation. In some embodiments, translation is terminated while the ribosome, e.g., at least one subunit of the ribosome, remains in contact with the circular polyribonucleotide.

In some embodiments, the circular polyribonucleotide includes a termination element at the end of one or more expression sequences. In some embodiments, one or more expression sequences comprises two or more termination elements in succession. In such embodiments, translation is terminated and rolling circle translation is terminated. In some embodiments, the ribosome completely disengages with the circular polyribonucleotide. In some such embodiments, production of a succeeding (e.g., second, third, fourth, fifth, etc.) expression sequence in the circular polyribonucleotide may require the ribosome to reengage with the circular polyribonucleotide prior to initiation of translation. Generally, termination elements include an in-frame nucleotide triplet that signals termination of translation, e.g., UAA, UGA, UAG. In some embodiments, one or more termination elements in the circular polyribonucleotide are frame-shifted termination elements, such as but not limited to, off-frame or −1 and +1 shifted reading frames (e.g., hidden stop) that may terminate translation. Frame-shifted termination elements include nucleotide triples, TAA, TAG, and TGA that appear in the second and third reading frames of an expression sequence. Frame-shifted termination elements may be important in preventing misreads of mRNA, which is often detrimental to the cell.

Stagger Element

In some embodiments, the circular polyribonucleotide includes at least one stagger element adjacent to an expression sequence. In some embodiments, the circular polyribonucleotide includes a stagger element adjacent to each expression sequence. In some embodiments, the stagger element is present on one or both sides of each expression sequence, leading to separation of the expression products, e.g., peptide(s) and or polypeptide(s). In some embodiments, the stagger element is a portion of the one or more expression sequences. In some embodiments, the circular polyribonucleotide comprises one or more expression sequences, and each of the one or more expression sequences is separated from a succeeding expression sequence by a stagger element on the circular polyribonucleotide. In some embodiments, the stagger element prevents generation of a single polypeptide (a) from two rounds of translation of a single expression sequence or (b) from one or more rounds of translation of two or more expression sequences. In some embodiments, the stagger element is a sequence separate from the one or more expression sequences. In some embodiments, the stagger element comprises a portion of an expression sequence of the one or more expression sequences.

In some embodiments, the circular polyribonucleotide includes a stagger element. To avoid production of a continuous expression product, e.g., peptide or polypeptide, while maintaining rolling circle translation, a stagger element may be included to induce ribosomal pausing during translation. In some embodiments, the stagger element is at 3' end of at least one of the one or more expression sequences. The stagger element can be configured to stall a ribosome during rolling circle translation of the circular polyribonucleotide. The stagger element may include, but is not limited to a 2A-like, or CHYSEL (cis-acting hydrolase element) sequence. In some embodiments, the stagger element encodes a sequence with a C-terminal consensus sequence that is $X_1X_2X_3EX_5NPGP$ (SEQ ID NO: 101), where $X_1$ is absent or G or H, $X_2$ is absent or D or G, $X_3$ is D or V or I or S or M, and $X_5$ is any amino acid. In some embodiments, this sequence comprises a non-conserved sequence of amino-acids with a strong alpha-helical propensity followed by the consensus sequence-D(V/I)ExNPG P (SEQ ID NO: 61), where x=any amino acid. Some nonlimiting examples of stagger elements includes GDVESNPGP (SEQ ID NO: 62), GDIEENPGP (SEQ ID NO: 63), VEPNPGP (SEQ ID NO: 64), IETNPGP (SEQ ID NO: 65), GDIESNPGP (SEQ ID NO: 66), GDVELNPGP (SEQ ID NO: 67), GDIETNPGP (SEQ ID NO: 68), GDVENPGP (SEQ ID NO: 69), GDVEENPGP (SEQ ID NO: 70), GDVEQNPGP (SEQ ID NO: 71), IESNPGP (SEQ ID NO: 72), GDIELNPGP (SEQ ID NO: 73), HDIETNPGP (SEQ ID NO: 74), HDVETNPGP (SEQ ID NO: 75), HDVEMNPGP (SEQ ID NO: 76), GDMESNPGP (SEQ ID NO: 77), GDVETNPGP (SEQ ID NO: 78), GDIEQNPGP (SEQ ID NO: 79), and DSEFNPGP (SEQ ID NO: 80).

In some embodiments, the stagger element described herein cleaves an expression product, such as between G and P of the consensus sequence described herein. As one non-limiting example, the circular polyribonucleotide includes at least one stagger element to cleave the expression product. In some embodiments, the circular polyribonucleotide includes a stagger element adjacent to at least one expression sequence. In some embodiments, the circular polyribonucleotide includes a stagger element after each expression sequence. In some embodiments, the circular polyribonucleotide includes a stagger element is present on one or both sides of each expression sequence, leading to translation of individual peptide(s) and or polypeptide(s) from each expression sequence.

In some embodiments, a stagger element comprises one or more modified nucleotides or unnatural nucleotides that induce ribosomal pausing during translation. Unnatural nucleotides may include peptide nucleic acid (PNA), Morpholino and locked nucleic acid (LNA), as well as glycol nucleic acid (GNA) and threose nucleic acid (TNA). Examples such as these are distinguished from naturally occurring DNA or RNA by changes to the backbone of the molecule. Exemplary modifications can include any modification to the sugar, the nucleobase, the internucleoside linkage (e.g. to a linking phosphate/to a phosphodiester linkage/to the phosphodiester backbone), and any combination thereof that can induce ribosomal pausing during translation. Some of the exemplary modifications provided herein are described elsewhere herein.

In some embodiments, the stagger element is present in the circular polyribonucleotide in other forms. For example, in some exemplary circular polyribonucleotides, a stagger element comprises a termination element of a first expression sequence in the circular polyribonucleotide, and a nucleotide spacer sequence that separates the termination element from a first translation initiation sequence of an expression succeeding the first expression sequence. In some examples, the first stagger element of the first expression sequence is upstream of (5' to) a first translation initiation sequence of the expression succeeding the first expression sequence in the circular polyribonucleotide. In some cases, the first expression sequence and the expression sequence succeeding the first expression sequence are two separate expression sequences in the circular polyribonucleotide. The distance between the first stagger element and the first translation initiation sequence can enable continuous translation of the first expression sequence and its succeeding expression sequence. In some embodiments, the first stagger element comprises a termination element and separates an expression product of the first expression sequence from an expression product of its succeeding expression sequences, thereby creating discrete expression products. In some cases, the circular polyribonucleotide comprising the first stagger element upstream of the first translation initiation sequence of the succeeding sequence in the circular polyribonucleotide is continuously translated, while a corresponding circular polyribonucleotide comprising a stagger element of a second expression sequence that is upstream of a second translation initiation sequence of an expression sequence succeeding the second expression sequence is not continuously translated. In some cases, there is only one expression sequence in the circular polyribonucleotide, and the first expression sequence and its succeeding expression sequence are the same expression sequence. In some exemplary circular polyribonucleotides, a stagger element comprises a first termination element of a first expression sequence in the circular polyribonucleotide, and a nucleotide spacer sequence that separates the termination element from a downstream translation initiation sequence. In some such examples, the first stagger element is upstream of (5' to) a first translation initiation sequence of the first expression sequence in the circular polyribonucleotide. In some cases, the distance between the first stagger element and the first translation initiation sequence enables continuous translation of the first expression sequence and any succeeding expression sequences. In some embodiments, the first stagger element separates one round expression product of the first expression sequence from the next round expression product of the first expression sequences, thereby creating discrete expression products. In some cases, the circular polyribonucleotide comprising the first stagger element upstream of the first translation initiation sequence of the first expression sequence in the circular polyribonucleotide is continuously translated, while a corresponding circular polyribonucleotide comprising a stagger element upstream of a second translation initiation sequence of a second expression sequence in the corresponding circular polyribonucleotide is not continuously translated. In some cases, the distance between the second stagger element and the second translation initiation sequence is at least 2×, 3×, 4×, 5×, 6×, 7×, 8×, 9×, or 10× greater in the corresponding circular polyribonucleotide than a distance between the first stagger element and the first translation initiation in the circular polyribonucleotide. In some cases, the distance between the first stagger element and the first translation initiation is at least 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, 40 nt, 45 nt, 50 nt, 55 nt, 60 nt, 65 nt, 70 nt, 75 nt, or greater. In some embodiments, the distance between the second stagger element and the second translation initiation is at least 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, 40 nt, 45 nt, 50 nt, 55 nt, 60 nt, 65 nt, 70 nt, 75 nt, or greater than the distance between the first stagger element and the first translation initiation. In some embodiments, the circular polyribonucleotide comprises more than one expression sequence.

Regulatory Nucleic Acids

In some embodiments, the circular polyribonucleotide comprises one or more expression sequences that encode regulatory nucleic acid, e.g., that modifies expression of an endogenous gene and/or an exogenous gene. In some embodiments, the expression sequence of a circular polyribonucleotide as provided herein can comprise a sequence that is antisense to a regulatory nucleic acid like a non-coding RNA, such as, but not limited to, tRNA, lncRNA, miRNA, rRNA, snRNA, microRNA, siRNA, piRNA, snoRNA, snRNA, exRNA, scaRNA, Y RNA, and hnRNA.

In one embodiment, the regulatory nucleic acid targets a host gene. The regulatory nucleic acids may include, but are not limited to, a nucleic acid that hybridizes to an endogenous gene (e.g., miRNA, siRNA, mRNA, lncRNA, RNA, DNA, an antisense RNA, gRNA as described herein elsewhere), nucleic acid that hybridizes to an exogenous nucleic acid such as a viral DNA or RNA, nucleic acid that hybridizes to an RNA, nucleic acid that interferes with gene transcription, nucleic acid that interferes with RNA translation, nucleic acid that stabilizes RNA or destabilizes RNA such as through targeting for degradation, and nucleic acid that modulates a DNA or RNA binding factor. In one embodiments, the sequence is an miRNA. In some embodiments, the regulatory nucleic acid targets a sense strand of a host gene. In some embodiments, the regulatory nucleic acid targets an antisense strand of a host gene In some embodiments, the circular polyribonucleotide comprises a regulatory nucleic acid, such as a guide RNA (gRNA). In some embodiments, the circular polyribonucleotide comprises a guide RNA or encodes the guide RNA. A gRNA short synthetic RNA composed of a "scaffold" sequence necessary for binding to the incomplete effector moiety and a user-defined ~20 nucleotide targeting sequence for a genomic target. In practice, guide RNA sequences are generally designed to have a length of between 17-24 nucleotides (e.g., 19, 20, or 21 nucleotides) and complementary to the targeted nucleic acid sequence. Custom gRNA generators and algorithms are available commercially for use in the design of effective guide RNAs. Gene editing has also been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing). Chemically modified sgRNAs have also been demonstrated to be effective in genome editing; see, for example, Hendel et al. (2015) Nature Biotechnol., 985-991.

The gRNA may recognize specific DNA sequences (e.g., sequences adjacent to or within a promoter, enhancer, silencer, or repressor of a gene).

In one embodiment, the gRNA is used as part of a CRISPR system for gene editing. For the purposes of gene editing, the circular polyribonucleotide may be designed to include one or multiple guide RNA sequences corresponding to a desired target DNA sequence; see, for example, Cong et al. (2013) Science, 339:819-823; Ran et al. (2013) Nature Protocols, 8:2281-2308. At least about 16 or 17 nucleotides of gRNA sequence are required by Cas9 for DNA cleavage to occur; for Cpf1 at least about 16 nucleotides of gRNA sequence is needed to achieve detectable DNA cleavage.

Certain regulatory nucleic acids can inhibit gene expression through the biological process of RNA interference (RNAi). RNAi molecules comprise RNA or RNA-like structures typically containing 15-50 base pairs (such as about 18-25 base pairs) and having a nucleobase sequence identical (complementary) or nearly identical (substantially complementary) to a coding sequence in an expressed target gene within the cell. RNAi molecules include, but are not limited to: short interfering RNAs (siRNAs), double-strand RNAs (dsRNA), micro RNAs (miRNAs), short hairpin RNAs (shRNA), meroduplexes, and dicer substrates (U.S. Pat. Nos. 8,084,599 8,349,809 and 8,513,207).

In some embodiments, the circular polyribonucleotide comprises regulatory nucleic acids that are RNA or RNA-like structures typically between about 5-500 base pairs (depending on the specific RNA structure, e.g., miRNA 5-30 bps, lncRNA 200-500 bps) and may have a nucleobase sequence identical (complementary) or nearly identical (substantially complementary) to a coding sequence in an expressed target gene within the cell.

Long non-coding RNAs (lncRNA) are defined as non-protein coding transcripts longer than 100 nucleotides. This somewhat arbitrary limit distinguishes lncRNAs from small regulatory RNAs such as microRNAs (miRNAs), short interfering RNAs (siRNAs), and other short RNAs. In general, the majority (~78%) of lncRNAs are characterized as tissue-specific. Divergent lncRNAs that are transcribed in the opposite direction to nearby protein-coding genes (comprise a significant proportion ~20% of total lncRNAs in mammalian genomes) may possibly regulate the transcription of the nearby gene. In one embodiment, the circular polyribonucleotide provided herein comprises a sense strand of a lncRNA. In one embodiment, the circular polyribonucleotide provided herein comprises an antisense strand of a lncRNA.

The circular polyribonucleotide may encode a regulatory nucleic acid substantially complementary, or fully complementary, to all or a fragment of an endogenous gene or gene product (e.g., mRNA). The regulatory nucleic acids may complement sequences at the boundary between introns and exons, in between exons, or adjacent to exon, to prevent the maturation of newly-generated nuclear RNA transcripts of specific genes into mRNA for transcription. The regulatory nucleic acids that are complementary to specific genes can hybridize with the mRNA for that gene and prevent its translation. The antisense regulatory nucleic acid can be DNA, RNA, or a derivative or hybrid thereof. In some embodiments, the regulatory nucleic acid comprises a protein-binding site that can bind to a protein that participates in regulation of expression of an endogenous gene or an exogenous gene.

The length of the circular polyribonucleotide may encode a regulatory nucleic acid that hybridizes to a transcript of interest that is between about 5 to 30 nucleotides, between about 10 to 30 nucleotides, or about 11, 12, 13, 14, 15, 16, 17, 18, 19, 20, 21, 22, 23, 24, 25, 26, 27, 28, 29, 30 or more nucleotides. The degree of identity of the regulatory nucleic acid to the targeted transcript should be at least 75%, at least 80%, at least 85%, at least 90%, or at least 95%.

The circular polyribonucleotide may encode a micro RNA (miRNA) molecule identical to about 5 to about 25 contiguous nucleotides of a target gene. In some embodiments, the miRNA sequence targets a mRNA and commences with the dinucleotide AA, comprises a GC-content of about 30-70% (about 30-60%, about 40-60%, or about 45%-55%), and does not have a high percentage identity to any nucleotide sequence other than the target in the genome of the mammal in which it is to be introduced, for example as determined by standard BLAST search.

In some embodiments, the circular polyribonucleotide comprises at least one miRNA, e.g., 2, 3, 4, 5, 6, or more. In some embodiments, the circular polyribonucleotide comprises a sequence that encodes an miRNA at least about 75%, 80%, 85%, 90% 95%, 96%, 97%, 98%, 99% or 100% nucleotide sequence identity to any one of the nucleotide sequences or a sequence that is complementary to a target sequence.

siRNAs and shRNAs resemble intermediates in the processing pathway of the endogenous microRNA (miRNA) genes (Bartel, Cell 116:281-297, 2004). In some embodiments, siRNAs can function as miRNAs and vice versa (Zeng et al., Mol Cell 9:1327-1333, 2002; Doench et al., Genes Dev 17:438-442, 2003). MicroRNAs, like siRNAs, use RISC to downregulate target genes, but unlike siRNAs, most animal miRNAs do not cleave the mRNA. Instead, miRNAs reduce protein output through translational suppression or polyA removal and mRNA degradation (Wu et al., Proc Natl Acad Sci USA 103:4034-4039, 2006). Known miRNA binding sites are within mRNA 3' UTRs; miRNAs seem to target sites with near-perfect complementarity to nucleotides 2-8 from the miRNA's 5' end (Rajewsky, Nat Genet 38 Suppl:S8-13, 2006; Lim et al., Nature 433:769-773, 2005). This region is known as the seed region. Because siRNAs and miRNAs are interchangeable, exogenous siRNAs downregulate mRNAs with seed complementarity to the siRNA (Birmingham et al., Nat Methods 3:199-204, 2006. Multiple target sites within a 3' UTR give stronger downregulation (Doench et al., Genes Dev 17:438-442, 2003).

Lists of known miRNA sequences can be found in databases maintained by research organizations, such as Wellcome Trust Sanger Institute, Penn Center for Bioinformatics, Memorial Sloan Kettering Cancer Center, and European Molecule Biology Laboratory, among others. Known effective siRNA sequences and cognate binding sites are also well represented in the relevant literature. RNAi molecules are readily designed and produced by technologies known in the art. In addition, there are computational tools that increase the chance of finding effective and specific sequence motifs (Lagana et al., Methods Mol. Bio., 2015, 1269:393-412).

The circular polyribonucleotide may modulate expression of RNA encoded by a gene. Because multiple genes can share some degree of sequence homology with each other, in some embodiments, the circular polyribonucleotide can be designed to target a class of genes with sufficient sequence homology. In some embodiments, the circular polyribonucleotide can contain a sequence that has complementarity to sequences that are shared amongst different gene targets or are unique for a specific gene target. In some embodiments, the circular polyribonucleotide can be designed to target conserved regions of an RNA sequence having homology between several genes thereby targeting several genes in a gene family (e.g., different gene isoforms, splice variants, mutant genes, etc.). In some embodiments, the circular polyribonucleotide can be designed to target a sequence that is unique to a specific RNA sequence of a single gene.

In some embodiments, the expression sequence has a length less than 5000 bps (e.g., less than about 5000 bps, 4000 bps, 3000 bps, 2000 bps, 1000 bps, 900 bps, 800 bps, 700 bps, 600 bps, 500 bps, 400 bps, 300 bps, 200 bps, 100 bps, 50 bps, 40 bps, 30 bps, 20 bps, 10 bps, or less). In some embodiments, the expression sequence has, independently or in addition to, a length greater than 10 bps (e.g., at least about 10 bps, 20 bps, 30 bps, 40 bps, 50 bps, 60 bps, 70 bps, 80 bps, 90 bps, 100 bps, 200 bps, 300 bps, 400 bps, 500 bps, 600 bps, 700 bps, 800 bps, 900 bps, 1000 kb, 1.1 kb, 1.2 kb, 1.3 kb, 1.4 kb, 1.5 kb, 1.6 kb, 1.7 kb, 1.8 kb, 1.9 kb, 2 kb, 2.1 kb, 2.2 kb, 2.3 kb, 2.4 kb, 2.5 kb, 2.6 kb, 2.7 kb, 2.8 kb, 2.9 kb, 3 kb, 3.1 kb, 3.2 kb, 3.3 kb, 3.4 kb, 3.5 kb, 3.6 kb, 3.7 kb, 3.8 kb, 3.9 kb, 4 kb, 4.1 kb, 4.2 kb, 4.3 kb, 4.4 kb, 4.5 kb, 4.6 kb, 4.7 kb, 4.8 kb, 4.9 kb, 5 kb or greater).

In some embodiments, the expression sequence comprises one or more of the features described herein, e.g., a sequence encoding one or more peptides or proteins, one or more regulatory element, one or more regulatory nucleic acids, e.g., one or more non-coding RNAs, other expression sequences, and any combination thereof.

Translation Efficiency

In some embodiments, the translation efficiency of a circular polyribonucleotide as provided herein is greater than a reference, e.g., a linear counterpart, a linear expression sequence, or a linear circular polyribonucleotide. In some embodiments, a circular polyribonucleotide as provided herein has the translation efficiency that is at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, 500%, 600%, 70%, 800%, 900%, 1000%, 2000%, 5000%, 10000%, 100000%, or more greater than that of a reference. In some embodiments, a circular polyribonucleotide has a translation efficiency 10% greater than that of a linear counterpart. In some embodiments, a circular polyribonucleotide has a translation efficiency 300% greater than that of a linear counterpart.

In some embodiments, the circular polyribonucleotide produces stoichiometric ratios of expression products. Rolling circle translation continuously produces expression products at substantially equivalent ratios. In some embodiments, the circular polyribonucleotide has a stoichiometric translation efficiency, such that expression products are produced at substantially equivalent ratios. In some embodiments, the circular polyribonucleotide has a stoichiometric translation efficiency of multiple expression products, e.g., products from 2, 3, 4, 5, 6, 7, 8, 9, 10, 11, 12, or more expression sequences.

Rolling Circle Translation

In some embodiments, once translation of the circular polyribonucleotide is initiated, the ribosome bound to the circular polyribonucleotide does not disengage from the circular polyribonucleotide before finishing at least one round of translation of the circular polyribonucleotide. In some embodiments, the circular polyribonucleotide as described herein is competent for rolling circle translation. In some embodiments, during rolling circle translation, once translation of the circular polyribonucleotide is initiated, the ribosome bound to the circular polyribonucleotide does not disengage from the circular polyribonucleotide before finishing at least 2 rounds, at least 3 rounds, at least 4 rounds, at least 5 rounds, at least 6 rounds, at least 7 rounds, at least 8 rounds, at least 9 rounds, at least 10 rounds, at least 11 rounds, at least 12 rounds, at least 13 rounds, at least 14 rounds, at least 15 rounds, at least 20 rounds, at least 30 rounds, at least 40 rounds, at least 50 rounds, at least 60 rounds, at least 70 rounds, at least 80 rounds, at least 90 rounds, at least 100 rounds, at least 150 rounds, at least 200 rounds, at least 250 rounds, at least 500 rounds, at least 1000 rounds, at least 1500 rounds, at least 2000 rounds, at least 5000 rounds, at least 10000 rounds, at least $10^5$ rounds, or at least $10^6$ rounds of translation of the circular polyribonucleotide.

In some embodiments, the rolling circle translation of the circular polyribonucleotide leads to generation of polypeptide product that is translated from more than one round of translation of the circular polyribonucleotide ("continuous" expression product). In some embodiments, the circular polyribonucleotide comprises a stagger element, and rolling circle translation of the circular polyribonucleotide leads to generation of polypeptide product that is generated from a single round of translation or less than a single round of translation of the circular polyribonucleotide ("discrete" expression product). In some embodiments, the circular polyribonucleotide is configured such that at least 10%, 20%, 30%, 40%, 50%, at least 60%, at least 70%, at least 80%, at least 90%, at least 95%, at least 96%, at least 97%, at least 98%, at least 99%, or 100% of total polypeptides (molar/molar) generated during the rolling circle translation of the circular polyribonucleotide are discrete polypeptides. In some embodiments, the amount ratio of the discrete products over the total polypeptides is tested in an in vitro translation system. In some embodiments, the in vitro translation system used for the test of amount ratio comprises rabbit reticulocyte lysate. In some embodiments, the amount ratio is tested in an in vivo translation system, such as a eukaryotic cell or a prokaryotic cell, a cultured cell or a cell in an organism.

Untranslated Regions

In some embodiments, the circular polyribonucleotide comprises untranslated regions (UTRs). UTRs of a genomic region comprising a gene may be transcribed but not translated. In some embodiments, a UTR may be included upstream of the translation initiation sequence of an expression sequence described herein. In some embodiments, a UTR may be included downstream of an expression sequence described herein. In some instances, one UTR for first expression sequence is the same as or continuous with or overlapping with another UTR for a second expression sequence. In some embodiments, the intron is a human intron. In some embodiments, the intron is a full length human intron, e.g., ZKSCAN1.

In some embodiments, the circular polyribonucleotide comprises a UTR with one or more stretches of Adenosines and Uridines embedded within. These AU rich signatures are may increase turnover rates of the expression product.

Introduction, removal or modification of UTR AU rich elements (AREs) may be useful to modulate the stability or immunogenicity of the circular polyribonucleotide. When engineering specific circular polyribonucleotides, one or more copies of an ARE may be introduced to the circular polyribonucleotide and the copies of an ARE may modulate translation and/or production of an expression product. Likewise, AREs may be identified and removed or engineered into the circular polyribonucleotide to modulate the intracellular stability and thus affect translation and production of the resultant protein.

It should be understood that any UTR from any gene may be incorporated into the respective flanking regions of the circular polyribonucleotide. As a non-limiting example, the UTR or a fragment thereof which may be incorporated is a UTR listed in U.S. Provisional Application Nos. 61/775,509 and U.S. 61/829,372, or in International Patent Application No. PCT/US2014/021522; the contents of each of which are herein incorporated by reference in its entirety. Furthermore, multiple wild-type UTRs of any known gene may be utilized. It is also within the scope of the present invention to provide artificial UTRs which are not variants of wild type genes. These UTRs or portions thereof may be placed in the same orientation as in the transcript from which they were selected or may be altered in orientation or location. Hence a 5' or 3' UTR may be inverted, shortened, lengthened, made chimeric with one or more other 5' UTRS or 3' UTRs. As used herein, the term "altered" as it relates to a UTR sequence, means that the UTR has been changed in some way in relation to a reference sequence. For example, a 3' or 5' UTR may be altered relative to a wild type or native UTR by the change in orientation or location as taught above or may be altered by the inclusion of additional nucleotides, deletion of nucleotides, swapping or transposition of nucleotides. Any of these changes producing an "altered" UTR (whether 3' or 5') comprise a variant UTR.

In one embodiment, a double, triple or quadruple UTR, such as a 5' or 3' UTR, may be used. As used herein, a "double" UTR is one in which two copies of the same UTR are encoded either in series or substantially in series. For example, a double beta-globin 3' UTR may be used as described in US Patent publication 20100129877, the contents of which are incorporated herein by reference in its entirety.

PolyA Sequence

In some embodiments, the circular polyribonucleotide may include a poly-A sequence. In some embodiments, the length of a poly-A sequence is greater than 10 nucleotides in length. In one embodiment, the poly-A sequence is greater than 15 nucleotides in length (e.g., at least or greater than about 10, 15, 20, 25, 30, 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides). In some embodiments, the poly-A sequence is from about 10 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In one embodiment, the poly-A sequence is designed relative to the length of the overall circular polyribonucleotide. This design may be based on the length of the coding region, the length of a particular feature or region (such as the first or flanking regions), or based on the length of the ultimate product expressed from the circular polyribonucleotide. In this context, the poly-A sequence may be 10, 20, 30, 40, 50, 60, 70, 80, 90, or 100% greater in length than the circular polyribonucleotide or a feature thereof. The poly-A sequence may also be designed as a fraction of circular polyribonucleotide to which it belongs. In this context, the poly-A sequence may be 10, 20, 30, 40, 50, 60, 70, 80, or 90% or more of the total length of the construct or the total length of the construct minus the poly-A sequence. Further, engineered binding sites and conjugation of circular polyribonucleotide for Poly-A binding protein may enhance expression.

In one embodiment, the circular polyribonucleotide is designed to include a polyA-G quartet. The G-quartet is a cyclic hydrogen bonded array of four guanine nucleotides that can be formed by G-rich sequences in both DNA and RNA. In one embodiment, the G-quartet is incorporated at the end of the poly-A sequence. The resultant circular polyribonucleotide construct is assayed for stability, protein production and/or other parameters including half-life at various time points. In some embodiments, the polyA-G quartet results in protein production equivalent to at least 75% of that seen using a poly-A sequence of 120 nucleotides (SEQ ID NO: 136) alone.

In some embodiments, the circular polyribonucleotide comprises a polyA, lacks a polyA, or has a modified polyA to modulate one or more characteristics of the circular polyribonucleotide. In some embodiments, the circular polyribonucleotide lacking a polyA or having modified polyA improves one or more functional characteristics, e.g., immunogenicity, half-life, expression efficiency, etc.

RNA-Binding

In some embodiments, the circular polyribonucleotide comprises one or more RNA binding sites. microRNAs (or miRNA) are short noncoding RNAs that bind to the 3'UTR of nucleic acid molecules and down-regulate gene expression either by reducing nucleic acid molecule stability or by inhibiting translation. The circular polyribonucleotide may comprise one or more microRNA target sequences, microRNA sequences, or microRNA seeds. Such sequences may correspond to any known microRNA, such as those taught in US Publication US2005/0261218 and US Publication US2005/0059005, the contents of which are incorporated herein by reference in their entirety.

A microRNA sequence comprises a "seed" region, i.e., a sequence in the region of positions 2-8 of the mature microRNA, which sequence has perfect Watson-Crick complementarity to the miRNA target sequence. A microRNA seed may comprise positions 2-8 or 2-7 of the mature microRNA. In some embodiments, a microRNA seed may comprise 7 nucleotides (e.g., nucleotides 2-8 of the mature microRNA), wherein the seed-complementary site in the corresponding miRNA target is flanked by an adenine (A) opposed to microRNA position 1. In some embodiments, a microRNA seed may comprise 6 nucleotides (e.g., nucleotides 2-7 of the mature microRNA), wherein the seed-complementary site in the corresponding miRNA target is flanked by an adenine (A) opposed to microRNA position 1. See for example, Grimson A, Farh K, Johnston W K, Garrett-Engele P, Lim L P, Barrel D P; Mol Cell. 2007 Jul. 6; 27(1):91-105; each of which is herein incorporated by reference in their entirety.

The bases of the microRNA seed are substantially complementary with the target sequence. By engineering microRNA target sequences into the circular polyribonucleotide, the circular polyribonucleotide may evade or be detected by the host's immune system, have modulated degradation, or modulated translation, provided the microRNA in question is available. This process will reduce the hazard of off target effects upon circular polyribonucleotide delivery. Identification of microRNA, microRNA target regions, and their expression patterns and role in biology have been reported (Bonauer et al., Curr Drug Targets 2010 11:943-949; Anand and Cheresh Curr Opin Hematol 2011 18: 171-176; Contreras and Rao Leukemia 2012 26:404-413 (2011 Dec. 20. doi: 10.1038/leu.2011.356); Barrel Cell 2009 136:215-233; Landgraf et al, Cell, 2007 129: 1401-1414; each of which is herein incorporated by reference in its entirety).

Conversely, microRNA binding sites can be engineered out of (i.e. removed from) the circular polyribonucleotide to modulate protein expression in specific tissues. Regulation of expression in multiple tissues can be accomplished through introduction or removal or one or several microRNA binding sites.

Examples of tissues where microRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126). MicroRNA can also regulate complex biological processes such as angiogenesis (miR-132) (Anand and Cheresh Curr Opin Hematol 2011 18: 171-176; herein incorporated by reference in its entirety). In the circular polyribonucleotide described herein, binding sites for microRNAs that are involved in such processes may be removed or introduced, in order to tailor the expression from the circular polyribonucleotide to biologically relevant cell types or to the context of relevant biological processes. A listing of MicroRNA, miR sequences and miR binding sites is listed in Table 9 of U.S. Provisional Application No. 61/753,661 filed Jan. 17, 2013, in Table 9 of U.S. Provisional Application No. 61/754,159 filed Jan. 18, 2013, and in Table 7 of U.S. Provisional Application No. 61/758,921 filed Jan. 31, 2013, each of which are herein incorporated by reference in their entireties. In some embodiments, the microRNA binding site includes, e.g. miR-7.

The circular polyribonucleotide disclosed herein can comprise a miRNA binding site that hybridize to any miRNA, such as any of those disclosed in miRNA databases such as miRBase, deepBase, miRBase, microRNA.org, miRGen 2.0; miRNAMap, PMRD, TargetScan, or VIRmiRNA. In some cases, the miRNA binding site can any site that is complementary to an miRNA whose target gene is disclosed in microRNA target genedatasese such as StarBase, StarScan, Cupid, TargetScan, TarBase, Diana-microT, miRecords, PicTar, PITA, RepTarm RNA22, miRTarBase, miRwalk, or MBSTAR.

Through an understanding of the expression patterns of microRNA in different cell types, the circular polyribonucleotide described herein can be engineered for more targeted expression in specific cell types or only under specific biological conditions. Through introduction of tissue-specific microRNA binding sites, the circular polyribonucleotide can be designed for optimal protein expression in a tissue or in the context of a biological condition. Examples of use of microRNA to drive tissue or disease-specific gene expression are listed (Getner and Naldini, Tissue Antigens. 2012, 80:393-403; herein incorporated by reference in its entirety).

In addition, microRNA seed sites may be incorporated into the circular polyribonucleotide to modulate expression in certain cells which results in a biological improvement. An example of this is incorporation of miR-142 sites. Incorporation of miR-142 sites into the circular polyribonucleotide described herein may modulate expression in hematopoietic cells, but also reduce or abolish immune responses to a protein encoded in the circular polyribonucleotide.

In some embodiments, the circular polyribonucleotide includes one or more large intergenic non-coding RNAs (lincRNA) binding sites. Large intergenic non-coding RNAs (lincRNAs) make up most of the long non-coding RNAs. LincRNAs are non-coding transcripts and, in some embodiments, are more than about 200 nucleotides long. In some embodiments, they have an exon-intron-exon structure, similar to protein-coding genes, but do not encompass open-reading frames and do not code for proteins. More than 8,000 lincRNAs have been described recently and are thought to be the largest subclass of RNAs, originating from the non-coding transcriptome in humans. Thousands of lincRNAs are known and some appear to be key regulators of diverse cellular processes. Determining the function of individual lincRNAs remains a challenge. lincRNA expression is strikingly tissue specific compared to coding genes, and that they are typically co-expressed with their neighboring genes, albeit to a similar extent to that of pairs of neighboring protein-coding genes.

In some embodiments, the circular polyribonucleotide includes one or more lincRNAs, such as FIRRE, LINC00969, PVT1, LINC01608, JPX, LINC01572, LINC00355, Clorf132, C3orf35, RP11-734, LINC01608, CC-499B15.5, CASC15, LINC00937, RP11-191, etc., or other lincRNAs or lncRNAs such as those from known lncRNA databases.

Protein-Binding

In some embodiments, the circular polyribonucleotide includes one or more protein binding sites that enable a protein, e.g., a ribosome, to bind to an internal site in the RNA sequence. By engineering protein binding sites, e.g., ribosome binding sites, into the circular polyribonucleotide, the circular polyribonucleotide may evade or have reduced detection by the host's immune system, have modulated degradation, or modulated translation, by masking the circular polyribonucleotide from components of the host's immune system.

In some embodiments, the circular polyribonucleotide comprises at least one immunoprotein binding site, for example to evade immune responses, e.g., CTL (cytotoxic T lymphocyte) responses. In some embodiments, the immunoprotein binding site is a nucleotide sequence that binds to an immunoprotein and aids in masking the circular polyribonucleotide as exogenous. In some embodiments, the immunoprotein binding site is a nucleotide sequence that binds to an immunoprotein and aids in hiding the circular polyribonucleotide as exogenous or foreign.

Traditional mechanisms of ribosome engagement to linear RNA involve ribosome binding to the capped 5' end of an RNA. From the 5' end, the ribosome migrates to an initiation codon, whereupon the first peptide bond is formed. According to the present invention, internal initiation (i.e., cap-independent) of translation of the circular polyribonucleotide does not require a free end or a capped end. Rather, a ribosome binds to a non-capped internal site, whereby the ribosome begins polypeptide elongation at an initiation codon. In some embodiments, the circular polyribonucleotide includes one or more RNA sequences comprising a ribosome binding site, e.g., an initiation codon.

Natural 5'UTRS bear features which play roles in for translation initiation. They harbor signatures like Kozak sequences which are commonly known to be involved in the process by which the ribosome initiates translation of many genes. Kozak sequences have the consensus CCR(A/G) CCAUGG, where R is a purine (adenine or guanine) three bases upstream of the start codon (AUG), which is followed by another 'G'. 5'UTR also have been known to form secondary structures which are involved in elongation factor binding.

In some embodiments, the circular polyribonucleotide encodes a protein binding sequence that binds to a protein. In some embodiments, the protein binding sequence targets or localizes the circular polyribonucleotide to a specific target. In some embodiments, the protein binding sequence specifically binds an arginine-rich region of a protein.

In some embodiments, the protein binding site includes, but is not limited to, a binding site to the protein such as ACIN1, AGO, APOBEC3F, APOBEC3G, ATXN2, AUH, BCCIP, CAPRIN1, CELF2, CPSF1, CPSF2, CPSF6, CPSF7, CSTF2, CSTF2T, CTCF, DDX21, DDX3, DDX3X, DDX42, DGCR8, EIF3A, EIF4A3, EIF4G2, ELAVL1, ELAVL3, FAM120A, FBL, FIP1L1, FKBP4, FMR1, FUS, FXR1, FXR2, GNL3, GTF2F1, HNRNPA1, HNRNPA2B1, HNRNPC, HNRNPK, HNRNPL, HNRNPM, HNRNPU, HNRNPUL1, IGF2BP1, IGF2BP2, IGF2BP3, ILF3, KHDRBS1, LARP7, LIN28A, LIN28B, m6A, MBNL2, METTL3, MOV10, MSI1, MSI2, NONO, NONO-, NOP58, NPM1, NUDT21, PCBP2, POLR2A, PRPF8, PTBP1, RBFOX2, RBM10, RBM22, RBM27, RBM47, RNPS1, SAFB2, SBDS, SF3A3, SF3B4, SIRT7, SLBP, SLTM, SMNDC1, SND1, SRRM4, SRSF1, SRSF3, SRSF7, SRSF9, TAF15, TARDBP, TIA1, TNRC6A, TOP3B, TRA2A, TRA2B, U2AF1, U2AF2, UNK, UPF1, WDR33, XRN2, YBX1, YTHDC1, YTHDF1, YTHDF2, YWHAG, ZC3H7B, PDK1, AKT1, and any other protein that binds RNA.

Encryptogen

As described herein, the circular polyribonucleotide comprises an encryptogen to reduce, evade or avoid the innate immune response of a cell. In one aspect, provided herein are circular polyribonucleotide which when delivered to cells, results in a reduced immune response from the host as compared to the response triggered by a reference compound, e.g. a linear polynucleotide corresponding to the described circular polyribonucleotide or a circular polyribonucleotide lacking an encryptogen. In some embodiments, the circular polyribonucleotide has less immunogenicity than a counterpart lacking an encryptogen.

In some embodiments, an encryptogen enhances stability. There is growing body of evidence about the regulatory roles played by the UTRs in terms of stability of a nucleic acid molecule and translation. The regulatory features of a UTR may be included in the encryptogen to enhance the stability of the circular polyribonucleotide.

In some embodiments, 5' or 3'UTRs can constitute encryptogens in a circular polyribonucleotide. For example, removal or modification of UTR AU rich elements (AREs) may be useful to modulate the stability or immunogenicity of the circular polyribonucleotide.

In some embodiments, removal of modification of AU rich elements (AREs) in expression sequence, e.g., translatable regions, can be useful to modulate the stability or immunogenicity of the circular polyribonucleotide In some embodiments, an encryptogen comprises miRNA binding site or binding site to any other non-coding RNAs. For example, incorporation of miR-142 sites into the circular polyribonucleotide described herein may not only modulate expression in hematopoietic cells, but also reduce or abolish immune responses to a protein encoded in the circular polyribonucleotide.

In some embodiments, an encyptogen comprises one or more protein binding sites that enable a protein, e.g., an immunoprotein, to bind to the RNA sequence. By engineering protein binding sites into the circular polyribonucleotide, the circular polyribonucleotide may evade or have reduced detection by the host's immune system, have modulated degradation, or modulated translation, by masking the circular polyribonucleotide from components of the host's immune system. In some embodiments, the circular polyribonucleotide comprises at least one immunoprotein binding site, for example to evade immune responses, e.g., CTL responses. In some embodiments, the immunoprotein binding site is a nucleotide sequence that binds to an immunoprotein and aids in masking the circular polyribonucleotide as exogenous.

In some embodiments, an encryptogen comprises one or more modified nucleotides. Exemplary modifications can include any modification to the sugar, the nucleobase, the internucleoside linkage (e.g. to a linking phosphate/to a phosphodiester linkage/to the phosphodiester backbone), and any combination thereof that can prevent or reduce immune response against the circular polyribonucleotide. Some of the exemplary modifications provided herein are described in details below.

In some embodiments, the circular polyribonucleotide includes one or more modifications as described elsewhere herein to reduce an immune response from the host as compared to the response triggered by a reference compound, e.g. a circular polyribonucleotide lacking the modifications. In particular, the addition of one or more inosine has been shown to discriminate RNA as endogenous versus viral. See for example, Yu, Z. et al. (2015) RNA editing by ADAR1 marks dsRNA as "self". Cell Res. 25, 1283-1284, which is incorporated by reference in its entirety.

In some embodiments, the circular polyribonucleotide includes one or more expression sequences for shRNA or an RNA sequence that can be processed into siRNA, and the shRNA or siRNA targets RIG-1 and reduces expression of RIG-1. RIG-1 can sense foreign circular RNA and leads to degradation of foreign circular RNA. Therefore, a circular polynucleotide harboring sequences for RIG-1-targeting shRNA, siRNA or any other regulatory nucleic acids can reduce immunity, e.g., host cell immunity, against the circular polyribonucleotide.

In some embodiments, the circular polyribonucleotide lacks a sequence, element or structure, that aids the circular polyribonucleotide in reducing, evading or avoiding an innate immune response of a cell. In some such embodiments, the circular polyribonucleotide may lack a polyA sequence, a 5' end, a 3' end, phosphate group, hydroxyl group, or any combination thereof.

Riboswitches

In some embodiments, the circular polyribonucleotide comprises one or more riboswitches.

A riboswitch is typically considered a part of the circular polyribonucleotide that can directly bind a small target molecule, and whose binding of the target affects RNA translation, the expression product stability and activity (Tucker B J, Breaker R R (2005), Curr Opin Struct Biol 15 (3): 342-8). Thus, the circular polyribonucleotide that includes a riboswitch is directly involved in regulating its own activity, depending on the presence or absence of its target molecule. In some embodiments, a riboswitch has a region of aptamer-like affinity for a separate molecule. Thus, in the broader context of the instant invention, any aptamer included within a non-coding nucleic acid could be used for sequestration of molecules from bulk volumes. Downstream reporting of the event via "(ribo)switch" activity may be especially advantageous.

In some embodiments, the riboswitch may have an effect on gene expression including, but not limited to, transcriptional termination, inhibition of translation initiation, mRNA self-cleavage, and in eukaryotes, alteration of splicing pathways. The riboswitch may function to control gene expression through the binding or removal of a trigger molecule. Thus, subjecting a circular polyribonucleotide that includes the riboswitch to conditions that activate, deactivate or block the riboswitch to alter expression. Expression can be altered as a result of, for example, termination of transcription or blocking of ribosome binding to the RNA. Binding of a trigger molecule or an analog thereof can, depending on the nature of the riboswitch, reduce or prevent expression of the RNA molecule or promote or increase expression of the RNA molecule. Some examples of riboswitches are described herein.

In some embodiments, the riboswitch is a Cobalamin riboswitch (also $B_{12}$-element), which binds adenosylcobalamin (the coenzyme form of vitamin $B_{12}$) to regulate the biosynthesis and transport of cobalamin and similar metabolites.

In some embodiments, the riboswitch is a cyclic di-GMP riboswitches, which bind cyclic di-GMP to regulate a variety of genes. Two non-structurally related classes exist—cyclic di-GMP-l and cyclic di-GMP-ll.

In some embodiments, the riboswitch is a FMN riboswitch (also RFN-element) which binds flavin mononucleotide (FMN) to regulate riboflavin biosynthesis and transport.

In some embodiments, the riboswitch is a glmS riboswitch, which cleaves itself when there is a sufficient concentration of glucosamine-6-phosphate.

In some embodiments, the riboswitch is a Glutamine riboswitches, which bind glutamine to regulate genes involved in glutamine and nitrogen metabolism. They also bind short peptides of unknown function. Such riboswitches fall into two classes, which are structurally related: the glnA RNA motif and Downstream-peptide motif.

In some embodiments, the riboswitch is a Glycine riboswitch, which binds glycine to regulate glycine metabolism genes. It comprises two adjacent aptamer domains in the same mRNA, and is the only known natural RNA that exhibits cooperative binding.

In some embodiments, the riboswitch is a Lysine riboswitch (also L-box), which binds lysine to regulate lysine biosynthesis, catabolism and transport.

In some embodiments, the riboswitch is a PreQ1 riboswitch, which binds pre-queuosine to regulate genes involved in the synthesis or transport of this precursor to queuosine. Two entirely distinct classes of PreGI riboswitches are known: PreQ1-l riboswitches and PreQ1-ll riboswitches. The binding domain of PreQ1-l riboswitches is unusually small among naturally occurring riboswitches. PreGI-II riboswitches, which are only found in certain species in the genera *Streptococcus* and *Lactococcus*, have a completely different structure, and are larger.

In some embodiments, the riboswitch is a Purine riboswitch, which binds purines to regulate purine metabolism and transport. Different forms of the purine riboswitch bind guanine (a form originally known as the G-box) or adenine. The specificity for either guanine or adenine depends completely upon Watson-Crick interactions with a single pyrimidine in the riboswitch at position Y74. In the guanine riboswitch, this residue is a cytosine (i.e. C74), in the adenine residue it is always a uracil (i.e. U74). Homologous types of purine riboswitches bind deoxyguanosine, but have more significant differences than a single nucleotide mutation.

In some embodiments, the riboswitch is a SAH riboswitch, which binds S-adenosylhomocysteine to regulate genes involved in recycling this metabolite which is produced when S-adenosylmethionine is used in methylation reactions.

In some embodiments, the riboswitch is a SAM riboswitch, which binds S-adenosyl methionine (SAM) to regulate methionine and SAM biosynthesis and transport. Three distinct SAM riboswitches are known: SAM-I (originally called S-box), SAM-II and the $S_MK$ box riboswitch. SAM-I is widespread in bacteria, but SAM-II is found only in α-, β- and a few γ-proteobacteria. The $S_MK$ box riboswitch is found only in the order Lactobacillales. These three varieties of riboswitch have no obvious similarities in terms of sequence or structure. A fourth variety, SAM-IV, appears to have a similar ligand-binding core to that of SAM-I, but in the context of a distinct scaffold.

In some embodiments, the riboswitch is a SAM-SAH riboswitch, which binds both SAM and SAH with similar affinities. Since they are always found in a position to regulate genes encoding methionine adenosyltransferase, it was proposed that only their binding to SAM is physiologically relevant.

In some embodiments, the riboswitch is a Tetrahydrofolate riboswitch, which binds tetrahydrofolate to regulate synthesis and transport genes.

In some embodiments, the riboswitch is a theophylline binding riboswitch or a thymine pyrophosphate binding riboswitch.

In some embodiments, the riboswitch is a *T. tengcongensis* glmS catalytic riboswitch, which senses glucosamine-6 phosphate (Klein and Ferre-D'Amare 2006).

In some embodiments, the riboswitch is a TPP riboswitch (also THI-box), which binds thiamine pyrophosphate (TPP) to regulate thiamine biosynthesis and transport, as well as transport of similar metabolites. It is the only riboswitch found so far in eukaryotes.

In some embodiments, the riboswitch is a Moco riboswitch, which binds molybdenum cofactor, to regulate genes involved in biosynthesis and transport of this coenzyme, as well as enzymes that use it or its derivatives as a cofactor.

In some embodiments, the riboswitch is a Adenine sensing add-A riboswitch, found in the 5' UTR of the adenine deaminase encoding gene of *Vibrio vulnificus.*

Aptazyme

In some embodiments, the circular polyribonucleotide comprises an aptazyme. Aptazyme is a switch for conditional expression in which an aptamer region is used as an allosteric control element and coupled to a region of catalytic RNA (a "ribozyme" as described below). In some embodiments, the aptazyme is active in cell type specific translation. In some embodiments, the aptazyme is active under cell state specific translation, e.g., virally infected cells or in the presence of viral nucleic acids or viral proteins.

A ribozyme (from ribonucleic acid enzyme, also called RNA enzyme or catalytic RNA) is a RNA molecule that catalyzes a chemical reaction. Many natural ribozymes catalyze either the hydrolysis of one of their own phosphodiester bonds, or the hydrolysis of bonds in other RNAs, but they have also been found to catalyze the aminotransferase activity of the ribosome. More recently it has been shown that catalytic RNAs can be "evolved" by in vitro methods [1. Agresti J J, Kelly B T, Jaschke A, Griffiths A D: Selection of ribozymes that catalyse multiple-turnover Diels-Alder cycloadditions by using in vitro compartmentalization. Proc Natl Acad Sci USA 2005, 102:16170-16175; 2. Sooter L J, Riedel T, Davidson E A, Levy M, Cox J C, Ellington A D: Toward automated nucleic acid enzyme selection. Biological Chemistry 2001, 382(9):1327-1334]. Winkler et al. have shown [Winkler W C, Nahvi A, Roth A, Collins J A, Breaker R R: Control of gene expression by a natural metabolite-responsive ribozyme. Nature 2004, 428:281-286.] that, similar to riboswitch activity discussed above, ribozymes and their reaction products can regulate gene expression. In the context of the instant invention, it may be particularly advantageous to place a catalytic RNA or ribozyme within a larger non-coding RNA such that the ribozyme is present at many copies within the cell for the purposes of chemical transformation of a molecule from a bulk volume. Furthermore, encoding both aptamers and ribozymes in the same non-coding RNA may be particularly advantageous.

Some nonlimiting examples of ribozymes include hammerhead ribozyme, VL ribozyme, leadzyme, hairpin ribozyme.

In some embodiments, the aptazyme is a ribozyme that can cleave RNA sequences and which can be regulated as a result of binding ligand/modulator. The ribozyme may also be a self-cleaving ribozyme. As such, they combine the properties of ribozymes and aptamers. Aptazymes offer advantages over conventional aptamers due to their potential for activity in trans, the fact that they act catalytically to inactivate expression and that inactivation, due to cleavage of their own or heterologous transcript, is irreversible.

In some embodiments, the aptazyme is included in an untranslated region of the circular polyribonucleotide and in the absence of ligand/modulator is inactive, allowing expression of the transgene. Expression can be turned off (or down-regulated) by addition of the ligand. It should be noted that aptazymes which are downregulated in response to the presence of a particular modulator can be used in control systems where upregulation of gene expression in response to modulator is desired.

Aptazymes may also permit development of systems for self-regulation of circular polyribonucleotide expression. For example, the protein product of the circular polyribonucleotide is the rate determining enzyme in the synthesis of a particular small molecule could be modified to include an aptazyme selected to have increased catalytic activity in the presence of that molecule, thereby providing an autoregulatory feedback loop for its synthesis. Alternatively, the aptazyme activity can be selected to be sensitive to accumulation of the protein product from the circular polyribonucleotide, or any other cellular macromolecule.

In some embodiments, the circular polyribonucleotide may include an aptamer sequence. Some nonlimiting examples include an RNA aptamer binding lysozyme, a Toggle-25t which is an RNA aptamer that includes 2'fluoropyrimidine nucleotides bind thrombins with high specificity and affinity, RNATat that binds human immunodeficiency virus trans-acting responsive element (HIV TAR), RNA aptamer-binding hemin, RNA aptamer-binding interferon γ, RNA aptamer binding vascular endothelial growth factor (VEGF), RNA aptamer binding prostate specific antigen (PSA), RNA aptamer binding dopamine, and RNA aptamer binding the non-classical oncogene, heat shock factor 1 (HSF1).

Circularization

In one embodiment, a linear circular polyribonucleotide may be cyclized, or concatemerized. In some embodiments, the linear circular polyribonucleotide may be cyclized in vitro prior to formulation and/or delivery. In some embodiments, the linear circular polyribonucleotide may be cyclized within a cell.

Extracellular Circularization

In some embodiments, the linear circular polyribonucleotide is cyclized, or concatemerized using a chemical method to form a circular polyribonucleotide. In some chemical methods, the 5'-end and the 3'-end of the nucleic acid (e.g., a linear circular polyribonucleotide) includes chemically reactive groups that, when close together, may form a new covalent linkage between the 5'-end and the 3'-end of the molecule. The 5'-end may contain an NHS-ester reactive group and the 3'-end may contain a 3'-amino-terminated nucleotide such that in an organic solvent the 3'-amino-terminated nucleotide on the 3'-end of a linear RNA molecule will undergo a nucleophilic attack on the 5'-NHS-ester moiety forming a new 5'-/3'-amide bond.

In one embodiment, a DNA or RNA ligase may be used to enzymatically link a 5'-phosphorylated nucleic acid molecule (e.g., a linear circular polyribonucleotide) to the 3'-hydroxyl group of a nucleic acid (e.g., a linear nucleic acid) forming a new phosphorodiester linkage. In an example reaction, a linear circular polyribonucleotide is incubated at 37° C. for 1 hour with 1-10 units of T4 RNA ligase (New England Biolabs, Ipswich, MA) according to the manufacturer's protocol. The ligation reaction may occur in the presence of a linear nucleic acid capable of base-pairing with both the 5'- and 3'-region in juxtaposition to assist the enzymatic ligation reaction. In one embodiment, the ligation is splint ligation. For example, a splint ligase, like SplintR® ligase, can be used for splint ligation. For splint ligation, a single stranded polynucleotide (splint), like a single stranded RNA, can be designed to hybridize with both termini of a linear polyribonucleotide, so that the two termini can be juxtaposed upon hybridization with the single-stranded splint. Splint ligase can thus catalyze the ligation of the juxtaposed two termini of the linear polyribonucleotide, generating a circular polyribonucleotide.

In one embodiment, a DNA or RNA ligase may be used in the synthesis of the circular polynucleotides. As a non-limiting example, the ligase may be a circ ligase or circular ligase.

In one embodiment, either the 5'- or 3'-end of the linear circular polyribonucleotide can encode a ligase ribozyme sequence such that during in vitro transcription, the resultant linear circular polyribonucleotide includes an active ribozyme sequence capable of ligating the 5'-end of the linear circular polyribonucleotide to the 3'-end of the linear circular polyribonucleotide. The ligase ribozyme may be derived from the Group I Intron, Hepatitis Delta Virus, Hairpin ribozyme or may be selected by SELEX (systematic evolution of ligands by exponential enrichment). The ribozyme ligase reaction may take 1 to 24 hours at temperatures between 0 and 37° C.

In one embodiment, a linear circular polyribonucleotide may be cyclized or concatemerized by using at least one non-nucleic acid moiety. In one aspect, the at least one non-nucleic acid moiety may react with regions or features near the 5' terminus and/or near the 3' terminus of the linear circular polyribonucleotide in order to cyclize or concatermerize the linear circular polyribonucleotide. In another aspect, the at least one non-nucleic acid moiety may be located in or linked to or near the 5' terminus and/or the 3' terminus of the linear circular polyribonucleotide. The non-nucleic acid moieties contemplated may be homologous or heterologous. As a non-limiting example, the non-nucleic acid moiety may be a linkage such as a hydrophobic linkage, ionic linkage, a biodegradable linkage and/or a cleavable linkage. As another non-limiting example, the non-nucleic acid moiety is a ligation moiety. As yet another non-limiting example, the non-nucleic acid moiety may be an oligonucleotide or a peptide moiety, such as an apatamer or a non-nucleic acid linker as described herein.

In one embodiment, a linear circular polyribonucleotide may be cyclized or concatemerized due to a non-nucleic acid moiety that causes an attraction between atoms, molecular surfaces at, near or linked to the 5' and 3' ends of the linear circular polyribonucleotide. As a non-limiting example, one or more linear circular polyribonucleotides may be cyclized or concatermized by intermolecular forces or intramolecular forces. Non-limiting examples of intermolecular forces include dipole-dipole forces, dipole-induced dipole forces, induced dipole-induced dipole forces, Van der Waals forces, and London dispersion forces. Non-limiting examples of intramolecular forces include covalent bonds, metallic bonds, ionic bonds, resonant bonds, agnostic bonds, dipolar bonds, conjugation, hyperconjugation and antibonding.

In one embodiment, the linear circular polyribonucleotide may comprise a ribozyme RNA sequence near the 5' terminus and near the 3' terminus. The ribozyme RNA sequence may covalently link to a peptide when the sequence is exposed to the remainder of the ribozyme. In one aspect, the peptides covalently linked to the ribozyme RNA sequence near the 5' terminus and the 3' terminus may associate with each other causing a linear circular polyribonucleotide to cyclize or concatemerize. In another aspect, the peptides covalently linked to the ribozyme RNA near the 5' terminus and the 3' terminus may cause the linear primary construct or linear mRNA to cyclize or concatemerize after being subjected to ligated using various methods known in the art such as, but not limited to, protein ligation. Non-limiting examples of ribozymes for use in the linear primary constructs or linear RNA of the present invention or a non-exhaustive listing of methods to incorporate and/or covalently link peptides are described in US patent application No. US20030082768, the contents of which is here in incorporated by reference in its entirety.

In some embodiments, the linear circular polyribonucleotide may include a 5' triphosphate of the nucleic acid converted into a 5' monophosphate, e.g., by contacting the 5' triphosphate with RNA 5' pyrophosphohydrolase (RppH) or an ATP diphosphohydrolase (apyrase). Alternately, converting the 5' triphosphate of the linear circular polyribonucleotide into a 5' monophosphate may occur by a two-step reaction comprising: (a) contacting the 5' nucleotide of the linear circular polyribonucleotide with a phosphatase (e.g., Antarctic Phosphatase, Shrimp Alkaline Phosphatase, or Calf Intestinal Phosphatase) to remove all three phosphates; and (b) contacting the 5' nucleotide after step (a) with a kinase (e.g., Polynucleotide Kinase) that adds a single phosphate.

In some embodiments, the circularization efficiency of the circularization methods provided herein is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 95%, or 100%. In some embodiments, the circularization efficiency of the circularization methods provided herein is at least about 40%.

Splicing Element

In some embodiment, the circular polyribonucleotide includes at least one splicing element. In a circular polyribonucleotide as provided herein, a splicing element can be a complete splicing element that can mediate splicing of the circular polyribonucleotide. Alternatively, the spicing element can also be a residual splicing element from a completed splicing event. For instance, in some cases, a splicing element of a linear polyribonucleotide can mediate a splicing event that results in circularization of the linear polyribonucleotide, thereby the resultant circular polyribonucleotide comprises a residual splicing element from such splicing-mediated circularization event. In some cases, the residual splicing element is not able to mediate any splicing. In other cases, the residual splicing element can still mediate splicing under certain circumstances. In some embodiments, the splicing element is adjacent to at least one expression sequence. In some embodiments, the circular polyribonucleotide includes a splicing element adjacent each expression sequence. In some embodiments, the splicing element is on one or both sides of each expression sequence, leading to separation of the expression products, e.g., peptide(s) and or polypeptide(s).

In some embodiments, the circular polyribonucleotide includes an internal splicing element that when replicated the spliced ends are joined together. Some examples may include miniature introns (<100 nt) with splice site sequences and short inverted repeats (30-40 nt) such as AluSq2, AluJr, and AluSz, inverted sequences in flanking introns, Alu elements in flanking introns, and motifs found in (suptable4 enriched motifs) cis-sequence elements proximal to backsplice events such as sequences in the 200 bp preceding (upstream of) or following (downstream from) a backsplice site with flanking exons. In some embodiments, the circular polyribonucleotide includes at least one repetitive nucleotide sequence described elsewhere herein as an internal splicing element. In such embodiments, the repetitive nucleotide sequence may include repeated sequences from the Alu family of introns. In some embodiments, a splicing-related ribosome binding protein can regulate circular polyribonucleotide biogenesis (e.g. the Muscleblind and Quaking (QKI) splicing factors).

In some embodiments, the circular polyribonucleotide may include canonical splice sites that flank head-to-tail junctions of the circular polyribonucleotide.

In some embodiments, the circular polyribonucleotide may include a bulge-helix-bulge motif, comprising a 4-base pair stem flanked by two 3-nucleotide bulges. Cleavage occurs at a site in the bulge region, generating characteristic fragments with terminal 5'-hydroxyl group and 2', 3'-cyclic phosphate. Circularization proceeds by nucleophilic attack of the 5'-OH group onto the 2', 3'-cyclic phosphate of the same molecule forming a 3', 5'-phosphodiester bridge.

In some embodiments, the circular polyribonucleotide may include a multimeric repeating RNA sequence that harbors a HPR element. The HPR comprises a 2',3'-cyclic phosphate and a 5'-OH termini. The HPR element self-processes the 5'- and 3'-ends of the linear circular polyribonucleotide, thereby ligating the ends together.

In some embodiments, the circular polyribonucleotide may include a sequence that mediates self-ligation. In one embodiment, the circular polyribonucleotide may include a HDV sequence (e.g., HDV replication domain conserved sequence, GGCUCAUCUCGACAAGAGGCGGCAGUCCUCAGUACUCUUACUCUUUUCUGUAAAGAGGAGAC UGCUGGACUCGCCGCCCAAGUUCGAGCAUGAGCC (SEQ ID NO: 102) or GGCUAGAGGCGGCAGUCCUCAGUACUCUUACUCUUUUCUGUAAAGAGGAGACUGCUGGACUC GCCGCCCGAGCC (SEQ ID NO: 103)) to self-ligate. In one embodiment, the circular polyribonucleotide may include loop E sequence (e.g. in PSTVd) to self-ligate. In another embodiment, the circular polyribonucleotide may include a self-circularizing intron, e.g., a 5' and 3' slice junction, or a self-circularizing catalytic intron such as a Group I, Group II or Group III Introns. Nonlimiting examples of group I intron self-splicing sequences may include self-splicing permuted intron-exon sequences derived from T4 bacteriophage gene td, and the intervening sequence (IVS) rRNA of Tetrahymena.

Other Circularization Methods

In some embodiments, linear circular polyribonucleotides may include complementary sequences, including either repetitive or nonrepetitive nucleic acid sequences within individual introns or across flanking introns. Repetitive nucleic acid sequence are sequences that occur within a segment of the circular polyribonucleotide. In some embodiments, the circular polyribonucleotide includes a repetitive nucleic acid sequence. In some embodiments, the repetitive nucleotide sequence includes poly CA or poly UG sequences. In some embodiments, the circular polyribonucleotide includes at least one repetitive nucleic acid sequence that hybridizes to a complementary repetitive nucleic acid sequence in another segment of the circular polyribonucleotide, with the hybridized segment forming an internal double strand. In some embodiments, repetitive nucleic acid sequences and complementary repetitive nucleic acid sequences from two separate circular polyribonucleotides hybridize to generate a single circularized polyribonucleotide, with the hybridized segments forming internal double strands. In some embodiments, the complementary sequences are found at the 5' and 3' ends of the linear circular polyribonucleotides. In some embodiments, the complementary sequences include about 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, or more paired nucleotides.

In some embodiments, chemical methods of circularization may be used to generate the circular polyribonucleotide.

Such methods may include, but are not limited to click chemistry (e.g., alkyne and azide based methods, or clickable bases), olefin metathesis, phosphoramidate ligation, hemiaminal-imine crosslinking, base modification, and any combination thereof.

In some embodiments, enzymatic methods of circularization may be used to generate the circular polyribonucleotide. In some embodiments, a ligation enzyme, e.g., DNA or RNA ligase, may be used to generate a template of the circular polyribonuclease or complement, a complementary strand of the circular polyribonuclease, or the circular polyribonuclease.

Circularization of the circular polyribonucleotide may be accomplished by methods known in the art, for example, those described in "RNA circularization strategies in vivo and in vitro" by Petkovic and Muller from Nucleic Acids Res, 2015, 43(4): 2454-2465, and "In vitro circularization of RNA" by Muller and Appel, from RNA Biol, 2017, 14(8): 1018-1027.

Replication Element

The circular polyribonucleotide may encode a sequence and/or motifs useful for replication. Replication of a circular polyribonucleotide may occur by generating a complement circular polyribonucleotide. In some embodiments, the circular polyribonucleotide includes a motif to initiate transcription, where transcription is driven by either endogenous cellular machinery (DNA-dependent RNA polymerase) or an RNA-depended RNA polymerase encoded by the circular polyribonucleotide. The product of rolling-circle transcriptional event may be cut by a ribozyme to generate either complementary or propagated circular polyribonucleotide at unit length. The ribozymes may be encoded by the circular polyribonucleotide, its complement, or by an RNA sequence in trans. In some embodiments, the encoded ribozymes may include a sequence or motif that regulates (inhibits or promotes) activity of the ribozyme to control circular RNA propagation. In some embodiments, unit-length sequences may be ligated into a circular form by a cellular RNA ligase. In some embodiments, the circular polyribonucleotide includes a replication element that aids in self amplification. Examples of such replication elements include, but are not limited to, HDV replication domains described elsewhere herein, RNA promotor of Potato Spindle Tuber Viroid (see for example Kolonko 2005 Virology), and replication competent circular RNA sense and/or antisense ribozymes such as

```
antigenomic
                                          (SEQ ID NO: 104)
5'-CGGGUCGGCAUGGCAUCUCCACCUCCUCGCGGUCCGACCUGGGCAU

CCGAAGGAGGACGCACGUCCACUCGGAUGGCUAAGGGAGAGCCA-3'
or

genomic
                                          (SEQ ID NO: 105)
5'-UGGCCGGCAUGGUCCCAGCCUCCUCGCUGGCGCCGGCUGGGCAACA

UUCCGAGGGGACCGUCCCCUCGGUAAUGGCGAAUGGGACCCA-3'.
```

In some embodiments, the circular polyribonucleotide includes at least one stagger element as described herein to aid in replication. A stagger element within the circular polyribonucleotide can cleave long transcripts replicated from the circular polyribonucleotide to a specific length that could subsequently circularize to form a complement to the circular polyribonucleotide.

In another embodiment, the circular polyribonucleotide includes at least one ribozyme sequence to cleave long transcripts replicated from the circular polyribonucleotide to a specific length, where another encoded ribozyme cuts the transcripts at the ribozyme sequence. Circularization forms a complement to the circular polyribonucleotide.

In some embodiments, the circular polyribonucleotide is substantially resistant to degradation, e.g., by exonucleases.

In some embodiments, the circular polyribonucleotide replicates within a cell. In some embodiments, the circular polyribonucleotide replicates within in a cell at a rate of between about 10%-20%, 20%-30%, 30%-40%, 40%-50%, 50%-60%, 60%-70%, 70%-75%, 75%-80%, 80%-85%, 85%-90%, 90%-95%, 95%-99%, or any percentage therebetween. In some embodiments, the circular polyribonucleotide is replicated within a cell and is passed to daughter cells. In some embodiments, a cell passes at least one circular polyribonucleotide to daughter cells with an efficiency of at least 25%, 50%, 60%, 70%, 80%, 85%, 90%, 95%, or 99%. In some embodiments, cell undergoing meiosis passes the circular polyribonucleotide to daughter cells with an efficiency of at least 25%, 50%, 60%, 70%, 80%, 85%, 90%, 95%, or 99%. In some embodiments, a cell undergoing mitosis passes the circular polyribonucleotide to daughter cells with an efficiency of at least 25%, 50%, 60%, 70%, 80%, 85%, 90%, 95%, or 99%.

In some embodiments, the circular polyribonucleotide replicates within the host cell. In one embodiment, the circular polyribonucleotide is capable of replicating in a mammalian cell, e.g., human cell.

While in some embodiments the circular polyribonucleotide replicates in the host cell, the circular polyribonucleotide does not integrate into the genome of the host, e.g., with the host's chromosomes. In some embodiments, the circular polyribonucleotide has a negligible recombination frequency, e.g., with the host's chromosomes. In some embodiments, the circular polyribonucleotide has a recombination frequency, e.g., less than about 1.0 cM/Mb, 0.9 cM/Mb, 0.8 cM/Mb, 0.7 cM/Mb, 0.6 cM/Mb, 0.5 cM/Mb, 0.4 cM/Mb, 0.3 cM/Mb, 0.2 cM/Mb, 0.1 cM/Mb, or less, e.g., with the host's chromosomes.

Other Sequences

In some embodiments, the circular polyribonucleotide further includes another nucleic acid sequence. In some embodiments, the circular polyribonucleotide may comprise other sequences that include DNA, RNA, or artificial nucleic acids. The other sequences may include, but are not limited to, genomic DNA, cDNA, or sequences that encode tRNA, mRNA, rRNA, miRNA, gRNA, siRNA, or other RNAi molecules. In one embodiment, the circular polyribonucleotide includes an siRNA to target a different loci of the same gene expression product as the circular polyribonucleotide. In one embodiment, the circular polyribonucleotide includes an siRNA to target a different gene expression product as the circular polyribonucleotide.

In some embodiments, the circular polyribonucleotide lacks a 5'-UTR. In some embodiments, the circular polyribonucleotide lacks a 3'-UTR. In some embodiments, the circular polyribonucleotide lacks a poly-A sequence. In some embodiments, the circular polyribonucleotide lacks a termination element. In some embodiments, the circular polyribonucleotide lacks an internal ribosomal entry site. In some embodiments, the circular polyribonucleotide lacks degradation susceptibility by exonucleases. In some embodiments, the fact that the circular polyribonucleotide lacks degradation susceptibility can mean that the circular polyribonucleotide is not degraded by an exonuclease, or only degraded in the presence of an exonuclease to a limited extent that is comparable to or similar to in the absence of exonuclease. In some embodiments, the circular polyribonucleotide lacks degradation by exonucleases. In some embodiments, the circular polyribonucleotide has reduced degradation when exposed to exonuclease. In some embodiments, the circular polyribonucleotide lacks binding to a cap-binding protein In some embodiments, the circular polyribonucleotide lacks a 5' cap.

In some embodiments, the circular polyribonucleotide lacks a 5'-UTR and is competent for protein express from its one or more expression sequences. In some embodiments, the circular polyribonucleotide lacks a 3'-UTR and is competent for protein express from its one or more expression sequences. In some embodiments, the circular polyribonucleotide lacks a poly-A sequence and is competent for protein express from its one or more expression sequences. In some embodiments, the circular polyribonucleotide lacks a termination element and is competent for protein express from its one or more expression sequences. In some embodiments, the circular polyribonucleotide lacks an internal ribosomal entry site and is competent for protein express from its one or more expression sequences. In some embodiments, the circular polyribonucleotide lacks a cap and is competent for protein express from its one or more expression sequences. In some embodiments, the circular polyribonucleotide lacks a 5'-UTR, a 3'-UTR, and an IRES, and is competent for protein express from its one or more expression sequences. In some embodiments, the circular polyribonucleotide comprises one or more of the following sequences: a sequence that encodes one or more miRNAs, a sequence that encodes one or more replication proteins, a sequence that encodes an exogenous gene, a sequence that encodes a therapeutic, a regulatory element (e.g., translation modulator, e.g., translation enhancer or suppressor), a translation initiation sequence, one or more regulatory nucleic acids that targets endogenous genes (siRNA, lncRNAs, shRNA), and a sequence that encodes a therapeutic mRNA or protein.

The other sequence may have a length from about 2 to about 10000 nts, about 2 to about 5000 nts, about 10 to about 100 nts, about 50 to about 150 nts, about 100 to about 200 nts, about 150 to about 250 nts, about 200 to about 300 nts, about 250 to about 350 nts, about 300 to about 500 nts, about 10 to about 1000 nts, about 50 to about 1000 nts, about 100 to about 1000 nts, about 1000 to about 2000 nts, about 2000 to about 3000 nts, about 3000 to about 4000 nts, about 4000 to about 5000 nts, or any range therebetween.

As a result of its circularization, the circular polyribonucleotide may include certain characteristics that distinguish it from linear RNA. For example, the circular polyribonucleotide is less susceptible to degradation by exonuclease as compared to linear RNA. As such, the circular polyribonucleotide is more stable than a linear RNA, especially when incubated in the presence of an exonuclease. The increased stability of the circular polyribonucleotide compared with linear RNA makes circular polyribonucleotide more useful as a cell transforming reagent to produce polypeptides and can be stored more easily and for longer than linear RNA. The stability of the circular polyribonucleotide treated with exonuclease can be tested using methods standard in art which determine whether RNA degradation has occurred (e.g., by gel electrophoresis).

Moreover, unlike linear RNA, the circular polyribonucleotide is less susceptible to dephosphorylation when the circular polyribonucleotide is incubated with phosphatase, such as calf intestine phosphatase.

Nucleotide Spacer Sequences

In some embodiments, the circular polyribonucleotide comprises a spacer sequence.

In some embodiments, the circular polyribonucleotide comprises at least one spacer sequence. In some embodiments, the circular polyribonucleotide comprises 1, 2, 3, 4, 5, 6, 7 or more spacer sequences.

In some embodiments, the circular polyribonucleotide comprises a ratio of spacer sequence to non-spacer sequence of the circular polyribonucleotide, e.g., expression sequences, of about 0.05:1, about 0.06:1, about 0.07:1, about 0.08:1, about 0.09:1, about 0.1:1, about 0.12:1, about 0.125:1, about 0.15:1, about 0.175:1, about 0.2:1, about 0.225:1, about 0.25:1, about 0.3:1, about 0.35:1, about 0.4:1, about 0.45:1, about 0.5:1, about 0.55:1, about 0.6:1, about 0.65:1, about 0.7:1, about 0.75:1, about 0.8:1, about 0.85:1, about 0.9:1, about 0.95:1, about 0.98:1, about 1:1, about 1.02:1, about 1.05:1, about 1.1:1, about 1.15:1, about 1.2:1, about 1.25:1, about 1.3:1, about 1.35:1, about 1.4:1, about 1.45:1, about 1.5:1, about 1.55:1, about 1.6:1, about 1.65:1, about 1.7:1, about 1.75:1, about 1.8:1, about 1.85:1, about 1.9:1, about 1.95:1, about 1.975:1, about 1.98:1, or about 2:1.

In some embodiments, the spacer sequence comprises a ratio of spacer sequence to a downstream (e.g., 3' of the spacer sequence) non-spacer element of the circular polyribonucleotide of about 0.5:1, about 0.06:1, about 0.07:1, about 0.08:1, about 0.09:1, about 0.1:1, about 0.12:1, about 0.125:1, about 0.15:1, about 0.175:1, about 0.2:1, about 0.225:1, about 0.25:1, about 0.3:1, about 0.35:1, about 0.4:1, about 0.45:1, about 0.5:1, about 0.55:1, about 0.6:1, about 0.65:1, about 0.7:1, about 0.75:1, about 0.8:1, about 0.85:1, about 0.9:1, about 0.95:1, about 0.98:1, about 1:1, about 1.02:1, about 1.05:1, about 1.1:1, about 1.15:1, about 1.2:1, about 1.3:1, about 1.4:1, about 1.5:1, about 1.6:1, about 1.7:1, about 1.8:1, about 1.9:1, about 1.95:1, about 1.975:1, about 1.98:1, about 2.1:1, about 2.2:1, about 2.3:1, about 2.4:1, about 2.5:1, about 2.6:1, about 2.7:1, about 2.8:1, about 2.9:1, about 3:1, about 3.1:1, about 3.2:1, about 3.3:1, about 3.4:1, about 3.5:1, about 3.6:1, about 3.7:1, about 3.8:1, about 3.85:1, about 3.9:1, about 3.95:1, about 3.98:1, or about 4:1. In some embodiments, the spacer sequence comprises a ratio of spacer sequence to an upstream (e.g., 5' of the spacer sequence) non-spacer element of the circular polyribonucleotide of about 0.5:1, about 0.06:1, about 0.07:1, about 0.08:1, about 0.09:1, about 0.1:1, about 0.12:1, about 0.125:1, about 0.15:1, about 0.175:1, about 0.2:1, about 0.225:1, about 0.25:1, about 0.3:1, about 0.35:1, about 0.4:1, about 0.45:1, about 0.5:1, about 0.55:1, about 0.6:1, about 0.65:1, about 0.7:1, about 0.75:1, about 0.8:1, about 0.85:1, about 0.9:1, about 0.95:1, about 0.98:1, about 1:1, about 1.02:1, about 1.05:1, about 1.1:1, about 1.15:1, about 1.2:1, about 1.3:1, about 1.4:1, about 1.5:1, about 1.6:1, about 1.7:1, about 1.8:1, about 1.9:1, about 1.95:1, about 1.975:1, about 1.98:1, about 2.1:1, about 2.2:1, about 2.3:1, about 2.4:1, about 2.5:1, about 2.6:1, about 2.7:1, about 2.8:1, about 2.9:1, about 3:1, about 3.1:1, about 3.2:1, about 3.3:1, about 3.4:1, about 3.5:1, about 3.6:1, about 3.7:1, about 3.8:1, about 3.85:1, about 3.9:1, about 3.95:1, about 3.98:1, or about 4:1.

In some embodiments, the spacer sequence comprises a sequence of at least 3 ribonucleotides, at least 4 ribonucleotides, at least 5 ribonucleotides, at least about 8 ribonucleotides, at least about 10 ribonucleotides, at least about 12 ribonucleotides, at least about 15 ribonucleotides, at least about 20 ribonucleotides, at least about 25 ribonucleotides, at least about 30 ribonucleotides, at least about 40 ribonucleotides, at least about 50 ribonucleotides, at least about 60 ribonucleotides, at least about 70 ribonucleotides, at least about 80 ribonucleotides, at least about 90 ribonucleotides, at least about 100 ribonucleotides, at least about 120 ribonucleotides, at least about 150 ribonucleotides, at least about 200 ribonucleotides, at least about 250 ribonucleotides, at least about 300 ribonucleotides, at least about 400 ribonucleotides, at least about 500 ribonucleotides, at least about 600 ribonucleotides, at least about 700 ribonucleotides, at least about 800 ribonucleotides, at least about 900 ribonucleotides, or at least about 100 ribonucleotides.

In some embodiments, the spacer sequence may be a nucleic acid sequence or molecule having low GC content, for example less than 65%, 60%, 55%, 50%, 55%, 50%, 45%, 40%, 39%, 38%, 37%, 36%, 35%, 34%, 33%, 32%, 31%, 30%, 29%, 28%, 27%, 26%, 25%, 24%, 23%, 22%, 20%, 19%, 18%, 17%, 16%, 15%, 14%, 13%, 12%, 11%, 10%, 9%, 8%, 7%, 6%, 5%, 4%, 3%, 2% or 1%, across the full length of the spacer, or across at least 50%, 60%, 70%, 80%, 90%, 91%, 92%, 93%, 94%, 95%, 96%, 97%, 98% or 99% contiguous nucleic acid residues of the spacer. In some embodiments, the spacer sequence may comprise at least 95%, 90%, 85%, 80%, 75%, 70%, 65%, 60%, 55%, 50%, 55%, 50%, 45%, 40%, 35%, 30%, 20% or any percentage therebetween of adenine ribonucleotides. In some embodiments, the spacer sequence comprises at least 5 or more adenine ribonucleotides in a row. In some embodiments, the spacer sequence comprises at least 6 adenine ribonucleotides in a row, at least 7 adenine ribonucleotides in a row, at least 8 ribonucleotides, at least about 10 adenine ribonucleotides in a row, at least about 12 adenine ribonucleotides in a row, at least about 15 adenine ribonucleotides in a row, at least about 20 adenine ribonucleotides in a row, at least about 25 adenine ribonucleotides in a row, at least about 30 adenine ribonucleotides in a row, at least about 40 adenine ribonucleotides in a row, at least about 50 adenine ribonucleotides in a row, at least about 60 adenine ribonucleotides in a row, at least about 70 adenine ribonucleotides in a row, at least about 80 adenine ribonucleotides in a row, at least about 90 adenine ribonucleotides in a row, at least about 95 adenine ribonucleotides in a row, at least about 100 adenine ribonucleotides in a row, at least about 150 adenine ribonucleotides in a row, at least about 200 adenine ribonucleotides in a row, at least about 250 adenine ribonucleotides in a row, at least about 300 adenine ribonucleotides in a row, at least about 350 adenine ribonucleotides in a row, at least about 400 adenine ribonucleotides in a row, at least about 450 adenine ribonucleotides in a row, at least about 500 adenine ribonucleotides in a row, at least about 550 adenine ribonucleotides in a row, at least about 600 adenine ribonucleotides in a row, at least about 700 adenine ribonucleotides in a row, at least about 800 adenine ribonucleotides in a row, at least about 900 adenine ribonucleotides in a row, or at least about 1000 adenine ribonucleotides in a row.

In some embodiments, the spacer sequence is situated between one or more elements. In some embodiments, the spacer sequence provides conformational flexibility between the elements. In some embodiments, the conformational flexibility is due to the spacer sequence being substantially free of a secondary structure. In some embodiments, the spacer sequence is substantially free of a secondary structure, such as less than 40 kcal/mol, less than −39, −38, −37, −36, −35, −34, −33, −32, −31, −30, −29, −28, −27, −26, −25, −24, −23, −22, −20, −19, −18, −17, −16, −15, −14, −13, −12, −11, −10, −9, −8, −7, −6, −5, −4, −3, −2 or −1 kcal/mol. The spacer may include a nucleic acid, such as DNA or RNA.

In some embodiments, the spacer sequence may encode an RNA sequence, and preferably a protein or peptide sequence, including a secretion signal peptide.

In some embodiments, the spacer sequence may be non-coding. Where the spacer is a non-coding sequence, a translation initiation sequence may be provided in the coding sequence of an adjacent sequence. In some embodiments, it is envisaged that the first nucleic acid residue of the coding sequence may be the A residue of a translation initiation sequence, such as AUG. Where the spacer encodes an RNA or protein or peptide sequence, a translation initiation sequence may be provided in the spacer sequence.

In some embodiments, the spacer is operably linked to another sequence described herein.

Non-Nucleic Acid Linkers

The circular polyribonucleotide described herein may also comprise a non-nucleic acid linker. In some embodiments, the circular polyribonucleotide described herein has a non-nucleic acid linker between one or more of the sequences or elements described herein. In one embodiment, one or more sequences or elements described herein are linked with the linker. The non-nucleic acid linker may be a chemical bond, e.g., one or more covalent bonds or non-covalent bonds. In some embodiments, the non-nucleic acid linker is a peptide or protein linker. Such a linker may be between 2-30 amino acids, or longer. The linker includes flexible, rigid or cleavable linkers described herein.

The most commonly used flexible linkers have sequences consisting primarily of stretches of Gly and Ser residues ("GS" linker). Flexible linkers may be useful for joining domains that require a certain degree of movement or interaction and may include small, non-polar (e.g. Gly) or polar (e.g. Ser or Thr) amino acids. Incorporation of Ser or Thr can also maintain the stability of the linker in aqueous solutions by forming hydrogen bonds with the water molecules, and therefore reduce unfavorable interactions between the linker and the protein moieties.

Rigid linkers are useful to keep a fixed distance between domains and to maintain their independent functions. Rigid linkers may also be useful when a spatial separation of the domains is critical to preserve the stability or bioactivity of one or more components in the fusion. Rigid linkers may have an alpha helix-structure or Pro-rich sequence, $(XP)_n$, with X designating any amino acid, preferably Ala, Lys, or Glu.

Cleavable linkers may release free functional domains in vivo. In some embodiments, linkers may be cleaved under specific conditions, such as the presence of reducing reagents or proteases. In vivo cleavable linkers may utilize the reversible nature of a disulfide bond. One example includes a thrombin-sensitive sequence (e.g., PRS) between the two Cys residues. In vitro thrombin treatment of CPRSC (SEQ ID NO: 131) results in the cleavage of the thrombin-sensitive sequence, while the reversible disulfide linkage remains intact. Such linkers are known and described, e.g., in Chen et al. 2013. Fusion Protein Linkers: Property, Design and Functionality. Adv Drug Deliv Rev. 65(10): 1357-1369. In vivo cleavage of linkers in fusions may also be carried out by proteases that are expressed in vivo under pathological conditions (e.g. cancer or inflammation), in specific cells or tissues, or constrained within certain cellular compartments. The specificity of many proteases offers slower cleavage of the linker in constrained compartments.

Examples of linking molecules include a hydrophobic linker, such as a negatively charged sulfonate group; lipids, such as a poly (—$CH_2$—) hydrocarbon chains, such as polyethylene glycol (PEG) group, unsaturated variants thereof, hydroxylated variants thereof, amidated or otherwise N-containing variants thereof, noncarbon linkers; carbohydrate linkers; phosphodiester linkers, or other molecule capable of covalently linking two or more polypeptides. Non-covalent linkers are also included, such as hydrophobic lipid globules to which the polypeptide is linked, for example through a hydrophobic region of the polypeptide or a hydrophobic extension of the polypeptide, such as a series of residues rich in leucine, isoleucine, valine, or perhaps also alanine, phenylalanine, or even tyrosine, methionine, glycine or other hydrophobic residue. The polypeptide may be linked using charge-based chemistry, such that a positively charged moiety of the polypeptide is linked to a negative charge of another polypeptide or nucleic acid.

Stability/Half-Life

In some embodiments, the circular polyribonucleotide provided herein has increase half-life over a reference, e.g., a linear polyribonucleotide having the same nucleotide sequence but is not circularized (linear counterpart). In some embodiments, the circular polyribonucleotide is substantially resistant to degradation, e.g., exonuclease. In some embodiments, the circular polyribonucleotide is resistant to self-degradation. In some embodiments, the circular polyribonucleotide lacks an enzymatic cleavage site, e.g., a dicer cleavage site. In some embodiments, the circular polyribonucleotide has a half-life at least about 5%, at least about 10%, at least about 20%, at least about 30%, at least about 40%, at least about 50%, at least about 60%, at least about 70%, at least about 80%, at least about 90%, at least about 100%, at least about 120%, at least about 140%, at least about 150%, at least about 160%, at least about 180%, at least about 200%, at least about 300%, at least about 400%, at least about 500%, at least about 600%, at least about 700% at least about 800%, at least about 900%, at least about 1000% or at least about 10000%, longer than a reference, e.g., a linear counterpart.

In some embodiments, the circular polyribonucleotide persists in a cell during cell division. In some embodiments, the circular polyribonucleotide persists in daughter cells after mitosis. In some embodiments, the circular polyribonucleotide is replicated within a cell and is passed to daughter cells. In some embodiments, the circular polyribonucleotide comprises a replication element that mediates self-replication of the circular polyribonucleotide. In some embodiments, the replication element mediates transcription of the circular polyribonucleotide into a linear polyribonucleotide that is complementary to the circular polyribonucleotide (linear complementary). In some embodiments, the linear complementary polyribonucleotide can be circularized in vivo in cells into a complementary circular polyribonucleotide. In some embodiments, the complementary polyribonucleotide can further self-replicate into another circular polyribonucleotide, which has the same or similar nucleotide sequence as the starting circular polyribonucleotide. One exemplary self-replication element includes HDV replication domain (as described by Beeharry et al, *Virol,* 2014, 450-451:165-173). In some embodiments, a cell passes at least one circular polyribonucleotide to daughter cells with an efficiency of at least 25%, 50%, 60%, 70%, 80%, 85%, 90%, 95%, or 99%. In some embodiments, cell undergoing meiosis passes the circular polyribonucleotide to daughter cells with an efficiency of at least 25%, 50%, 60%, 70%, 80%, 85%, 90%, 95%, or 99%. In some embodiments, a cell undergoing mitosis passes the circular polyribonucleotide to daughter cells with an efficiency of at least 25%, 50%, 60%, 70%, 80%, 85%, 90%, 95%, or 99%.

Modifications

The circular polyribonucleotide may include one or more substitutions, insertions and/or additions, deletions, and covalent modifications with respect to reference sequences, in particular, the parent polyribonucleotide, are included within the scope of this invention.

In some embodiments, the circular polyribonucleotide includes one or more post-transcriptional modifications (e.g., capping, cleavage, polyadenylation, splicing, poly-A sequence, methylation, acylation, phosphorylation, methylation of lysine and arginine residues, acetylation, and nitrosylation of thiol groups and tyrosine residues, etc). The one or more post-transcriptional modifications can be any post-transcriptional modification, such as any of the more than one hundred different nucleoside modifications that have been identified in RNA (Rozenski, J, Crain, P, and McCloskey, J. (1999). *The RNA Modification Database:* 1999 *update. Nucl Acids Res* 27: 196-197) In some embodiments, the first isolated nucleic acid comprises messenger RNA (mRNA). In some embodiments, the mRNA comprises at least one nucleoside selected from the group consisting of pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine. In some embodiments, the mRNA comprises at least one nucleoside selected from the group consisting of 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine. In some embodiments, the mRNA comprises at least one nucleoside selected from the group consisting of 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine. In some embodiments, mRNA comprises at least one nucleoside selected from the group consisting of inosine, 1-methyl-inosine, wyosine, wybutosine, 7-deaza-guanosine, 7-deaza aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethyl-guanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

The circular polyribonucleotide may include any useful modification, such as to the sugar, the nucleobase, or the internucleoside linkage (e.g. to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof). Additional modifications are described herein.

In some embodiments, the circular polyribonucleotide includes at least one N(6)methyladenosine (m6A) modification to increase translation efficiency. In some embodiments, the N(6)methyladenosine (m6A) modification can reduce immunogenicity of the circular polyribonucleotide.

In some embodiments, the modification may include a chemical or cellular induced modification. For example, some nonlimiting examples of intracellular RNA modifications are described by Lewis and Pan in “RNA modifications and structures cooperate to guide RNA-protein interactions” from Nat Reviews Mol Cell Biol, 2017, 18:202-210.

In some embodiments, chemical modifications to the ribonucleotides of the circular polyribonucleotide may enhance immune evasion. The circular polyribonucleotide may be synthesized and/or modified by methods well established in the art, such as those described in “Current protocols in nucleic acid chemistry,” Beaucage, S. L. et al. (Eds.), John Wiley & Sons, Inc., New York, NY, USA, which is hereby incorporated herein by reference. Modifications include, for example, end modifications, e.g., 5' end modifications (phosphorylation (mono-, di- and tri-), conjugation, inverted linkages, etc.), 3' end modifications (conjugation, DNA nucleotides, inverted linkages, etc.), base modifications (e.g., replacement with stabilizing bases, destabilizing bases, or bases that base pair with an expanded repertoire of partners), removal of bases (abasic nucleotides), or conjugated bases. The modified ribonucleotide bases may also include 5-methylcytidine and pseudouridine. In some embodiments, base modifications may modulate expression, immune response, stability, subcellular localization, to name a few functional effects, of the circular polyribonucleotide. In some embodiments, the modification includes a bi-orthogonal nucleotides, e.g., an unnatural base. See for example, Kimoto et al, Chem Commun (Camb), 2017, 53:12309, DOI: 10.1039/c7cc06661a, which is hereby incorporated by reference.

In some embodiments, sugar modifications (e.g., at the 2' position or 4' position) or replacement of the sugar one or more ribonucleotides of the circular polyribonucleotide may, as well as backbone modifications, include modification or replacement of the phosphodiester linkages. Specific examples of circular polyribonucleotide include, but are not limited to circular polyribonucleotide including modified backbones or no natural internucleoside linkages such as internucleoside modifications, including modification or replacement of the phosphodiester linkages. Circular polyribonucleotides having modified backbones include, among others, those that do not have a phosphorus atom in the backbone. For the purposes of this application, and as sometimes referenced in the art, modified RNAs that do not have a phosphorus atom in their internucleoside backbone can also be considered to be oligonucleosides. In particular embodiments, the circular polyribonucleotide will include ribonucleotides with a phosphorus atom in its internucleoside backbone.

Modified circular polyribonucleotide backbones may include, for example, phosphorothioates, chiral phosphorothioates, phosphorodithioates, phosphotriesters, aminoalkylphosphotriesters, methyl and other alkyl phosphonates such as 3'-alkylene phosphonates and chiral phosphonates, phosphinates, phosphoramidates such as 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. In some embodiments, the circular polyribonucleotide may be negatively or positively charged.

The modified nucleotides, which may be incorporated into the circular polyribonucleotide, can be modified on the internucleoside linkage (e.g., phosphate backbone). Herein, in the context of the polynucleotide backbone, the phrases “phosphate” and “phosphodiester” are used interchangeably. Backbone phosphate groups can be modified by replacing one or more of the oxygen atoms with a different substituent. Further, the modified nucleosides and nucleotides can include the wholesale replacement of an unmodified phosphate moiety with another internucleoside linkage as described herein. Examples of modified phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be modified by the replacement of a linking oxygen with nitrogen (bridged phosphoramidates), sulfur (bridged phosphorothioates), and carbon (bridged methylene-phosphonates).

The a-thio substituted phosphate moiety is provided to confer stability to RNA and DNA polymers through the unnatural phosphorothioate backbone linkages. Phosphorothioate DNA and RNA have increased nuclease resistance and subsequently a longer half-life in a cellular environment. Phosphorothioate linked to the circular polyribonucleotide is expected to reduce the innate immune response through weaker binding/activation of cellular innate immune molecules.

In specific embodiments, a modified nucleoside includes an alpha-thio-nucleoside (e.g., 5'-0-(l-thiophosphate)-adenosine, 5'-0-(l-thiophosphate)-cytidine (a-thio-cytidine), 5'-0-(l-thiophosphate)-guanosine, 5'-0-(l-thiophosphate)-uridine, or 5'-0-(l-thiophosphate)-pseudouridine).

Other internucleoside linkages that may be employed according to the present invention, including internucleoside linkages which do not contain a phosphorous atom, are described herein.

In some embodiments, the circular polyribonucleotide may include one or more cytotoxic nucleosides. For example, cytotoxic nucleosides may be incorporated into circular polyribonucleotide, such as bifunctional modification. Cytotoxic nucleoside may include, but are not limited to, adenosine arabinoside, 5-azacytidine, 4'-thio-aracytidine, cyclopentenylcytosine, cladribine, clofarabine, cytarabine, cytosine arabinoside, l-(2-C-cyano-2-deoxy-beta-D-arabino-pentofuranosyl)-cytosine, decitabine, 5-fluorouracil, fludarabine, floxuridine, gemcitabine, a combination of tegafur and uracil, tegafur ((RS)-5-fluoro-l-(tetrahydrofuran-2-yl)pyrimidine-2,4(1H,3H)-dione), troxacitabine, tezacitabine, 2'-deoxy-2'-methylidenecytidine (DMDC), and 6-mercaptopurine. Additional examples include fludarabine phosphate, N4-behenoyl-l-beta-D-arabinofuranosylcytosine, N4-octadecyl-1-beta-D-arabinofuranosylcytosine, N4-palmitoyl-l-(2-C-cyano-2-deoxy-beta-D-arabino-pentofuranosyl) cytosine, and P-4055 (cytarabine 5'-elaidic acid ester).

The circular polyribonucleotide may or may not be uniformly modified along the entire length of the molecule. For example, one or more or all types of nucleotide (e.g., naturally-occurring nucleotides, purine or pyrimidine, or any one or more or all of A, G, U, C, I, pU) may or may not be uniformly modified in the circular polyribonucleotide, or in a given predetermined sequence region thereof. In some embodiments, the circular polyribonucleotide includes a pseudouridine. In some embodiments, the circular polyribonucleotide includes an inosine, which may aid in the immune system characterizing the circular polyribonucleotide as endogenous versus viral RNAs. The incorporation of inosine may also mediate improved RNA stability/reduced degradation. See for example, Yu, Z. et al. (2015) RNA editing by ADAR1 marks dsRNA as "self". Cell Res. 25, 1283-1284, which is incorporated by reference in its entirety.

In some embodiments, all nucleotides in the circular polyribonucleotide (or in a given sequence region thereof) are modified. In some embodiments, the modification may include an m6A, which may augment expression; an inosine, which may attenuate an immune response; pseudouridine, which may increase RNA stability, or translational readthrough (stagger element), an m5C, which may increase stability; and a 2,2,7-trimethylguanosine, which aids subcellular translocation (e.g., nuclear localization).

Different sugar modifications, nucleotide modifications, and/or internucleoside linkages (e.g., backbone structures) may exist at various positions in the circular polyribonucleotide. One of ordinary skill in the art will appreciate that the nucleotide analogs or other modification(s) may be located at any position(s) of the circular polyribonucleotide, such that the function of the circular polyribonucleotide is not substantially decreased. A modification may also be a noncoding region modification. The circular polyribonucleotide may include from about 1% to about 100% modified nucleotides (either in relation to overall nucleotide content, or in relation to one or more types of nucleotide, i.e. any one or more of A, G, U or C) or any intervening percentage (e.g., from 1% to 20%>, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%).

Structure

In some embodiments, the circular polyribonucleotide comprises a higher order structure, e.g., a secondary or tertiary structure. In some embodiments, complementary segments of the circular polyribonucleotide fold itself into a double stranded segment, held together with hydrogen bonds between pairs, e.g., A-U and C-G. In some embodiments, helices, also known as stems, are formed intramolecularly, having a double-stranded segment connected to an end loop. In some embodiments, the circular polyribonucleotide has at least one segment with a quasi-double-stranded secondary structure. In some embodiments, a segment having a quasi-double-stranded secondary structure has at least 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, or more paired nucleotides. In some embodiments, the circular polyribonucleotide has one or more segments (e.g., 2, 3, 4, 5, 6, or more) having a quasi-double-stranded secondary structure. In some embodiments, the segments are separated by 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, or more nucleotides.

In some embodiments, one or more sequences of the circular polyribonucleotide include substantially single stranded vs double stranded regions. In some embodiments, the ratio of single stranded to double stranded may influence the functionality of the circular polyribonucleotide.

In some embodiments, one or more sequences of the circular polyribonucleotide that are substantially single stranded. In some embodiments, one or more sequences of the circular polyribonucleotide that are substantially single stranded may include a protein- or RNA-binding site. In some embodiments, the circular polyribonucleotide sequences that are substantially single stranded may be conformationally flexible to allow for increased interactions. In some embodiments, the sequence of the circular polyribonucleotide is purposefully engineered to include such secondary structures to bind or increase protein or nucleic acid binding.

In some embodiments, the circular polyribonucleotide sequences that are substantially double stranded. In some embodiments, one or more sequences of the circular polyribonucleotide that are substantially double stranded may include a conformational recognition site, e.g., a riboswitch or aptazyme. In some embodiments, the circular polyribonucleotide sequences that are substantially double stranded may be conformationally rigid. In some such instances, the conformationally rigid sequence may sterically hinder the circular polyribonucleotide from binding a protein or a nucleic acid. In some embodiments, the sequence of the circular polyribonucleotide is purposefully engineered to include such secondary structures to avoid or reduce protein or nucleic acid binding.

There are 16 possible base-pairings, however of these, six (AU, GU, GC, UA, UG, CG) may form actual base-pairs. The rest are called mismatches and occur at very low frequencies in helices. In some embodiments, the structure of the circular polyribonucleotide cannot easily be disrupted without impact on its function and lethal consequences, which provide a selection to maintain the secondary structure. In some embodiments, the primary structure of the stems (i.e., their nucleotide sequence) can still vary, while still maintaining helical regions. The nature of the bases is secondary to the higher structure, and substitutions are possible as long as they preserve the secondary structure. In some embodiments, the circular polyribonucleotide has a quasi-helical structure. In some embodiments, the circular polyribonucleotide has at least one segment with a quasi-helical structure. In some embodiments, a segment having a quasi-helical structure has at least 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, or more nucleotides. In some embodiments, the circular polyribonucleotide has one or more segments (e.g., 2, 3, 4, 5, 6, or more) having a quasi-helical structure. In some embodiments, the segments are separated by 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, or more nucleotides. In some embodiments, the circular polyribonucleotide includes at least one of a U-rich or A-rich sequence or a combination thereof. In some embodiments, the U-rich and/or A-rich sequences are arranged in a manner that would produce a triple quasi-helix structure. In some embodiments, the circular polyribonucleotide has a double quasi-helical structure. In some embodiments, the circular polyribonucleotide has one or more segments (e.g., 2, 3, 4, 5, 6, or more) having a double quasi-helical structure. In some embodiments, the circular polyribonucleotide includes at least one of a C-rich and/or G-rich sequence. In some embodiments, the C-rich and/or G-rich sequences are arranged in a manner that would produce triple quasi-helix structure. In some embodiments, the circular polyribonucleotide has an intramolecular triple quasi-helix structure that aids in stabilization.

In some embodiments, the circular polyribonucleotide has two quasi-helical structure (e.g., separated by a phosphodiester linkage), such that their terminal base pairs stack, and the quasi-helical structures become colinear, resulting in a "coaxially stacked" substructure.

In some embodiments, the circular polyribonucleotide comprises a tertiary structure with one or more motifs, e.g., a pseudoknot, a g-quadruplex, a helix, and coaxial stacking.

In some embodiments, the circular polyribonucleotide has at least one binding site, e.g., at least one protein binding site, at least one miRNA binding site, at least one lncRNA binding site, at least one tRNA binding site, at least one rRNA binding site, at least one snRNA binding site, at least one siRNA binding site, at least one piRNA binding site, at least one snoRNA binding site, at least one snRNA binding site, at least one exRNA binding site, at least one scaRNA binding site, at least one Y RNA binding site, at least one hnRNA binding site, and/or at least one tRNA motif.

Delivery

The circular polyribonucleotide described herein may also be included in pharmaceutical compositions with a delivery carrier.

Pharmaceutical compositions described herein may be formulates for example including a carrier, such as a pharmaceutical carrier and/or a polymeric carrier, e.g., a liposome, and delivered by known methods to a subject in need thereof (e.g., a human or non-human agricultural or domestic animal, e.g., cattle, dog, cat, horse, poultry). Such methods include, but not limited to, transfection (e.g., lipid-mediated, cationic polymers, calcium phosphate, dendrimers); electroporation or other methods of membrane disruption (e.g., nucleofection), viral delivery (e.g., lentivirus, retrovirus, adenovirus, AAV), microinjection, microprojectile bombardment ("gene gun"), fugene, direct sonic loading, cell squeezing, optical transfection, protoplast fusion, impalefection, magnetofection, exosome-mediated transfer, lipid nanoparticle-mediated transfer, and any combination thereof. Methods of delivery are also described, e.g., in Gori et al., Delivery and Specificity of CRISPR/Cas9 Genome Editing Technologies for Human Gene Therapy. Human Gene Therapy. July 2015, 26(7): 443-451. doi: 10.1089/hum.2015.074; and Zuris et al. Cationic lipid-mediated delivery of proteins enables efficient protein-based genome editing in vitro and in vivo. Nat Biotechnol. 2014 Oct. 30; 33(1):73-80.

The invention is further directed to a host or host cell comprising the circular polyribonucleotide described herein. In some embodiments, the host or host cell is a plant, insect, bacteria, fungus, vertebrate, mammal (e.g., human), or other organism or cell.

In some embodiments, the circular polyribonucleotide is non-immunogenic in the host. In some embodiments, the circular polyribonucleotide has a decreased or fails to produce a response by the host's immune system as compared to the response triggered by a reference compound, e.g. a linear polynucleotide corresponding to the described circular polyribonucleotide or a circular polyribonucleotide lacking an encryptogen. Some immune responses include, but are not limited to, humoral immune responses (e.g. production of antigen-specific antibodies) and cell-mediated immune responses (e.g. lymphocyte proliferation).

In some embodiments, a host or a host cell is contacted with (e.g., delivered to or administered to) the circular polyribonucleotide. In some embodiments, the host is a mammal, such as a human. The amount of the circular polyribonucleotide, expression product, or both in the host can be measured at any time after administration. In certain embodiments, a time course of host growth in a culture is determined. If the growth is increased or reduced in the presence of the circular polyribonucleotide, the circular polyribonucleotide or expression product or both is identified as being effective in increasing or reducing the growth of the host.

Methods of Production

In some embodiments, the circular polyribonucleotide includes a deoxyribonucleic acid sequence that is non-naturally occurring and can be produced using recombinant technology (methods described in detail below; e.g., derived in vitro using a DNA plasmid) or chemical synthesis.

It is within the scope of the invention that a DNA molecule used to produce an RNA circle can comprise a DNA sequence of a naturally-occurring original nucleic acid sequence, a modified version thereof, or a DNA sequence encoding a synthetic polypeptide not normally found in nature (e.g., chimeric molecules or fusion proteins). DNA and RNA molecules can be modified using a variety of techniques including, but not limited to, classic mutagenesis techniques and recombinant techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof.

The circular polyribonucleotide may be prepared according to any available technique including, but not limited to chemical synthesis and enzymatic synthesis. In some embodiments, a linear primary construct or linear mRNA may be cyclized, or concatemerized to create a circular polyribonucleotide described herein. The mechanism of cyclization or concatemerization may occur through methods such as, but not limited to, chemical, enzymatic, splint ligation), or ribozyme catalyzed methods. The newly formed 5'-/3'-linkage may be an intramolecular linkage or an intermolecular linkage.

Methods of making the circular polyribonucleotides described herein are described in, for example, Khudyakov & Fields, Artificial DNA: Methods and Applications, CRC Press (2002); in Zhao, Synthetic Biology: Tools and Applications, (First Edition), Academic Press (2013); and Egli & Herdewijn, Chemistry and Biology of Artificial Nucleic Acids, (First Edition), Wiley-VCH (2012).

Various methods of synthesizing circular polyribonucleotides are also described in the art (see, e.g., U.S. Pat. Nos. 6,210,931, 5,773,244, 5,766,903, 5,712,128, 5,426,180, US Publication No. US20100137407, International Publication No. WO1992001813 and International Publication No. WO2010084371; the contents of each of which are herein incorporated by reference in their entireties).

In some embodiments, the circular polyribonucleotides may be cleaned up after production to remove production impurities, e.g., free ribonucleic acids, linear or nicked RNA, DNA, proteins, etc. In some embodiments, the circular polyribonucleotides may be purified by any known method commonly used in the art. Examples of nonlimiting purification methods include, column chromatography, gel excision, size exclusion, etc.

Pharmaceutical Compositions

The present invention includes compositions in combination with one or more pharmaceutically acceptable excipients. Pharmaceutical compositions may optionally comprise one or more additional active substances, e.g. therapeutically and/or prophylactically active substances. Pharmaceutical compositions of the present invention may be sterile and/or pyrogen-free. General considerations in the formulation and/or manufacture of pharmaceutical agents may be found, for example, in Remington: The Science and Practice of Pharmacy 21st ed., Lippincott Williams & Wilkins, 2005 (incorporated herein by reference).

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product.

Methods of Expression

The present invention includes a method for protein expression, comprising translating at least a region of the circular polyribonucleotide provided herein.

In some embodiments, the methods for protein expression comprises translation of at least 10%, at least 20%, at least 30%, at least 40%, at least 50%, at least 60%, at least 70%, at least 80%, at least 90%, or at least 95% of the total length of the circular polyribonucleotide into polypeptides. In some embodiments, the methods for protein expression comprises translation of the circular polyribonucleotide into polypeptides of at least 5 amino acids, at least 10 amino acids, at least 15 amino acids, at least 20 amino acids, at least 50 amino acids, at least 100 amino acids, at least 150 amino acids, at least 200 amino acids, at least 250 amino acids, at least 300 amino acids, at least 400 amino acids, at least 500 amino acids, at least 600 amino acids, at least 700 amino acids, at least 800 amino acids, at least 900 amino acids, or at least 1000 amino acids. In some embodiments, the methods for protein expression comprises translation of the circular polyribonucleotide into polypeptides of about 5 amino acids, about 10 amino acids, about 15 amino acids, about 20 amino acids, about 50 amino acids, about 100 amino acids, about 150 amino acids, about 200 amino acids, about 250 amino acids, about 300 amino acids, about 400 amino acids, about 500 amino acids, about 600 amino acids, about 700 amino acids, about 800 amino acids, about 900 amino acids, or about 1000 amino acids. In some embodiments, the methods comprise translation of the circular polyribonucleotide into continuous polypeptides as provided herein, discrete polypeptides as provided herein, or both.

In some embodiments, the translation of the at least a region of the circular polyribonucleotide takes place in vitro, such as rabbit reticulocyte lysate. In some embodiments, the translation of the at least a region of the circular polyribonucleotide takes place in vivo, for instance, after transfection of a eukaryotic cell, or transformation of a prokaryotic cell such as a bacteria.

In some aspects, the present disclosure provides methods of in vivo expression of one or more expression sequences in a subject, comprising: administering a circular polyribonucleotide to a cell of the subject wherein the circular polyribonucleotide comprises the one or more expression sequences; and expressing the one or more expression sequences from the circular polyribonucleotide in the cell. In some embodiments, the circular polyribonucleotide is configured such that expression of the one or more expression sequences in the cell at a later time point is equal to or higher than an earlier time point. In some embodiments, the circular polyribonucleotide is configured such that expression of the one or more expression sequences in the cell over a time period of at least 7, 8, 9, 10, 12, 14, 16, 18, 20, 22, 23 or more days does not decrease by greater than about 40%. In some embodiments, the circular polyribonucleotide is configured such that expression of the one or more expression sequences in the cell is maintained at a level that does not vary by more than about 40% for at least 7, 8, 9, 10, 12, 14, 16, 18, 20, 22, 23 or more days. In some embodiments, the administration of the circular polyribonucleotide is conducted using any delivery method described herein. In some embodiments, the circular polyribonucleotide is administered to the subject via intravenous injection. In some embodiments, the administration of the circular polyribonucleotide includes, but is not limited to, prenatal administration, neonatal administration, postnatal administration, oral, by injection (e.g., intravenous, intraarterial, intraperitoneal, intradermal, subcutaneous and intramuscular), by ophthalmic administration and by intranasal administration.

In some embodiments, the methods for protein expression comprise modification, folding, or other post-translation modification of the translation product. In some embodiments, the methods for protein expression comprise post-translation modification in vivo, e.g., via cellular machinery.

All references and publications cited herein are hereby incorporated by reference.

The above described embodiments can be combined to achieve the afore-mentioned functional characteristics. This is also illustrated by the below examples which set forth exemplary combinations and functional characteristics achieved. Table 1 provides an exemplary overview which shows how different elements described above can be combined and the functional characteristics observed.

TABLE 1

Exemplary Elements in EXAMPLES

| | Elements (e.g. start codon, stagger element, encryptogen, IRES etc.) | | | | | | |
|---|---|---|---|---|---|---|---|
| Exemplary function | Replication element Transcription start | Expression sequence Coding for product | Stagger element Ribosomal pausing; rolling circle translation | Regulatory element Expression modifier | Encryptogen Modulating immune response | Quasi-double strand secondary structure | Effect of Circular Polyribonucleotide |
| Example 3 | | x | x | | x | | Greater translation efficiency than a linear counterpart |
| Example 4 | | x | x | | x | | Stochiometric translation efficiency of mutliple translation products |
| Example 5<br>Example 9<br>Example 44<br>Example 47 | | x | | | x | | Less immunogenicity than counterpart lacking an encryptogen |
| Example 13 | x | | | | | | |
| Example 14 | | x | x | | x | | Increased half-life over a linear counterpart |
| Example 15 | | x | x | | x | | Persistence during cell division |
| Example 18<br>Example 29 | | x | x | | | | Increased half-life over a linear counterpart |
| Example 30 | | x | x | x | | | Increased half-life over a linear counterpart |
| Example 38<br>Example 39 | | x | x | x | | | Greater translation efficiency than a linear counterpart |
| Example 10<br>Example 12<br>Example 40<br>Example 41 | | | | | | x | |
| Example 48 | | x | | | | | Persistence during cell division |
| Example 49 | | x | x | | | | Greater translation efficiency than a linear counterpart |
| Example 6<br>Example 52 | | x | | x | | | |
| Example 53 | | x | | | x | | Less immunogenicity than counterpart lacking an encryptogen |

TABLE 1-continued

Exemplary Elements in EXAMPLES

| Exemplary function | Elements (e.g. start codon, stagger element, encryptogen, IRES etc.) Replication element Transcription start | Expression sequence Coding for product | Stagger element Ribosomal pausing; rolling circle translation | Regulatory element Expression modifier | Encryptogen Modulating immune response | Quasi-double strand secondary structure | Effect of Circular Polyribonucleotide |
|---|---|---|---|---|---|---|---|
| Example 54 Example 55 | | x | | | x | | Greater translation efficiency than a linear counterpart; Increased half-life over a linear counterpart; Less immunogenicity than counterpart lacking an encryptogen |

EXAMPLES

The following examples are provided to further illustrate some embodiments of the present invention, but are not intended to limit the scope of the invention; it will be understood by their exemplary nature that other procedures, methodologies, or techniques known to those skilled in the art may alternatively be used.

Example 1: In Vitro Circular RNA Production

This example demonstrates in vitro production of a circular RNA.

Figure 2:
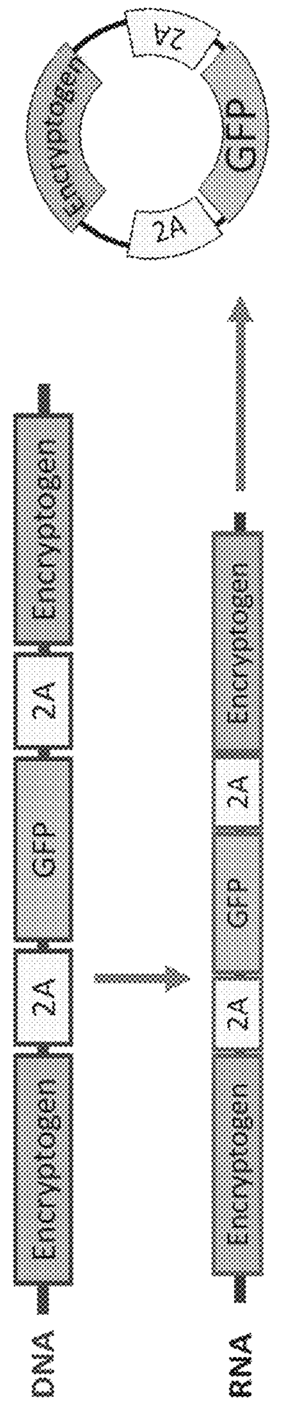
FIG. 2 shows a schematic of an exemplary in vitro production process of a circular RNA that contains a start-codon, an ORF (open reading frame) coding for GFP, a stagger element (2A), an encryptogen, and an IRES (internal ribosome entry site).

A circular RNA is designed with a start-codon (SEQ ID NO:1), ORF(s) (SEQ ID NO:2), stagger element(s) (SEQ ID NOS 3, 132, and 133), encryptogen(s) (SEQ ID NOS 4 and 134), and an IRES (SEQ ID NO:5), shown in FIG. 2. Circularization enables rolling circle translation, multiple open reading frames (ORFs) with alternating stagger elements for discrete ORF expression and controlled protein stoichiometry, encryptogen(s) to attenuate or mitigate RNA immunogenicity, and an optional IRES that targets RNA for ribosomal entry without poly-A sequence.

In this Example, the circular RNA is generated as follows. Unmodified linear RNA is synthesized by in vitro transcription using T7 RNA polymerase from a DNA segment having 5'- and 3'-ZKSCAN1 introns and an ORF encoding GFP linked to 2A sequences. Transcribed RNA is purified with an RNA purification system (QIAGEN), treated with alkaline phosphatase (ThermoFisher Scientific, EF0652) following the manufacturer's instructions, and purified again with the RNA purification system.

Splint ligation circular RNA is generated by treatment of the transcribed linear RNA and a DNA splint using T4 DNA ligase (New England Bio, Inc., M0202M), and the circular RNA is isolated following enrichment with RNase R treatment. RNA quality is assessed by agarose gel or through automated electrophoresis (Agilent).

Example 2: In Vivo Circular RNA Production, Cell Culture

This example demonstrates in vivo production of a circular RNA.

Figure 3:
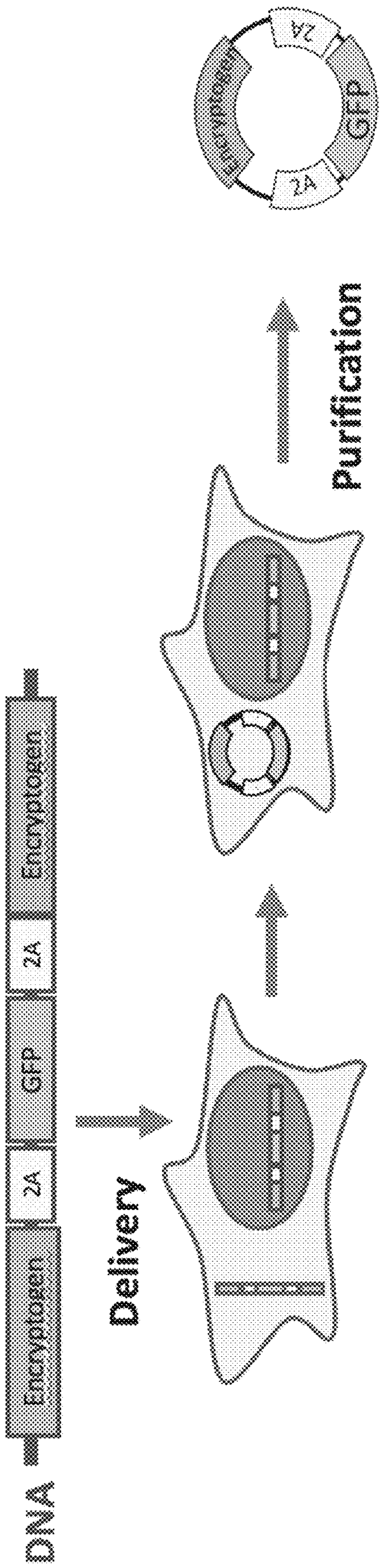
FIG. 3 shows a schematic of an exemplary in vivo production process of a circular RNA.

GFP (SEQ ID NO: 2) is cloned into an expression vector, e.g. pcDNA3.1(+) (Addgene) (SEQ ID NO: 6). This vector is mutagenized to induce circular RNA production in cells (SEQ ID NO: 6 and described by Kramer et al 2015), shown in FIG. 3.

HeLa cells are grown at 37° C. and 5% $CO_2$ in Dulbecco's modified Eagle's medium (DMEM) with high glucose (Life Technologies), supplemented with penicillin-streptomycin and 10% fetal bovine serum. One microgram of the above described expression plasmid is transfected using lipid transfection reagent (Life Technologies), and total RNA from the transfected cells is isolated using a phenol-based RNA isolation reagent (Life Technologies) as per the manufacturer's instructions between 1 hour and 20 days after transfection.

To measure GFP circular RNA and mRNA levels, qPCR reverse transcription using random hexamers is performed. In short, for RT-qPCR Hela cells' total RNA and RNase R-digested RNA from the same source are used as templates for the RT-PCR. To prepare the cDNAs of GFP mRNAs and circular GFP RNAs, the reverse transcription reactions are performed with a reverse transcriptase (Super-Script II: RNase H; Invitrogen) and random hexamers in accordance with the manufacturer's instruction. The amplified PCR products are analyzed using a 6% PAGE and visualized by ethidium bromide staining. To estimate the enrichment factor, the PCR products are quantified by densitometry (ImageQuant; Molecular Dynamics) and the concentrations of total RNA samples are measured by UV absorbance.

An additional RNA measurement is performed with northern blot analysis. Briefly, whole cell extract was obtained using a phenol based reagent (TRIzol) or nuclear and cytoplasmic protein extracts are obtained by fractionation of the cells with a commercial kit (CelLytic NuCLEAR Extraction Kit, Sigma). To inhibit RNA polymerase II transcription, cells are treated with flavopiridol (1 mM final concentration; Sigma) for 0-6 h at 37° C. For RNase R treatments, 10 mg of total RNA is treated with 20 U of RNase R (Epicentre) for 1 h at 37° C.

Northern blots using oligonucleotide probes are performed as follows. Oligonucleotide probes, PCR primers are designed using standard primer designing tools. T7 promoter sequence is added to the reverse primer to obtain an antisense probe in in vitro transcription reaction. In vitro transcription is performed using T7 RNA polymerase with a DIG-RNA labeling mix according to manufacturer's instruction. DNA templates are removed by DNAs I digestion and RNA probes purified by phenol chloroform extraction and subsequent precipitation. Probes are used at 50 ng/ml. Total RNA (2 μg-10 μg) is denatured using Glyoxal load dye (Ambion) and resolved on 1.2% agarose gel in MOPS buffer. The gel is soaked in 1×TBE for 20 min and transferred to a Hybond-N+ membrane (GE Healthcare) for 1 h (15 V) using a semi-dry blotting system (Bio-Rad). Membranes are dried and UV-crosslinked (at 265 nm) 1× at 120,000 μJ cm-2. Pre-hybridization is done at 68° C. for 1 h and DIG-labelled in-vitro transcribed RNA probes are hybridized overnight. The membranes are washed three times in 2×SSC, 0.1% SDS at 68° C. for 30 min, followed by three 30 min washes in 0.2×SSC, 0.1% SDS at 68° C. The immunodetection is performed with anti-DIG directly-conjugated with alkaline phosphatase antibodies. Immunoreactive bands are visualized using chemiluminescent alkaline phosphatase substrate (CDP star reagent) and an image detection and quantification system (LAS-4000 detection system).

Example 3: Preparation of Circular RNA and In Vitro Translation

This example demonstrates gene expression and detection of the gene product from a circular RNA.

Figure 4:
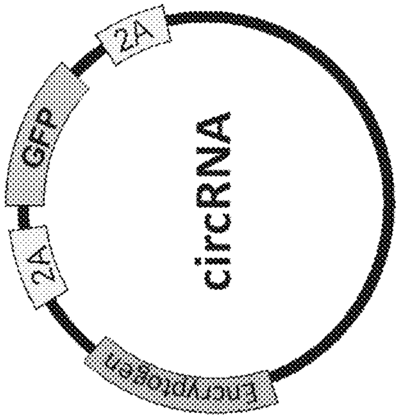
FIG. 4 shows design of an exemplary circular RNA that comprises a start-codon, an ORF coding for GFP, a stagger element (2A), and an encryptogen.

In this Example, the circular RNA is designed with a start-codon (SEQ ID NO:1), a GFP ORF (SEQ ID NO:2), stagger element(s) (SEQ ID NOS 3, 132, and 133), human-derived encryptogen(s) (SEQ ID NOS 4 and 134), and with or without an IRES (SEQ ID NO:5), see FIG. 4. In this Example, the circular RNA is generated either in vitro or in cells as described in Example 1 and 2.

The circular RNA is incubated for 5 h or overnight in rabbit reticulocyte lysate (Promega, Fitchburg, WI, USA) at 30° C. The final composition of the reaction mixture includes 70% rabbit reticulocyte lysate, 10 μM methionine and leucine, 20 μM amino acids other than methionine and leucine, and 0.8 U/μL RNase inhibitor (Toyobo, Osaka, Japan). Aliquots are taken from the mixture and separated on 10-20% gradient polyacrylamide/sodium dodecyl sulfate (SDS) gels (Atto, Tokyo, Japan). The supernatant is removed and the pellet is dissolved in 2×SDS sample buffer (0.125 M Tris-HCl, pH 6.8, 4% SDS, 30% glycerol, 5% 2-mercaptoethanol, 0.01% bromophenol blue) at 70° C. for 15 min. The hemoglobin protein is removed during this process whereas proteins other than hemoglobin are concentrated.

After centrifugation at 1,400×g for 5 min, the supernatant is analyzed on 10-20% gradient polyacrylamide/SDS gels. A commercially available standard (BioRad) is used as the size marker. After being electrotransferred to a polyvinylidene fluoride (PVDF) membrane (Millipore) using a semi-dry method, the blot is visualized using a chemiluminescent kit (Rockland).

It is expected that the GFP protein is visualized in cell lysates and is detected in higher quantities in circular RNA than linear RNA, as a result of rolling circle translation.

Example 4: Stoichiometric Protein Expression from Circular RNA

This example demonstrates the ability of circular RNA to stoichiometrically express of proteins.

Figure 5A:
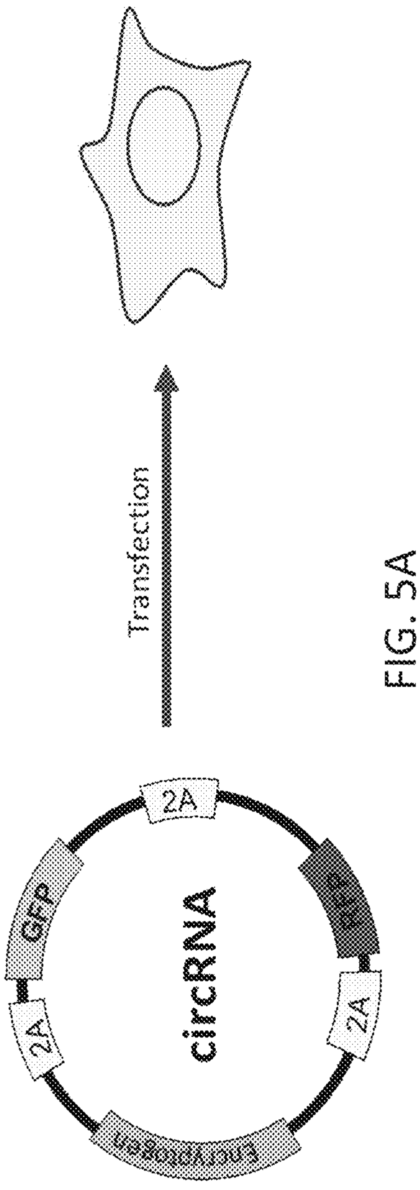
FIGS. 5A and 5B are schematics demonstrating in vivo stoichiometric protein expression of two different circular RNAs.
Figure 5B:
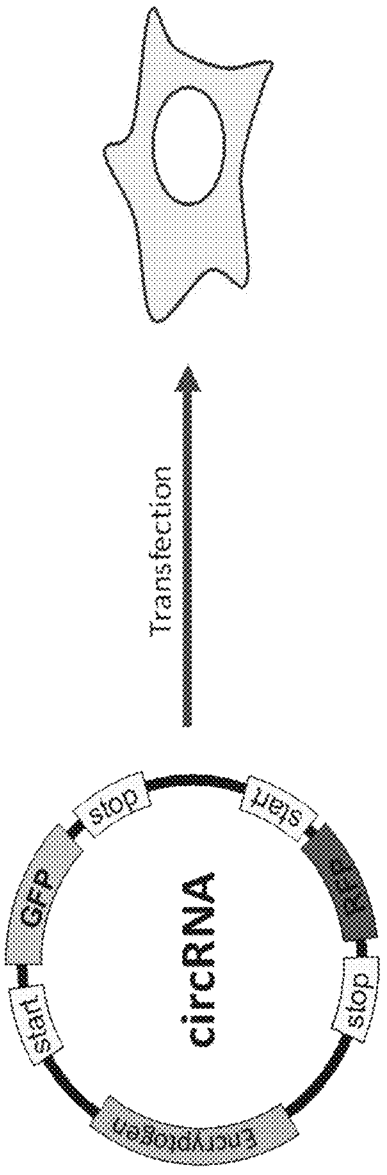

In this Example, one circular RNA is designed to include encryptogens (SEQ ID NOS 4 and 134) and an ORF encoding GFP (SEQ ID NO: 2) and an ORF encoding RFP (SEQ ID NO:8) with stagger elements (SEQ ID NOS 3, 132, and 133) flanking the GFP and RFP ORFs, see FIG. 5. Another circular RNA is designed similarly, however instead of flanking 2A sequences it will have a Stop and Start codon in between the GFP and RFP ORFs. The circular RNAs are generated either in vitro or in cells as described in Example 1 and 2.

The circular RNAs are incubated for 5 h or overnight in rabbit reticulocyte lysate (Promega, Fitchburg, WI, USA) at 30° C. The final composition of the reaction mixture includes 70% rabbit reticulocyte lysate, 10 μM methionine and leucine, 20 μM amino acids other than methionine and leucine, and 0.8 U/μL RNase inhibitor (Toyobo, Osaka, Japan). Aliquots are taken from the mixture and separated on 10-20% gradient polyacrylamide/sodium dodecyl sulfate (SDS) gels (Atto, Tokyo, Japan). The supernatant is removed and the pellet is dissolved in 2×SDS sample buffer (0.125 M Tris-HCl, pH 6.8, 4% SDS, 30% glycerol, 5% 2-mercaptoethanol, 0.01% bromophenol blue) at 70° C. for 15 min. The hemoglobin protein is removed during this process whereas proteins other than hemoglobin are concentrated.

After centrifugation at 1,400×g for 5 min, the supernatant is analyzed on 10-20% gradient polyacrylamide/SDS gels. A commercially available standard (BioRad) is used as the size marker. After being electrotransferred to a polyvinylidene fluoride (PVDF) membrane (Millipore) using a semi-dry method, the blot is visualized using a chemiluminescent kit (Rockland).

It is expected that circular RNA with GFP and RFP ORFs not separated by a Stop and start codon will have equal amounts of either protein, while cells treated with the circular RNA including the start and stop codon in between the ORFs will have different amounts of either protein.

Example 5: Non-Immunogenicity in Cell Culture

This example demonstrates in vivo assessment of immunogenicity of the circular RNA after cell infection.

Figure 6:
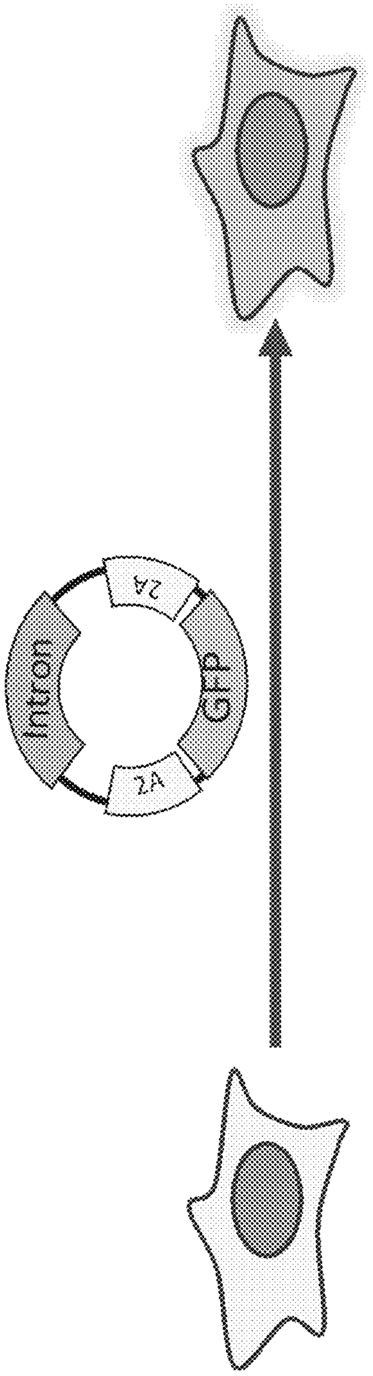
FIG. 6 shows a schematic of a control circular RNA that has an intron and expresses GFP.

In this Example, circular RNAs designed to include an encryptogen e.g. a ZKSCAN1 intron and a GFP ORF. In addition, control circular RNA is designed to include a GFP ORF with and without introns, see FIG. 6. The circular RNA is generated either in vitro or in cells as described in Example 1 and 2. HeLa cells are transfected with 500 ng of circular RNAs.

Transfection of the circular RNA include the following conditions: (1) naked circular RNA in cell culture media (Lingor et al 2004); (2) electroporation (Muller et al 2015); (3) cationic lipids (SNALP, Vaxfectin) (Chesnoy and Huang, 2000); (3) cationic polymers (PEI, polybrene, DEAE-dextran) (Turbofect); (4) virus-like particles (L1 from HPV, VP1 from polyomavirus) (Tonges et al 2006); (5) exosomes (Exo-Fect from SBI); (6) nanostructured calcium phosphate (nanoCaP)(Olton et al 2006); (6) peptide transduction domains (TAT, polyR, SP, pVEC, SynB1, etc) (Zhang et al 2009); (7) vesicles (VSV-G, TAMEL) (Liu et al 2017); (8) cell squeezing; (SQZ Biotechnologies) (9) nanoparticles (Neuhaus et al 2016); and/or (10) magnetofection (Mair et al 2009). Transfection methods are performed in cell culture media (DMEM 10% FBS) and cells are subsequently cultured for 24-48 hrs.

After 2-48 hrs post-transfection, media is removed and relative expression of the indicated RNA and transfected RNA is measured by qRT-PCR.

For qRT-PCR analysis, total RNA is isolated from cells using a phenol based RNA isolation solution (TRIzol) and an RNA isolation kit (QIAGEN) following the manufacturer's instructions. qRT-PCR analysis is performed in triplicate using a PCR master mix (Brilliant II SYBR Green qRT-PCR Master Mix) and a PCR cycler (LightCycler 480). mRNA levels for well-known innate immunity regulators such as RIG-I, MDA5, OAS, OASL, and PKR are quantified and normalized to actin, GAPDH, or HPRT values. Relative expression of indicated RNA genes for circular RNA transfection are normalized by level of transfected RNA and compared to the expression level of cells with circular RNA transfection that does not contain encryptogen(s).

In addition to qRT-PCR analysis, western blot analysis and immuno-histochemistry are used, as described above in Example 4, to assess GFP expression efficiency.

It is expected that GFP positive cells containing encryptogen(s) will show an attenuated immunogenicity response.

In addition, (1) primary murine dendritic cells; (2) Human embryonic kidney 293 cells stabile expressing TLR-7, 8 or 9 (InvivoGen); (3) monocyte derived dendritic cells (AllCells) or (4) Raw 264.7 cells are transfected with a DNA plasmid including ZKSCAN1 or td introns that produce a circular RNA encoding GFP as described above. After 6-48 hrs post-transfection, cell culture supernatant is collected and cytokine expression is measured using ELISA. When cell culture supernatant is collected, cells are collected for Northern blot, gene expression array and FACS analysis.

For ELISA, ELISA kits for interferon-β (IFN-β), chemokine (C-C motif) ligand 5 (CCL5), IL-12 (BD Biosciences), IFN-α, TNF-α and IL-8 (Biosource International) are used. ELISAs are performed according to the manufacturers' recommendations. Expression of indicated cytokines for circular RNA transfected cells are compared to the level of control RNA transfected cells. It is expected that cells transfected with circular RNA with an encryptogen will have reduced cytokine expression compared to control transfected cells.

For Northern blot analysis. Samples are processed and analyzed as previously described. Probes are derived from plasmids and are specific for the coding regions of human IFN-alpha 13, IFN-beta (Open Biosystems), TNF-alpha, or GAPDH (ATCC). It is expected that cells transfected with circular RNA with an encryptogen will have reduced cytokine expression compared to control transfected cells.

For the gene expression array, RNA is isolated using a phenol based solution (TRIzol) and/or an RNA isolation kit (RNeasy Qiagen). RNA is amplified and analyzed (e.g. Illumina Human HT12v4 chip in an Illumina BeadStation 500GX). Levels in mock control treated cells are used as the baseline for the calculation of fold increase. It is expected that cells transfected with circular RNA with an encryptogen will have reduced cytokine expression compared to control transfected cells.

For FACS analysis, cells are stained with a directly conjugated antibodies against CD83 (Research Diagnostics Inc), HLA-DR, CD80 or CD86 and analyzed on a flow cytometer. It is expected that cells transfected with circular RNA with an encryptogen will show reduced expression of these markers compared to control transfected cells.

Example 6: Riboswitches for Selective Expression

This example demonstrates the ability to control protein expression from circular RNA in vivo.

Figure 7:
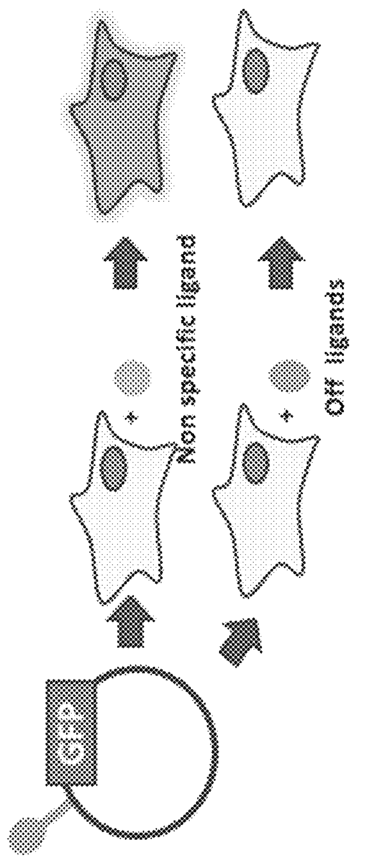
FIG. 7 shows a schematic of an exemplary circular RNA that has a synthetic riboswitch (in red) regulating the expression of the GFP from the circular RNA in the presence or absence of ligands to the riboswitch.

For this Example, circular RNAs designed to include encryptogen(s) (SEQ ID NOS 4 and 134), a synthetic riboswitch (SEQ ID NO: 9) regulating the expression of the ORF encoding GFP (SEQ ID NO:2) with stagger elements (2A sequences) (SEQ ID NOS 3, 132, and 133) flanking the GFP ORF, see FIG. 7. The circular RNA is generated either in vitro or in cells as described in Example 1 and 2.

Theophylline induces activation of the riboswitch, resulting in an off-switch of gene expression (as described by Auslander et al 2010). It is expected that the riboswitch controls GFP expression from the circular RNA. In the presence of theophylline, no GFP expression is expected to be observed.

HeLa cells are transfected with 500 ng of the described circular RNA encoding GFP under the control of the theophylline dependent synthetic riboswitch (SEQ ID NO:9) to assess selective expression. Transfection methods are described in Example 5.

After 24 hr of culture at 37° C. and 5% CO2, cells are treated with and without theophylline with concentrations ranging from 1 nM-3 mM. After 24 hrs of continuous culture, cells are fixed in 4% paraformaldehyde for 15 minutes at room temperature, blocked and permeabilized for 45 minutes with 10% FBS in PBS with 0.2% detergent. Samples are then incubated with primary antibodies against GFP (Invitrogen) and secondary antibodies conjugated with Alexa 488 and DAPI (Invitrogen) in PBS with 10% FBS and 0.1% detergent for 2 hrs at room temperature or overnight at 4° C. Cells are then washed with PBS and subsequently analyzed using a fluorescent microscope for GFP expression.

Example 7: In Vivo Expression

This example demonstrates the ability to express protein from a circular RNA in vivo.

Figure 8:
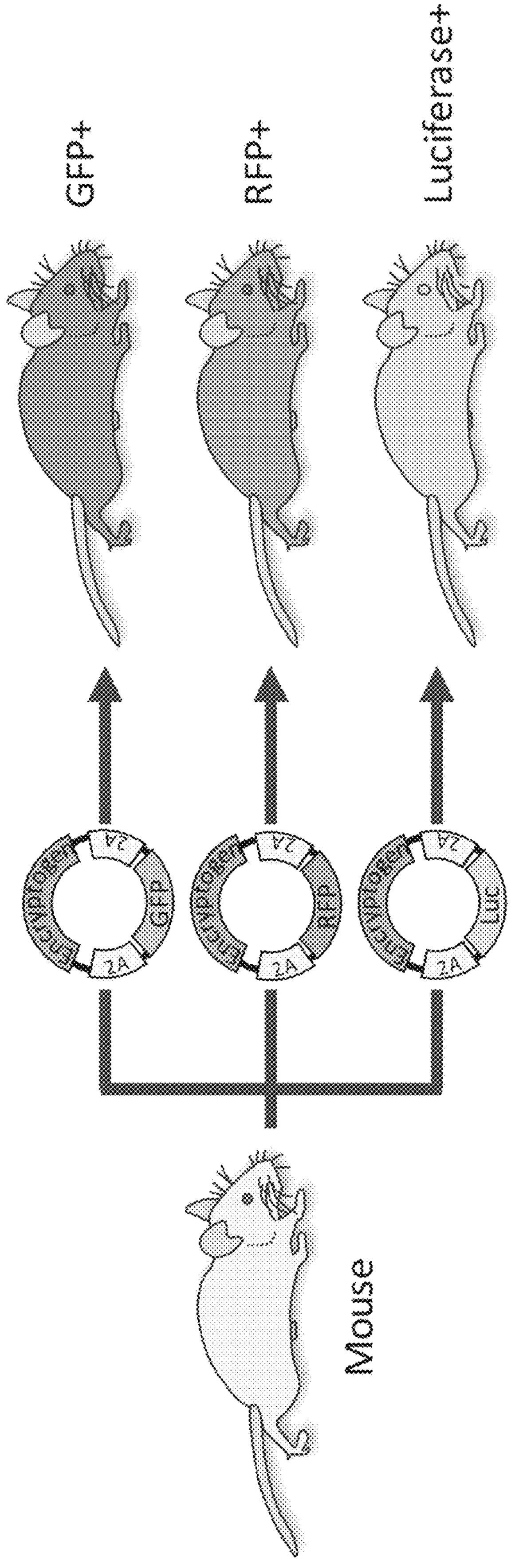
FIG. 8 is a schematic demonstrating in vivo protein expression in mouse model from exemplary circular RNAs.

For this Example, circular RNAs designed to include including encryptogen(s) (SEQ ID NOS 4 and 134) and an ORF encoding GFP (SEQ ID NO:2) or RFP (SEQ ID NO:8) or Luciferase (SEQ ID NO:10) with stagger elements (SEQ ID NOS 3, 132, and 133) flanking the GFP, RFP or Luciferase ORF, see FIG. 8. The circular RNA is generated either in vitro or in cells as described in Example 1 and 2.

Male BALB/c mice 6-8 weeks old receive 300 mg/kg (6 mg) circular RNA (50 uL vol) with GFP, RFP, or luciferase ORFs, as described herein, or linear RNA as a control, via intradermal (ID), intramuscular (IM), oral (PO), intraperitoneal (IP), or intravenous (IV) administration. Animals receive a single dose or three injections (day 1, day 3, day 5).

Blood, heart, lung, spleen, kidney, liver, and skin injection sites are collected from non-dosed control mice and at 2, 4, 8, 24, 48, 72, 96 120, 168, and 264 hr post-dosing (n=4 mice/time point). Blood samples are collected from jugular venipuncture at study termination.

Circular RNA quantification for both serum and tissues is performed using quantification of branched DNA (bDNA) (Panomics/Affymetrix). A standard curve on each plate of known amounts of RNA (added to untreated tissue samples) is used to quantitate the RNA in treated tissues. The calculated amount in picograms (pg) is normalized to the amount of weighed tissue in the lysate applied to the plate. Protein expression (RFP or GFP) is evaluated by FACS or western blot in each tissue as described in a previous Example.

A separate group of mice dosed with luciferase circular RNA are injected with 3 mg luciferin at 6, 24, 48, 72, and 96 hr post-dosing and the animals are imaged on an in vivo imaging system (IVIS Spectrum, PerkinElmer). At 6 hr post-dosing, three animals are sacrificed and dissected, and the muscle, skin, draining lymph nodes, liver, and spleen are imaged ex vivo.

It is expected that mice express GFP, RFP, or luciferase in treated tissues.

Example 8: In Vivo Biodistribution

This example demonstrates the ability to control and measure biodistribution of circular RNA in vivo.

Figure 9:
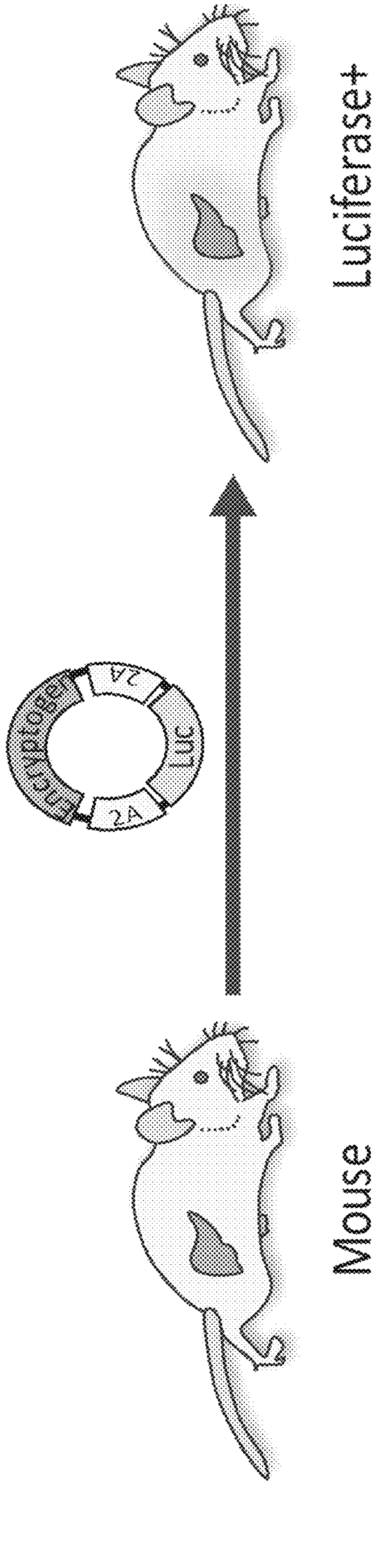
FIG. 9 is a schematic demonstrating in vivo biodistribution of an exemplary circular RNA in a mouse model.

In this Example, mice are treated with the circular RNA encoding luciferase as described in Example 9. In short, circular RNAs designed to include including encryptogen(s) (SEQ ID NOS 4 and 134) and an ORF encoding Luciferase (SEQ ID NO:10) with stagger elements (SEQ ID NO 3, 132, and 133) flanking the Luciferase ORF, see FIG. 9. The circular RNA is generated either in vitro or in cells as described in Example 1 and 2.

Mice are dosed with luciferase circular RNA by injected with 3 mg luciferin, at 6, 24, 48, 72, and 96 hr post-dosing and the animals are imaged on an in vivo imaging system (IVIS Spectrum, PerkinElmer). At 6 hr post-dosing, three animals are sacrificed and dissected, and the muscle, skin, draining lymph nodes, liver, and spleen are imaged ex vivo Circular RNA quantification for both serum and tissues is performed by using quantification of branched DNA (bDNA) (Panomics/Affymetrix). A standard curve on each plate of known amounts of RNA (added to untreated tissue samples) is used to quantitate the RNA in treated tissues. The calculated amount in picograms (pg) is normalized to the amount of weighed tissue in the lysate applied to the plate.

A separate group of male BALB/c mice 6-8 weeks old are dosed with luciferase circular RNA via IM or ID administration at four dose levels: 10, 2, 0.4, and 0.08 mg (n=6 per group). At 6, 24, 48, 72, and 96 hr post-dosing, animals are injected with 3 mg luciferin and imaged on an in vivo imaging system (IVIS Spectrum, PerkinElmer). At 6 hr post-dosing, three animals are sacrificed and dissected, and the muscle, skin, draining lymph nodes, liver, and spleen are imaged ex vivo. Tissues from the mice are also assessed for luciferase expression as described in Example 9 and tissue distribution of this expression is analyzed.

It is expected that mice show expression of luciferase in the treated tissues.

Example 9: Non-Immunogenicity In Vivo

This example demonstrates in vivo assessment of immunogenicity of the circular RNA after cell infection.

Figure 10:
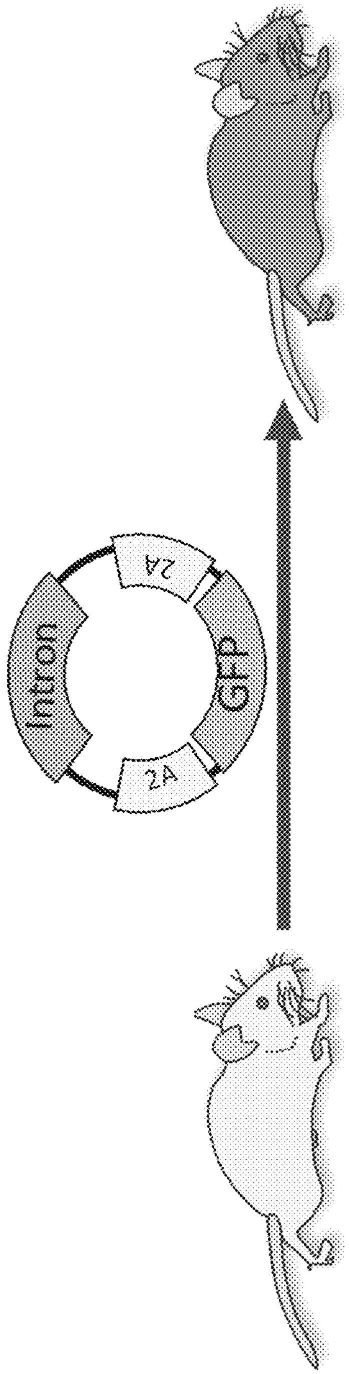
FIG. 10 is a schematic demonstrating in vivo protein expression in mouse model from an exemplary circular RNA that harbors an encryptogen (intron).

This Example describes quantification and comparison of the immune response after administrations of circular RNA harboring an encryptogen, see FIG. 10. In an embodiment, any of the circular RNA with an encryptogen, will have a reduced (e.g., reduced compared to administration of control RNA) immunogenic response following one or more administrations of the circular RNA compared to control.

A measure of immunogenicity for circular RNA are the cytokine levels in serum.

In this Example, cytokine serum levels are examined after one or more administrations of circular RNA. Circular RNA from any one of the previous Examples is administered via intradermal (ID), intramuscular (IM), oral (PO), intraperitoneal (IP), or intravenous (IV) into BALB/c mice 6-8 weeks old. Serum is drawn from the different cohorts: mice injected systemically and/or locally with injection(s) of circular RNA harboring an encryptogen and circular RNA without an encryptogen.

Collected serum samples are diluted 1-10× in PBS and analyzed for mouse IFN-α by enzyme-linked immunosorbent assay (PBL Biomedical Labs, Piscataway, NJ) and TNF-α (R&D, Minneapolis, MN).

In addition to cytokine levels in serum, expression of inflammatory markers is another measure of immunogenicity. In this Example, spleen tissue from mice treated with vehicle (no circular RNA), linear RNA, or circular RNA will be harvested 1, 4, and 24 hours post administration. Samples will be analyzed using the following techniques qRT-PCR analysis, Northern blot or FACS analysis.

For qRT-PCR analysis mRNA levels for RIG-I, MDA5, OAS, OASL, TNF-alpha and PKR are quantified as described previously.

For Northern blot analysis. Samples are processed and analyzed for IFN-alpha 13, IFN-beta (Open Biosystems), TNF-alpha, or GAPDH (ATCC) as described above.

For FACS analysis, cells are stained with a directly conjugated antibodies against CD83 (Research Diagnostics Inc), HLA-DR, CD80 or CD86 and analyzed on a flow cytometer.

In an embodiment, circular RNA with an encryptogen will have decreased cytokine levels (as measured by ELISA, Northern blot, FACS and/or qRT-PCR) after one or multiple administrations, as compared control RNA.

Example 10: Circular RNA Includes at Least One Double-Stranded RNA Segment

This example demonstrates that circular RNA includes at least one double-stranded RNA segment.

Figure 11:
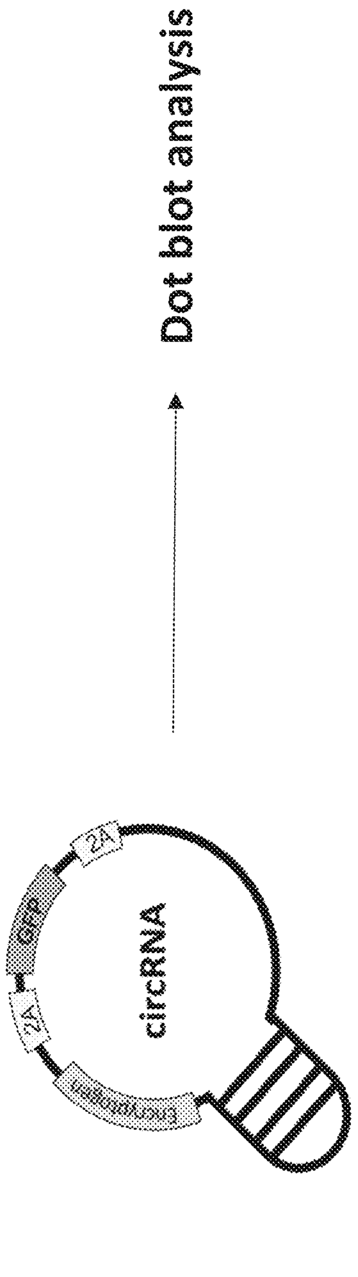
FIG. 11 shows a schematic of an exemplary circular RNA that has one double-stranded RNA segment, which can be subject to dot blot analysis for its structural information.

In this Example, circular RNA is synthesized through one of the methods described previously, to include a GFP ORF and an IRES, see FIG. 11. Dot blot assays with J2 and K1 monoclonal antibodies will be utilized to measure double stranded RNA structures of at least 40 bp in length. Circular RNA (200 ng) is blotted onto a nylon membrane (super charged Nytran), dried, blocked with 5% non-fat dried milk in TBS-T buffer (50 mM Tris-HCl, 150 mM NaCl, 0.05% Tween-20, pH 7.4), and incubated with dsRNA-specific mAb J2 or K1 (English & Scientific Consulting) for 60 min. Membranes are washed six times with TBS-T then treated with HRP-conjugated donkey anti-mouse Ig (Jackson Immunology), then washed six times and dots are visualized with an enhanced chemiluminescence western blot detection reagent (Amersham).

It is expected that a circular RNA creates an internal quasi-double stranded RNA segment.

Example 11: Circular RNA Includes a Quasi-Double-Stranded Structure

This example demonstrates that circular RNA includes a quasi-double-stranded structure.

In this Example, circular RNA is synthesized through one of the methods described previously, with and without addition of the expression of HDVmin (Griffin et al 2014).

Figure 12:
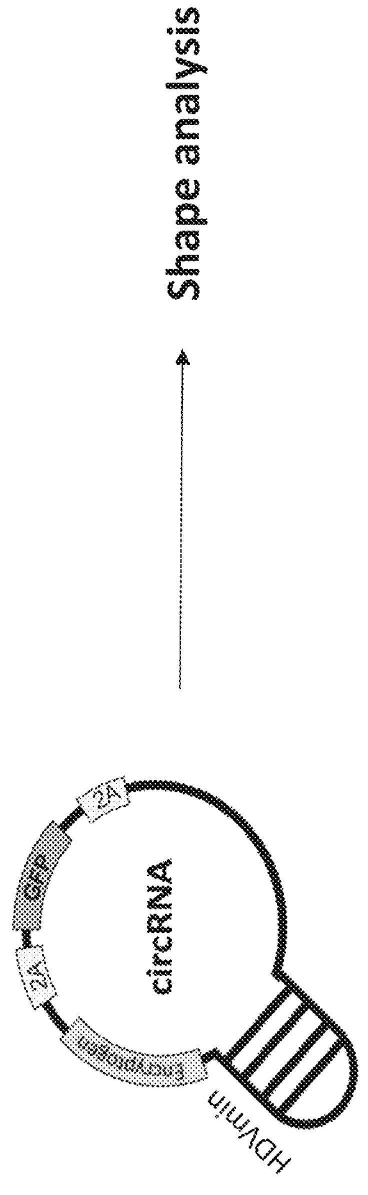
FIG. 12 shows a schematic of an exemplary circular RNA that has a quasi-helical structure (HDVmin), which can be subject to SHAPE analysis for its structural information.

This RNA sequence forms a quasi-helical structure, see FIG. 12, and is used as a positive control (as shown by Griffin et al 2014).

To test if circular RNA structure includes a functional quasi-double-stranded structure we will determine the secondary structure using selective 2'OH acylation analyzed by primer extension (SHAPE). SHAPE assesses local backbone flexibility in RNA at single-nucleotide resolution. The reactivity of base positions to the SHAPE electrophile is related to secondary structure: base-paired positions are weakly reactive, while unpaired positions are more highly reactive.

SHAPE is performed on circular RNA, HDVmin, and linear RNA containing. SHAPE is performed with N-methylisatoic anhydride (NMIA) or benzoyl cyanide (BzCN) essentially as reported by Wilkinson et al 2006 and Griffin 2014 et al respectively. In brief for SHAPE with BzCN, 1 ul of 800 mM BzCN in dimethyl sulfoxide (DMSO) is added to a 20 ul reaction mixture containing 3 to 6 pmol of RNA in 160 mM Tris, pH 8.0, 1 U/l RNAse inhibitor (e.g. SuperaseIn RNase inhibitor) and incubated for 1 min at 37° C. Control reaction mixtures include 1 ul DMSO without BzCN. After incubation with BzCN, RNAs is extracted with phenol chloroform, and purified (e.g using a RNA Clean & Concentrator-5 kit) as directed by the manufacturer, and resuspended in 6 ul 10 mM Tris, pH 8.0. A one-dye system is used to detect BzCN adducts. RNAs are annealed with a primer labeled with 6-carboxyfluorescein (6-FAM). Primer extension is performed using a reverse transcriptase (SuperScript III-Invitrogen) according to the manufacturer's recommendations with the following modifications to the incubation conditions: 5 min at 42° C., 30 min at 55° C., 25 min at 65° C., and 15 min at 75° C. Two sequencing ladders are generated using either 0.5 mM ddATP or 0.5 mM ddCTP in the primer extension reaction. Primer extension products are precipitated with ethanol, washed to remove excess salt, and resolved by capillary electrophoresis along with a commercial size standard (e.g. Liz size standard Genewiz Fragment Analysis Service).

Raw electropherograms are analyzed using a primary fragment analysis tool (e.g. PeakScanner Applied Bio-systems). The peaks at each position in the electropherograms are then integrated. For each RNA analyzed, y axis scaling to correct for loading error is performed so that the background for each primer extension reaction is normalized to that of a negative-control reaction performed on RNA that is not treated with BzCN. A signal decay correction is applied to the data for each reaction. The peaks are aligned to a ladder created from two sequencing reactions. At each position, the peak area of the negative control is subtracted from the peak area in BzCN-treated samples; these values are then converted to normalized SHAPE reactivities by dividing the subtracted peak areas by the average of the highest 2% to 10% of the subtracted peak areas.

In addition to SHAPE analysis we will perform NMR (Marchanka et al 2015); Hydroxyl radical probing (Ding et al 2012); or a combination of DMS and CMTC and Kethoxal (Tijerina et al 2007 and Ziehler et al 2001).

It is expected that a circular RNA will have a quasi-double-stranded structure.

Example 12: Circular RNA Includes a Functional Quasi-Helical Structure

This example demonstrates that circular RNA includes a functional quasi-helical structure.

Figure 13:
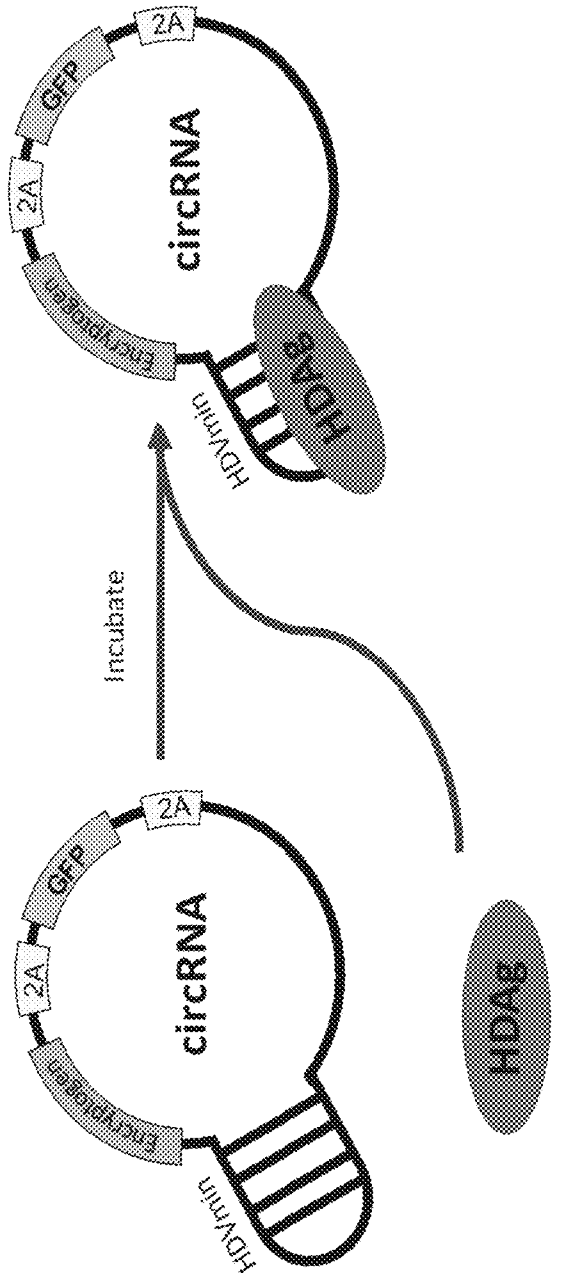
FIG. 13 shows a schematic of an exemplary circular RNA that has a functional quasi-helical structure (HDVmin), which demonstrates HDAg binding activity.

In this Example, circular RNA is synthesized through one of the methods described previously, with the addition of the expression of 395L (Defenbaugh et al 2009). This RNA sequence forms a quasi-helical structure (as shown above, by RNA secondary structure folding algorithm mfold and Defenbaugh et al 2009), FIG. 13. This structure is essential for complex formation with hepatitis D antigen (HDAg).

Therefore, to test if circular RNA structure includes a functional quasi-structure we will incubate circular RNA and linear RNA with HDAg-160 or HDAg-195 and analyze binding using EMSA assays. Binding reactions are done in 25 ul including 10 mM Tris-HCl (pH 7.0), 25 mM KCl, 10 mM NaCl, 0.1 g/l bovine serum albumin (New England Biolabs), 5% glycerol, 0.5 mM DTT, 0.2 U/l RNase inhibitor (Applied Biosystems), and 1 mM phenylmethylsulfonyl fluoride solution. circular RNA is incubated with HDAg protein (obtained as described by Defenbaugh et al 2009) at concentrations ranging from 0-110 nM. Reaction mixtures are assembled on ice, incubated at 37° C. for 1 h, and electrophoresed on 6% native polyacrylamide gels in 0.5 Tris-borate-EDTA at 240 V for 2.5 h. Levels of free and bound RNA are determined using nucleic acid staining (e.g. gelred). Binding will be calculated as the intensity of unbound RNA relative to the intensity of the entire lane minus the background.

It is expected that a circular RNA will have a functional quasi-helical structure.

Example 13: Self-Transcription/Replication

Figure 14:
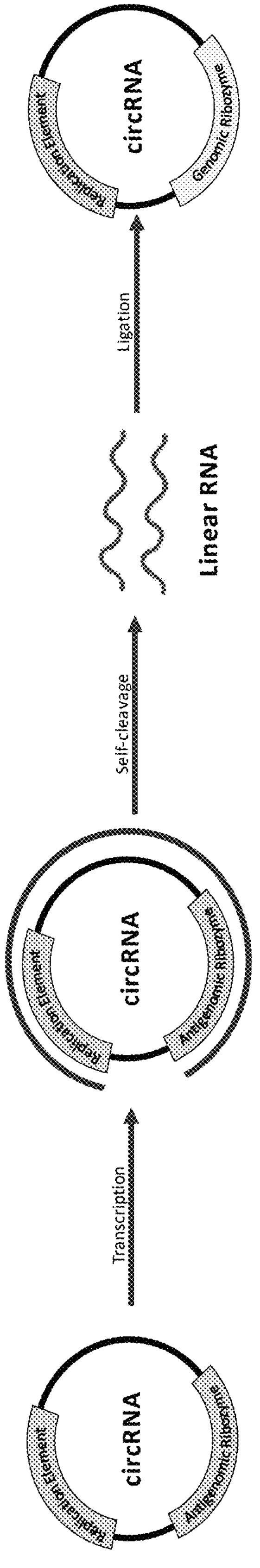
FIG. 14 is a schematic demonstrating transcription, self-cleavage, and ligation of an exemplary self-replicable circular RNA.

In this Example, circular RNA is synthesized through one of the methods described previously, with the addition of the expression of the HDV replication domain(s) (as described by Beeharry et al 2014), the antigenomic replication competent ribozyme and a nuclear localization signal. These RNA sequences allow for circular RNA to be located in the nucleus where the host RNA polymerase will bind and transcribe the RNA. Then this RNA is self-cleaved using the ribozyme. RNA is then ligated and self-replicated again, see FIG. 14.

Circular RNA (1-5 microgram) will be transfected into HeLa cells using techniques described above. HeLa cells are grown at 37° C. and 5% $CO_2$ in Dulbecco's modified Eagle's medium (DMEM) with high glucose (Life Technologies), supplemented with penicillin-streptomycin and 10% fetal bovine serum. After transfection HeLa cells are cultured for an additional 4-72 hr, then total RNA from the transfected cells is isolated using a phenol-based RNA isolation reagent (Life Technologies) as per the manufacturer's instructions between 1 hour and 20 days after transfection and total amount of circular RNA encoding the HDV domains will be determined and compared to control circular RNA using qPCR as described herein.

Example 14: Circular RNA Stability/Half-Life

Figure 15:
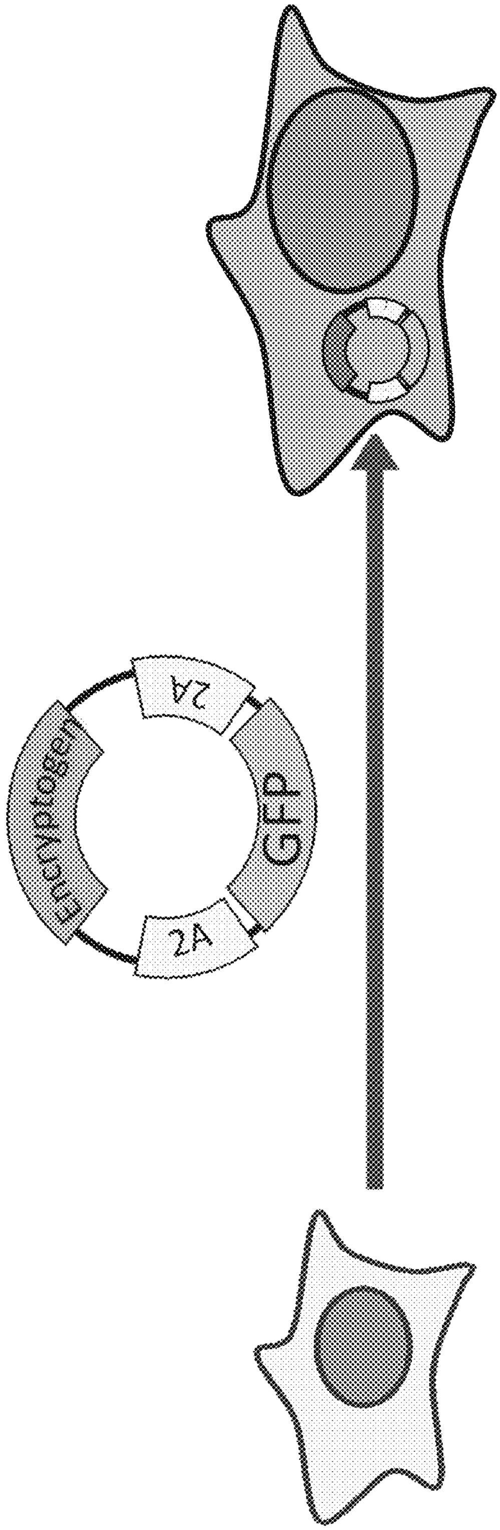
FIG. 15 shows a schematic of an exemplary circular RNA that is expressed in vivo and has improved in vivo stability.

In this Example, circular RNA is synthesized through one of the methods described previously. A circular RNA is designed to include encryptogens (SEQ ID NOS 4 and 134) and an ORF encoding GFP (SEQ ID NO: 2) with stagger elements (SEQ ID NOS 3, 132, and 133) flanking the GFP ORF, see FIG. 15.

Human fibroblast (e.g. IMR-90) are grown to confluency in Dulbecco's modified Eagle's medium (DMEM; Invitrogen) supplemented with 10% fetal bovine serum (FBS; Invitrogen) at 37° C. under 5% CO2 on tissue culture treated plates. When fibroblast reach confluency, they stop dividing due to contact inhibition (Leontieva et al 2014). Lipid transfection reagent (2 μL; Invitrogen) is added to a mixture of 1 μg circular RNA or linear RNA (described above) and 145 μL reduced serum medium (Opti-MEM I solution) in one well of a 12-well tissue culture treated plate. After incubation at room temperature for 15 min, ~1x10^5 cells suspended in DMEM with 10% FBS are added to the circular RNA solution (described above).

Cells will be cultured and then collected at day 1, 2, 3, 4, 5, 10, 20 and 30 after circular RNA transfection. Cells will be isolated for q-rt-PCR and another subset for FACS analysis. To measure GFP circular RNA and mRNA levels, qPCR reverse transcription using random hexamers is performed, as described in Example 2. Cells will be analyzed with FACS using GFP antibodies as described herein.

It is expected that circular RNA will persist in cells for at least several days and that they retain functional expression of GFP protein.

Example 15: Circular RNA Preservation in Daughter Cells

Figure 16:
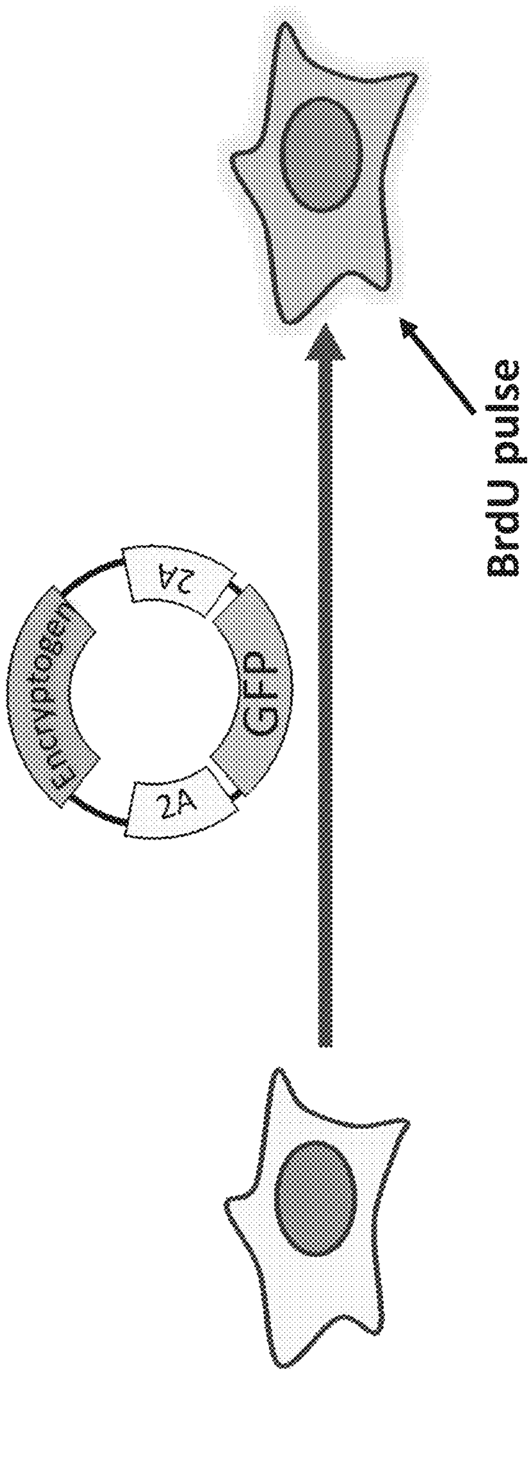
FIG. 16 shows a schematic of an exemplary circular RNA that is preserved during mitosis and persists in daughter cells. BrdU pulse as shown is used for labeling the divided cells.

In this Example, circular RNA is synthesized through one of the methods described previously. A circular RNA is designed to include encryptogens (SEQ ID NO 4 and 134) and an ORF encoding GFP (SEQ ID NO: 2) with stagger elements (SEQ ID NOS 3, 132, and 133) flanking the GFP ORF, see FIG. 16.

Human Fibroblasts (e.g. IMR-90) are grown in Dulbecco's modified Eagle's medium (DMEM; Invitrogen) supplemented with 10% fetal bovine serum (FBS; Invitrogen) at 37° C. under 5% CO2 on tissue culture treated plates. Cells are passaged regularly to maintain exponential growth. Lipid transfection reagent (2 μL; Invitrogen) is added to a mixture of 1 μg circular RNA or linear RNA (described above) and 145 μL reduced serum medium (Opti-MEM I solution) in one well of a 12-well tissue culture treated plate. After incubation at room temperature for 15 min, 1x10^5 HeLa cells suspended in DMEM with 10% FBS are added to the circular RNA solution (described above). After incubation for 24 h at 37° C. and 5% CO2, the cells are pulsed with BrdU (e.g. Sigma-Aldrich). BrdU, labeling duration is optimized for each cell type according to their specific population doubling time, e.g. IMR-90 human fibroblasts have a doubling time of 27 hrs and are pulsed for 8-9 hrs as described by Elabd et al 2013.

Cells will be collected at day 1, 2, 3, 4, 5 and 10 after BrdU pulse. A subset of the cells will be isolated q-rt-PCR and another subset for FACS analysis. To measure GFP circular RNA and mRNA levels, qPCR reverse transcription using random hexamers is performed, as described in Example 2. Cells will be analyzed with FACS using BrdU and GFP antibodies as described herein.

It is expected that circular RNA will persist in daughter cells and that daughter cells will express GFP protein.

Example 16: Circular RNA Circularization

This Example demonstrates in vitro production of circular RNA using splint ligation.

A non-naturally occurring circular RNA can be engineered to include one or more desirable properties and may be produced using recombinant DNA technology. As shown in the following Example, splint ligation circularized linear RNA.

CircRNA1 was designed to encode triple FLAG tagged EGF without stop codon (264 nts). It has a Kozak sequence (SEQ ID NO: 11) at the start codon for translation initiation. CirRNA2 has identical sequences with circular RNA1 except it has a termination element (triple stop codons) (273 nts, SEQ ID NO: 12). Circular RNA3 was designed to encode triple FLAG tagged EGF flanked by a stagger element (2A sequence, SEQ ID NO: 13), without a termination element (stop codon) (330 nts). CircRNA4 has identical sequences with circular RNA3 except it has a termination element (triple stop codon) (339 nts).

In this example, the circular RNA was generated as follows. DNA templates for in vitro transcription were amplified from gBlocks gene fragment with corresponding sequences (IDT) with T7 promoter-harboring forward primer and 2-O-methylated nucleotide with a reverse primer. Amplified DNA templates were gel-purified with a DNA gel purification kit (Qiagen). 250-500 ng of purified DNA template was subjected to in vitro transcription. Linear, 5'-mono phosphorylated in vitro transcripts were generated using T7 RNA polymerase from each DNA template having corresponding sequences in the presence of 7.5 mM GMP, 1.5 mM GTP, 7.5 mM UTP, 7.5 mM CTP and 7.5 mM ATP. Around 40 μg of linear RNA was generated in each reaction. After incubation, each reaction was treated with DNase to remove the DNA template. The in vitro transcribed RNA was precipitated with ethanol in the presence of 2.5M ammonium acetate to remove unincorporated monomers.

Transcribed linear RNA was circularized using T4 RNA ligase 2 on a 20 nt splint DNA oligomer (SEQ ID NO: 14) as template. Splint DNA was designed to anneal 10 nt of each 5' or 3'end of linear RNA. After annealing with the splint DNA (3 μM), 1 μM linear RNA was incubated with 0.5 U/μl T4 RNA ligase 2 at 37 C or 4 hr. Mixture without T4 RNA ligase 2 was used as the negative control.

Figure 17:
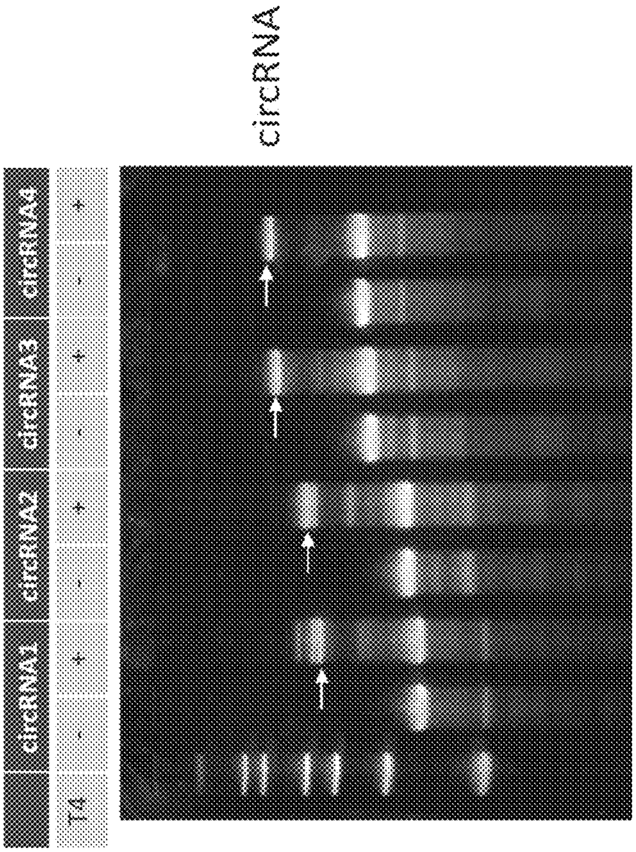
FIG. 17 is a denaturing PAGE gel image demonstrating in vitro production of different exemplary circular RNAs.

The circularization of linear RNA was monitored by separating RNA on 6% denaturing PAGE. Slower migrating RNA bands correspond with circular RNA rather than linear RNA on denaturing polyacrylamide gels because of their circular structure. As seen in FIG. 17, the addition of ligase (+lanes) to the RNA mixtures generated new bands to appear above the linear RNA bands that were present in the mixtures that lacked ligase (−lanes). Slower migrating bands appeared in all RNA mixtures indicating successful splint ligation (e.g., circularization) occurred with multiple constructs as compared to negative control.

Example 17: RNA Circularization Efficiency

This Example demonstrates circularization efficiencies of RNA splint ligation.

A non-naturally occurring circular RNA engineered to include one or more desirable properties may be produced using splint mediated circularization. As shown in the following Example, splint ligation circularized linear RNA with higher efficiency than controls.

CircRNA1, CircRNA2, CircRNA3, and CircRNA4 as described in Example 1 were also used here. CircRNA5 was designed to encode FLAG tagged EGF flanked by a 2A sequence and followed by FLAG tagged nano luciferase (873 nts, SEQ ID NO: 17). CircRNA6 has identical sequence with circular RNAS except it included a a termination element (triple stop codon) between the EGF and nano luciferase genes, and a termination element (triple stop codon) at the end of the nano luciferase sequence (762 nts, SEQ ID NO: 18).

In this Example, to measure circularization efficiency of RNA, 6 different sizes of linear RNA (264 nts, 273 nts, 330 nts, 339 nts, 873 nts and 762 nts) were generated and circularized as described in Example 1. The circular RNAs were resolved by 6% denaturing PAGE and corresponding RNA bands on the gel for linear or circular RNA were excised for purification. Excised RNA gel bands were crushed and RNA was eluted with 8000 of 300 mM NaCl overnight. Gel debris was removed by centrifuge filters and RNA was precipitated with ethanol in the presence of 0.3M sodium acetate.

Figure 18:
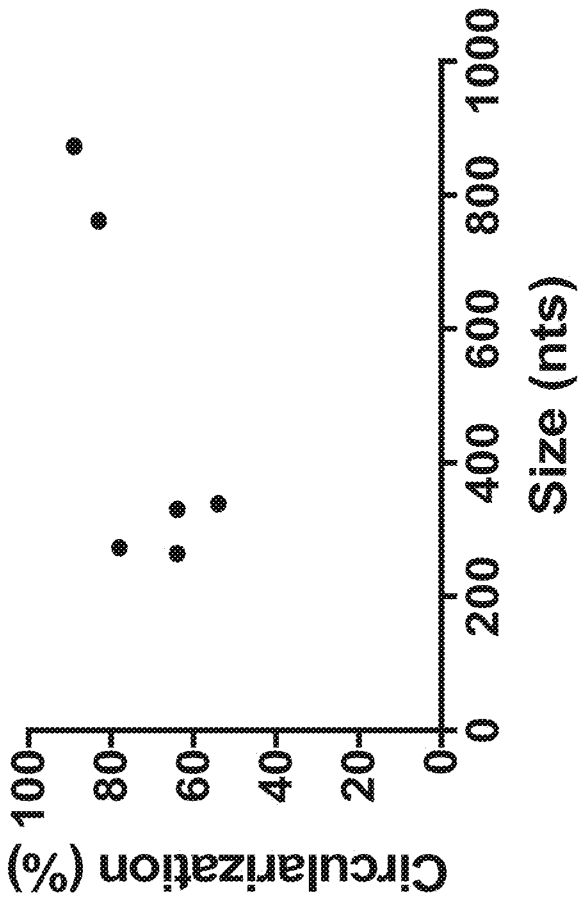
FIG. 18 is a graph summarizing circularization efficiencies of different exemplary circular RNAs.

Circularization efficiency was calculated as follows. The amount of eluted circular RNA was divided by the total eluted RNA amount (circular+linear RNA) and the result was depicted as a graph in FIG. 18.

Ligation of linear RNAs using T4 RNAse ligase 2 produced circular RNA at efficiency rates higher than control. Trending data indicated larger constructs circularized at higher rates.

Example 18: Circular RNA Lacking Degradation Susceptibility

This Example demonstrates circular RNA susceptibility to degradation by RNAse R compared to linear RNA.

Circular RNA is more resistant to exonuclease degradation than linear RNA due to the lack of 5' and 3' ends. As shown in the following Example, circular RNA was less susceptible to degradation than its linear RNA counterpart.

CircRNA5 was generated and circularized as described in Example 2 for use in the assay described herein.

To test circularization of CircRNA5, 20 ng/μl of linear or CircRNA5 was incubated with 2 U/μl of RNAse R, a 3' to 5' exoribonuclease that digests linear RNAs but does not digest lariat or circular RNA structures, at 37° C. for 30 min. After incubation, the reaction mixture was analyzed by 6% denaturing PAGE.

Figure 19:
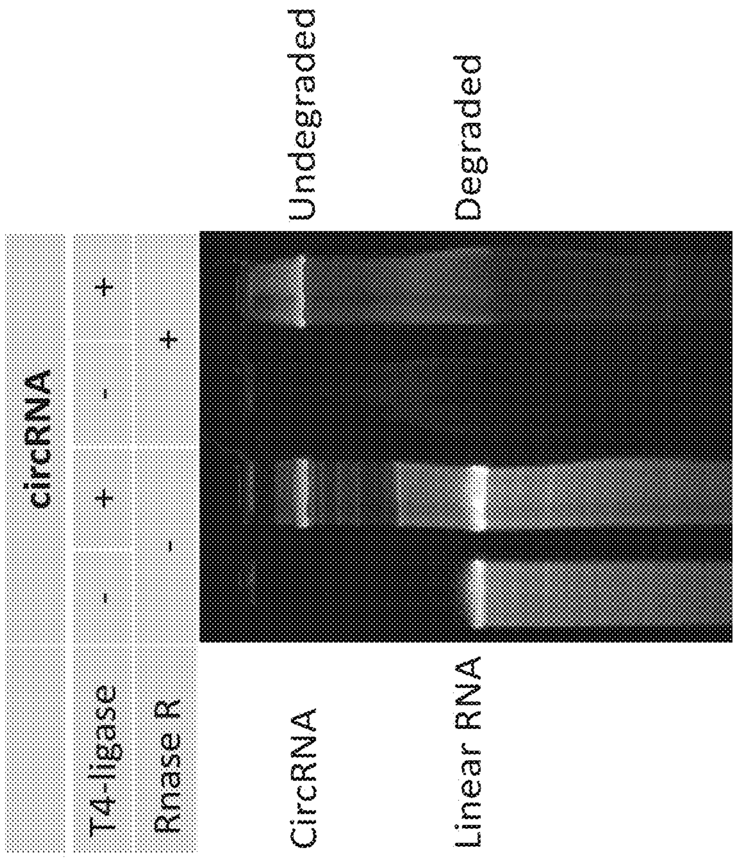
FIG. 19 is a denaturing PAGE gel image demonstrating decreased degradation susceptibility of an exemplary circular RNA as compared to its linear counterpart.

The linear RNA bands present in the lanes lacking exonuclease were absent in the CircRNA5 lane (see FIG. 19) indicating CircRNA5 showed higher resistance to exonuclease treatment as compared to linear RNA control.

Example 19: Isolation and Purification of Circular RNA

This Example demonstrates circular RNA purification.

In certain embodiments, circular RNAs, as described in the previous Examples, may be isolated and purified before expression of the encoded protein products. This Example describes isolation using UREA gel separation. As shown in the following Example, circular RNA was isolated and purified.

CircRNA1, CircRNA2, CircRNA3, CircRNA4, CircRNA5, and CircRNA6, as described in Example 2, were isolated as described herein.

Figure 20:
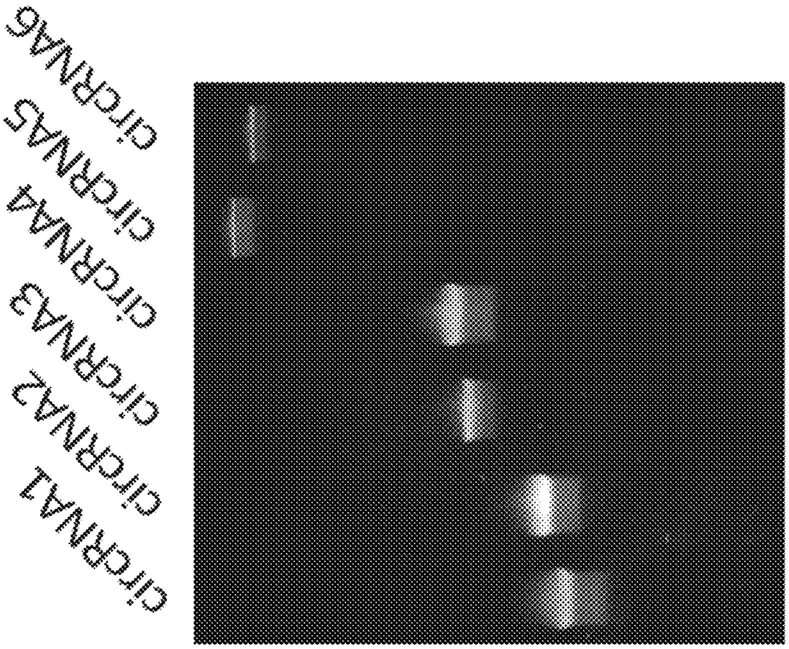
FIG. 20 is a denaturing PAGE gel image demonstrating exemplary circular RNA after an exemplary purification process.

In this Example, linear and circular RNA were generated as described. To purify the circular RNAs, ligation mixtures were resolved on 6% denaturing PAGE and RNA bands corresponding to each of the circular RNAs were excised. Excised RNA gel fragments were crushed and RNA was eluted with 800 μl of 300 mM NaCl overnight. Gel debris was removed by centrifuge filters and RNA was precipitated with ethanol in the presence of 0.3M sodium acetate. Eluted circular RNA was analyzed by 6% denaturing PAGE, see FIG. 20.

Single bands were visualized by PAGE for the circular RNAs having variable sizes.

Example 20: Detection of Protein Expression

This Example demonstrates in vitro protein expression from a circular RNA.

Protein expression is the process of generating a specific protein from mRNA. This process includes the transcription of DNA into messenger RNA (mRNA), followed by the translation of mRNA into polypeptide chains, which are ultimately folded into functional proteins and may be targeted to specific subcellular or extracellular locations.

As shown in the following Example, a protein was expressed in vitro from a circular RNA sequence.

Circular RNA was designed to encode triple FLAG tagged EGF flanked by a 2A sequence without a termination element (stop codon) (330 nts, SEQ ID NO: 19).

Linear or circular RNA was incubated for 5 hr in rabbit reticulocyte lysate at 30° C. in a volume of 25 μl. The final composition of the reaction mixture contained 70% rabbit reticulocyte lysate, 20 μM amino acids, 0.8 U/μl RNase inhibitor and 1 μg of linear or circular RNA. After incubation, hemoglobin protein was removed by adding acetic acid (0.32 μl) and water (300 μl) to the reaction mixture (16 μl) and centrifuging at 20,817×g for 10 min at 15° C. The supernatant was removed and the pellet was dissolved in 30° l of 2×SDS sample buffer and incubated at 70° C. for 15 min. After centrifugation at 1400×g for 5 min, the supernatant was analyzed on a 10-20% gradient polyacrylamide/SDS gel.

Figure 21:
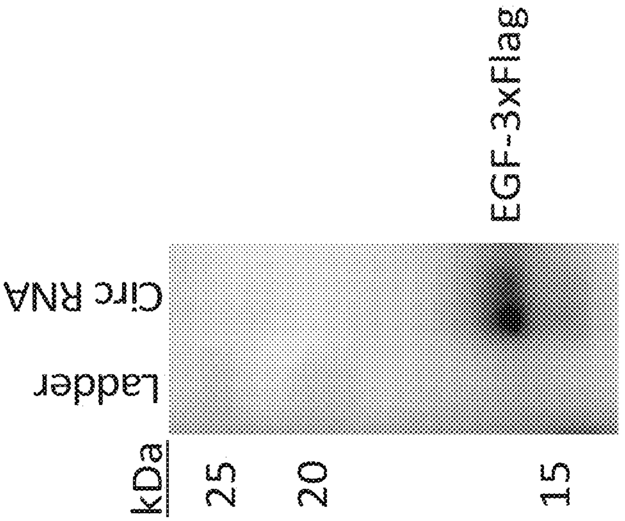
FIG. 21 is a Western blot image demonstrating expression of Flag protein (~15 kDa) by an exemplary circular RNA that lacks IRES, cap, 5' and 3' UTRs.

After being electrotransferred to a nitrocellulose membrane using dry transfer method, the blot was incubated with an anti-FLAG antibody and anti-mouse IgG peroxidase. The blot was visualized with an ECL kit (see FIG. 21) and western blot band intensity was measured by ImageJ.

Fluorescence was detected indicated expression product was present. Thus, circular RNA was shown to drive expression of a protein.

Example 21: IRES-Independent Expression

This Example demonstrates circular RNA driving expression in the absence of an IRES.

An IRES, or internal ribosome entry site, is an RNA element that allows translation initiation in a cap-independent manner. Circular RNA was shown to be drive expression of Flag protein in the absence of an IRES.

Circular RNA was designed to encode triple FLAG tagged EGF flanked by a 2A sequence without a termination element (stop codon) (330 nts, SEQ ID NO: 19).

Linear or circular RNA was incubated for 5 hr in rabbit reticulocyte lysate at 30° C. in a volume of 25 μl. The final composition of the reaction mixture included 70% rabbit reticulocyte lysate, 20 μM amino acids, 0.8 U/μl RNase inhibitor and 1 μg of linear or circular RNA. After incubation, hemoglobin protein was removed by adding acetic acid (0.32 μl) and water (300 μl) to the reaction mixture (16 μl) and centrifuging at 20,817×g for 10 min at 15° C. The supernatant was removed and the pellet was dissolved in 30° l of 2×SDS sample buffer and incubated at 70° C. for 15 min. After centrifugation at 1400×g for 5 min, the supernatant was analyzed on a 10-20% gradient polyacrylamide/SDS gel.

After being electrotransferred to a nitrocellulose membrane using dry transfer method, the blot was incubated with an anti-FLAG antibody and anti-mouse IgG peroxidase. The blot was visualized with an enhanced chemiluminescence (ECL) kit (see FIG. 21) and western blot band intensity was measured by ImageJ.

Expression product was detected in the circular RNA reaction mixture even in the absence of an IRES.

Example 22: Cap-Independent Expression

This Example demonstrates circular RNA is able to drive expression in the absence of a cap.

A cap is a specially altered nucleotide on the 5' end of mRNA. The 5' cap is useful for stability, as well as the translation initiation, of linear mRNA. Circular RNA drove expression of product in the absence of a cap.

Circular RNA was designed to encode triple FLAG tagged EGF flanked by a 2A sequence without a termination element (stop codon) (330 nts, SEQ ID NO: 19).

Linear or circular RNA was incubated for 5 hr in rabbit reticulocyte lysate at 30° C. in a volume of 25 μl. The final composition of the reaction mixture included 70% rabbit reticulocyte lysate, 20 μM amino acids, 0.8 U/μl RNase inhibitor and 1 μg of linear or circular RNA. After incubation, hemoglobin protein was removed by adding acetic acid (0.32 μl) and water (300 μl) to the reaction mixture (16 μl) and centrifuging at 20,817×g for 10 min at 15° C. The supernatant was removed and the pellet was dissolved in 30 μl of 2×SDS sample buffer at 70° C. for 15 min. After centrifugation at 1400×g for 5 min, the supernatant was analyzed on 10-20% gradient polyacrylamide/SDS gel.

After being electrotransferred to a nitrocellulose membrane using dry transfer method, the blot was incubated with an anti-FLAG antibody and anti-mouse IgG peroxidase. The blot was visualized with an ECL kit (see FIG. 21) and western blot band intensity was measured by ImageJ.

Expression product was detected in the circular RNA reaction mixture even in the absence of a cap.

Example 23: Expression without a 5'-UTR

This Example demonstrates in vitro protein expression from a circular RNA lacking 5' untranslated regions.

The 5' untranslated region (5' UTR) is the region directly upstream of an initiation codon that aids in downstream protein translation of a RNA transcript.

As shown in the following Example, a 5'-untranslated region in the circular RNA sequence was not necessary for in vitro protein expression.

Circular RNA was designed to encode triple FLAG tagged EGF flanked by a 2A sequence without a termination element (stop codon) (330 nts, SEQ ID NO: 19).

Linear or circular RNA was incubated for 5 hr in rabbit reticulocyte lysate at 30° C. in a volume of 25 μl. The final composition of the reaction mixture included 70% rabbit reticulocyte lysate, 20 μM amino acids, 0.8 U/μl RNase inhibitor and 1 μg of linear or circular RNA. After incubation, hemoglobin protein was removed by adding acetic acid (0.32 μl) and water (300 μl) to the reaction mixture (16 μl) and centrifuging at 20,817×g for 10 min at 15° C. The supernatant was removed and the pellet was dissolved in 30° l of 2×SDS sample buffer and incubated at 70° C. for 15 min. After centrifugation at 1400×g for 5 min, the supernatant was analyzed on a 10-20% gradient polyacrylamide/SDS gel.

After being electrotransferred to a nitrocellulose membrane using dry transfer method, the blot was incubated with an anti-FLAG antibody and anti-mouse IgG peroxidase. The blot was visualized with an ECL kit (see FIG. 21) and western blot band intensity was measured by ImageJ.

Expression product was detected in the circular RNA reaction mixture even in the absence of a 5' UTR.

Example 24: Expression without a 3'-UTR

This Example demonstrates in vitro protein expression from a circular RNA lacking a 3'-UTR.

The 3' untranslated region (3'-UTR) is the region directly downstream of a translation termination codon and includes regulatory regions that may post-transcriptionally influence gene expression. The 3'-untranslated region may also play a role in gene expression by influencing the localization, stability, export, and translation efficiency of an mRNA. In addition, the structural characteristics of the 3'-UTR as well as its use of alternative polyadenylation may play a role in gene expression.

As shown in the following Example, a 3'-UTR in the circular RNA sequence was not necessary for in vitro protein expression.

Circular RNA was designed to encode triple FLAG tagged EGF flanked by a 2A sequence without a termination element (stop codon) (330 nts, SEQ ID NO: 19).

Linear or circular RNA was incubated for 5 hr in rabbit reticulocyte lysate at 30° C. in a volume of 25 μl. The final composition of the reaction mixture included 70% rabbit reticulocyte lysate, 20 μM amino acids, 0.8 U/μl RNase inhibitor and 1 μg of linear or circular RNA. After incubation, hemoglobin protein was removed by adding acetic acid (0.32 μl) and water (300 μl) to the reaction mixture (16 μl) and centrifuging at 20,817×g for 10 min at 15° C. The supernatant was removed and the pellet was dissolved in 30° l of 2×SDS sample buffer and incubated at 70° C. for 15 min. After centrifugation at 1400×g for 5 min, the supernatant was analyzed on a 10-20% gradient polyacrylamide/SDS gel.

After being electrotransferred to a nitrocellulose membrane using dry transfer method, the blot was incubated with an anti-FLAG antibody and anti-mouse IgG peroxidase. The blot was visualized with an ECL kit (see FIG. 21) and western blot band intensity was measured by ImageJ.

Expression product was detected in the circular RNA reaction mixture even in the absence of a 3'UTR.

Example 25: Expression without a Termination Codon

This Example demonstrates generation of a polypeptide product following rolling circle translation from a circular RNA lacking a termination codon.

Proteins are based on polypeptides, which are comprised of unique sequences of amino acids. Each amino acid is encoded in mRNA by nucleotide triplets called codon. During protein translation, each codon in mRNA corresponds to the addition of an amino acid in a growing polypeptide chain. Termination element or stop codons signal the termination of this process by binding release factors, which cause the ribosomal subunits to disassociate, releasing the amino acid chain.

As shown in the following Example, a circular RNA lacking a termination codon generated a large polypeptide product comprised of repeated polypeptide sequences via rolling circle translation.

Circular RNA was designed to encode triple FLAG tagged EGF without a termination element (stop codon) (264 nts, SEQ ID NO: 20), and included a Kozak sequence at the start codon to favor translation initiation.

Linear or circular RNA was incubated for 5 hr in rabbit reticulocyte lysate at 30° C. in a volume of 25 μl. The final composition of the reaction mixture included 70% rabbit reticulocyte lysate, 20 μM amino acids, 0.8 U/μl RNase inhibitor and 1 μl of linear or circular RNA. After incubation, hemoglobin protein was removed by adding acetic acid (0.32 μl) and water (300 μl) to the reaction mixture (16 μl) and centrifuging at 20,817×g for 10 min at 15° C. The supernatant was removed and the pellet was dissolved in 30° l of 2×SDS sample buffer and incubated at 70° C. for 15 min. After centrifugation at 1400×g for 5 min, the supernatant was analyzed on a 10-20% gradient polyacrylamide/SDS gel.

Figure 22:
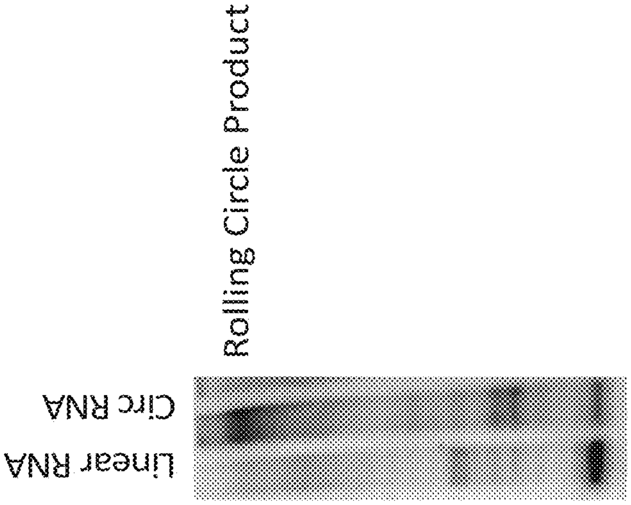
FIG. 22 is Western blot image demonstrating rolling-circle translation of an exemplary circular RNA.

After being electrotransferred to a nitrocellulose membrane using dry transfer method, the blot was incubated with an anti-FLAG antibody and anti-mouse IgG peroxidase. The blot was visualized with an ECL kit (see FIG. 22) and western blot band intensity was measured by ImageJ.

Expression product was detected in the circular RNA reaction mixture even in the absence of a termination codon.

Example 26: Expression of Discrete Proteins without a Termination Element (Stop Codon)

This Example demonstrates generation of a discrete protein products translated from a circular RNA lacking a termination element (stop codons).

Stagger elements, such as 2A peptides, may include short amino acid sequences, ~20 aa, that allow for the production of equimolar levels of multiple genes from a single mRNA. The stagger element may function by making the ribosome skip the synthesis of a peptide bond at the C-terminus of the 2A element, leading to separation between the end of the 2A sequence and the next peptide downstream. The separation occurs between Glycine and Proline residues found on the C-terminus and the upstream cistron has a few additional residues added to the end, while the downstream cistron starts with a Proline.

Figure 23:
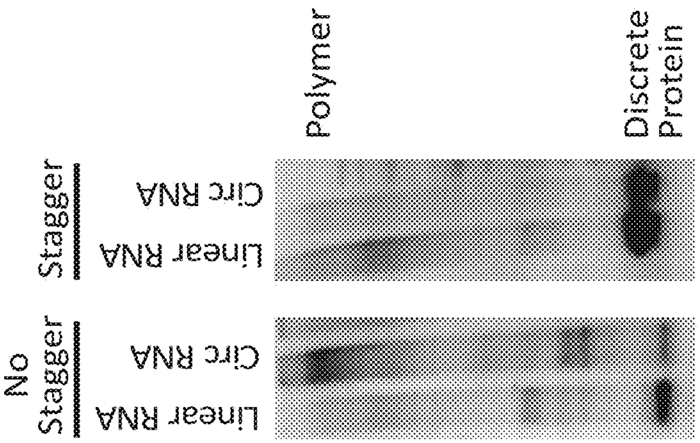
FIG. 23 shows Western blot images demonstrating production of discrete proteins or continuous long peptides from different exemplary circular RNAs with or without an exemplary stagger element.

As shown in the following Example, the circular RNA lacking a termination element (stop codon) generated a large polypeptide polymer (FIG. 23 left panel: no stagger-circular RNA lane) and inclusion of a 2A sequence at the 3' end of the coding region resulted in production of discrete protein at a size comparable to that generated by the equivalent linear RNA construct (FIG. 23 right panel: stagger-circular RNA lane).

Circular RNA was designed to encode triple FLAG tagged EGF without a termination element (stop codon) (264 nts, SEQ ID NO: 20) and without a stagger element. A second circular RNA was designed to encode triple FLAG tagged EGF flanked by a 2A sequence without a termination element (stop codon) (330 nts, SEQ ID NO: 19).

Linear or circular RNA was incubated for 5 hr in rabbit reticulocyte lysate at 30° C. in a volume of 25 μl. The final composition of the reaction mixture included 70% rabbit reticulocyte lysate, 20 μM amino acids, 0.8 U/μl RNase inhibitor and 1 μg of linear or circular RNA. After incubation, hemoglobin protein was removed by adding acetic acid (0.32 μl) and water (300 μl) to the reaction mixture (16 μl) and centrifuging at 20,817×g for 10 min at 15° C. The supernatant was removed and the pellet was dissolved in 30° l of 2×SDS sample buffer and incubated at 70° C. for 15 min. After centrifugation at 1400×g for 5 min, the supernatant was analyzed on a 10-20% gradient polyacrylamide/SDS gel.

After being electrotransferred to a nitrocellulose membrane using dry transfer method, the blot was incubated with an anti-FLAG antibody and anti-mouse IgG peroxidase. The blot was visualized with an ECL kit (see FIG. 23) and western blot band intensity was measured by ImageJ.

Discrete expression products were detected indicating circular RNA comprising a stagger element drove expression of the individual proteins even in the absence of a termination element (stop codons).

Example 27: Rolling Circle Translation

This Example demonstrates elevated in vitro biosynthesis of a protein from circular RNA using a stagger element.

A non-naturally occurring circular RNA was engineered to include a stagger element to compare protein expression with circular RNA lacking a stagger element. As shown in the following Example, a stagger element overexpressed protein as compared to an otherwise identical circular RNA lacking such a sequence.

Circular RNA was designed to encode triple FLAG tagged EGF with a termination element (e.g., three stop codons in tandem) (273 nts, SEQ ID NO: 21). A second circular RNA was designed to encode triple FLAG tagged EGF flanked by a 2A sequence without a termination element (stop codon) (330 nts, SEQ ID NO: 19).

Linear or circular RNA was incubated for 5 hr in rabbit reticulocyte lysate at 30° C. in a volume of 25 μl. The final composition of the reaction mixture contained 70% rabbit reticulocyte lysate, 20 μM amino acids, 0.8 U/μl RNase inhibitor and 1 μg of linear or circular RNA. After incubation, hemoglobin protein was removed by adding acetic acid (0.32 μl) and water (300 μl) to the reaction mixture (16 μl) and centrifuging at 20,817×g for 10 min at 15° C. The supernatant was removed and the pellet was dissolved in 30° l of 2×SDS sample buffer and incubated at 70° C. for 15 min. After centrifugation at 1400×g for 5 min, the supernatant was analyzed on a 10-20% gradient polyacrylamide/SDS gel.

Figure 24A:
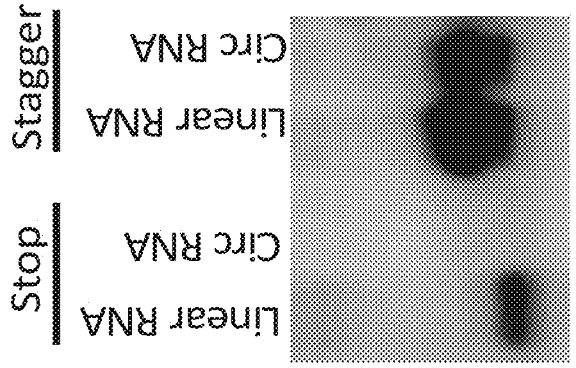
FIG. 24A is a Western blot image showing the comparison of protein expression between different exemplary circular RNAs with an exemplary stagger element or a termination element (stop codon).
Figure 24B:
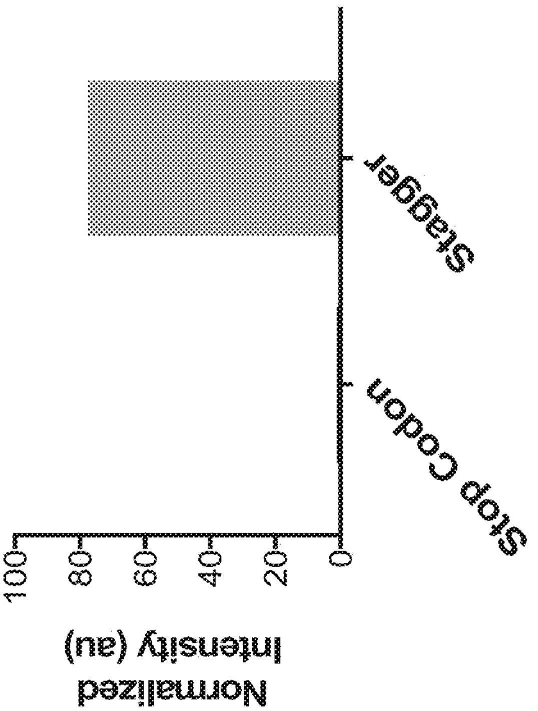
FIG. 24B is a graph summarizing the signal intensity from Western blot analysis of the protein products translated from the two exemplary circular RNAs.

After being electrotransferred to a nitrocellulose membrane using dry transfer method, the blot was incubated with an anti-FLAG antibody and anti-mouse IgG peroxidase. The blot was visualized with an ECL kit (see FIG. 24) and western blot band intensity was measured by ImageJ.

Discrete expression products were detected indicating circular RNA comprising a stagger element drove expression of the individual proteins even in the absence of a termination element (stop codons).

Example 28: Expression of a Biologically Active Protein In Vitro

This Example demonstrates in vitro biosynthesis of a biologically active protein from circular RNA.

A non-naturally occurring circular RNA was engineered to express a biologically active therapeutic protein. As shown in the following Example, a biologically active protein was expressed from the circular RNA in reticulocyte lysate.

Circular RNA was designed to encode FLAG tagged EGF flanked by a 2A sequence and followed by FLAG tagged nano-luciferase (873 nts, SEQ ID NO:17).

Linear or circular RNA was incubated for 5 hr in rabbit reticulocyte lysate at 30° C. in a volume of 25 μl. The final composition of the reaction mixture contained 70% rabbit reticulocyte lysate, 20 μM amino acids, 0.8 U/μl RNase inhibitor. Luciferase activity in the translation mixture was monitored using a luciferase assay system according to manufacturer's protocol (Promega).

Figure 25:
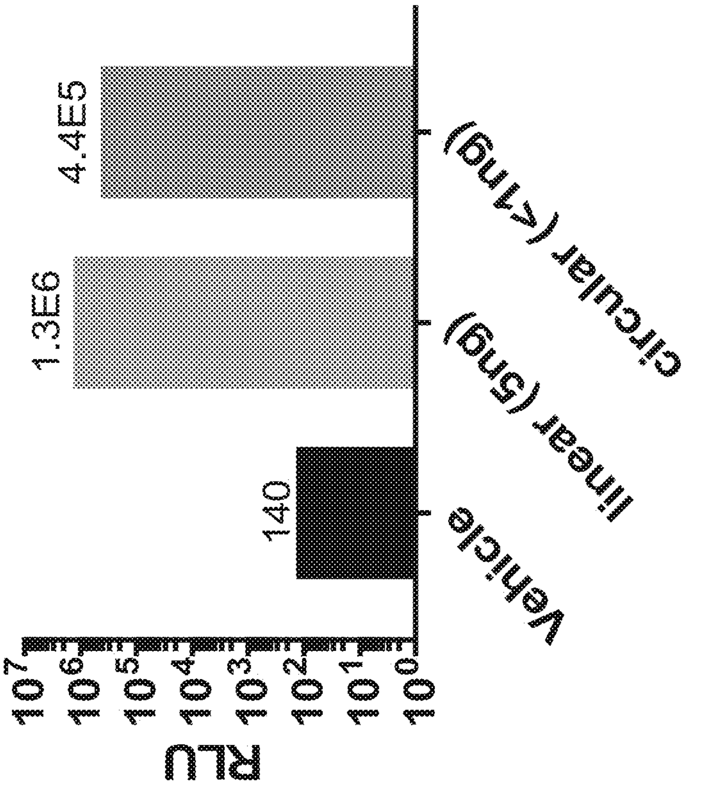
FIG. 25 is a graph summarizing the luciferase activity of translation products of an exemplary circular RNA and its linear counterpart, in comparison with a vehicle control RNA.

As shown in FIG. 25, much higher fluorescence was detected with both circular RNA and linear RNA than the control vehicle RNA, indicating expression product was present. Thus, circular RNA was shown to express a biologically active protein.

Example 29: Circular RNA with a Longer Half-Life than Linear RNA Counterpart

This Example demonstrates circular RNA engineered to have a prolonged half-life as compared to a linear RNA.

Circular RNA encoding a therapeutic protein provided recipient cells with the ability to produce greater levels of the encoded protein stemming from a prolonged biological half-life, e.g., as compared to linear RNA. As shown in the following Example, a circular RNA had a greater half-life than its linear RNA counterpart in reticulocyte lysate.

A circular RNA was designed to encode FLAG tagged EGF flanked by a 2A sequence and followed by FLAG tagged nano luciferase (873 nts, SEQ ID NO: 17).

In this Example, a time-course experiment was performed to monitor RNA stability. 100 ng of linear or circular RNA was incubated with rabbit reticulocyte lysate and samples were collected at 1 hr, 5 hr, 18 hr and 30 hr. Total RNA was isolated from lysate using a phenol-based reagent (Invitrogen) and cDNA was generated by reverse transcription. qRT-PCR analysis was performed using a dy-based quantitative PCR reaction mix (BioRad).

Figure 26:
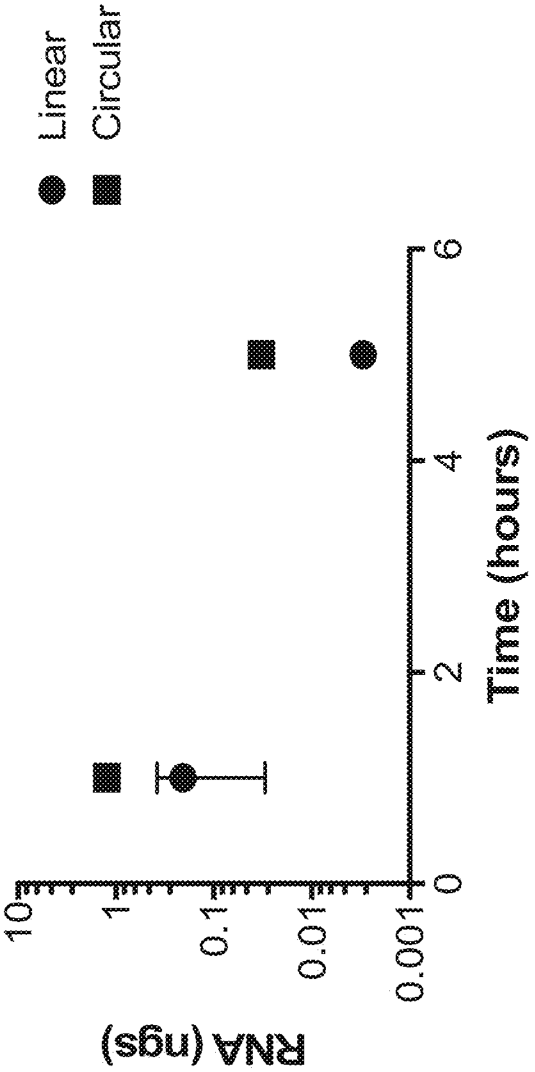
FIG. 26 is a graph summarizing RNA quantities at different collection time points in a time course experiment testing half-life of an exemplary circular RNA.

As shown in FIG. 26, greater concentrations of circular RNA were detected in the later timepoints than linear RNA. Thus, the circular RNA was more stable or had an increased half-life as compared to its linear counterpart.

Example 30: Circular RNA Demonstrated a Longer Half-Life than Linear RNA in Cells This Example demonstrates circular RNA delivered into cells and has an increased half-life in cells compared with linear RNA.

A non-naturally occurring circular RNA was engineered to express a biologically active therapeutic protein. As shown in the following Example, circular RNA was present at higher levels compared to its linear RNA counterpart, demonstrating a longer half-life for circular RNA.

In this Example, circular RNA and linear RNA were designed to encode a Kozak, EGF, flanked by a 2A, a stop or no stop sequence (SEQ ID NOs: 11, 19, 20, 21). To monitor half-life of RNA in cells, $0.1\times10^6$ cells were plated onto each well of a 12 well plate. After 1 day, 1 μg of linear or circular RNA was transfected into each well using a lipid-based transfection reagent (Invitrogen). Twenty-four hours after transfection, total RNA was isolated from cells using a phenol-based extraction reagent (Invitrogen). Total RNA (500 ng) was subjected to reverse transcription to generate cDNA. qRT-PCR analysis was performed using a dye-based quantitative PCR mix (BioRad). Primer sequences were as follow: Primers for linear or circular RNA, F: ACGACGGTGTGTGCATGTAT (SEQ ID NO: 106), R: TTCCCACCACTTCAGGTCTC (SEQ ID NO: 107); primers for circular RNA, F: TACGCCTGCAACTGTGTTGT (SEQ ID NO: 108), R: TCGATGATCTTGTCGTCGTC (SEQ ID NO: 109).

Figure 27A:
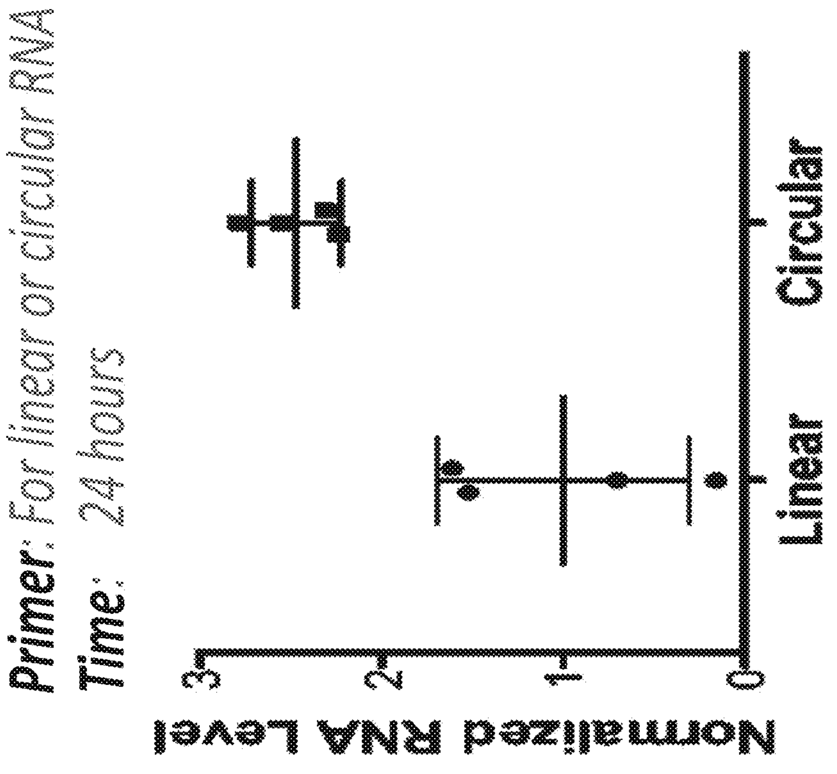
FIG. 27A is a graph showing qRT-PCR analysis of linear and circular RNA levels 24 hours after delivery to cells using primers that captured both linear and circular RNA.
Figure 27B:
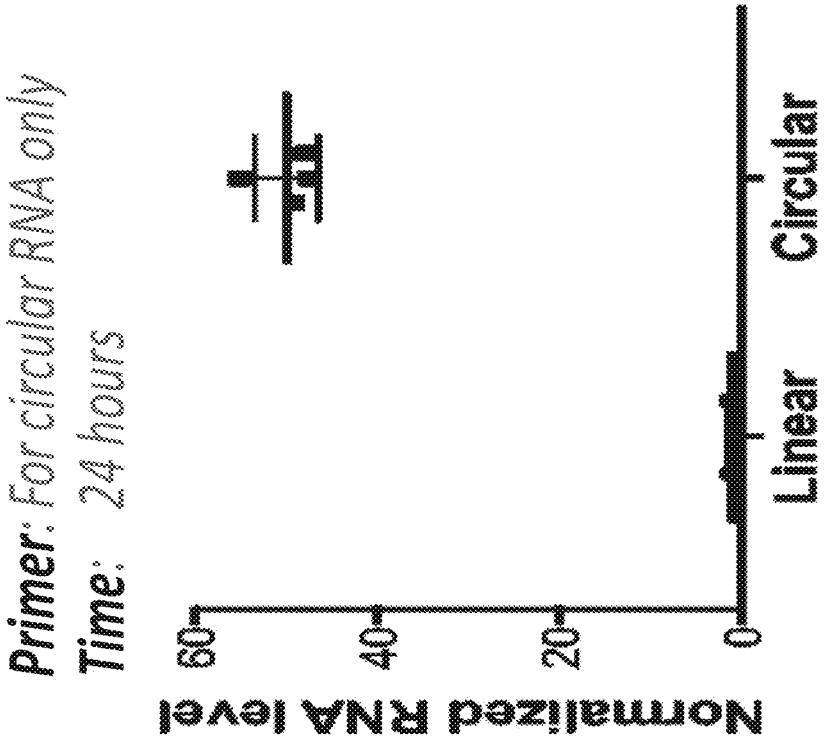
FIG. 27B is a graph showing qRT-PCR analysis of linear and circular RNA levels using a primer specific for the circular RNA.

Circular RNA was successfully transfected into 293T cells, as was its linear counterpart. After 24 hours, the circular and linear RNA that remained were measured using qPCR. As shown in FIGS. 27A and B, circular RNA was shown to have a longer half-life in cells compared to linear RNA.

Example 31: Synthetic Circular RNA were Translated in Cells, and Synthetic Circular RNA was Translated Via Rolling Circle Translation This Example demonstrates translation of synthetic circular RNA in cells.

As shown in the following Example, circular RNA and linear RNA were designed to encode a Kozak, 3×FLAG-EGF sequence with no termination element (SEQ ID NO: 11). Circular RNA was translated into polymeric EGF, while linear RNA was not, demonstrating that cells performed rolling circle translation of a synthetic circular RNA.

In this Example, $0.1\times10^6$ cells were plated onto each well of a 12 well plate to monitor translation efficiency of linear or circular RNA in cells. After 1 day, 1 μg of linear or circular RNA was transfected into each well using a lipid-based transfection reagent (Invitrogen). Twenty-four hours after transfection, cells were harvested by adding 200 μl of RIPA buffer onto each well. Next, 10 μg of cell lysate proteins were analyzed on 10-20% gradient polyacrylamide/SDS gel. After electrotransfer to a nitrocellulose membrane using dry transfer method, the blot was incubated with an anti-FLAG antibody and anti-mouse IgG peroxidase. As a loading control, anti-beta tubulin antibody was used. The blot was visualized with an enhanced chemiluminescent (ECL) kit. Western blot band intensity was measured by ImageJ.

Figure 28:
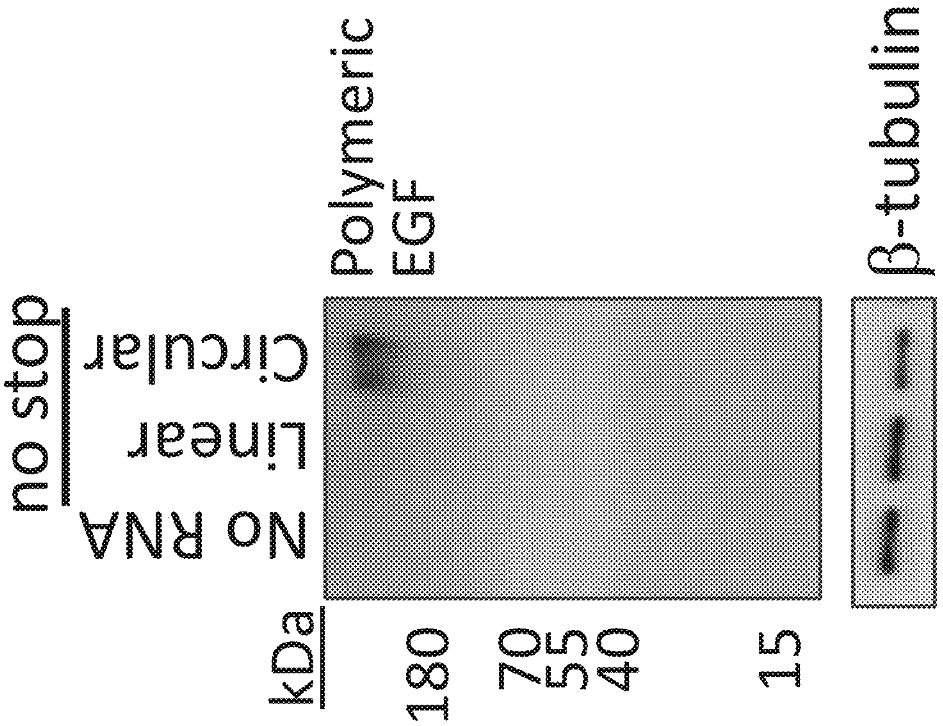
FIG. 28 is an image showing a blot of cell lysates from circular RNA and linear RNA probed for EGF protein and a beta-tubulin loading control.

Circular RNA was successfully transfected into 293T cells, as was its linear counterpart. However, FIG. 28 shows that 24 hours after transfection, EGF protein was detected in the circular RNA transfected cells, while none was detected in the linear RNA transfected cells. Thus, circular RNA was translated in cells via rolling circle translation as compared to linear RNA.

Example 32: Synthetic Circular RNA Demonstrated Reduced Immunogenic Gene Expression in Cells This Example demonstrates circular RNA engineered to have reduced immunogenicity as compared to a linear RNA.

Circular RNA that encoded a therapeutic protein provided a reduced induction of immunogenic related genes (RIG-I, MDA5, PKA and IFN-beta) in recipient cells, as compared to linear RNA. RIG-I can recognize short 5' triphosphate uncapped double stranded or single stranded RNA, while MDA5 can recognize longer dsRNAs. RIG-I and MDA5 can both be involved in activating MAVS and triggering antiviral responses. PKR can be activated by dsRNA and induced by interferons, such as IFN-beta. As shown in the following Example, circular RNA was shown to have a reduced activation of an immune related genes in 293T cells than an analogous linear RNA, as assessed by expression of RIG-I, MDA5, PKR and IFN-beta by q-PCR.

The circular RNA and linear RNA were designed to encode either (1) a Kozak, 3×FLAG-EGF sequence with no termination element (SEQ ID NO:11); (2) a Kozak, 3×FLAG-EGF, flanked by a termination element (stop codon) (SEQ ID NO:21); (3) a Kozak, 3×FLAG-EGF, flanked by a 2A sequence (SEQ ID NO:19); or (4) a Kozak, 3×FLAG-EGF sequence flanked by a 2A sequence followed by a termination element (stop codon) (SEQ ID NO:20).

In this Example, the level of innate immune response genes were monitored in cells by plating $0.1\times10^6$ cells into each well of a 12 well plate. After 1 day, 1 μg of linear or circular RNA was transfected into each well using a lipid-based transfection reagent (Invitrogen). Twenty-four hours after transfection, total RNA was isolated from cells using a phenol-based extraction reagent (Invitrogen). Total RNA (500 ng) was subjected to reverse transcription to generate cDNA. qRT-PCR analysis was performed using a dye-based quantitative PCR mix (BioRad).

Primer sequences used: Primers for GAPDH, F: AGGGCTGCTTTTAACTCTGGT (SEQ ID NO: 110), R: CCCCACTTGATTTTGGAGGGA (SEQ ID NO: 111); RIG-I, F: TGTGGGCAATGTCATCAAAA (SEQ ID NO: 40), R: GAAGCACTTGCTACCTCTTGC (SEQ ID NO: 41); MDA5, F: GGCACCATGGGAAGTGATT (SEQ ID NO: 42), R: ATTTGGTAAGGCCTGAGCTG (SEQ ID NO: 43); PKR, F: TCGCTGGTATCACTCGTCTG (SEQ ID NO: 44), R: GATTCTGAAGACCGCCAGAG (SEQ ID NO: 45); IFN-beta, F: CTCTCCTGTTGTGCTTCTCC (SEQ ID NO: 46), R: GTCAAAGTTCATCCTGTCCTTG (SEQ ID NO: 47).

Figure 29:
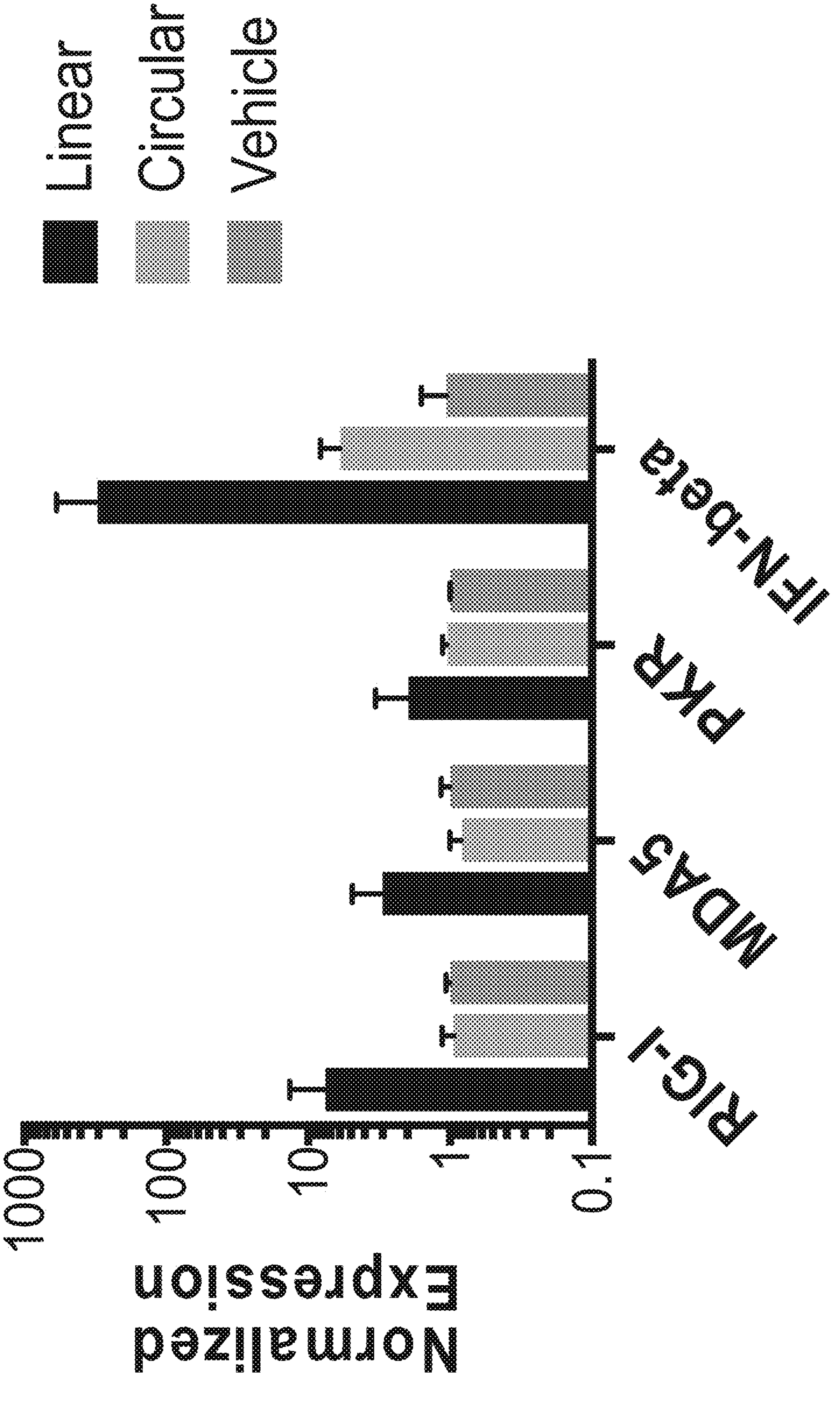
FIG. 29 is a graph showing qRT-PCR analysis of immune related genes from 293T cells transfected with circular RNA or linear RNA.

As shown in FIG. 29, qRT-PCR levels of immune related genes from 293T cells transfected with circular RNA showed reduction of RIG-I, MDA5, PKR and IFN-beta as compared to linear RNA transfected cells. Thus, induction of immunogenic related genes in recipient cells was reduced in circular RNA transfected cells, as compared to linear RNA transfected cells.

Example 33: Increased Expression from Synthetic Circular RNA Via Rolling Circle Translation in Cells This Example demonstrates increased expression from rolling circle translation of synthetic circular RNA in cells.

Circular RNAs were designed to include an IRES with a nanoluciferase gene or an EGF negative control gene without a termination element (stop codon). Cells were transfected with EGF negative control (SEQ ID NO:22); nLUC stop (SEQ ID NO:23): EMCV IRES, stagger sequence (2A sequence), 3× FLAG tagged nLUC sequences, stagger sequence (2A sequence), and a stop codon; or nLUC stagger (SEQ ID NO:24): EMCV IRES, stagger sequence (2A sequence), 3× FLAG tagged nLUC sequences, and stagger sequence (2A sequence). As shown in the FIG. 30, both circular RNAs produced translation product having functional luciferase activity.

In this Example, translation of circular RNA was monitored in cells. Specifically, $0.1\times10^6$ cells were plated onto each well of a 12 well plate. After 1 day, 300 ng of circular RNA was transfected into each well using a lipid-based transfection reagent (Invitrogen). After 24 hrs, cells were harvested by adding 100 μl of RIPA buffer. Nanoluciferase activity in lysates was measured using a luciferase assay system according to its manufacturer's protocol (Promega).

Figure 30:
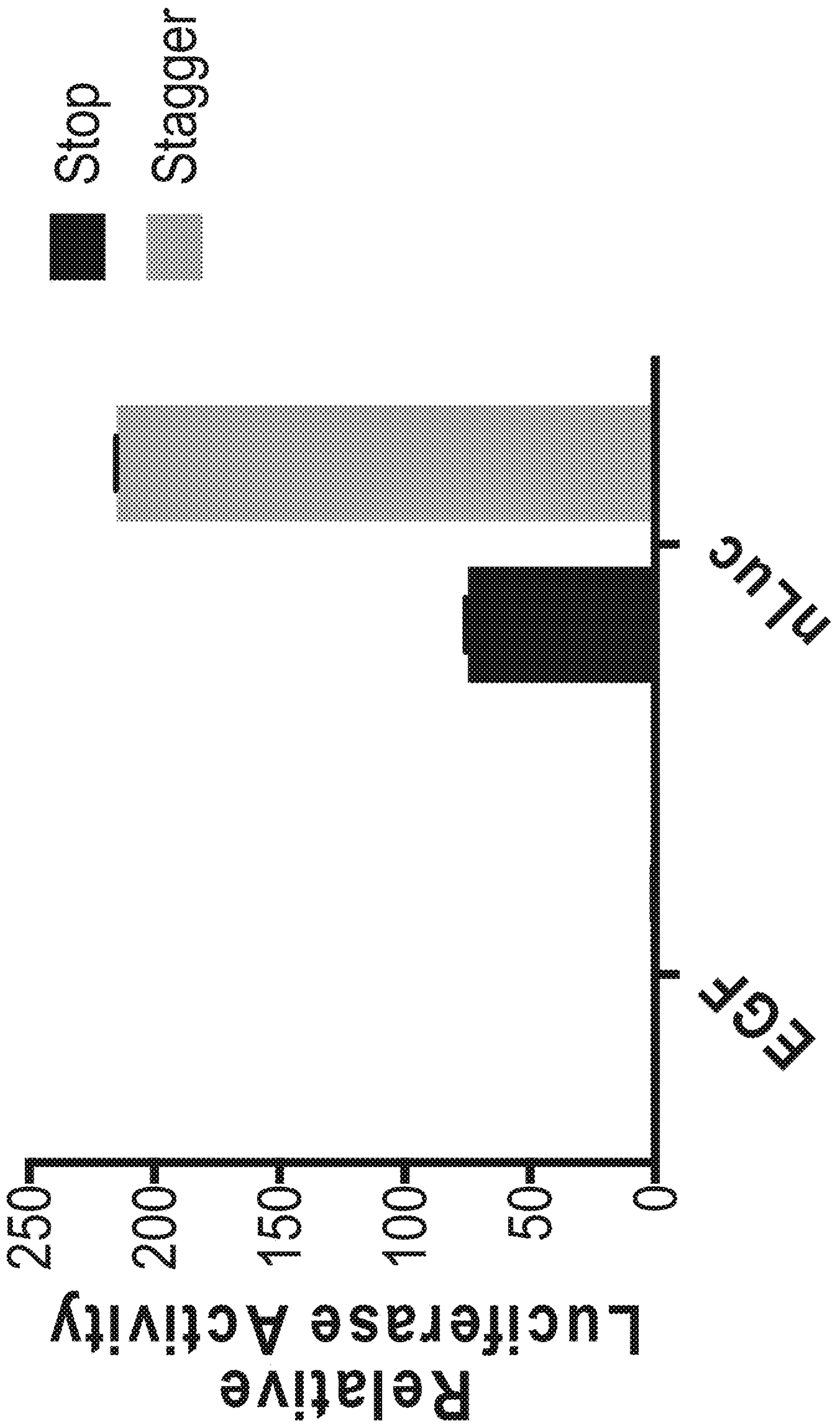
FIG. 30 is a graph showing luciferase activity of protein expressed from circular RNA via rolling circle translation.

As shown in FIG. 30, both circular RNAs expressed protein in cells. However, circular RNA with a stagger element, e.g., 2A sequence, that lacks a termination element (stop codon), produced higher levels of protein product having functional luciferase activity than circular RNA with a termination element (stop codon).

Example 34: Synthetic Circular RNA Translated in Cells

This Example demonstrates synthetic circular RNA translation in cells. Additionally, this Example shows that circular RNA produced more expression product than its linear counterpart.

Figure 31:
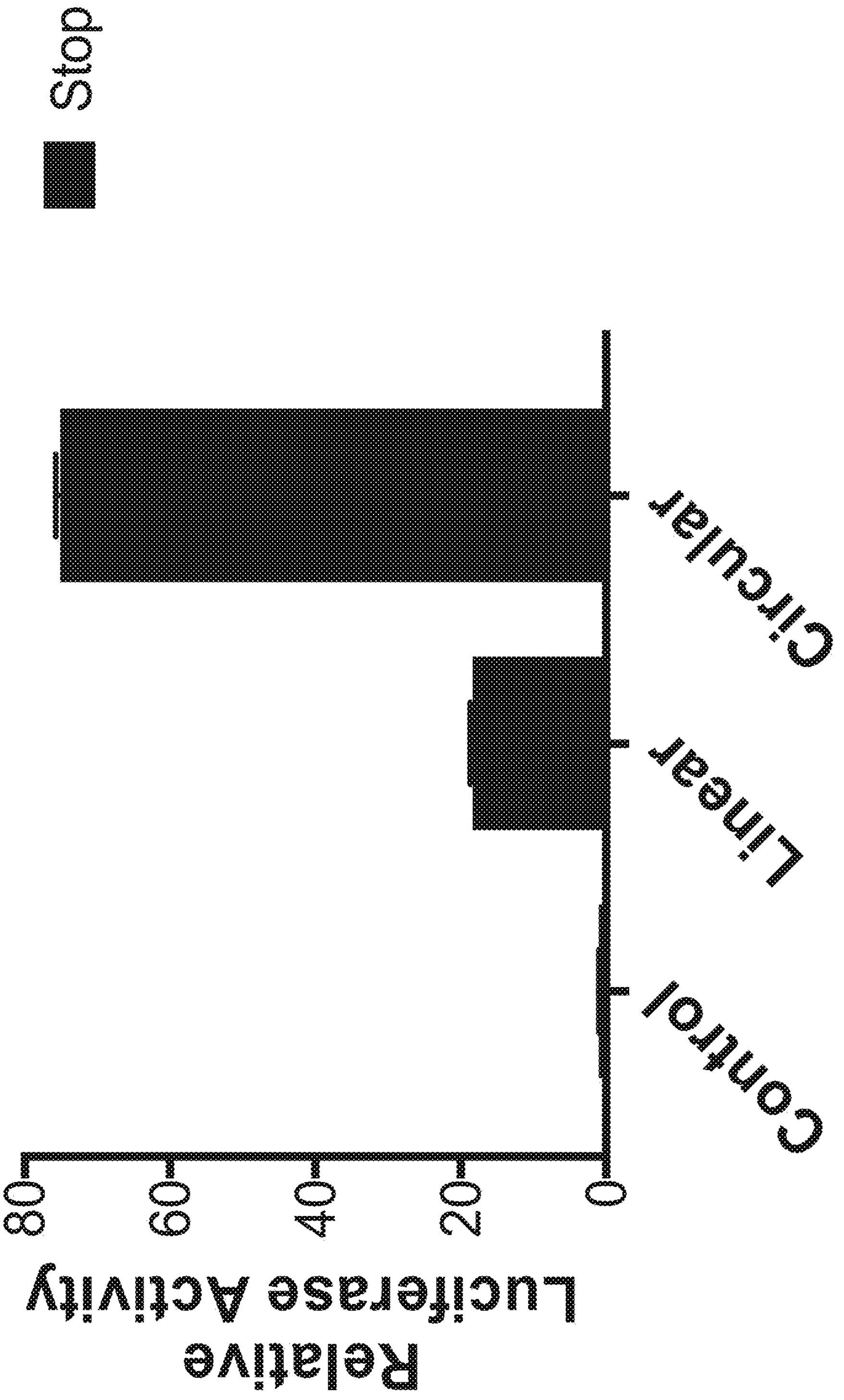
FIG. 31 is a graph showing luciferase activity of protein expressed from circular RNA or linear RNA.

Circular RNA was successfully transfected into 293T cells, as was its linear counterpart. Cells were transfected with circular RNA encoding EGF as a negative control (SEQ ID NO:22): EMCV IRES, stagger sequence (2A sequence), 3× FLAG tagged EGF sequences, stagger sequence (2A sequence); linear or circular nLUC (SEQ ID NO:23): EMCV IRES, stagger sequence (2A sequence), 3× FLAG tagged nLuc sequences, a stagger sequence (2A sequence), and stop codon. As shown in FIG. 31, circular RNA was translated into nanoluciferase in cells.

Linear or circular RNA translation was monitored in cells. Specifically, $0.1\times10^6$ cells were plated onto each well of a 12 well plate. After 1 day, 300 ng of linear or circular RNA was transfected into each well using a lipid-based transfection reagent (Invitrogen). After 24 hrs, cells were harvested by adding 100 μl of RIPA buffer. Nanoluciferase activity in lysates was measured using a luciferase assay system according to its manufacturer's protocol (Promega).

As shown in FIG. 31, circular RNA translation product was detected in cells. In particular, circular RNA had higher levels of luciferase activity or increased protein produced as compared to its linear RNA counterpart.

Example 35: Rolling Circle Translation from Synthetic Circular RNA Produced Functional Protein Product in Cells This Example demonstrates rolling circle translation of functional protein product from synthetic circular RNA lacking a termination element (stop codon), e.g., having a stagger element lacking a termination element (stop codon), in cells. Additionally, this Example shows that circular RNA with a stagger element expressed more functional protein product than its linear counterpart.

Figure 32:
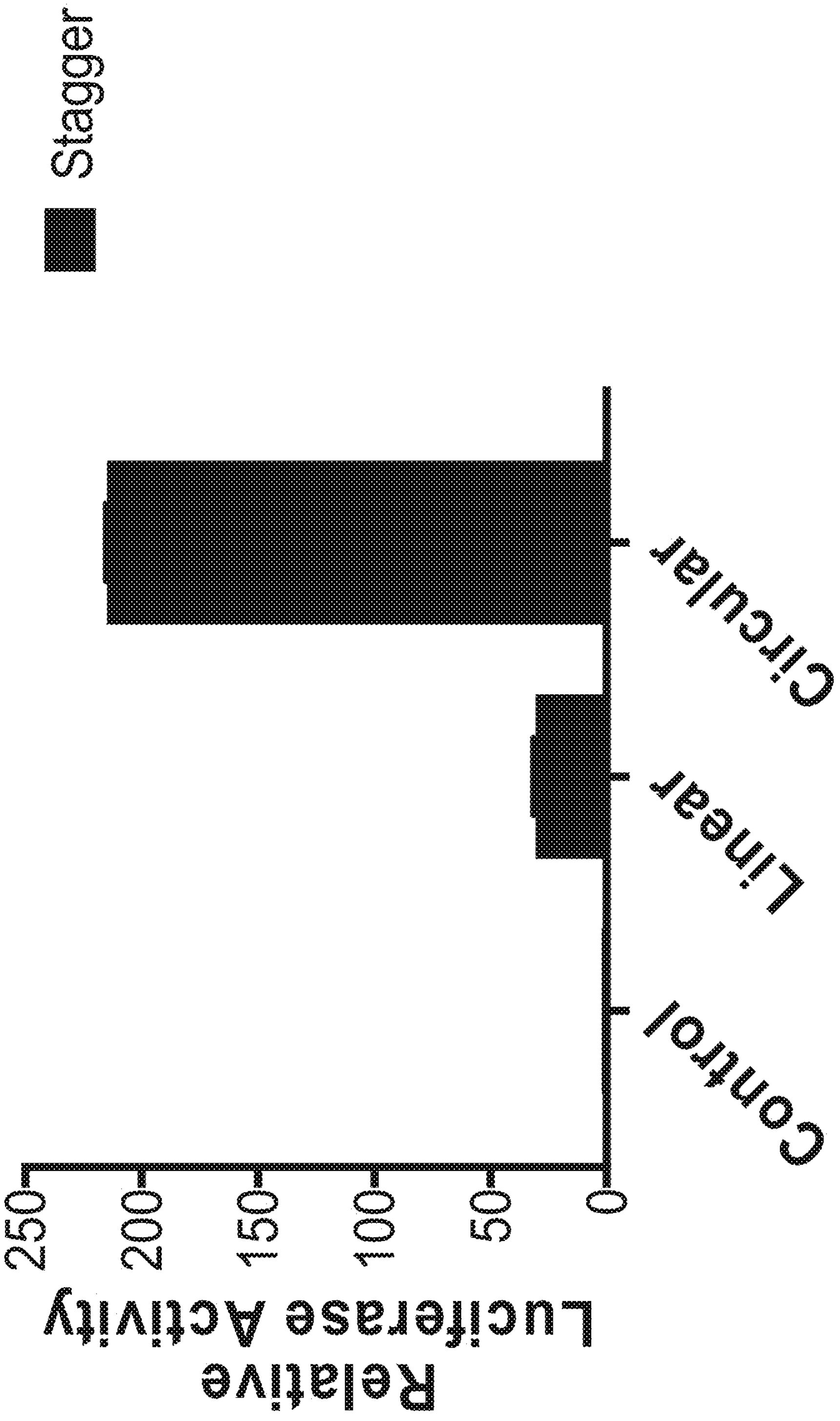
FIG. 32 is a graph showing luciferase activity of protein expressed from linear RNA or circular RNA via rolling circle translation.

Circular RNA was successfully transfected into 293T cells, as was its linear counterpart. Cells were transfected with circular RNA EGF negative control (SEQ ID NO:22); linear and circular nLUC (SEQ ID NO:24): EMCV IRES, stagger sequence (2A sequence), 3× FLAG tagged nLuc sequences, a stagger sequence (2A sequence). As shown in FIG. 32, circular RNA was translated into nanoluciferase in cells.

Linear or circular RNA translation was monitored in cells. Specifically, $0.1\times10^6$ cells were plated onto each well of a 12 well plate. After 1 day, 300 ng of linear or circular RNA was transfected into each well using a lipid-based transfection reagent (Invitrogen). After 24 hrs, cells were harvested by adding 100 μl of RIPA buffer. Nanoluciferase activity in lysates was measured using a luciferase assay system according to its manufacturer's protocol (Promega).

As shown in FIG. 32, circular RNA translation product was detected in cells. In particular, circular RNA without a termination element (stop codon) produced higher levels of protein product having functional luciferase activity than its linear RNA counterpart.

Example 36: Synthetic Circular RNA Translated Via IRES Initiation in Cells

This Example demonstrates synthetic circular RNA translation initiation with an IRES in cells.

Circular RNAs were designed to include a Kozak sequence or IRES with a nanoluciferase gene or an EGF negative control gene. Cells were transfected with EGF negative control (SEQ ID NO:22), nLUC Kozak (SEQ ID NO:25): Kozak sequence, 1× FLAG tagged EGF sequence, a stagger sequence (T2A sequence), 1× FLAG tagged nLUC, stagger sequence (P2A sequence), and a stop codon; or nLUC IRES (SEQ ID NO:23): EMCV IRES, stagger sequence (2A sequence), 3× FLAG tagged nLUC sequences, stagger sequence (2A sequence) and a stop codon. As shown in the FIG. 33, the circular RNA with an IRES demonstrated higher levels of luciferase activity, corresponding to higher protein levels, as compared to circular RNA with a Kozak sequence.

In this Example, translation of circular RNA was monitored in cells. Specifically, $0.1 \times 10^6$ cells were plated onto each well of a 12 well plate. After 1 day, 300 ng of circular RNA was transfected into each well using a lipid-based transfection reagent (Invitrogen). After 24 hrs, cells were harvested by adding 100 μl of RIPA buffer. Nanoluciferase activity in lysates was measured using a luciferase assay system according to its manufacturer's protocol (Promega).

Figure 33:
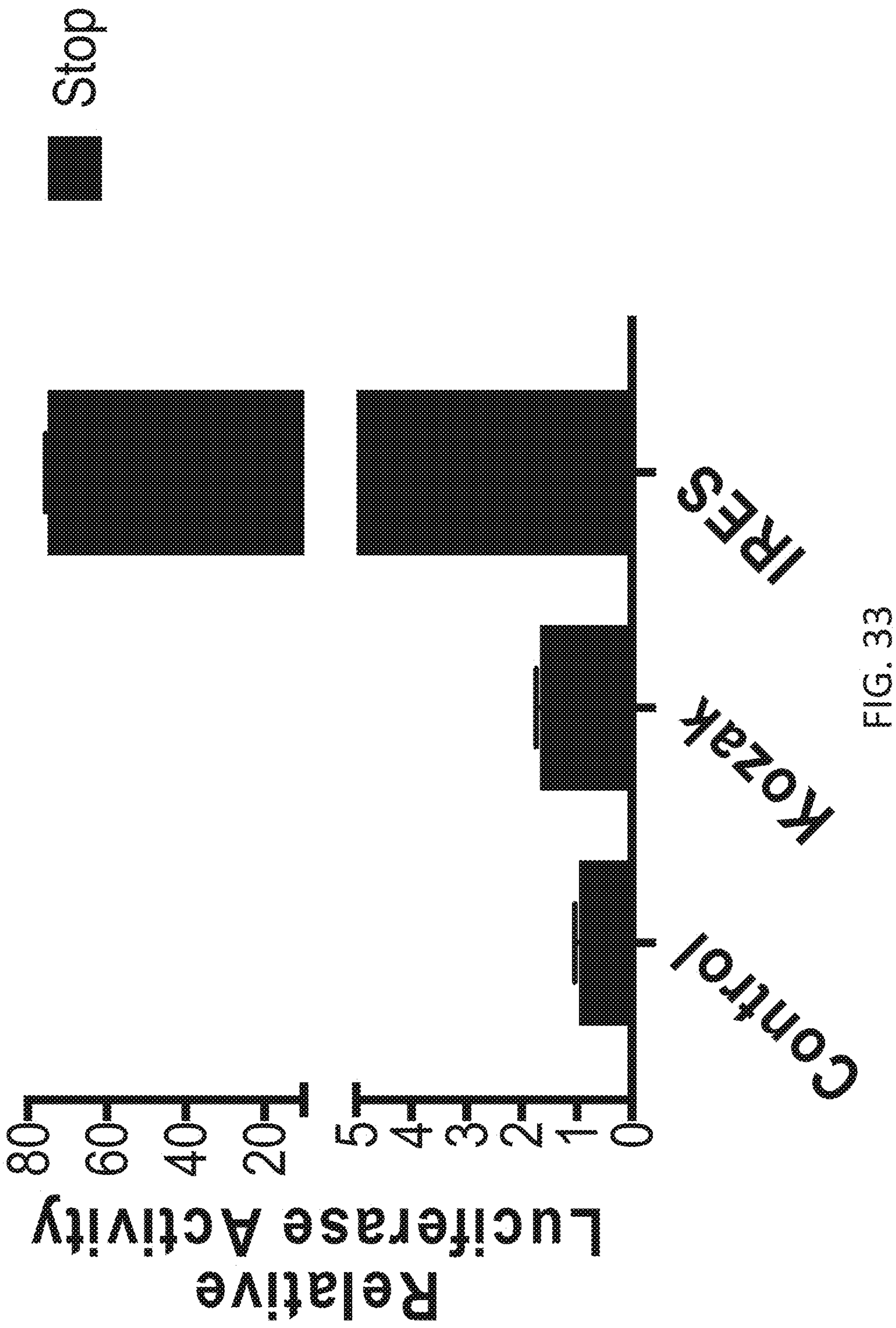
FIG. 33 is a graph showing luciferase activity of protein expressed from circular RNA via IRES translation initiation.

As shown in FIG. 33, circular RNA initiated protein expression with an IRES and produced higher levels of protein product having functional luciferase activity than circular RNA with Kozak initiated protein expression.

Example 37: Rolling Circle Translation of Synthetic Circular RNA in Cells

This Example demonstrates greater protein production via rolling circle translation of synthetic circular RNA in cells that initiated protein production with an IRES.

Circular RNAs were designed to include an a Kozak sequence or IRES with a nanoluciferase gene or an EGF negative control with or without a termination element (stop codon). Cells were transfected with EGF negative control (SEQ ID NO:22); nLUC IRES stop (SEQ ID NO:23): EMCV IRES, stagger sequence (2A sequence), 3× FLAG tagged nLUC sequences, stagger sequence (2A sequence) and a stop codon; or nLUC IRES stagger (SEQ ID NO:24): EMCV IRES, stagger sequence (2A sequence), 3× FLAG tagged nLUC sequences, and stagger sequence (2A sequence). As shown in the FIG. 34, both circular RNAs produced expression product demonstrated rolling circle translation and the circular RNA without a termination element an IRES (e.g., without a Kozak sequence) initiated and produced higher levels of protein product with functional luciferase activity than circular RNA with a termination element out an IRES (e.g., with a Kozak sequence), demonstrating rolling circle translation.

In this Example, translation of circular RNA was monitored in cells. Specifically, $0.1 \times 10^6$ cells were plated onto each well of a 12 well plate. After 1 day, 300 ng of circular RNA was transfected into each well using a lipid-based transfection reagent (Invitrogen). After 24 hrs, cells were harvested by adding 100 μl of RIPA buffer. Nanoluciferase activity in lysates was measured using a luciferase assay system according to its manufacturer's protocol (Promega).

Figure 34:
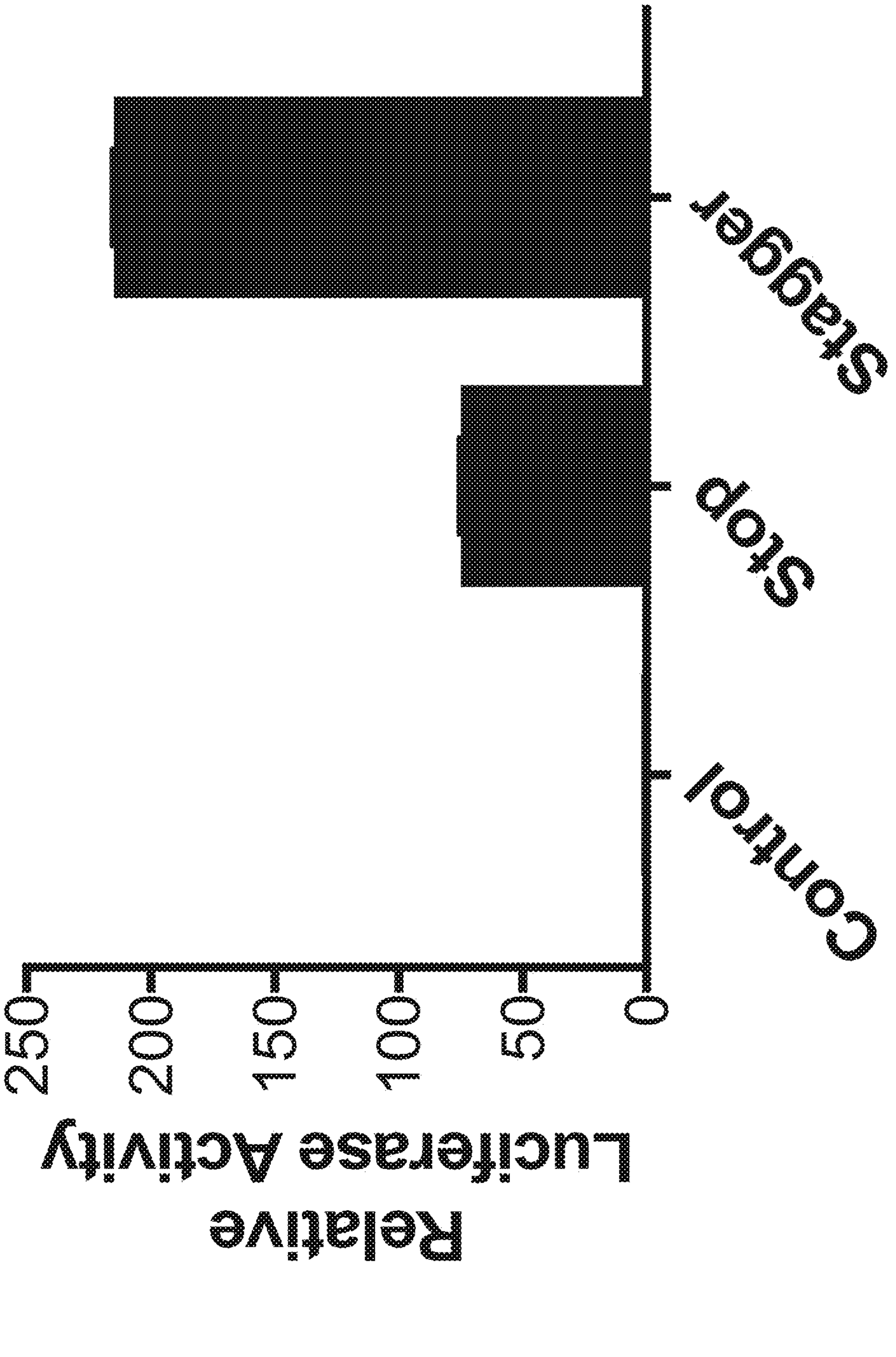
FIG. 34 is a graph showing luciferase activity of protein expressed from circular RNA via IRES initiation and rolling circle translation.

As shown in FIG. 34, circular RNA was translated into protein in cells via a rolling circle method given from both circular RNAs. However, the circular RNA that lacked a termination element (stop codon). However, the rolling circle translation of the circular RNA initiated greater protein production with an IRES and produced more protein product having functional luciferase activity as compared to a circular RNA with a termination element Kozak translation initiation.

Example 38: Increased Protein Expressed from Circular RNA

This Example demonstrates demonstrates synthetic circular RNA translation in cells. Additionally, this Example shows that circular RNA produced more expression product of the correct molecular weight than its linear counterpart.

Linear and circular RNAs were designed to include a nanoluciferase gene with a termination element (stop codon). Cells were transfected with vehicle: transfection reagent only; linear nLUC (SEQ ID NO:23): EMCV IRES, stagger element (2A sequence), 3× FLAG tagged nLuc sequences, a stagger element (2A sequence), and termination element (stop codon); or circular nLUC (SEQ ID NO:23): EMCV IRES, stagger element (2A sequence), 3× FLAG tagged nLuc sequences, a stagger element (2A sequence), and a termination element (stop codon). As shown in the FIG. 35, circular RNA produced greater levels of protein having the correct molecular weight as compared to linear RNA.

After 24 hrs, cells were harvested by adding 100 μl of RIPA buffer. After centrifugation at 1400×g for 5 min, the supernatant was analyzed on a 10-20% gradient polyacrylamide/SDS gel.

After being electrotransferred to a nitrocellulose membrane using dry transfer method, the blot was incubated with an anti-FLAG antibody and anti-mouse IgG peroxidase. The blot was visualized with an ECL kit and western blot band intensity was measured by ImageJ.

Figure 35:
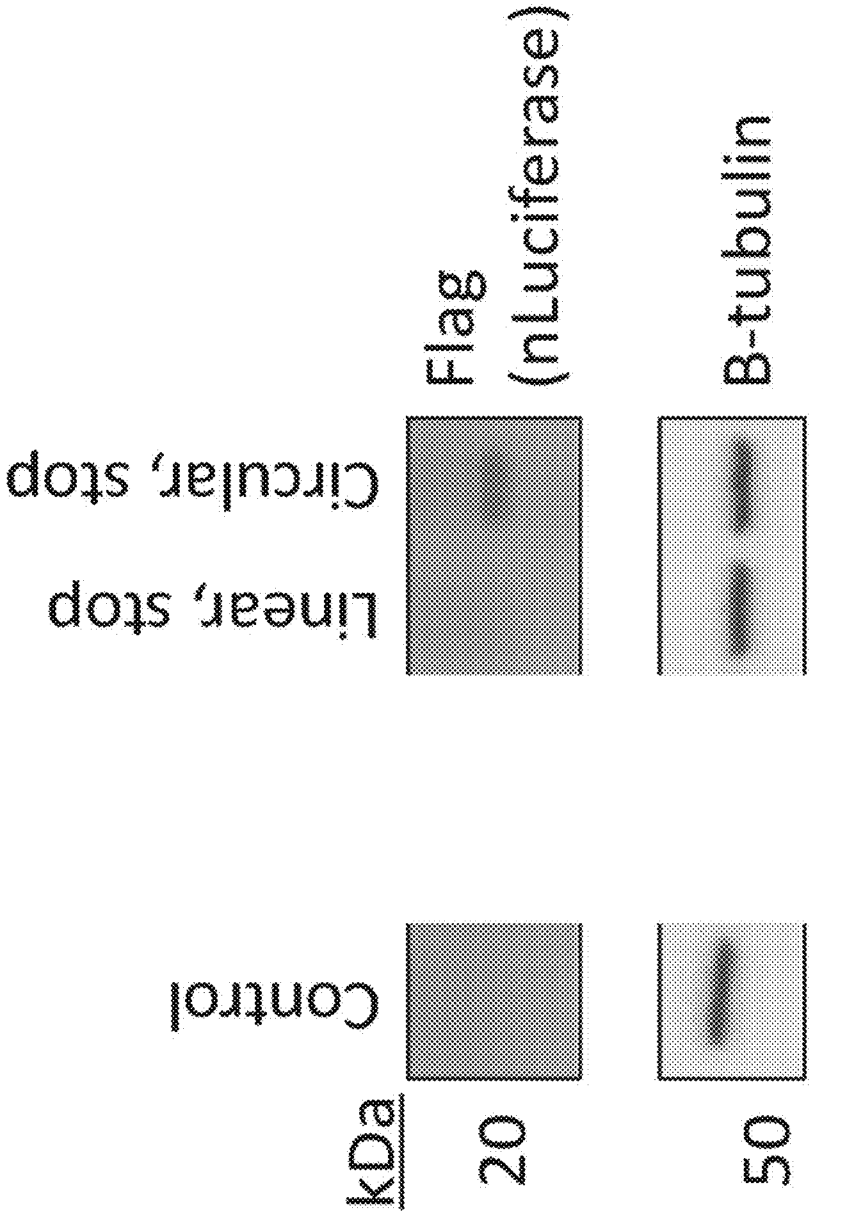
FIG. 35 is an image showing a protein blot of expression products from circular RNA or linear RNA.

As shown in FIG. 35, circular RNA was translated into protein in cells. In particular, circular RNA produced higher levels of protein having the correct molecular weight as compared to its linear RNA counterpart.

Example 39: Rolling Circle Translation of Synthetic Circular RNA Produced Discrete Protein Products in Cells This Example demonstrates discrete protein products were translated via rolling circle translation from synthetic circular RNA lacking a termination element (stop codon), e.g., having a stagger element in lieu of a termination element (stop codon), in cells. Additionally, this Example shows that circular RNA with a stagger element expressed more protein product having the correct molecular weight than its linear counterpart.

Circular RNAs were designed to include a nanoluciferase gene with a stagger element in place of a termination element (stop codon). Cells were transfected with vehicle: transfection reagent only; linear nLUC (SEQ ID NO:24): EMCV IRES, stagger element (2A sequence), 3× FLAG tagged nLuc sequences, and a stagger element (2A sequence); or circular nLUC (SEQ ID NO:24): EMCV IRES, stagger element (2A sequence), 3× FLAG tagged nLuc sequences, and a stagger element (2A sequence). As shown in the FIG. 36, circular RNA produced greater levels of protein having the correct molecular weight as compared to linear RNA.

After 24 hrs, cells were harvested by adding 100 μl of RIPA buffer. After centrifugation at 1400×g for 5 min, the supernatant was analyzed on a 10-20% gradient polyacrylamide/SDS gel.

After being electrotransferred to a nitrocellulose membrane using dry transfer method, the blot was incubated with an anti-FLAG antibody and anti-mouse IgG peroxidase. The blot was visualized with an ECL kit and western blot band intensity was measured by ImageJ.

Figure 36:
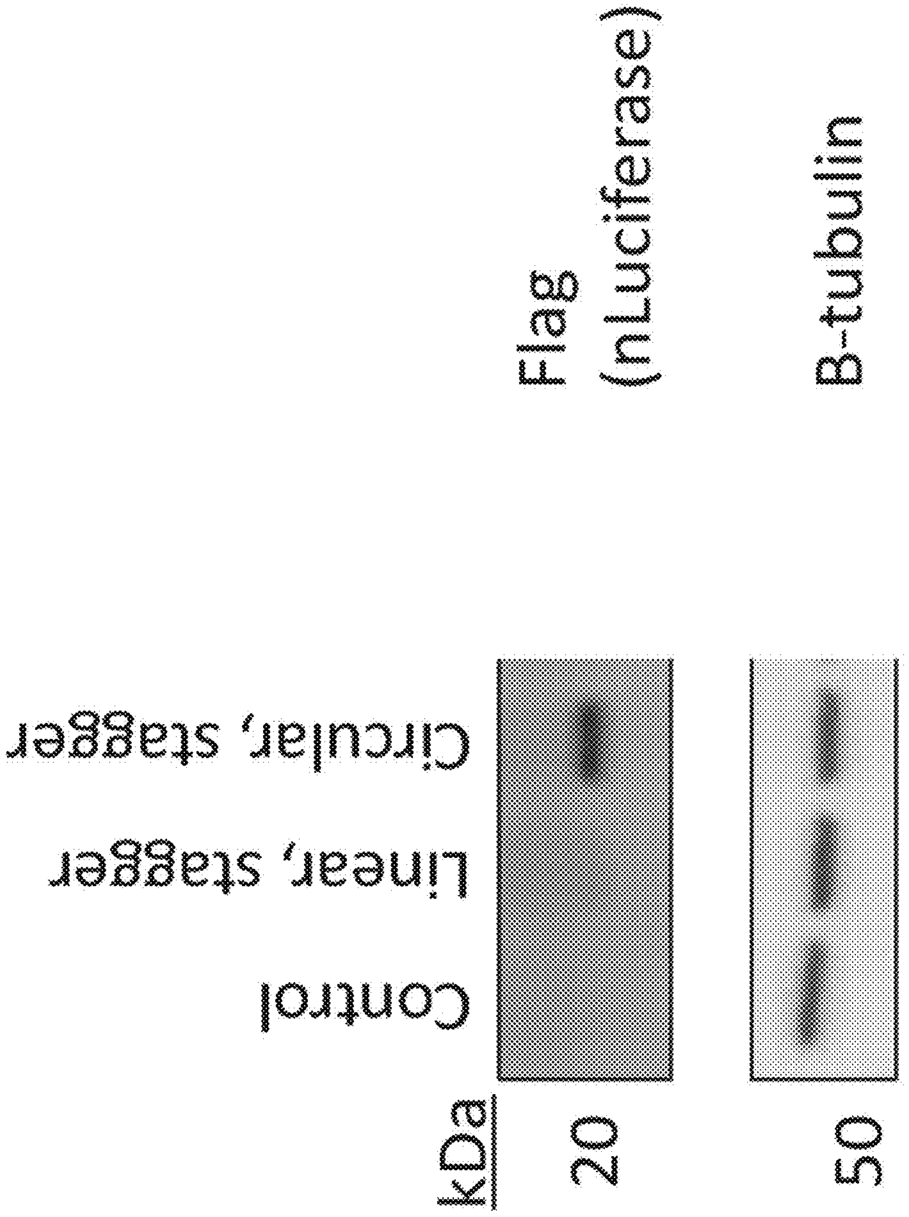
FIG. 36 is an image showing a protein blot of expression products from circular RNA or linear RNA.

As shown in FIG. 36, circular RNA translation product was detected in cells. In particular, circular RNA without a termination element (stop codon) produced higher levels of discrete protein product having the correct molecular weight than its linear RNA counterpart.

Example 40: Preparation of Circular RNA with a Quasi-Double Stranded, Helical Structure This Example demonstrates circular RNA possessed both quasi-double stranded and helical structure.

A non-naturally occurring circular RNA was engineered to adopt a quasi-double stranded, helical structure. A similar structure was shown to be involved in condensation of a naturally occurring circular RNA that possessed a uniquely long in vivo half-life (Griffin et al 2014, *J Virol.* 2014 July; 88(13):7402-11. doi: 10.1128/JVI.00443-14, Guedj et al, *Hepatology.* 2014 December; 60(6):1902-10. doi: 10.1002/hep.27357).

In this Example, circular RNA was designed to encode a EMCV IRES, Nluc tagged with 3×FLAG as ORF and stagger sequence (EMCV 2A 3×FLAG Nluc 2A no stop). To evaluate RNA secondary structure, thermodynamic RNA structure prediction tool (RNAfold) was used (Vienna RNA). Additionally, RNA tertiary structure was analyzed using an RNA modeling algorithm.

Figure 37:
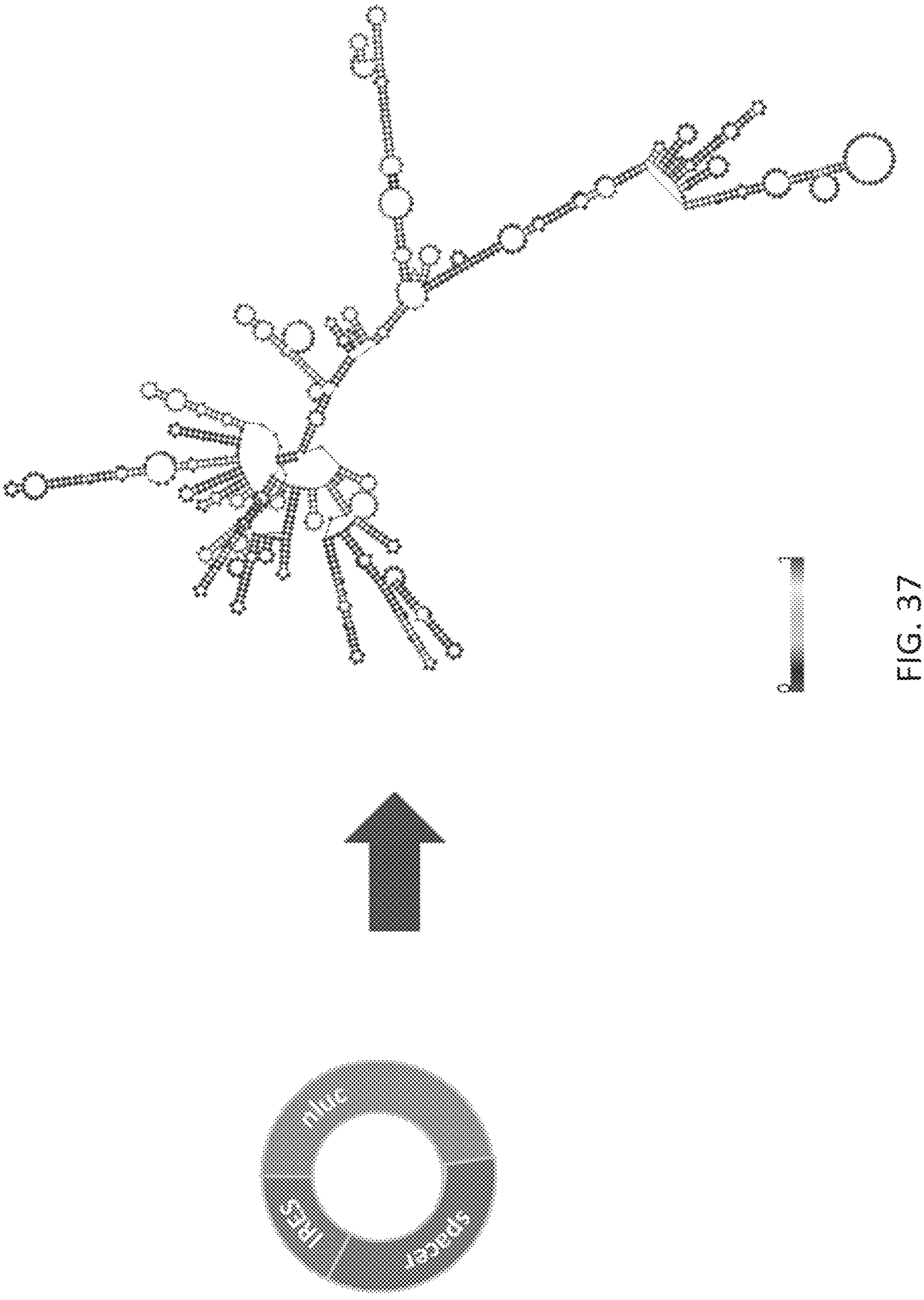
FIG. 37 shows predicted structure with a quasi-double stranded structure of an exemplary circular RNA.
Figure 38:
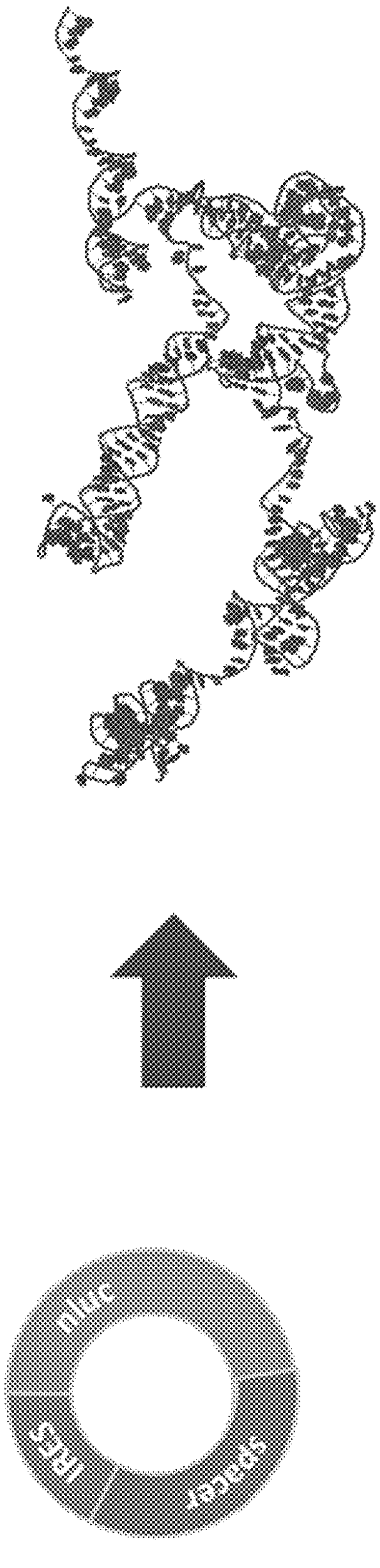
FIG. 38 shows predicted structure with a quasi-helical structure of an exemplary circular RNA.

As shown in FIGS. 37 and 38, circular RNA is modeled to have adopted a quasi-double stranded, helical structure.

Example 41: Preparation of Circular RNA with a Quasi-Helical Structure Linked with a Repetitive Sequence This Example demonstrates circular RNA can be designed to possess a quasi-helical structure linked with a repetitive sequence.

A non-naturally occurring circular RNA was engineered to adopt a quasi-helical structure linked with a repetitive sequence. A similar structure was shown to be involved in condensation of a naturally occurring circular RNA that possessed a uniquely long in vivo half-life (Griffin et al 2014, Guedj et al 2014).

In this Example, circular RNA was designed to encode a EMCV IRES, Nluc and spacer including a repetitive sequence (SEQ ID NO: 26). To evaluate RNA tertiary structure, an RNA modeling algorithm was used.

Figure 39:
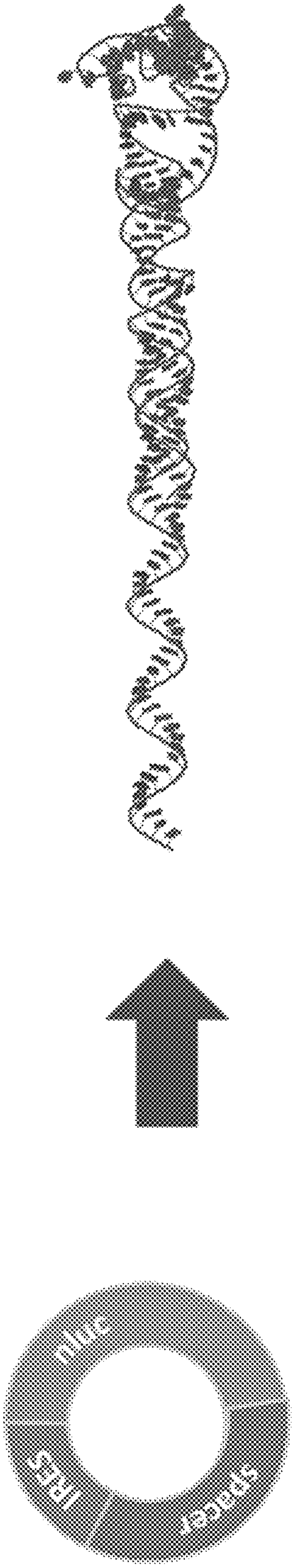
FIG. 39 shows predicted structure with a quasi-helical structure linked with a repetitive sequence of an exemplary circular RNA.

As shown in FIG. 39, circular RNA is modeled to have adopted a quasi-helical structure.

Example 42: Circularized RNA is Circular and not Concatemeric

This Example demonstrates circular RNA degradation by RNAse H produced nucleic acid degradation products consistent with a circular and not a concatemeric RNA.

RNA, when incubated with a ligase, can either not react or form an intra- or intermolecular bond, generating a circular (no free ends) or a concatemeric RNA, respectively. Treatment of each type of RNA with a complementary DNA primer and RNAse H, a nonspecific endonuclease that recognizes DNA/RNA duplexes, is expected to produce a unique number of degradation products of specific sizes depending on the starting RNA material.

As shown in the following Example, a ligated RNA was shown to be circular and not concatemeric based on the number and size of RNAs produced by RNAse H degradation.

Circular RNA and linear RNA containing EMCV T2A 3×FLAG-Nluc P2A were generated.

To test circularization status of the RNA (1299 nts), 0.05 pmole/μl of linear or circular RNA was incubated with 0.25 U/μl of RNAse H, an endoribonuclease that digests DNA/RNA duplexes, and 0.3 pmole/μl oligomer against 1037-1046 nts of RNA (CACCGCTCAGGACAATCCTT, SEQ ID NO: 55) at 37° C. for 20 min. After incubation, the reaction mixture was analyzed by 6% denaturing PAGE.

For the linear RNA used described above, it is expected that after binding of the DNA primer and subsequent cleavage by RNAse H two cleavage products are obtained of 1041 nt and 258 nt. A concatemer is expected to produce three cleavage products of 258, 1041 and 1299 nt. A circular is expected to produce a single 1299 nt cleavage product.

Figure 40:
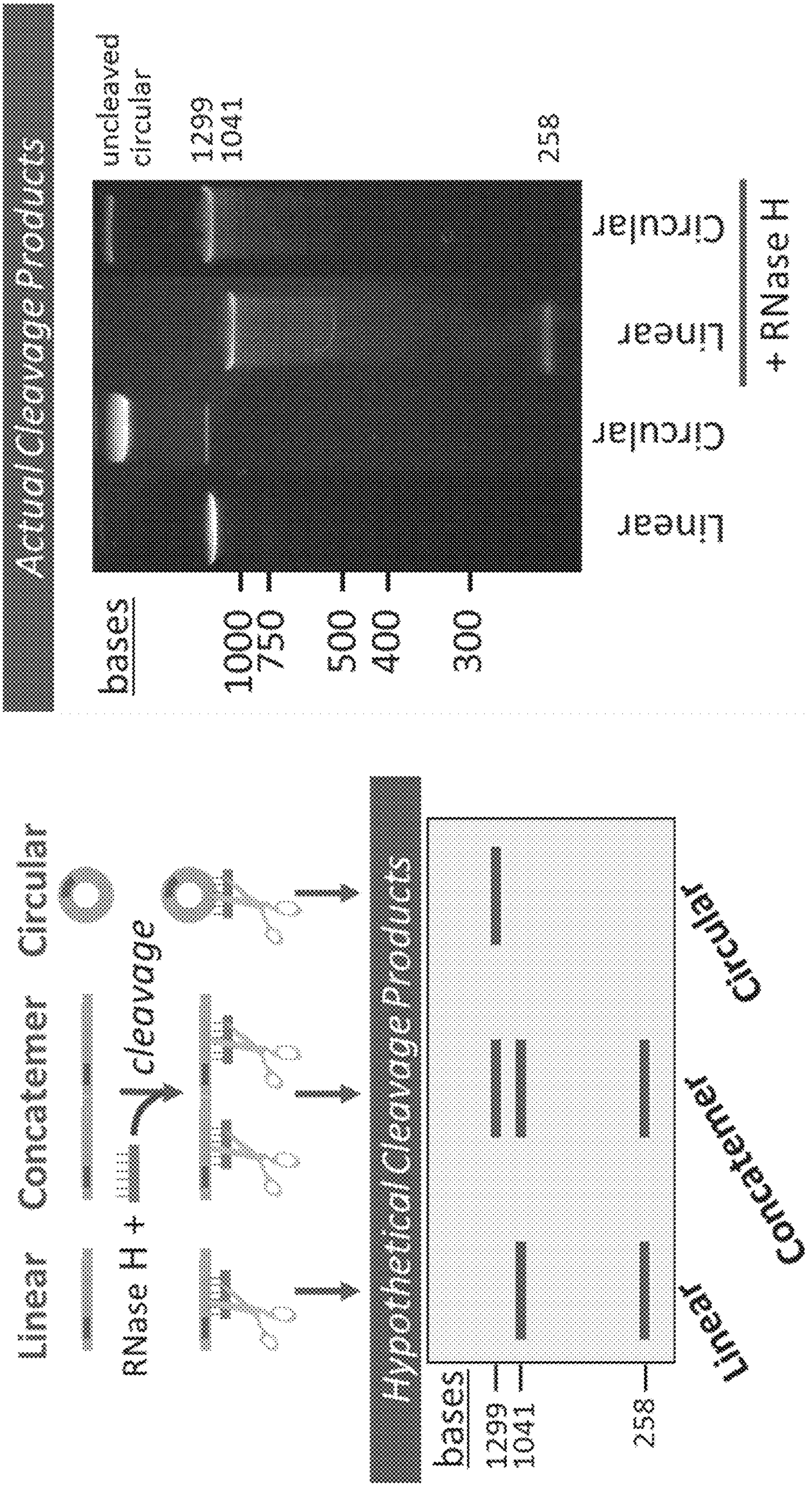
FIG. 40 demonstrates experimental data that degradation by RNAse H of an exemplary circular RNA produced nucleic acid degradation products consistent with a circular and not a concatemeric RNA.

The number of bands in the linear RNA lane incubated with RNAse endonuclease produced two bands of 1041 nt and 258 nt as expected, whereas a single band of 1299 nt was produced in the circular RNA lane (see FIG. 40), indicating that the circular RNA was in fact circular and not concatemeric.

Example 43: Preparation of Large circRNAs

This Example demonstrates the generation of circular polyribonucleotide from in the range of about 20 bases to about 6.2 Kb.

A non-naturally occurring circular RNA engineered to include one or more desirable properties was produced in a range of sizes depending on the desired function. As shown in the following Example, linear RNA of up to 6200 nt was circularized.

The plasmid pCDNA3.1/CAT (6.2 kb) was used here. Primers were designed to anneal to pCDNA3.1/CAT at regular intervals to generate DNA oligonucleotides corresponding to 500 nts, 1000 nts, 2000 nts, 4000 nts, 5000 nts and 6200 nts. In vitro transcription of the indicated DNA oligonucleotides was performed to generate linear RNA of the corresponding sizes. Circular RNAs were generated from these RNA oligonucleotides using splint DNA.

To measure circularization efficiency of RNA, 6 different sizes of linear RNA (500 nts, 1000 nts, 2000 nts, 4000 nts, 5000 nts and 6200 nts) were generated. They were circularized using a DNA splint and T4 DNA ligase 2. As a control, one reaction was performed without T4 RNA ligase. Half of the circularized sample was treated with RNAse R to remove linear RNA.

Figure 41:
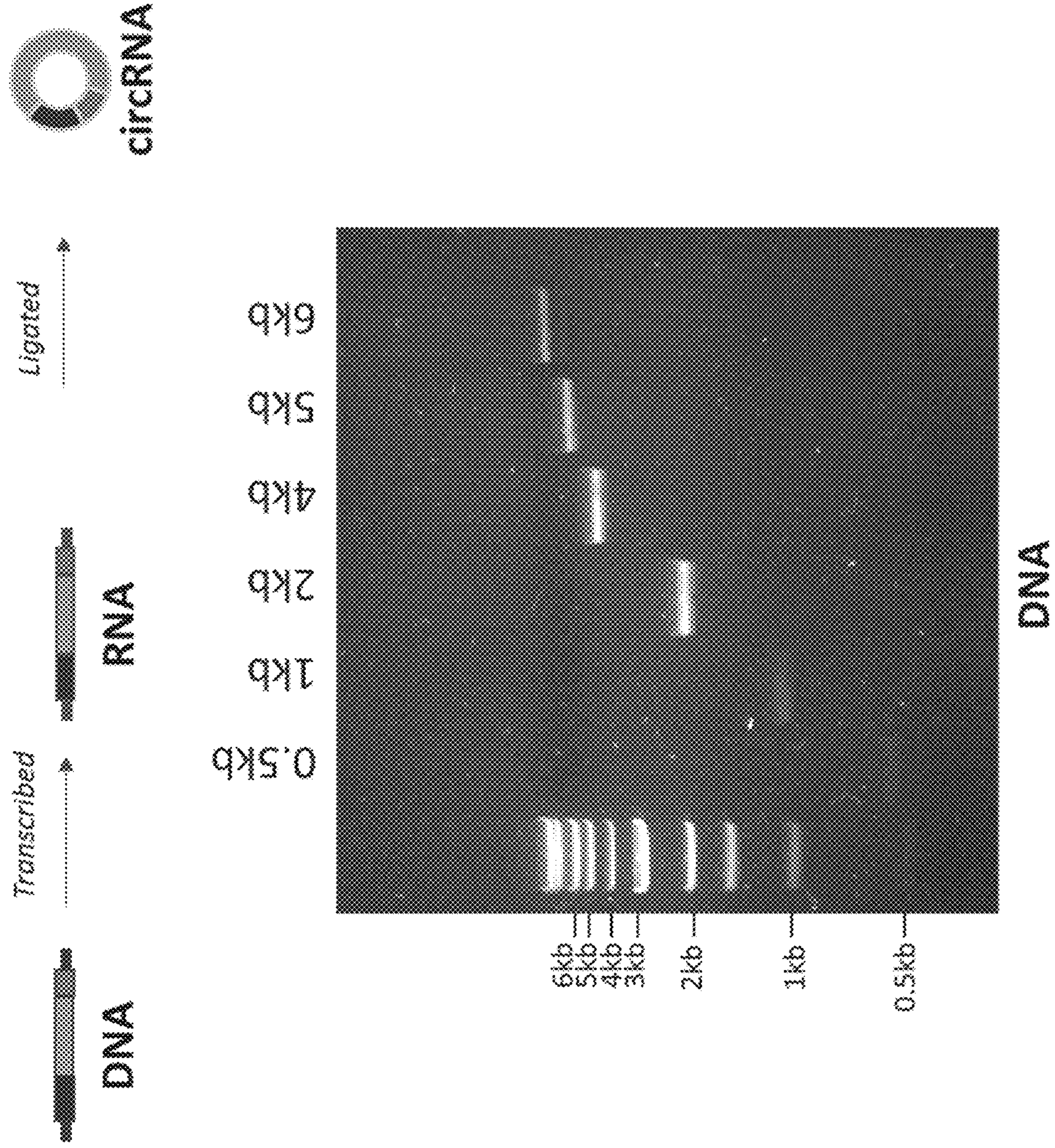
FIG. 41 shows an electrophoresis image of the different lengths of DNA that were generated for the creation of a wide variety of RNA lengths.
Figure 42:
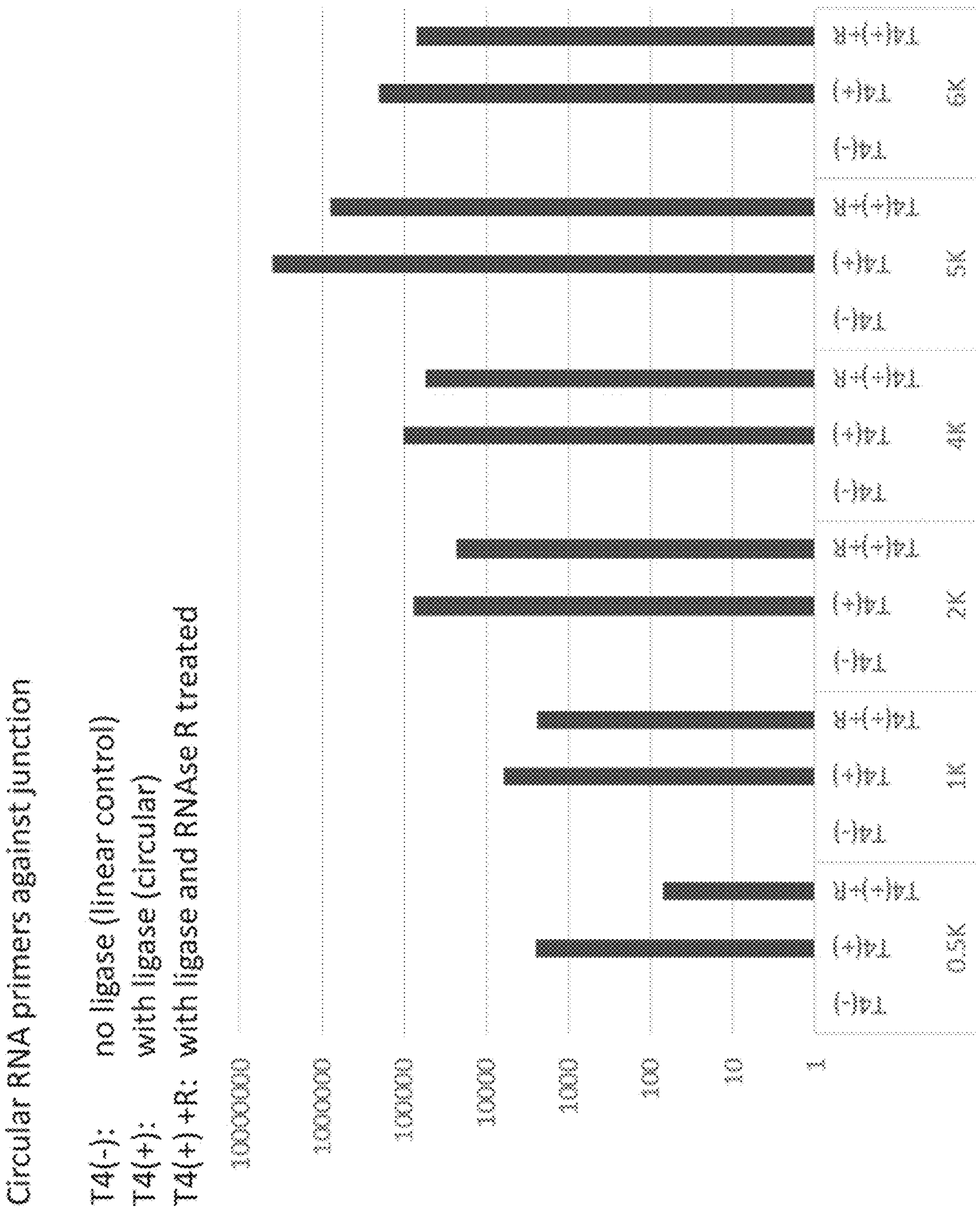
FIG. 42 shows experimental data that confirmed the circularization of RNAs using RNAse R treatment and qPCR analysis against circular junctions of a wide variety of lengths.

To monitor circularization efficiency, each sample was analyzed using qPCR. As shown in FIG. 41, circular RNA was generated from a wide variety of DNA of different lengths. As shown in FIG. 42, circularization of RNA was confirmed using RNAse R treatment and qPCR analysis against circular junctions. This Example demonstrates circular RNA production for a variety of lengths.

Example 44: Circular RNA Engineered with a Protein Binding Site

This Example demonstrates generation of a circular RNA with a protein binding site.

Figure 45:
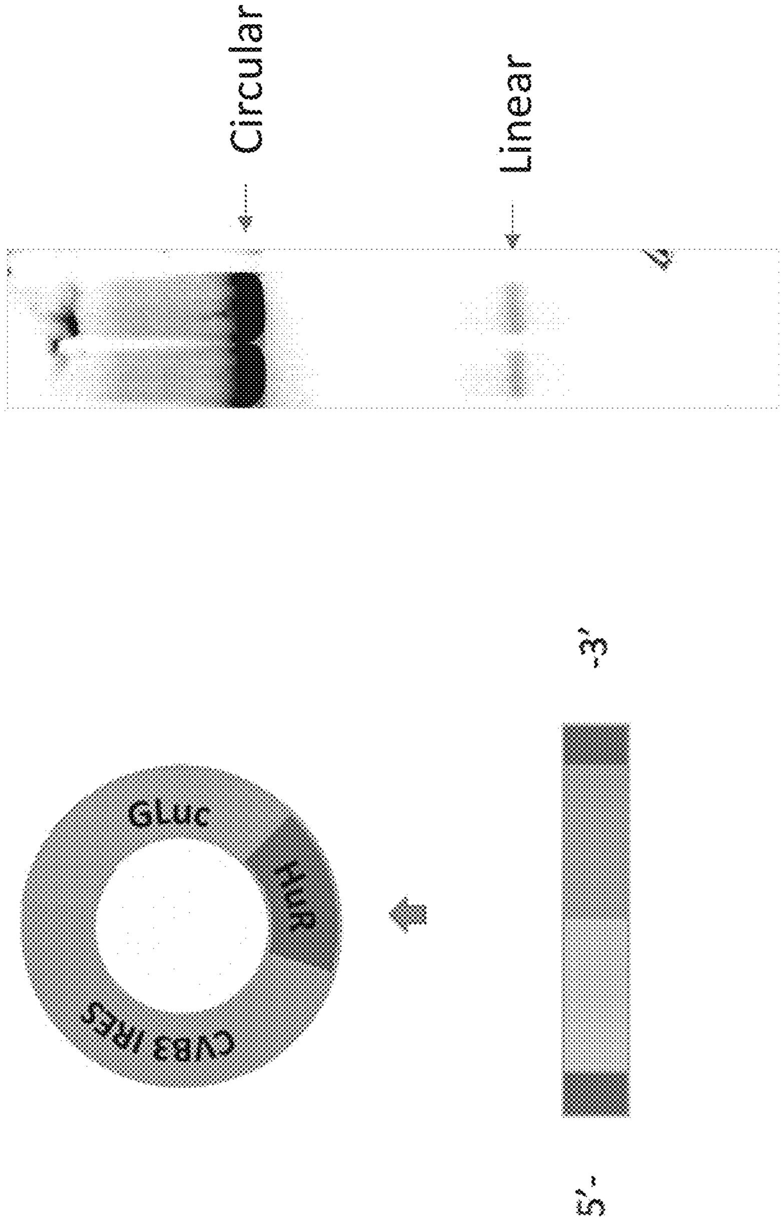
FIG. 45 shows generation of exemplary circular RNA with a protein binding site.

In this Example, one circular RNA is designed to include CVB3 IRES (SEQ ID NO:56), and an ORF encoding *Gaussia* luciferase (Gluc) (SEQ ID NO:57) followed by at least one protein binding site. For a specific example, a HuR binding sequence (SEQ ID NO:52) from Sindbis virus 3'UTR is used to test the effect of protein binding to circular RNA immunogenicity. HuR binding sequence comprises two elements, URE (U-rich element; SEQ ID NO: 50) and CSE (Conserved sequence element; SEQ ID NO: 51). Circular RNA without HuR binding sequence or with URE is used as a control. Part of the *Anabaena* autocatalytic intron and exon sequences are located prior to the CVB3 IRES (SEQ ID NO:56). The circular RNAs are generated in vitro as described. As shown in FIG. 45, circular RNA was generated to contain an HuR binding site.

To monitor the effect of RNA binding protein on circular RNA immunogenicity, cells are plated into each well of a 96 well plate. After 1 day, 500 ng of circular RNA is transfected into each well using a lipid-based transfection reagent (Invitrogen). Translation efficiency/RNA stability/immunogenicity are monitored daily, up to 72 hrs. Media is harvested to monitor Gluc activity. Cell lysate for measuring RNA level is prepared with a kit that allows measurements of relative gene expression by real-time RT-PCR (Invitrogen).

Translation efficiency is monitored by measuring Gluc activity with *Gaussia* luciferase flash assay kit according to the manufacturer's instruction (Pierce).

For qRT-PCR analysis, cDNA is generated with cell lysate preparation kit according to manufacturer's instruction (Invitrogen). qRT-PCR analysis is performed in triplicate using a PCR master mix (Brilliant II SYBR Green qRT-PCR Master Mix) and a PCR cycler (LightCycler 480). Circular RNA stability is measured by primers against Nluc. mRNA levels for well-known innate immunity regulators such as RIG-I, MDA5, OAS, OASL, and PKR are quantified and normalized to actin values.

Example 45: Preparation of Circular RNA with Regulatory Nucleic Acid Sites

This Example demonstrates in vitro production of circular RNA with a regulatory RNA binding site.

Different cell types possess unique nucleic acid regulatory machinery to target specific RNA sequences. Encoding these specific sequences in a circular RNA could confer unique properties in different cell types. As shown in the following Example, circular RNA was engineered to encode a microRNA binding site.

In this Example, circular RNA included a sequence encoding a WT EMCV IRES, a mir692 microRNA binding site (GAGGUGCUCAAAGAGAU (SEQ ID NO: 112)), and two spacer elements flanking the IRES-ORF.

The circular RNA was generated in vitro. Unmodified linear RNA was in vitro transcribed from a DNA template including all the motifs listed above, in addition to the T7 RNA polymerase promoter to drive transcription. Transcribed RNA was purified with an RNA cleanup kit (New England Biolabs, T2050), treated with RNA 5'-phosphohydrolase (RppH) (New England Biolabs, M0356) following the manufacturer's instructions, and purified again with an RNA purification column. RppH treated RNA was circularized using a splint DNA (GGCTATTCCCAATAGCCGTT (SEQ ID NO: 113)) and T4 RNA ligase 2 (New England Biolabs, M0239). Circular RNA was Urea-PAGE purified (FIG. 43), eluted in a buffer (0.5M Sodium Acetate, 0.1% SDS, 1 mM EDTA), ethanol precipitated and resuspended in RNase free water.

Figure 43:
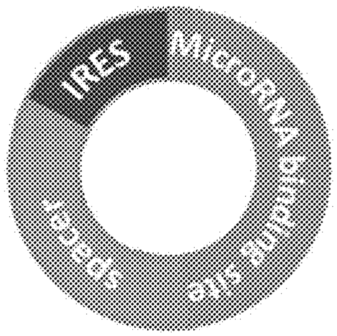
FIG. 43 shows generation of exemplary circular RNA with a miRNA binding site (SEQ ID NOS 112 and 129, respectively, in order of appearance).
Figure 43:
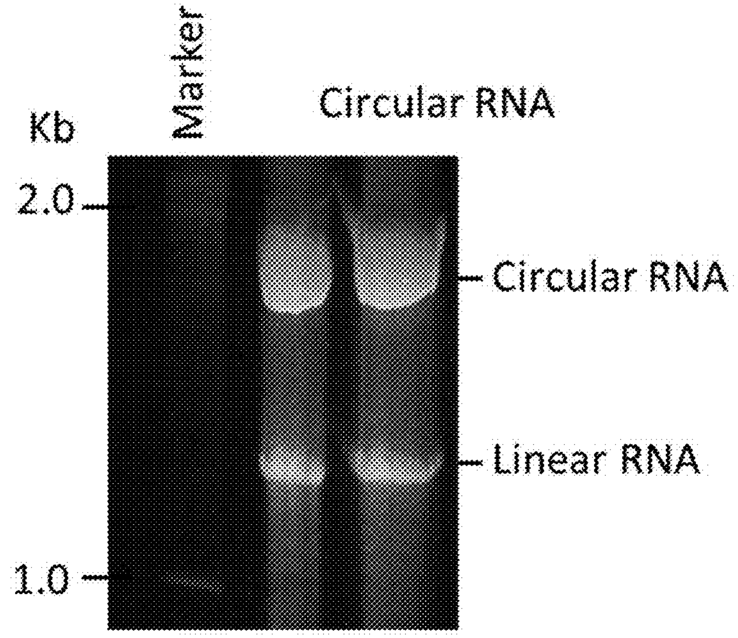

As shown in FIG. 43, circular RNA was generated with a miRNA binding site.

Example 46: Self-Splicing of Circular RNA

This example demonstrates the ability to produce a circular RNA by self-splicing.

For this Example, circular RNAs included a CVB3 IRES, an ORF encoding *Gaussia* Luciferase (GLuc), and two spacer elements flanking the IRES-ORF.

The circular RNA was generated in vitro. Unmodified linear RNA was in vitro transcribed from a DNA template including all the motifs listed above. In vitro transcription reactions included 1 μg of template DNA T7 RNA polymerase promoter, 10×T7 reaction buffer, 7.5 mM ATP, 7.5 mM CTP, 7.5 mM GTP, 7.5 mM UTP, 10 mM DTT, 40 U RNase Inhibitor, and T7 enzyme. Transcription was carried out at 37° C. for 4 h. Transcribed RNA was DNase treated with 1 U of DNase I at 37° C. for 15 min. To favor circularization by self splicing, additional GTP was added to a final concentration of 2 mM, incubated at 55° C. for 15 min. RNA was then column purified and visualized by UREA-PAGE.

Figure 44:
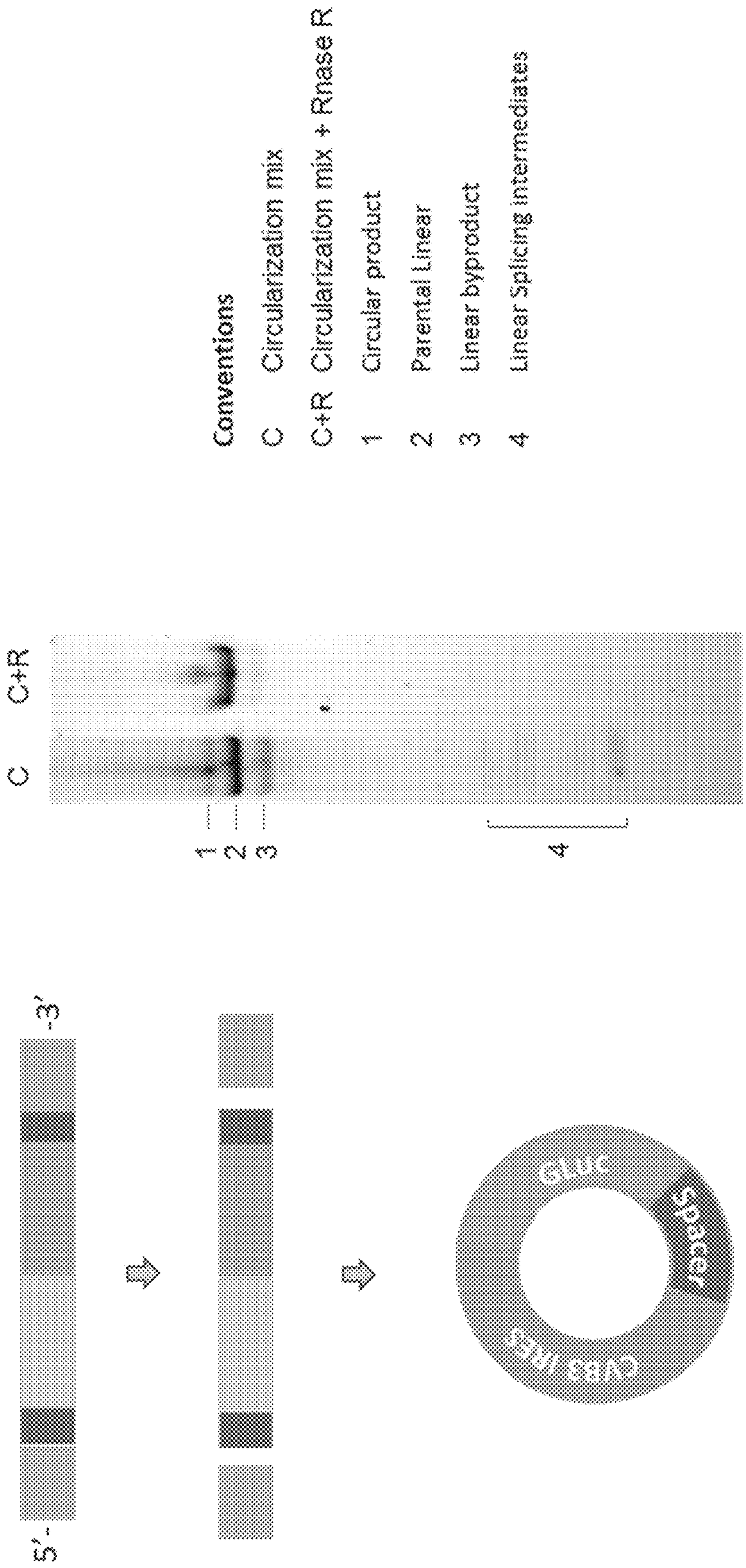
FIG. 44 shows generation of exemplary circular RNA by self-splicing.

FIG. 44 shows circular RNA generated by self-splicing.

Example 47: Circular RNA with a Splicing Element Comprising an Encryptogen

This Example demonstrates a circular RNA engineered to have reduced immunogenicity.

For this Example, a circular RNAs included a CVB3 IRES, an ORF encoding *Gaussia* Luciferase (GLuc), and two spacer elements flanking the IRES-ORF, these two spacer elements comprise a splicing element that are part of the *Anabaena* autocatalytic intron and exon sequences (SEQ ID NOS 59 and 135).

The circular RNA is generated in vitro.

In this Example, the level of innate immune response genes is monitored in cells by plating cells into each well of a 12 well plate. After 1 day, 1 μg of linear or circular RNA is transfected into each well using a lipid-based transfection reagent (Invitrogen). Twenty-four hours after transfection, total RNA is isolated from cells using a phenol-based extraction reagent (Invitrogen). Total RNA (500 ng) is subjected to reverse transcription to generate cDNA. qRT-PCR analysis is performed using a dye-based quantitative PCR mix (BioRad).

qRT-PCR levels of immune related genes from BJ cells transfected with circular RNA comprising a splicing element are expected to show a reduction of RIG-I, MDA5, PKR and IFN-beta as compared to linear RNA transfected cells. Thus, induction of immunogenic related genes in recipient cells is expected to be reduced in circular RNA transfected cells, as compared to linear RNA transfected cells.

Example 48: Persistence of Circular RNA During Cell Division

This Example demonstrates the persistence of circular polyribonucleotide during cell division. A non-naturally occurring circular RNA engineered to include one or more desirable properties may persist in cells through cell division without being degraded. As shown in the following Example, circular RNA expressing *Gaussia* luciferase (GLuc) was monitored over 72 h days in HeLa cells.

In this Example, a 1307 nt circular RNA included a CVB3 IRES, an ORF encoding *Gaussia* Luciferase (GLuc), and two spacer elements flanking the IRES-ORF.

Persistence of circular RNA over cell division was monitored in HeLa cells. 5000 cells/well in a 96-well plate were suspension transfected with circular RNA. Bright cell imaging was performed in a Avos imager (ThermoFisher) and cell counts were performed using luminescent cell viability assay (Promega) at 0 h, 24 h, 48 h, 72 h, and 96 h. *Gaussia* Luciferase enzyme activity was monitored daily as measure of protein expression and gLuc expression was monitored daily in supernatant removed from the wells every 24 h by using the *Gaussia* Luciferase activity assay (Thermo Scientific Pierce). 50 μl of 1× Gluc substrate was added to 5 μl of plasma to carry out the Gluc luciferase activity assay. Plates were read right after mixing on a luminometer instrument (Promega).

Figure 46:
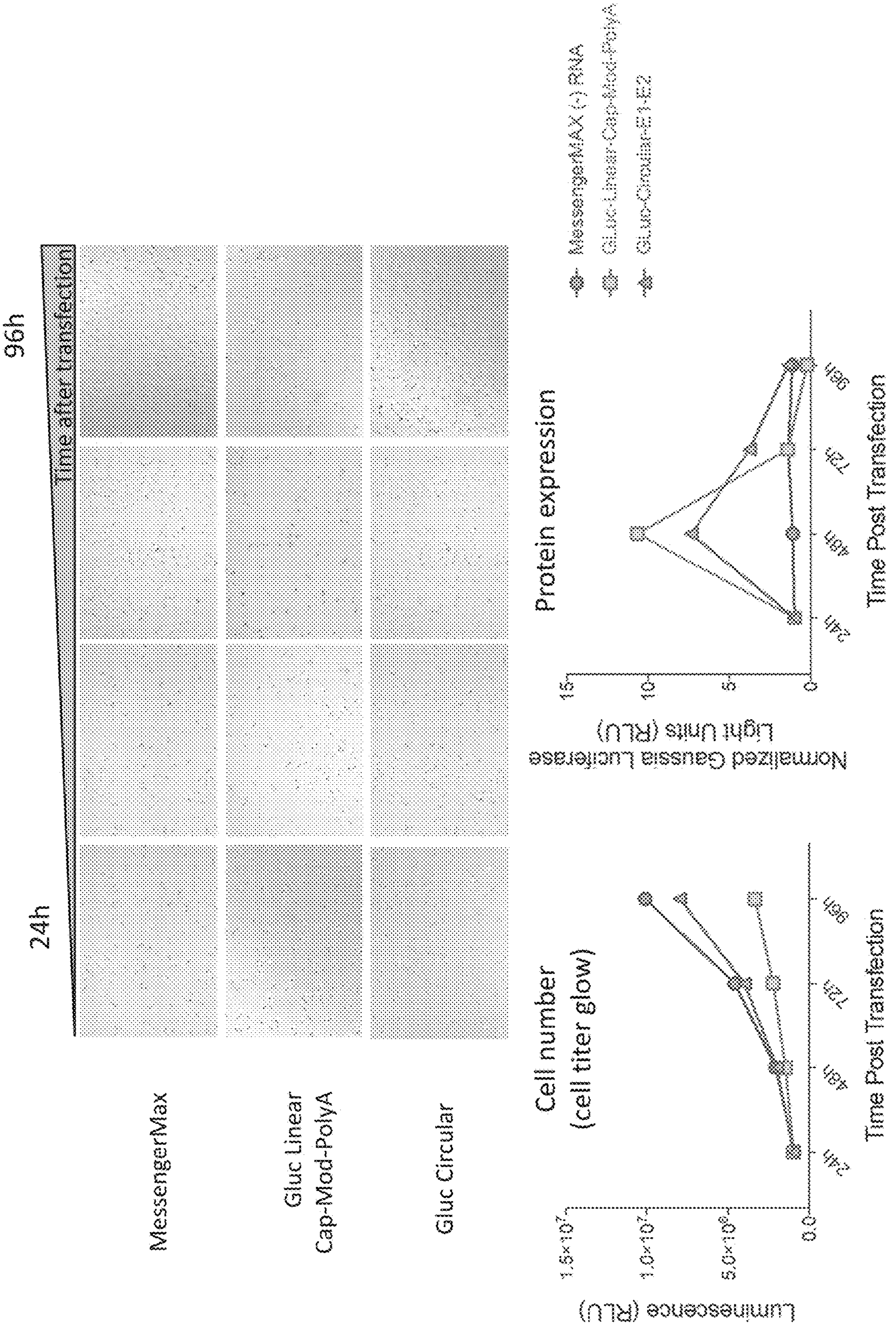
FIG. 46 shows experimental data demonstrating the higher stability of circular RNA in a dividing cell as compared to linear controls.

Expression of protein from circular RNA was detected at higher levels than linear RNA in dividing cells (FIG. 46). Cells with circular RNA had higher cell division rates as compared to linear RNA at all timepoints measured. This Example demonstrates increased detection of circular RNA during cell division than its linear RNA counterpart.

Example 49: Rolling Circle Translation Produced a Plurality of Expression Sequences This Example demonstrates the ability of circular RNA to express multiple proteins from a single construct. Additionally, this Example demonstrates rolling circle translation of circular RNA encoding multiple ORFs. This Example further demonstrates expression of two proteins from a single construct.

One circular RNA (mtEMCV T2A 3×FLAG-GFP F2A 3×FLAG-Nluc P2A IS spacer) was designed for rolling circle translation to include EMCV IRES (SEQ ID NO:58), and an ORF encoding GFP with 3×FLAG tag and an ORF encoding Nanoluciferase (Nluc) with 3×FLAG tag. Stagger elements (2A) were flanking the GFP and Nluc ORFs. Another circular RNA was designed similarly, but included a triple stop codon inbetween the Nluc ORF and the spacer. Part of the *Anabaena* autocatalytic intron and exon sequences were included prior to the EMCV IRES. The circular RNAs were generated either in vitro as described.

The expression of proteins from circular RNA was monitored either in vitro or in cells. For in vitro analysis, the circular RNAs were incubated for 3 h in rabbit reticulocyte lysate (Promega, Fitchburg, WI, USA) at 30° C. The final composition of the reaction mixture included 70% rabbit reticulocyte lysate, 20 μM complete amino acids, and 0.8 U/μL, RNase inhibitor (Toyobo, Osaka, Japan).

After incubation, hemoglobin protein was removed by adding acetic acid (0.32 μl) and water (300 μl) to the reaction mixture (16 μl) and centrifuging at 20,817×g for 10 min at 15° C. The supernatant was removed and the pellet was dissolved in 2×SDS sample buffer and incubated at 70° C. for 15 min. After centrifugation at 1400×g for 5 min, the supernatant was analyzed on a 10-20% gradient polyacrylamide/SDS gel.

For analysis in cells, cells were plated into each well of a 12 well plate to monitor translation efficiency of circular RNA in cells. After 1 day, 500 ng of circular RNA was transfected into each well using a lipid-based transfection reagent (Invitrogen). 48 hours after transfection, cells were harvested by adding 200 μl of RIPA buffer onto each well. Next, 10 μg of cell lysate proteins were analyzed on 10-20% gradient polyacrylamide/SDS gel.

After electrotransfer of samples from reticulocyte lysate and cells to a nitrocellulose membrane using dry transfer method, the blot was incubated with an anti-FLAG antibody and anti-mouse IgG peroxidase. As a loading control, anti-beta tubulin antibody was used. The blot was visualized with an enhanced chemiluminescent (ECL) kit. Western blot band intensity was measured by ImageJ.

Figure 47:
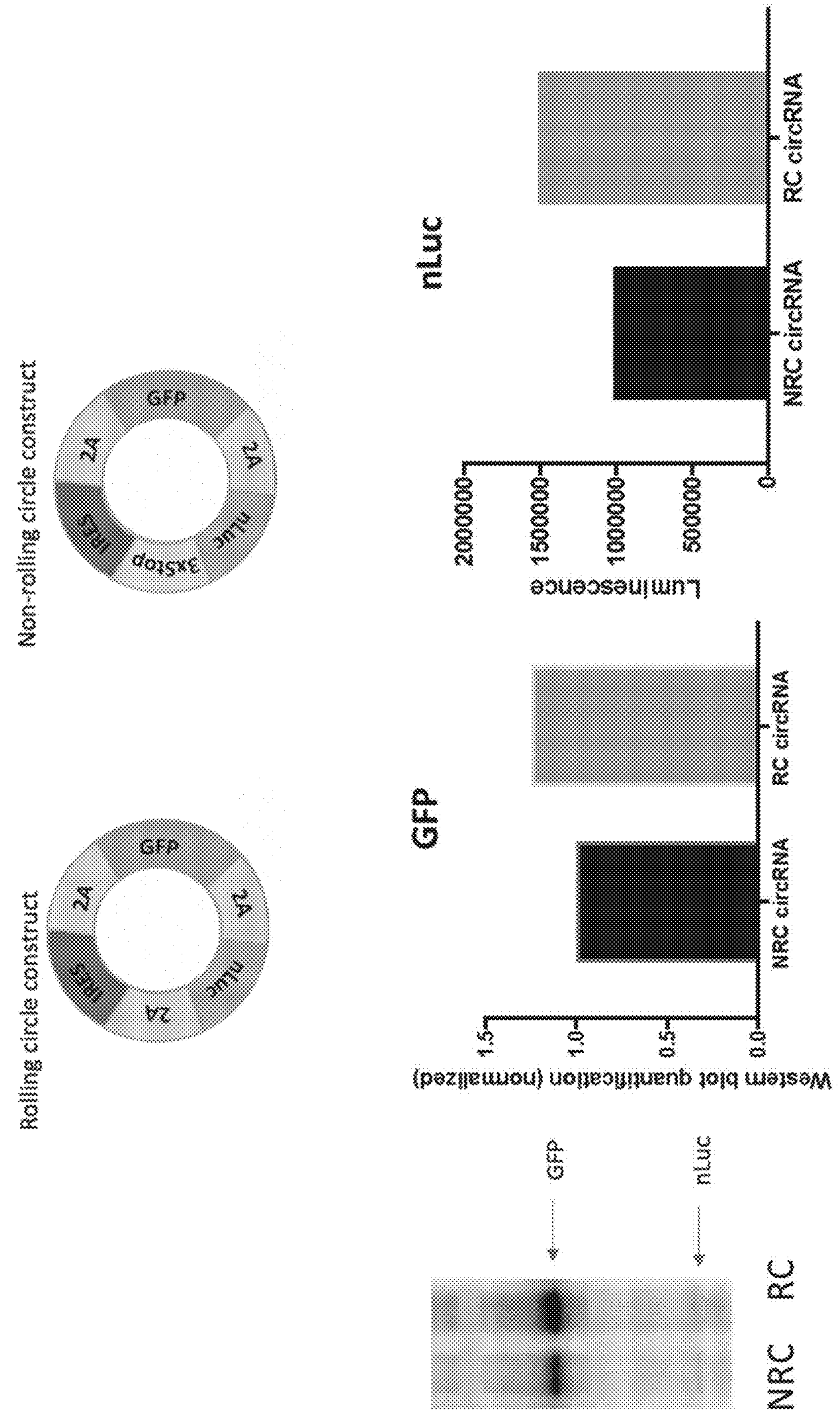
FIG. 47 shows experimental data demonstrating the protein expression from exemplary circular RNAs with a plurality of expression sequences and the rolling circle translation of exemplary circular RNAs with multiple expression sequences.

As shown in FIG. 47, the circular RNA encoding GFP and nLuc produced 2 protein products. Translation from the circular RNA without the triple stop generated more of both protein products than circular RNA with the triple stop codon. Finally, both circular RNA with and without the triple stop expressed proteins at 1/3.24 and 1/3.37 ratios, respectively.

Example 50: Circular RNA Shows Reduced Toxicity Compared to Linear RNA

This Example demonstrates that circular RNA is less toxic than linear RNA.

For this Example, the circular RNA includes an EMCV IRES, an ORF encoding NanoLuc with a 3×FLAG tag and flanked on either side by stagger elements (2A) and a termination element (Stop codon). The circular RNA was generated in vitro and purified as described herein. The linear RNA used in this Example was cap-modified-poly A tailed RNA or cap-unmodified-poly A tailed RNA encoding nLuc with globin UTRs.

To monitor toxicity of RNA in cells, BJ human fibroblast cells were plated onto each well of a 96 well plate. 50 ng of either circular or cap-modified-polyA tailed linear RNA were transfected after zero, forty-eight, and seventy-two hours, using a lipid-based transfection reagent (ThermoFisher) following the manufacturer's recommendations. Bright cell imaging was performed in a Avos imager (ThermoFisher) at 96 h. Total cells per condition were analyzed using ImageJ.

Figure 48:
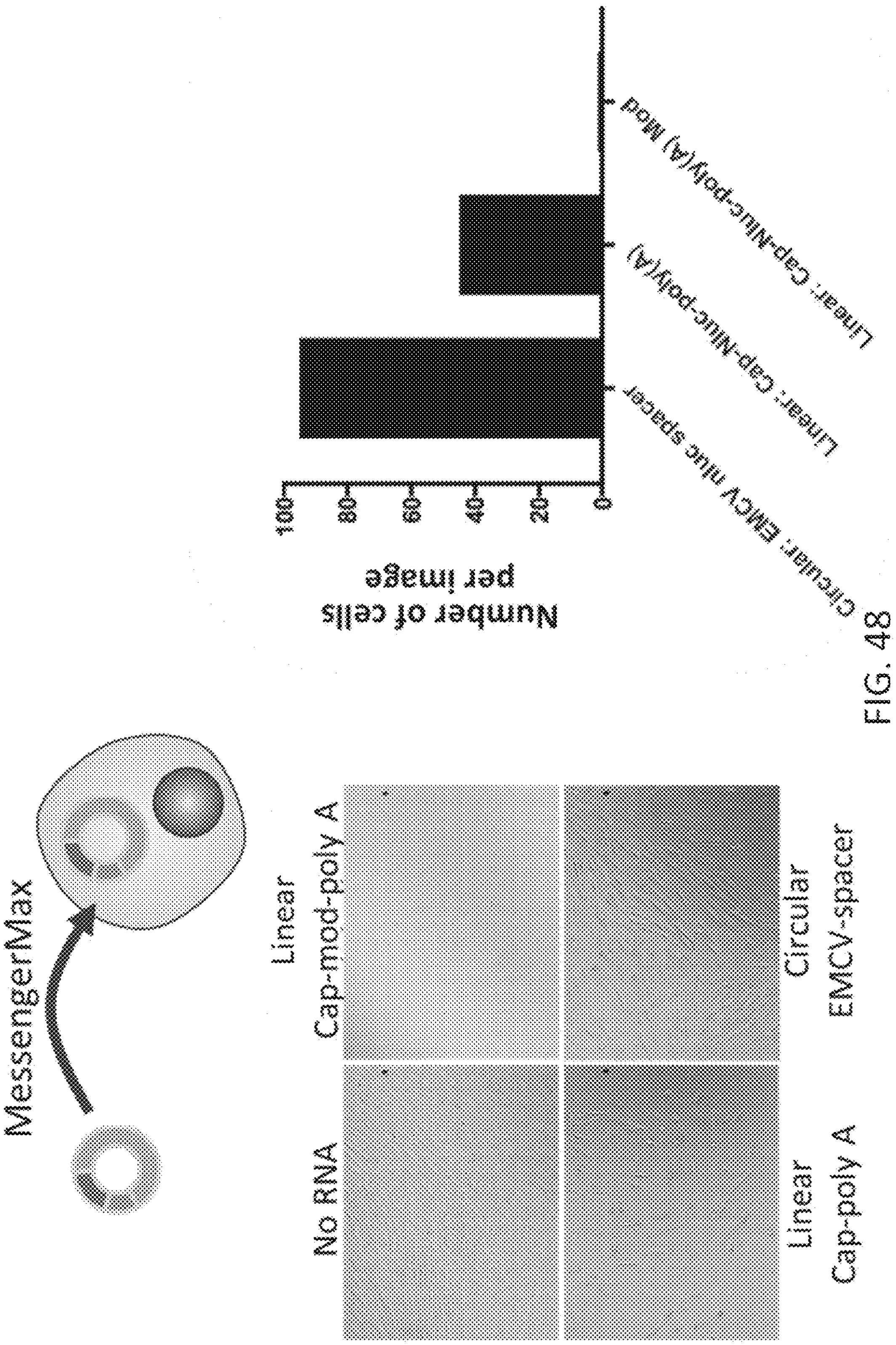
FIG. 48 shows experimental data demonstrating the reduced toxicity to transfected cells of an exemplary circular RNA as compared to linear control.

As shown in FIG. 48, transfection of circular RNA demonstrated reduced toxicity compared to linear RNA.

Example 51: Expression Under Stress Conditions

This Example demonstrates that circular RNA expressed better under stress conditions than linear RNA.

For this Example, the circular RNAs includes an EMCV IRES, an ORF encoding NanoLuc with a 3×FLAG tag, and flanked by stagger elements. The circular RNA was generated in vitro and purified as described. The linear RNA used in this Example was capped-poly A tailed RNA encoding nLuc with globin UTRs.

To monitor expression of *Gaussia* Luciferase from cells, BJ human fibroblast cells were plated into each well of a 96 well plate. 50 ng of either circular or cap-polyA tailed linear RNA was transfected after zero, forty-eight, and seventy-two hours, using a lipid-based transfection reagent following the manufacturer's recommendations. *Gaussia* Luciferase enzyme activity was monitored daily as measure of protein expression and gLuc expression was monitored daily in supernatant removed from the wells every 24 h by using the *Gaussia* Luciferase activity assay (Thermo Scientific Pierce). 50 μl of 1×Gluc substrate was added to 5 μl of plasma to carry out the Gluc luciferase activity assay. Plates were read right after mixing on a luminometer instrument (Promega).

Figure 49:
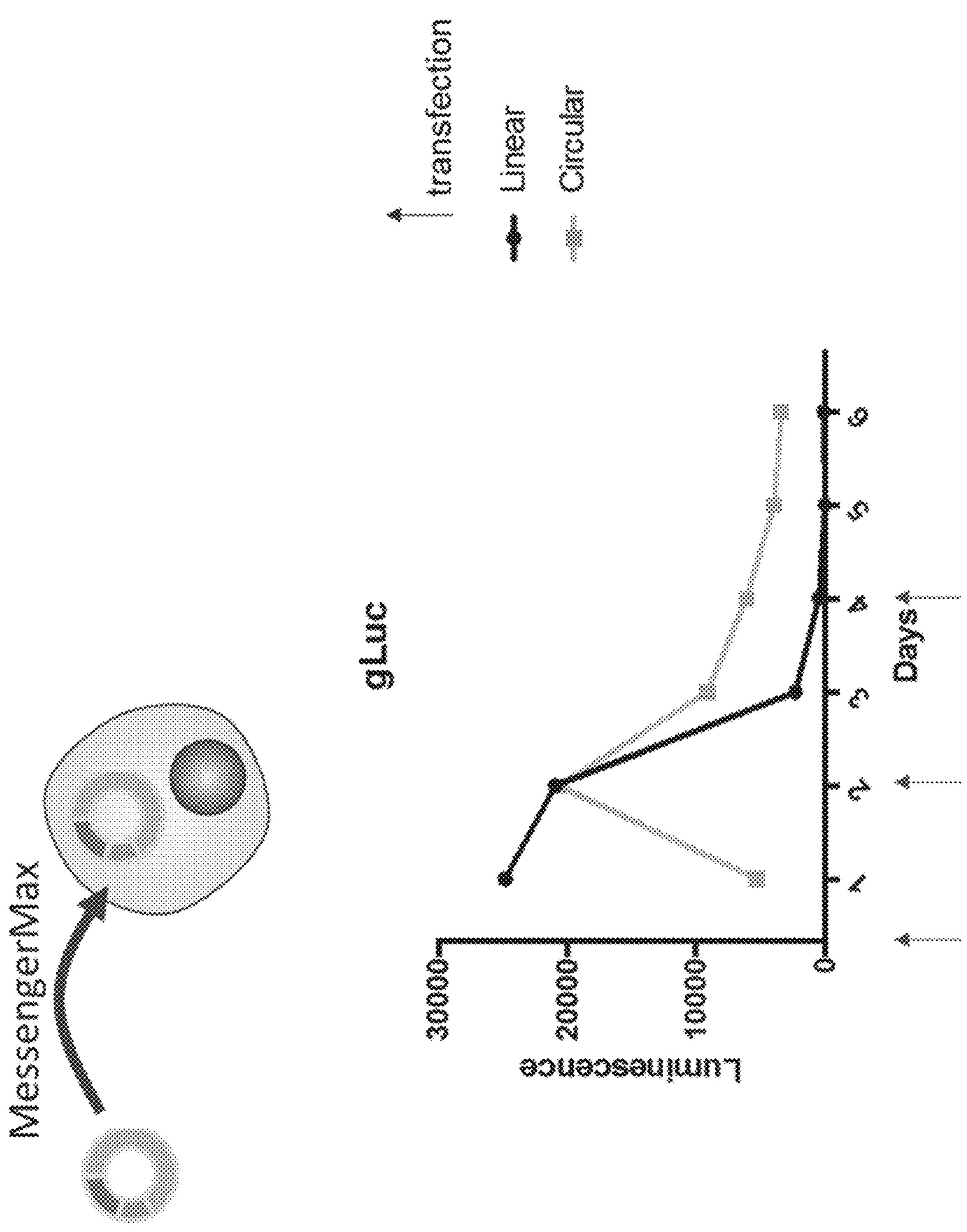
FIG. 49 shows that exemplary circular RNA was translated at a higher level as compared to linear RNA under stress condition.

As shown in FIG. 49, circular RNA was translated at a higher level as compared to linear RNA under stress condition.

Example 52: Riboswitches for Selective Expression

This Example demonstrates the ability to control protein expression from circular RNA.

Figure 50:
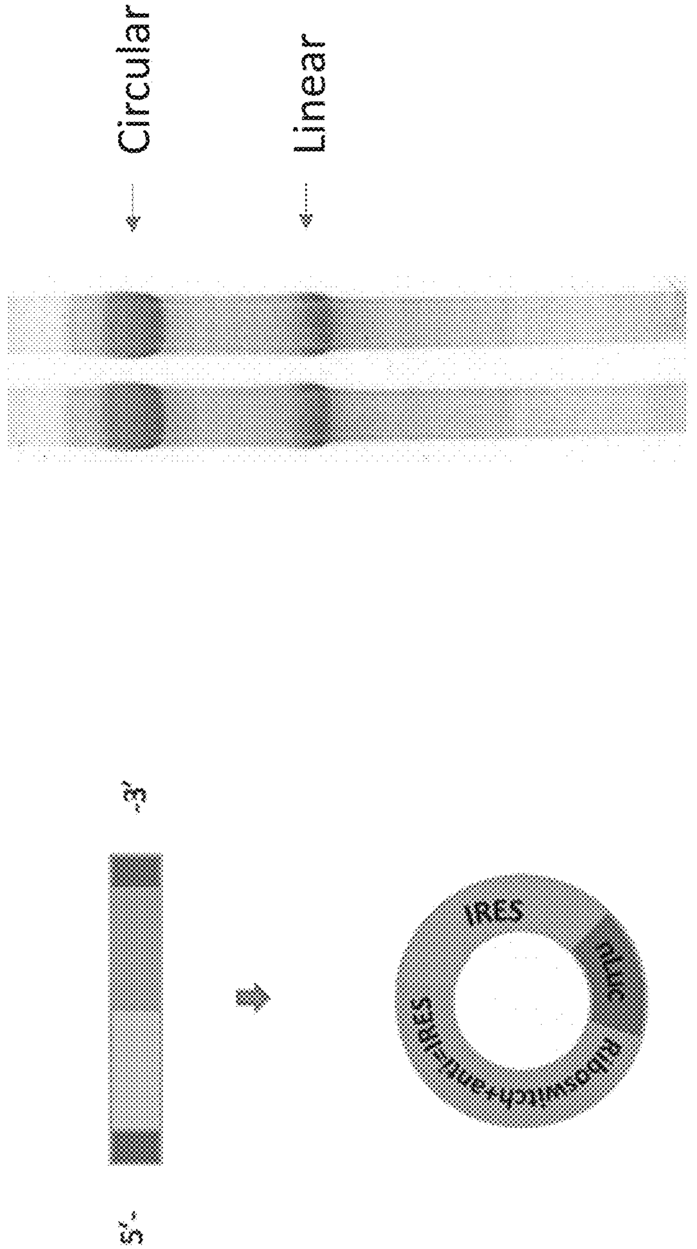
FIG. 50 shows generation of circular RNAs with a riboswitch.

For this Example, circular RNAs was designed to include a synthetic riboswitch (SEQ ID NO: 60) regulating the expression of the ORF encoding NanoLuc, see FIG. 50. The circular RNA was generated in vitro. Unmodified linear RNA was in vitro transcribed from a DNA template including all the motifs listed above, in addition the T7 RNA polymerase promoter to drive transcription. Transcribed RNA was purified with an RNA cleanup kit (New England Biolabs, T2050), treated with RNA 5'-phosphohydrolase (RppH) (New England Biolabs, M0356) following the manufacturer's instructions, and purified again with an RNA purification column. RppH treated RNA was circularized using a splint DNA (CCGTTGTGGTCTCCCAGA-TAAACAGTATTTTGTCC (SEQ ID NO: 114)) and T4 RNA ligase 2 (New England Biolabs, M0239). Circular RNA was Urea-PAGE purified (FIG. 50).

Theophylline or Tetracycline induce the activation of its specific riboswitch, resulting in an off-switch of gene expression (as described by Auslander et al Mol Biosyst. 2010 May; 6(5):807-14 and Ogawa et al, RNA. 2011 March; 17(3):478-88. doi: 10.1261/rna.2433111. Epub 2011 Jan. 11). It is expected that the riboswitch controls GFP or NLuc expression from the circular RNA. Thus, no GFP or NLuc expression is expected after the addition of theophylline or tetracycline.

The efficiency of the riboswitch is tested in a cell-free translation system and in HeLa cells. Cell-free translation is carried out by using a cell-free translation kit (Promega, L4140) following manufacturer's recommendations and measuring luminescence with a luminometer instrument (Promega) for the NLuc ORF and a cell imaging multi-mode reader (BioTek) for the GFP ORF.

For cellular assays, HeLa cells/well are transfected with 1 nM of the described circular RNA encoding GFP or NLuc under the control of either the theophylline or the tetracycline dependent synthetic riboswitch (first PCR forward primer for theoN5, ATACCAGCCGAAAGGCCCTTGGCAGAGAGGTCT-GAAAAGACCTCTGCTGACTATGTGATCTTAT TAAAATTAGG (SEQ ID NO: 115), second PCR forward primer for theoN5, GAAATTAATACGACTCACTATAGG-GAGACCACAACGGTTTCCCTCCTC-TATACCAGCCGAAAGG CCCTTGGCAG (SEQ ID NO: 116); first PCR forward primer for tc-N5, ACATACCAGAT-TTCGATCTGGAGAGGTGAAGAATACGAC-CACCTAGAGGTCTGAAAAGACCTCT GCTGAC-TATGTGATC (SEQ ID NO: 117), second PCR forward primer for tc-N5, GAAATTAATACGACTCACTATAGG-GAGACCACAACGGTTTCCCTCCTCTAAAACAT-ACCAGATT TCGATC (SEQ ID NO: 118)) to assess selective expression. Lipid-based transfection reagent is used according to the manufacturer's recommendations.

After 24 hr of culture at 37° C. and 5% CO2, cells are treated with and without theophylline or tetracycline, depending on the riboswitch encoded in the circular RNA, with concentrations ranging from 1 nM-3 mM. After 24 hrs of continuous culture, fluorescence or luminescence is evaluated. For GFP, live cells are imaged in a fluorescence neutral DMEM media with 5% FBS and penicillin/streptomycin and a stain for the nuclei. For NLuc, luminescence is evaluated using a luciferase system, following the manufacturer's instructions using a luminometer instrument (Promega).

DNA template for NLuc (Blue: *Plautia stali* intestine virus IRES, Orange: NLuc ORF)

(SEQ ID NO: 119)

```
GACACGCGGCCTTCCAAGCAGTTAGGGAAACCGACTTCTTTGAAGAAGA
AAGCTGACTATGTGATCTTATTAAAATTAGGTTAAATTTCGAGGTTAAA
AATAGTTTTAATATTGCTATAGTCTTAGAGGTCTTGTATATTTATACTT
ACCACACAAGATGGACCGGAGCAGCCCTCCAATATCTAGTGTACCCTCG
TGCTCGCTCAAACATTAAGTGGTGTTGTGCGAAAAGAATCTCACTTCAA
GAAAAAGAAACTAGTATGGTCTTCACACTCGAAGATTTCGTTGGGGACT
GGCGACAGACAGCCGGCTACAACCTGGACCAAGTCCTTGAACAGGGAGG
TGTGTCCAGTTTGTTTCAGAATCTCGGGGTGTCCGTAACTCCGATCCAA
AGGATTGTCCTGAGCGGTGAAAATGGGCTGAAGATCGACATCCATGTCA
TCATCCCGTATGAAGGTCTGAGCGGCGACCAAATGGGCCAGATCGAAAA
AATTTTTAAGGTGGTGTACCCTGTGGATGATCATCACTTTAAGGTGATC
CTGCACTATGGCACACTGGTAATCGACGGGGTTACGCCGAACATGATCG
ACTATTTCGGACGGCCGTATGAAGGCATCGCCGTGTTCGACGGCAAAAA
GATCACTGTAACAGGGACCCTGTGGAACGGCAACAAAATTATCGACGAG
CGCCTGATCAACCCCGACGGCTCCCTGCTGTTCCGAGTAACCATCAACG
GAGTGACCGGCTGGCGGCTGTGCGAACGCATTCTGGCGTAACTCGAGCT
CGGTACCTGTCCGCGGTCGCGACGTACGCGGGCGGCCGCCATAAATTGG
ATCCATATATAGGGCCCGGGTTATAATTACCTCAGGTCGACGTCCCATG
GTTTTGTATAGAATTTACGGCTAGCGCCGGATGCGACGCCGGTCGCGTC
TTATCCGGCCTTCCTATATCAGGCGGTGTTTAAGACGCCGCCGCTTCGC
CCAAATCCTTATGCCGGTTCGACGACTGGACAAAATACTGTTTATCT
```

DNA template for eGFP (Blue: *Plautia stali* intestine virus IRES, Orange: eGFP ORF)

(SEQ ID NO: 120)

```
GACACGCGGCCTTCCAAGCAGTTAGGGAAACCGACTTCTTTGAAGAAGA
AAGCTGACTATGTGATCTTATTAAAATTAGGTTAAATTTCGAGGTTAAA
AATAGTTTTAATATTGCTATAGTCTTAGAGGTCTTGTATATTTATACTT
ACCACACAAGATGGACCGGAGCAGCCCTCCAATATCTAGTGTACCCTCG
TGCTCGCTCAAACATTAAGTGGTGTTGTGCGAAAAGAATCTCACTTCAA
GAAAAAGAAACTAGTATGGTGAGCAAGGGCGAGGAGCTGTTCACCGGGG
TGGTGCCCATCCTGGTCGAGCTGGACGGCGACGTAAACGGCCACAAGTT
CAGCGTGTCCGGCGAGGGCGAGGGCGATGCCACCTACGGCAAGCTGACC
CTGAAGTTCATCTGCACCACCGGCAAGCTGCCCGTGCCCTGGCCCACCC
TCGTGACCACCCTGACCTACGGCGTGCAGTGCTTCAGCCGCTACCCCGA
CCACATGAAGCAGCACGACTTCTTCAAGTCCGCCATGCCCGAAGGCTAC
GTCCAGGAGCGCACCATCTTCTTCAAGGACGACGGCAACTACAAGACCC
GCGCCGAGGTGAAGTTCGAGGGCGACACCCTGGTGAACCGCATCGAGCT
GAAGGGCATCGACTTCAAGGAGGACGGCAACATCCTGGGGCACAAGCTG
GAGTACAACTACAACAGCCACAACGTCTATATCATGGCCGACAAGCAGA
AGAACGGCATCAAGGTGAACTTCAAGATCCGCCACAACATCGAGGACGG
```

-continued

```
CAGCGTGCAGCTCGCCGACCACTACCAGCAGAACACCCCCATCGGCGAC

GGCCCCGTGCTGCTGCCCGACAACCACTACCTGAGCACCCAGTCCGCCC

TGAGCAAAGACCCCAACGAGAAGCGCGATCACATGGTCCTGCTGGAGTT

CGTGACCGCCGCCGGGATCACTCTCGGCATGGACGAGCTGTACAAGTAA

CTCGAGCTCGGTACCTGTCCGCGGTCGCGACGTACGCGGGCGGCCGCCA

TAAATTGGATCCATATATAGGGCCCGGGTTATAATTACCTCAGGTCGAC

GTCCCATGGTTTTGTATAGAATTTACGGCTAGCGCCGGATGCGACGCCG

GTCGCGTCTTATCCGGCCTTCCTATATCAGGCGGTGTTTAAGACGCCGC

CGCTTCGCCCAAATCCTTATGCCGGTTCGACGACTGGACAAAATACTGT

TTATCT
```

Primer Sequences

```
Forward primer for 2 (underlined: T7 promoter)
                                  (SEQ ID NO: 121)
GAAATTAATACGACTCACTATAGGGAGACCACAACGGTTTCCCTGACTA

TGTGATC

Forward primer in the 1st PCR for theoN5 (orange:
aptamer; red: aIRES; purple: aaIRES)
                                  (SEQ ID NO: 115)
ATACCAGCCGAAAGGCCCTTGGCAGAGAGGTCTGAAAAGACCTCTGCTG

ACTATGTGATCTTATTAAAATTAGG

TheoN5 2nd PCR
                                  (SEQ ID NO: 116)
GAAATTAATACGACTCACTATAGGGAGACCACAACGGTTTCCCTCCTCT

ATACCAGCCGAAAGGCCCTTGGCAG

Forward primer in the 1st PCR for tc-N5
                                  (SEQ ID NO: 117)
ACATACCAGATTTCGATCTGGAGAGGTGAAGAATACGACCACCTAGAGG

TCTGAAAAGACCTCTGCTGACTATGTGATC

Forward primer in the 2nd PCR for tc-N5
                                  (SEQ ID NO: 118)
GAAATTAATACGACTCACTATAGGGAGACCACAACGGTTTCCCTCCTCT

AAAACATACCAGATTTCGATC

Reverse primer in all PCRs
                                  (SEQ ID NO: 122)
AGATAAACAGTATTTTGTCCAGTCGTCGAAC

Junction
                                  (SEQ ID NO: 123)
GGACAAAATACTGTTTATCTGGGAGACCACAACGG

Splint
                                  (SEQ ID NO: 114)
5'-CCG TTG TGG TCT CCC AGA TAA ACA GTA TTT TGT

CC-3'
```

Example 53: Circular RNA with Modified Nucleotides was Generated, Translated, and Reduced Immunogenicity of Circular RNA This Example demonstrates the generation of modified circular polyribonucleotide that produced protein product. In addition, this Example demonstrates circular RNA engineered with nucleotide modifications had reduced immunogenicity as compared to a linear RNA.

A non-naturally occurring circular RNA engineered to include one or more desirable properties and with complete or partial incorporation of modified nucleotides was produced. As shown in the following Example, full length modified linear RNA or a hybrid of modified and unmodified linear RNA was circularized and expression of nLuc was assessed. In addition, modified circular RNA was shown to have reduced activation of immune related genes (q-PCR of MDA5, OAS and IFN-beta expression) in BJ cells, as compared to a non-modified circular RNA.

Figure 51A:
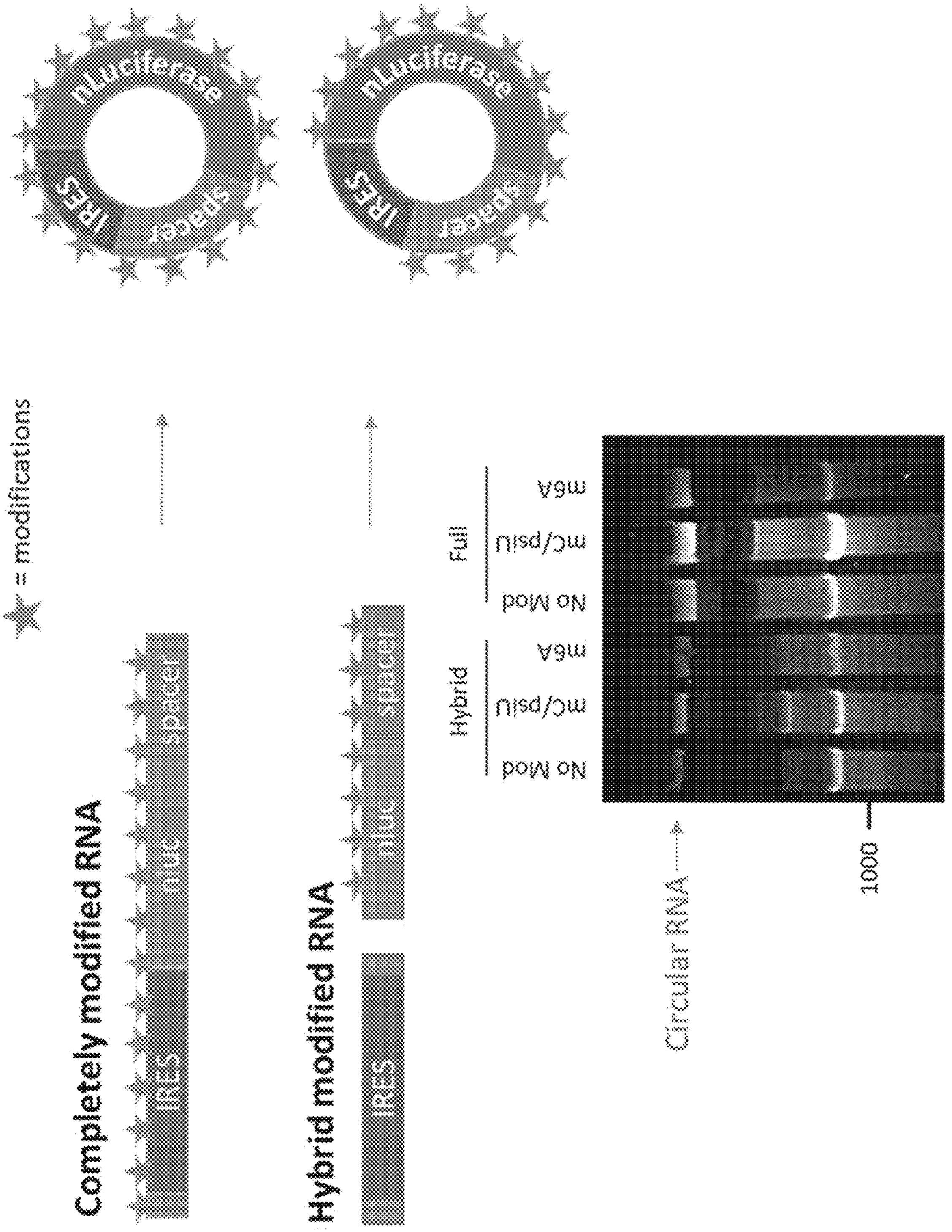
FIGS. 51A, 51B, and 51C show that the modified circular RNAs were translated in cells.

Circular RNA with a WT EMCV Nluc stop spacer was generated. For complete modification substitution, the modified nucleotides, pseudouridine and methylcytosine or m6A, were added in place of the standard unmodified nucleotides, uridine and cytosine or adenosine, respectively, during the in vitro transcription reaction. For the hybrid construct, the WT EMCV IRES was synthesized separately from the nLuc ORF. The WT EMCV IRES was synthesized using either modified or non-modified nucleotides. In contrast, the nLuc ORF sequence was synthesized using the modified nucleotides, pseudouridine and methylcytosine or m6A, in place of the standard unmodified nucleotides, uridine and cytosine or adenosine, respectively, during the in vitro transcription reaction. Following synthesis of the modified or unmodified IRES and the modified ORF, these two oligonucleotides were ligated together using T4 DNA ligase. As shown in FIG. 51A modified circular RNA was generated.

To measure expression efficiency of nLuc from the fully modified or hybrid modified constructs, 0.1 pmol of linear and circular RNA was transfected into BJ fibroblasts for 6 h. nLuc expression was measured at 6 h, 24 h, 48 h and 72 h post-transfection.

The level of innate immune response genes was monitored in cells from total RNA isolated from the cells using a phenol-based extraction reagent (Invitrogen). Total RNA (500 ng) was subjected to reverse transcription to generate cDNA. qRT-PCR analysis was performed using a dye-based quantitative PCR mix (BioRad).

Figure 51B:
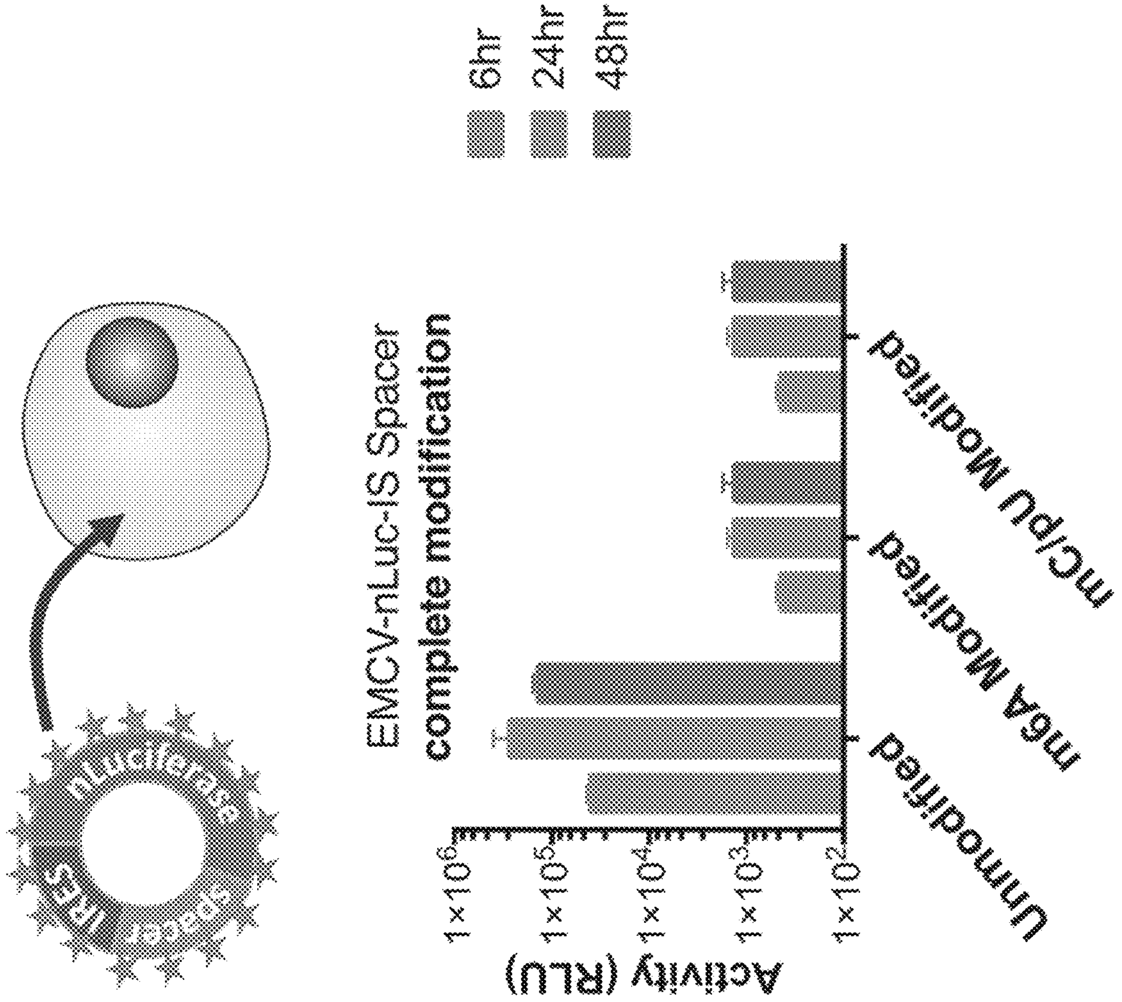
Figure 51C:
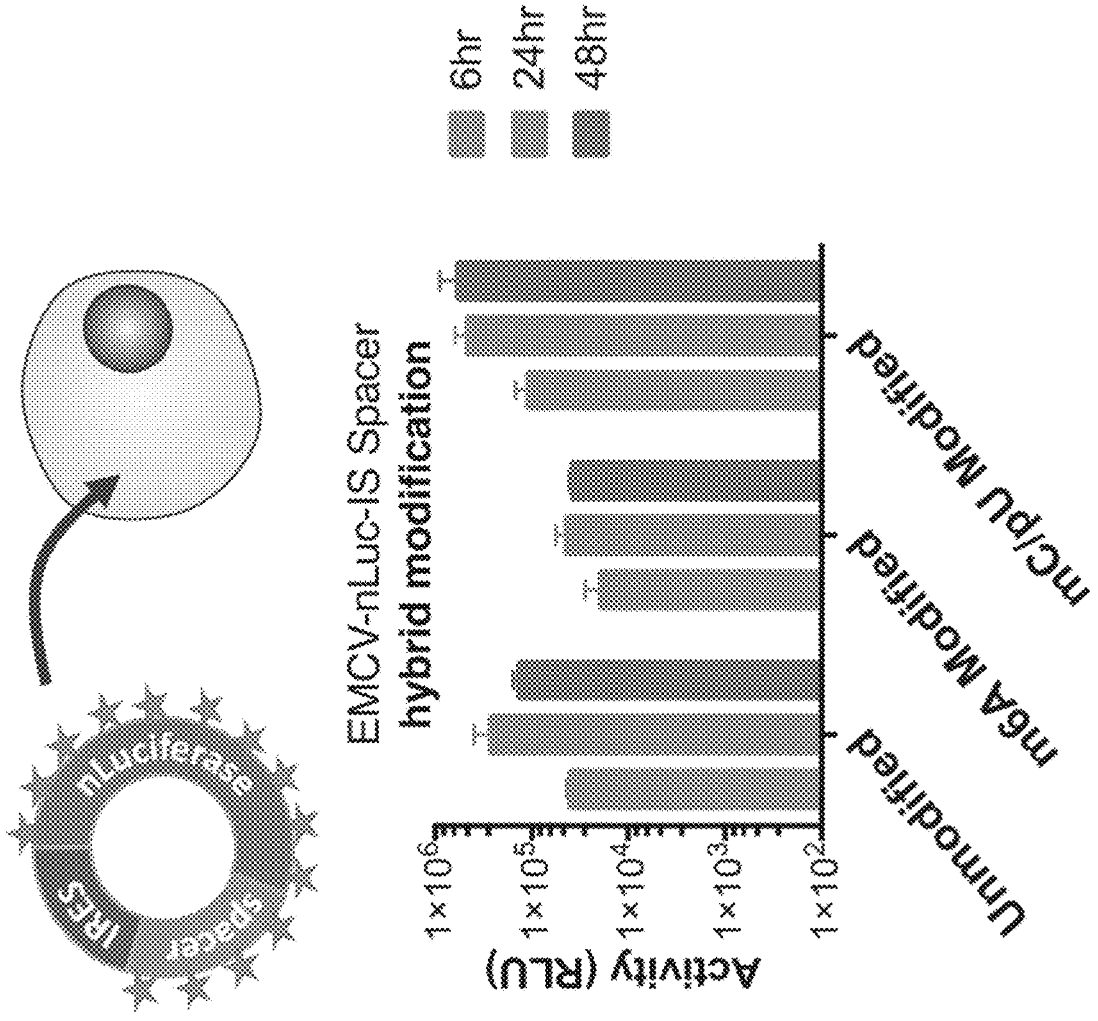
Figure 52A:
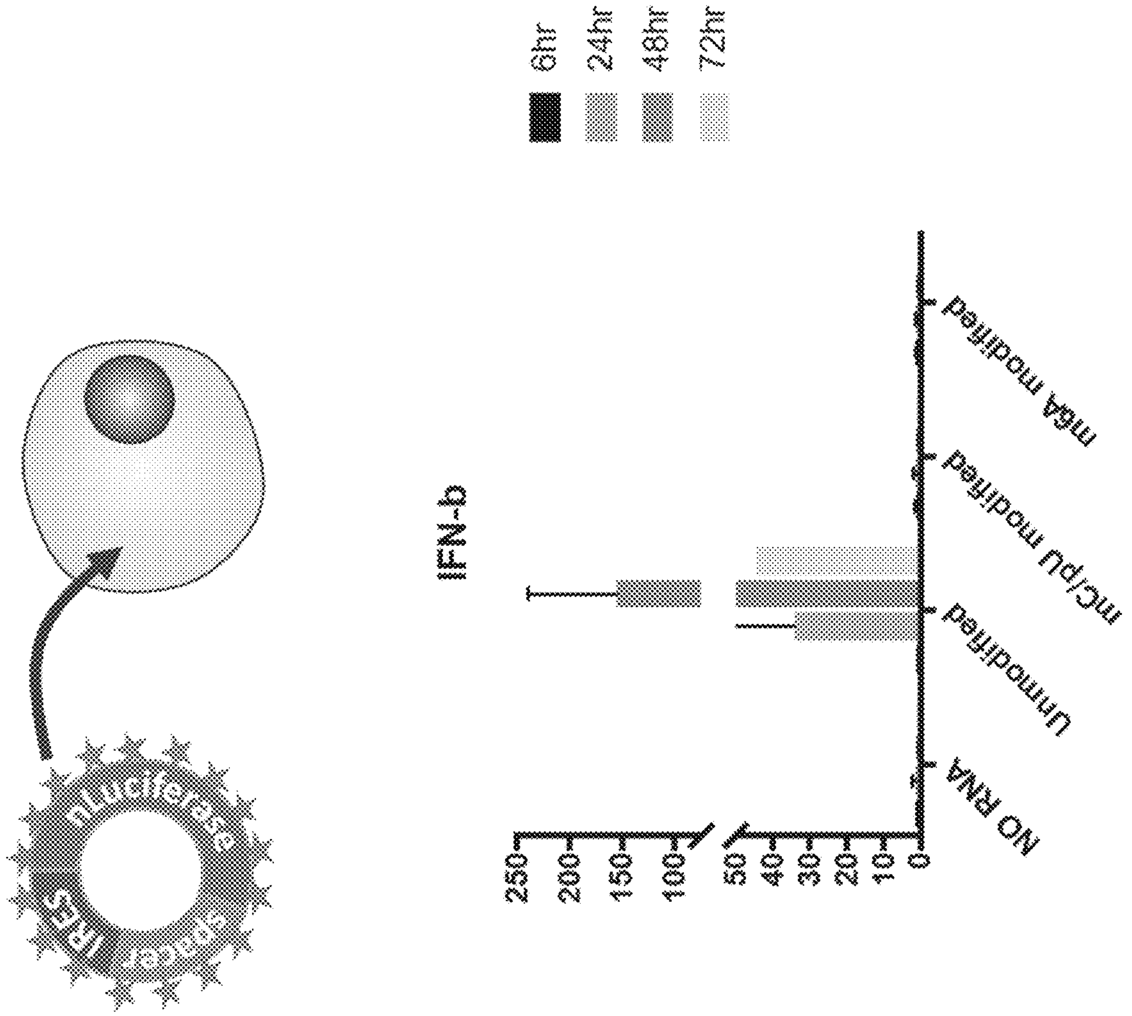
FIGS. 52A-52C show that modified circular RNAs have reduced immunogenicity as compared to unmodified circular RNAs to cells as assessed by MDA5, OAS and IFN-beta expression in the transfected cells.
Figure 52B:
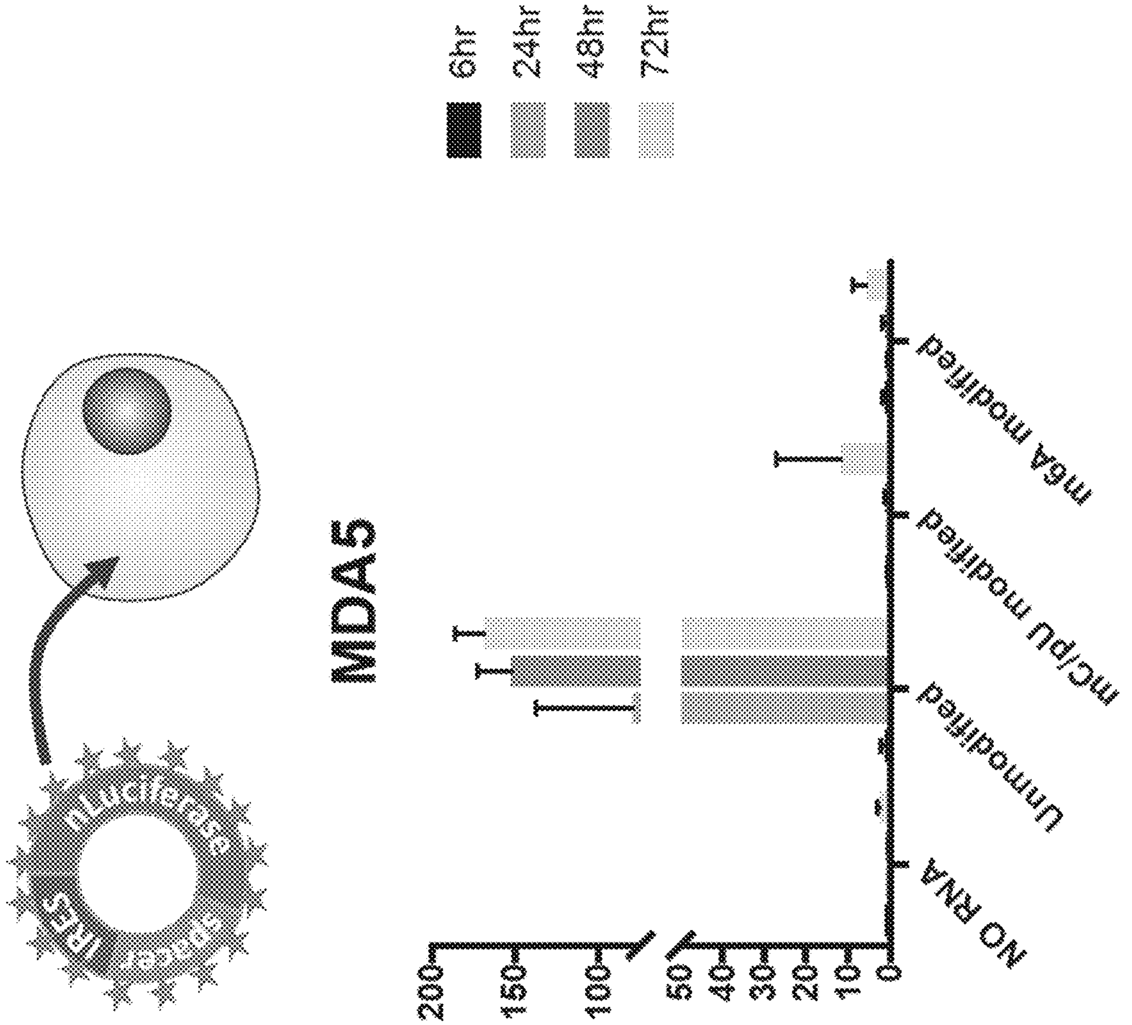
Figure 52C:
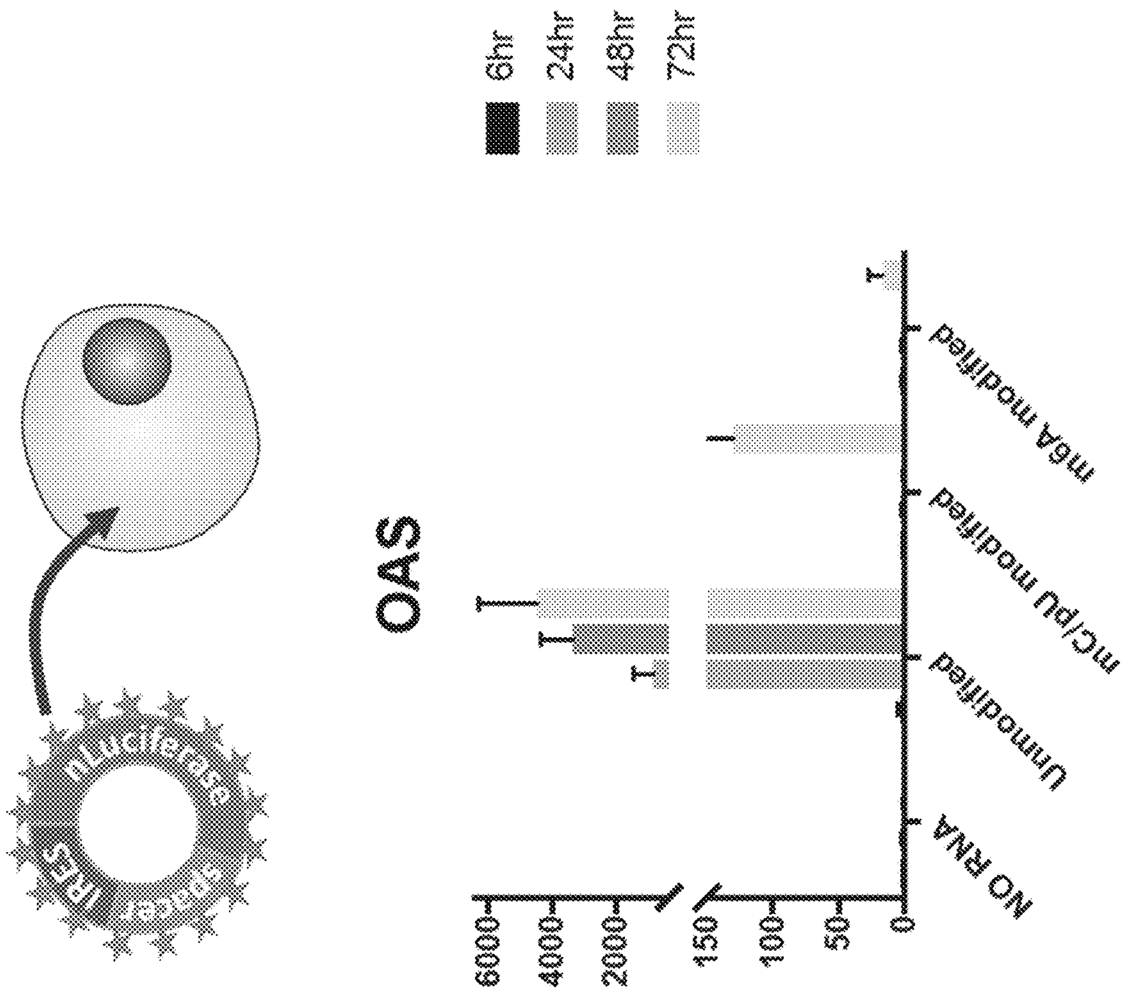

As shown in FIGS. 51B and 51C, modified circular RNA was translated. As shown in FIGS. 52A-C, qRT-PCR levels of immune related genes from BJ cells transfected with circular RNA showed reduction of MDA5, OAS and IFN-beta expression as compared to unmodified circular RNA transfected cells. Thus, induction of immunogenic related genes in recipient cells was reduced in cells transfected with modified circular RNA, as compared to unmodified circular RNA transfected cells.

Example 54: Circular RNA Administrated In Vivo and Displayed a Longer Half-Life/Increased Stability This Example demonstrates the ability to deliver circular RNA and the increased stability of circular RNA compared to linear RNA in vivo.

For this Example, circular RNAs were designed to include an EMCV IRES with an ORF encoding Nanoluciferase (Nluc) and stagger sequence (EMCV 2A 3×FLAG Nluc 2A no stop and EMCV 2A 3×FLAG Nluc 2A stop). The circular RNA was generated in vitro.

Balb/c mice were injected with circular RNA with Nluc ORF, or linear RNA as a control, via intravenous (IV) tail vein administration. Animals received a single dose of 5 μg of RNA formulated in a lipid-based transfection reagent (Minis) according to manufacturer's instructions.

Mice were sacrificed, and livers were collected at 3, 4, and 7 days post-dosing (n=2 mice/time point). The livers were collected and stored in an RNA stabilization reagent (Invitrogen). The tissue was homogenized in RIPA buffer with micro tube homogenizer (Fisher scientific) and RNA was extracted using a phenol-based RNA extraction reagent for cDNA synthesis. qPCR was used to measure the presence of both linear and circular RNA in the liver.

RNA detection in tissues was performed by qPCR. To detect linear and circular RNA primers that amplify the Nluc ORF were used. (F: AGATTTCGTTGGGGACTGGC (SEQ ID NO: 124), R: CACCGCTCAGGACAATCCTT (SEQ ID NO: 125)). To detect only circular RNA, primers that amplified the 5'-3' junction allowed for detection of circular but not linear RNA constructs (F: CTGGAGACGTGGAGGAGAAC (SEQ ID NO: 126), R: CCAAAAGACGGCAATATGGT (SEQ ID NO: 127)).

Figure 53:
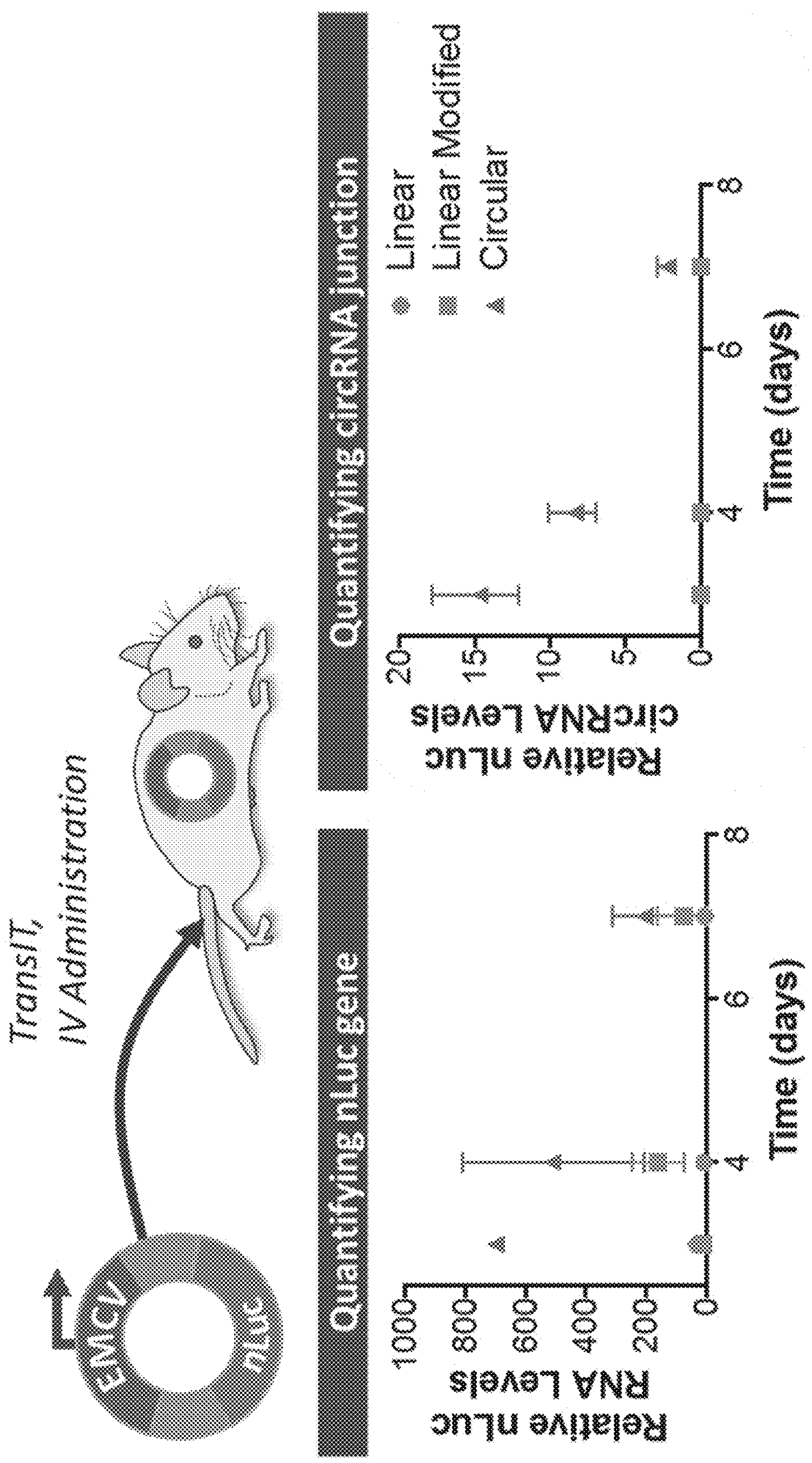
FIG. 53 shows that after injection into mice, circular RNA was detected at higher levels than linear RNA in livers of mice at 3, 4, and 7 days post-injection.

Circular RNA was detected at higher levels than linear RNA in livers of mice at 3, 4- and 7-days post-injection (FIG. 53). Therefore, circular RNA was administered and detectable in vivo for at least 7 days post administration.

Example 55: In Vivo Expression, Half-Life, and Non-Immunogenicity of Circular RNA This Example demonstrates the ability to drive expression from circular RNA in vivo. It demonstrates increased half-life of circular RNA compared to linear RNA. Finally, it demonstrates that circular RNA was engineered to be non-immunogenic in vivo For this Example, circular RNAs included a CVB3 IRES, an ORF encoding *Gaussia* Luciferase (GLuc), and two spacer elements flanking the IRES-ORF.

The circular RNA was generated in vitro. Unmodified linear RNA was in vitro transcribed from a DNA template including all the motifs listed above, as well as a T7 RNA polymerase promoter to drive transcription. Transcribed RNA was purified with an RNA cleanup kit (New England Biolabs, T2050), treated with RNA 5'-phosphohydrolase (RppH) (New England Biolabs, M0356) following the manufacturer's instructions, and purified again with an RNA purification column. RppH treated RNA was circularized using a splint DNA (GTCAACGGATTTTCCCAAGTCCGTAGCGTCTC (SEQ ID NO: 128)) and T4 RNA ligase 2 (New England Biolabs, M0239). Circular RNA was Urea-PAGE purified, eluted in a buffer (0.5M Sodium Acetate, 0.1% SDS, 1 mM EDTA), ethanol precipitated and resuspended in RNase free water.

Mice received a single tail vein injection dose of 2.5 μg of circular RNA with the *Gaussia* Luciferase ORF, or linear RNA as a control, both formulated in a lipid-based transfection reagent (Minis) as a carrier.

Blood samples (50 μl) were collected from the tail-vein of each mouse into EDTA tubes, at 1, 2, 7, 11, 16, and 23 days post-dosing. Plasma was isolated by centrifugation for 25 min at 1300 g at 4° C. and the activity of *Gaussia* Luciferase, a secreted enzyme, was tested using a *Gaussia* Luciferase activity assay (Thermo Scientific Pierce). 50 μl of 1×Gluc substrate was added to 5 μl of plasma to carry out the Gluc luciferase activity assay. Plates were read right after mixing in a luminometer instrument (Promega).

Figure 54A:
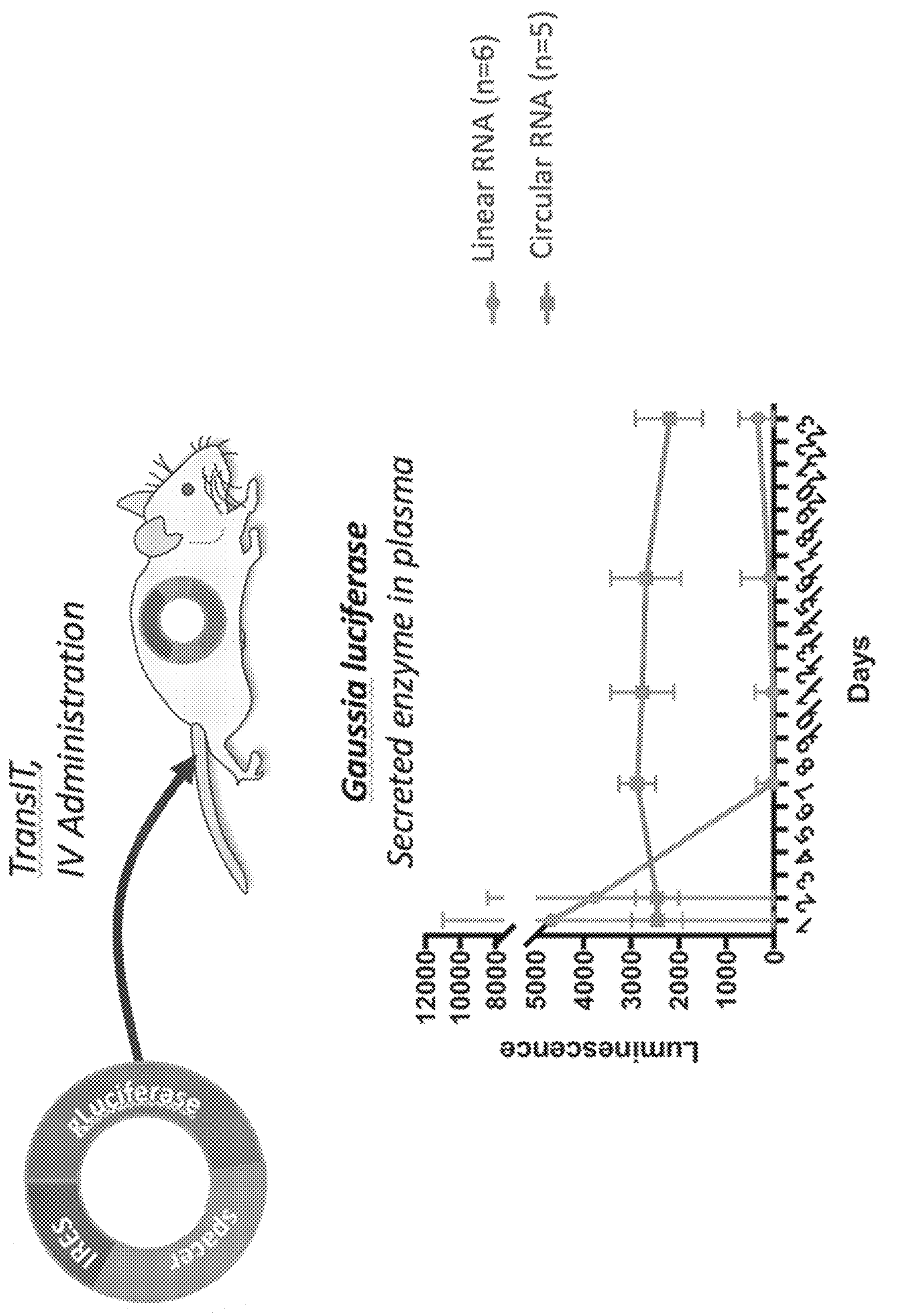
FIGS. 54A and 54B show that after injection of circular RNA or linear RNA expressing *Gaussia* Luciferase into mice, *Gaussia* Luciferase activity was detected in plasma at 1, 2, 7, 11, 16, and 23 days post-dosing of circular RNA, while its activity was only detected in plasma at 1, and 2 days post-dosing of modified linear RNA.
Figure 54B:
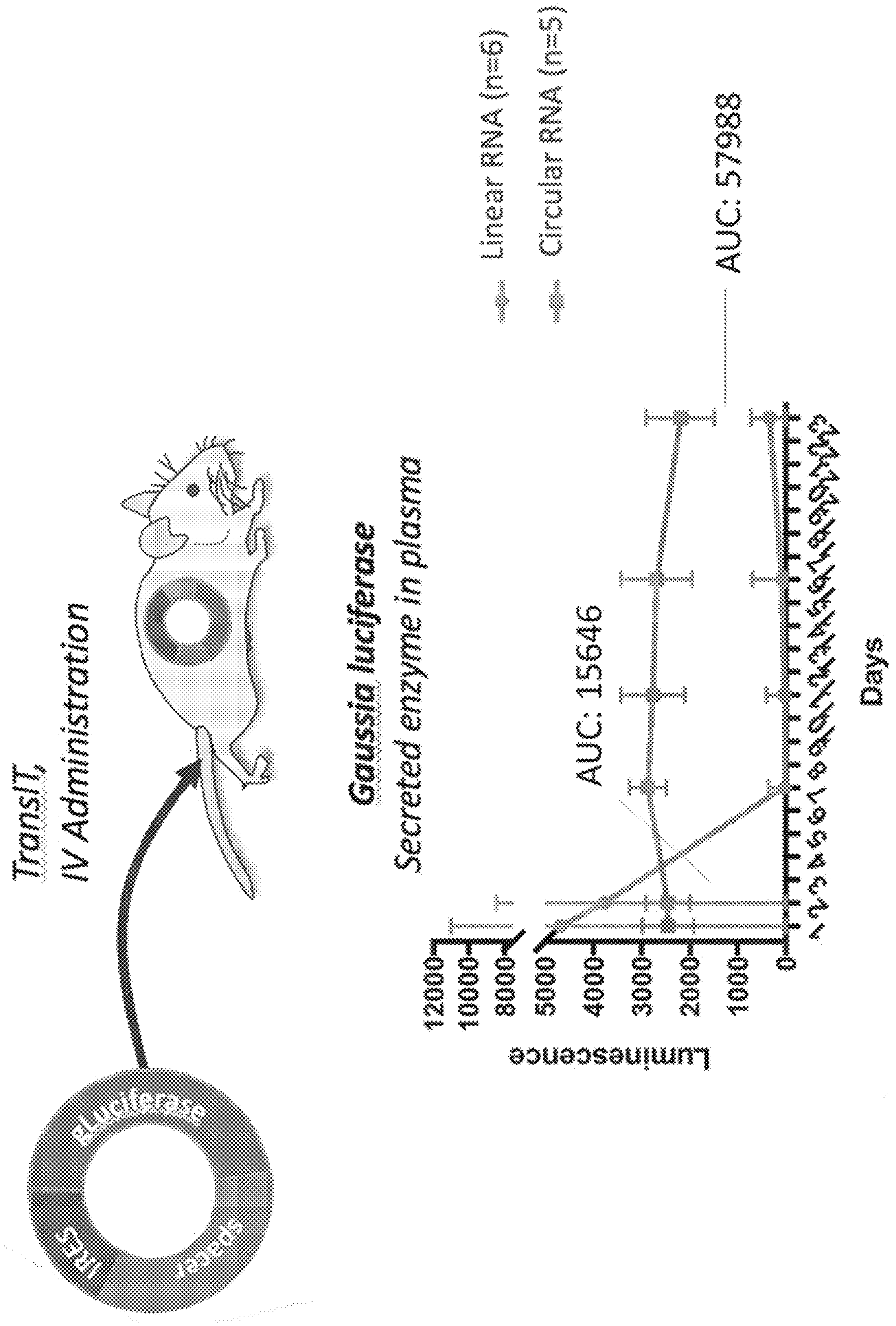

*Gaussia* Luciferase activity was detected in plasma at 1, 2, 7, 11, 16, and 23 days post-dosing of circular RNA (FIGS. 54A-B).

In contrast, *Gaussia* Luciferase activity was only detected in plasma at 1, and 2 days post-dosing of modified linear RNA. Enzyme activity from linear RNA derived protein was not detected above background levels at day 6 or beyond (FIGS. 54A-B).

At day 16, livers were dissected from three animals and total RNA was isolated from cells using a phenol-based extraction reagent (Invitrogen). Total RNA (500 ng) was subjected to reverse transcription to generate cDNA. qRT-PCR analysis was performed using a dye-based quantitative PCR mix (BioRad).

Figure 55:
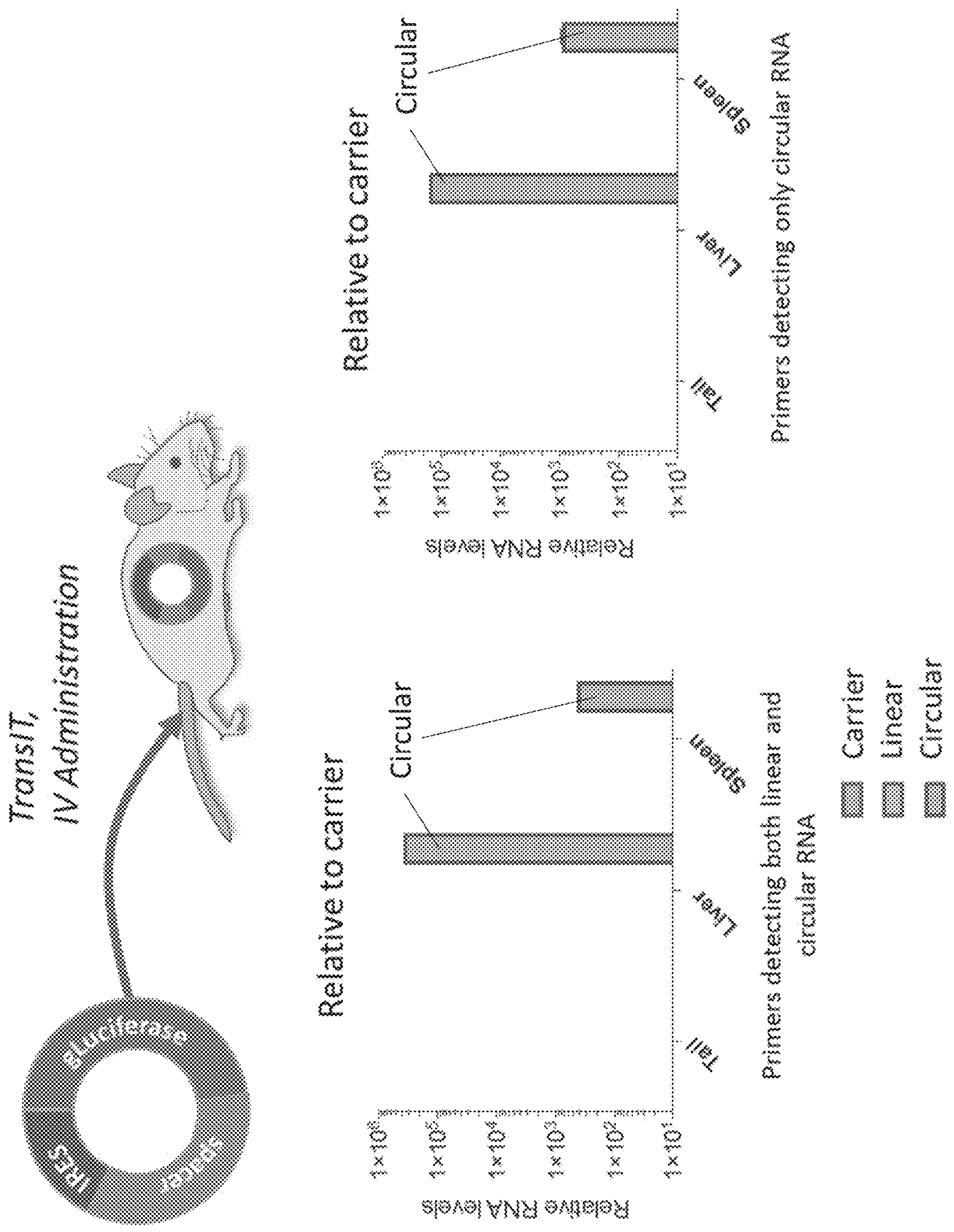
FIG. 55 show that after injection of RNA, circular RNA but not linear RNA, was detected in the liver and spleen at 16 days post-administration of RNA.
Figure 56:
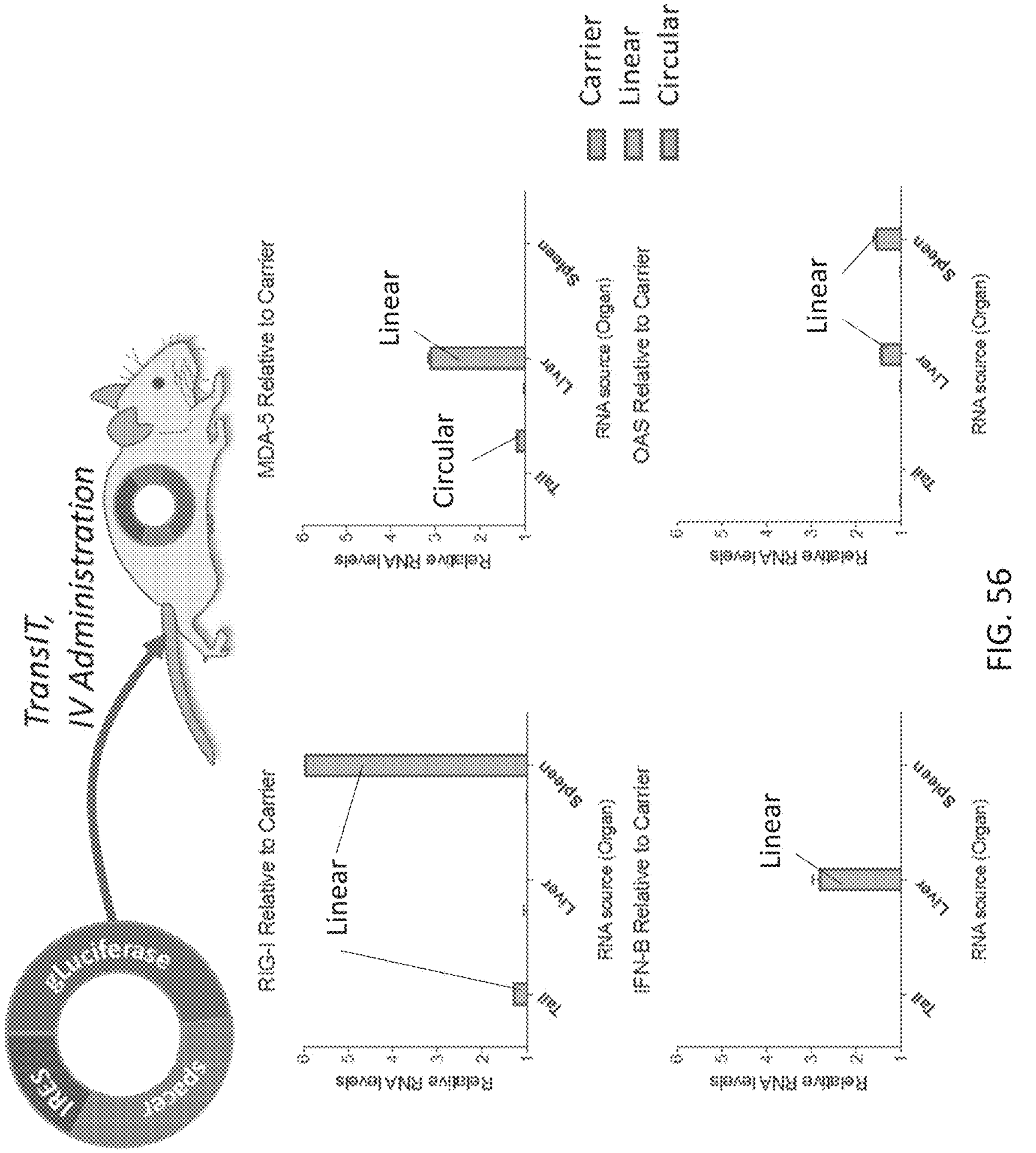
FIG. 56 show that after injection of RNA, linear RNA but not circular RNA, showed immunogenicity as assessed by RIG-I, MDA-5, IFN-B and OAS.

As shown in FIG. 55, qRT-PCR levels of circular RNA but not linear RNA were detected in both liver and spleen at day 16. As shown in FIG. 56, immune related genes from livers transfected with linear RNA showed increased expression of RIG-I, MDA5, IFN-B and OAS, while livers transfected with circular RNA did not show increased expression RIG-I, MDA5, PKR and IFN-beta of these markers as compared to carrier transfected animals at day 16. Thus, induction of immunogenic related genes in recipient cells was not present in circular RNA from transfected livers.

This Example demonstrated that circular RNA expressed protein in vivo for prolonged periods of time, with levels of protein activity in the plasma at multiple days post injection. Given the half-life of Gaussian Luciferase in mouse plasma is about 20 mins (see Tannous, Nat Protoc., 2009, 4(4):582-591), the similar levels of activity indicate continual expression from circular RNA. Further, circular RNA displayed a longer expression profile than its modified linear RNA counterpart without inducing immune related genes.

Sequence listing

SEQ ID NO: 1

(Start Codon)
AUG

SEQ ID NO: 2

(GFP)
EGFP:

SEQ ID NO: 3

(stagger element)
atggtgagcaagggcgaggagctgttcaccggggtggtgcccatcctggtcgagctggacggcgacgtaaacggcc acaagttcagcgtgtccggcgagggcgagggcgatgccacctacggcaagctgaccctgaagttcatctgcaccac cggcaagctgcccgtgccctggcccaccctcgtgaccaccctgacctacggcgtgcagtgcttcagccgctacccc gaccacatgaagcagcacgacttcttcaagtccgccatgcccgaaggctacgtccaggagcgcaccatcttcttca aggacgacggcaactacaagacccgcgccgaggtgaagttcgagggcgacaccctggtgaaccgcatcgagctgaa gggcatcgacttcaaggaggacggcaacatcctggggcacaagctggagtacaactacaacagccacaacgtctat -continued

| Sequence listing |
|---|

atcatggccgacaagcagaagaacggcatcaaggtgaacttcaagatccgccacaacatcgaggacggcagcgtgc agctcgccgaccactaccagcagaacacccccatcggcgacggccccgtgctgctgcccgacaaccactacctgag cacccagtccgccctgagcaaagaccccaacgagaagcgcgatcacatggtcctgctggagttcgtgaccgccgcc gggatcactctcggcatggacgagctgtacaag (SEQ ID NO: 3)
P2A: gctactaacttcagcctgctgaagcaggctggcgacgtggaggagaaccctggacct (SEQ ID NO: 132)
T2A: gagggcaggggaagtctactaacatgcggggacgtggaggaaaatcccggccca (SEQ ID NO: 133)
E2A: cagtgtactaattatgctctcttgaaattggctggagatgttgagagcaacccaggtccc Others: F2A, BmCPV2A, BmIFV2A
SEQ ID NO: 4 ZKSCAN introns
(SEQ ID NO: 4)
GTAAAAAGAGGTGAAACCTATTATGTGTGAGCAGGGCACAGACGTTGAAACTGGAGCCAGGAG

AAGTATTGGCAGGCTTTAGGTTATTAGGTGGTTACTCTGTCTTAAAAATGTTCTGGCTTTCTTCCT

GCATCCACTGGCATACTCATGGTCTGTTTTTAAATATTTTAATTCCCATTTACAAAGTGATTTACC

CACAAGCCCAACCTGTCTGTCTTCAG
Or
(SEQ ID NO: 134)
GTAAGAAGCAAGGTTTCATTTAGGGGAAGGGAAATGATTCAGGACGAGAGTCTTTGTGCTGCTG

AGTGCCTGTGATGAAGAAGCATGTTAGTcctgggcaacgtagcgagaccccatctctacaaaaaatagaaaaatta gccaggtatagtggcgcacacctgtgattccagctacgcaggaggctgaggtgggaggattgcttgagcccaggag gttgaggctgcagtgagctgtaatcatgccactactccaacctgggcaacacagcaaggaccctgtctcaaaaGCT ACTTACAGAAAAGAATTAggctcggcacggtagctcacacctgtaatcccagcactagggaggctgaggcgggcag atcacttgaggtcaggagtttgagaccagcctggccaacatggtgaaaccttgtctctactaaaaatatgaaaatt agccaggcatggtggcacattcctgtaatcccagctactcgggaggctgaggcaggagaatcacttgaacccagga ggtggaggttgcagtaagccgagatcgtaccactgtgctctagccttggtgacagagcgagactgtcttaaaaaaa aaaaaaaaaaaaaaagaattaattaaaaatttaaaaaaaaatgaaaaaaaGCTGCATGCTTGTTTTTTGTTTTTAG

TTATTCTACATTGTTGTCATTATTACCAAATATTGGGGAAAATACAACTTACAGACCAATCTCAGGAGTTAAATGT

TACTACGAAGGCAAATGAACTATGCGTAATGAACCTGGTAGGCATTA

SEQ ID NO: 5
(IRES)
IRES (EMCV):
Acgttactggccgaagccgcttggaataaggccggtgtgcgtngtctatatgttattttccaccatattgccgtct tttggcaatgtgagggcccggaaacctggccctgtcttcttgacgagcattcctaggggtattcccctctcgccaa aggaatgcaaggtctgttgaatgtcgtgaaggaagcagttcctctggaagcttcttgaagacaaacaacgtctgta gcgaccctttgcaggcagcggaaccccccacctggcgacaggtgcctctgcggccaaaagccacgtgtataagata cacctgcaaaggcggcacaaccccagtgccacgttgtgagttggatagttgtggaaagagtcaaatggctctcctc aagcgtattcaacaaggggctgaaggatgcccagaaggtaccccattgtatgggatctgatctggggcctcggtgc acatgctttacatgtgtnagtcgaggttaaaaaacgtctaggccccccgaaccacggggacgtggttttcctttga aaaacacgatgataata SEQ ID NO: 6
(addgene p3.1 laccase)
pcDNA3.1(+) Laccase2 MCS Exon Vector sequence 6926 bps
GACGGATCGGGAGATCTCCCGATCCCCTATGGTGCACTCTCAGTACAATCTGCTCTGATGCCGC

ATAGTTAAGCCAGTATCTGCTCCCTGCTTGTGTGTTGGAGGTCGCTGAGTAGTGCGCGAGCAAA

-continued

| Sequence listing |
| --- |

ATTTAAGCTACAACAAGGCAAGGCTTGACCGACAATTGCATGAAGAATCTGCTTAGGGTTAGGC

GTTTTGCGCTGCTTCGCGATGTACGGGCCAGATATACGCGTTGACATTGATTATTGACTAGTTAT

TAATAGTAATCAATTACGGGGTCATTAGTTCATAGCCCATATATGGAGTTCCGCGTTACATAACT

TACGGTAAATGGCCCGCCTGGCTGACCGCCCAACGACCCCCGCCCATTGACGTCAATAATGACG

TATGTTCCCATAGTAACGCCAATAGGGACTTTCCATTGACGTCAATGGGTGGAGTATTTACGGT

AAACTGCCCACTTGGCAGTACATCAAGTGTATCATATGCCAAGTACGCCCCCTATTGACGTCAA

TGACGGTAAATGGCCCGCCTGGCATTATGCCCAGTACATGACCTTATGGGACTTTCCTACTTGGC

AGTACATCTACGTATTAGTCATCGCTATTACCATGGTGATGCGGTTTTGGCAGTACATCAATGGG

CGTGGATAGCGGTTTGACTCACGGGGATTTCCAAGTCTCCACCCCATTGACGTCAATGGGAGTT

TGTTTTGGCACCAAAATCAACGGGACTTTCCAAAATGTCGTAACAACTCCGCCCCATTGACGCA

AATGGGCGGTAGGCGTGTACGGTGGGAGGTCTATATAAGCAGAGCTCTCTGGCTAACTAGAGA

ACCCACTGCTTACTGGCTTATCGAAATTAATACGACTCACTATAGGGAGACCCAAGCTGGCTAG

CGTTTAAACTTAAGCTTGGTACCGAGCTCGGATCCACTAGTCCAGTGTGGTGGAATTCCATTGA

GAAATGACTGAGTTCCGGTGCTCTCAAGTCATTGATCTTTGTCGACTTTTATTTGGTCTCTGTAAT

AACGACTTCAAAAACATTAAATTCTGTTGCGAAGCCAGTAAGCTACAAAAAGAAAaaacaagagagaa tgctatagtcgtatagtatagMcccgactatctgatacccattacttatctaggggaatgcgaacccaaaatttt atcagttttctcggatatcgatagatattggggaataaatttaaataaataaattttgggcgggtttagggcgtgg caaaaagtttttggcaaatcgctagaaatttacaagacttataaaattatgaaaaaatacaacaaaattttaaac acgtgggcgtgacagttttggGcggttttagggcgttagagtaggcgaggacagggttacatcgactaggctttga tcctgatcaagaatatatatactttataccgcttccttctacatgttacctatttttcaacgaatctagtatacct ttttactgtacgatttatgggtataaTAATAAGCTAAATCGAGACTAAGttttattgttatatatattttttttat tttatGCAGAAATTAATTAAACCGGTCCTGCAGGTGATCAGGCGCGCCGGTTACCGGCCGGCCCCGCGGAGCGTAA

GTATTCAAAATTCCAAAATTTTTTACTAGAAATATTCGATTTTTTAATAGGCAGTTTCTATACTATTGTATACTAT

TGtagattcgttgaaaagtatgtaacaggaagaataaagcatttccgaccatgtaaagtatatatattcttaataa ggatcaatagccgagtcgatctcgccatgtccgtctgtcttattGattaccgccgagacatcaggaactataaaag ctagaaggatgagttttagcatacagattctagagacaaggacgcagagcaagtttgttgatccatgctgccacgc tttaactttctcaaattgcccaaaactgccatgcccacaltttgaactattttcgaaatttttcataattgtat tactcgtgtaaatttccatcaatttgccaaaaactttttgtcacgcgttaacgccctaaagccgccaataggtca cgcccacactattgaGcaattatcaaatttttctcattttattccccaatatctatcgatatccccgattatgaa attattaaatttcgcgttcgcattcacactagctgagtaacgagtatctgatagttggggaaatcgactTATTTTT

TATATACAATGAAAATGAATTTAATCATATGAATATCGATTATAGCTTTTTATTTAATATGAATATTTATTTGGGC

TTAAGGTGTAACCTcctcgacataagactcacatggcgcaggcacattgaagacaaaaatactcaTTGTCGGGTCT

CGCACCCTCCAGCAGCACCTAAAATTATGTCTTCAATTATTGCCAACATTGGAGACACAATTAGTCTGTGGCACCT

CAGGCGGCCGCTCGAGTCTAGAGGGCCCGTTTAAACCCGCTGATCAGCCTCGACTGTGCCTTCTAGTTGCCAGCCA

TCTGTTGTTTGCCCCTCCCCCGTGCCTTCCTTGACCCTGGAAGGTGCCACTCCCACTGTCCTTTCCTA

ATAAAATGAGGAAATTGCATCGCATTGTCTGAGTAGGTGTCATTCTATTCTGGGGGGTGGGGTG

GGGCAGGACAGCAAGGGGGAGGATTGGGAAGACAATAGCAGGCATGCTGGGGATGCGGTGGG

CTCTATGGCTTCTGAGGCGGAAAGAACCAGCTGGGGCTCTAGGGGGTATCCCCACGCGCCCTGT

-continued

| Sequence listing |
| --- |
| AGCGGCGCATTAAGCGCGGCGGGTGTGGTGGTTACGCGCAGCGTGACCGCTACACTTGCCAGCG |
| CCCTAGCGCCCGCTCCTTTCGCTTTCTTCCCTTCCTTTCTCGCCACGTTCGCCGGCTTTCCCCGTC |
| AAGCTCTAAATCGGGGGCTCCCTTTAGGGTTCCGATTTAGTGCTTTACGGCACCTCGACCCCAAA |
| AAACTTGATTAGGGTGATGGTTCACGTAGTGGGCCATCGCCCTGATAGACGGTTTTTCGCCCTTT |
| GACGTTGGAGTCCACGTTCTTTAATAGTGGACTCTTGTTCCAAACTGGAACAACACTCAACCCTA |
| TCTCGGTCTATTCTTTTGATTTATAAGGGATTTTGCCGATTTCGGCCTATTGGTTAAAAAATGAG |
| CTGATTTAACAAAAATTTAACGCGAATTAATTCTGTGGAATGTGTGTCAGTTAGGGTGTGGAAA |
| GTCCCCAGGCTCCCCAGCAGGCAGAAGTATGCAAAGCATGCATCTCAATTAGTCAGCAACCAGG |
| TGTGGAAAGTCCCCAGGCTCCCCAGCAGGCAGAAGTATGCAAAGCATGCATCTCAATTAGTCAG |
| CAACCATAGTCCCGCCCCTAACTCCGCCCATCCCGCCCCTAACTCCGCCCAGTTCCGCCCATTCT |
| CCGCCCCATGGCTGACTAATTTTTTTTATTTATGCAGAGGCCGAGGCCGCCTCTGCCTCTGAGCT |
| ATTCCAGAAGTAGTGAGGAGGCTTTTTTGGAGGCCTAGGCTTTTGCAAAAAGCTCCCGGGAGCT |
| TGTATATCCATTTTCGGATCTGATCAAGAGACAGGATGAGGATCGTTTCGCATGATTGAACAAG |
| ATGGATTGCACGCAGGTTCTCCGGCCGCTTGGGTGGAGAGGCTATTCGGCTATGACTGGGCACA |
| ACAGACAATCGGCTGCTCTGATGCCGCCGTGTTCCGGCTGTCAGCGCAGGGGCGCCCGGTTCTT |
| TTTGTCAAGACCGACCTGTCCGGTGCCCTGAATGAACTGCAGGACGAGGCAGCGCGGCTATCGT |
| GGCTGGCCACGACGGGCGTTCCTTGCGCAGCTGTGCTCGACGTTGTCACTGAAGCGGGAAGGGA |
| CTGGCTGCTATTGGGCGAAGTGCCGGGGCAGGATCTCCTGTCATCTCACCTTGCTCCTGCCGAG |
| AAAGTATCCATCATGGCTGATGCAATGCGGCGGCTGCATACGCTTGATCCGGCTACCTGCCCAT |
| TCGACCACCAAGCGAAACATCGCATCGAGCGAGCACGTACTCGGATGGAAGCCGGTCTTGTCG |
| ATCAGGATGATCTGGACGAAGAGCATCAGGGGCTCGCGCCAGCCGAACTGTTCGCCAGGCTCA |
| AGGCGCGCATGCCCGACGGCGAGGATCTCGTCGTGACCCATGGCGATGCCTGCTTGCCGAATAT |
| CATGGTGGAAAATGGCCGCTTTTCTGGATTCATCGACTGTGGCCGGCTGGGTGTGGCGGACCGC |
| TATCAGGACATAGCGTTGGCTACCCGTGATATTGCTGAAGAGCTTGGCGGCGAATGGGCTGACC |
| GCTTCCTCGTGCTTTACGGTATCGCCGCTCCCGATTCGCAGCGCATCGCCTTCTATCGCCTTCTTG |
| ACGAGTTCTTCTGAGCGGGACTCTGGGGTTCGAAATGACCGACCAAGCGACGCCCAACCTGCCA |
| TCACGAGATTTCGATTCCACCGCCGCCTTCTATGAAAGGTTGGGCTTCGGAATCGTTTTCCGGGA |
| CGCCGGCTGGATGATCCTCCAGCGCGGGGATCTCATGCTGGAGTTCTTCGCCCACCCCAACTTGT |
| TTATTGCAGCTTATAATGGTTACAAATAAAGCAATAGCATCACAAATTTCACAAATAAAGCATT |
| TTYTTCACTGCATTCTAGTTGTGGTTTGTCCAAACTCATCAATGTATCTTATCATGTCTGTATACC |
| GTCGACCTCTAGCTAGAGCTTGGCGTAATCATGGTCATAGCTGTTTCCTGTGTGAAATTGTTATC |
| CGCTCACAATTCCACACAACATACGAGCCGGAAGCATAAAGTGTAAAGCCTGGGGTGCCTAAT |
| GAGTGAGCTAACTCACATTAATTGCGTTGCGCTCACTGCCCGCTTTCCAGTCGGGAAACCTGTCG |
| TGCCAGCTGCATTAATGAATCGGCCAACGCGCGGGGAGAGGCGGTTTGCGTATTGGGCGCTCTT |
| CCGCTTCCTCGCTCACTGACTCGCTGCGCTCGGTCGTTCGGCTGCGGCGAGCGGTATCAGCTCAC |
| TCAAAGGCGGTAATACGGTTATCCACAGAATCAGGGGATAACGCAGGAAAGAACATGTGAGCA |
| AAAGGCCAGCAAAAGGCCAGGAACCGTAAAAAGGCCGCGTTGCTGGCGTTTTTCCATAGGCTC |
| CGCCCCCCTGACGAGCATCACAAAAATCGACGCTCAAGTCAGAGGTGGCGAAACCCGACAGGA |
| CTATAAAGATACCAGGCGTTTCCCCCTGGAAGCTCCCTCGTGCGCTCTCCTGTTCCGACCCTGCC |

-continued

| Sequence listing |
|---|
| GCTTACCGGATACCTGTCCGCCTTTCTCCCTTCGGGAAGCGTGGCGCTTTCTCATAGCTCACGCT |
| GTAGGTATCTCAGTTCGGTGTAGGTCGTTCGCTCCAAGCTGGGCTGTGTGCACGAACCCCCCGTT |
| CAGCCCGACCGCTGCGCCTTATCCGGTAACTATCGTCTTGAGTCCAACCCGGTAAGACACGACT |
| TATCGCCACTGGCAGCAGCCACTGGTAACAGGATTAGCAGAGCGAGGTATGTAGGCGGTGCTA |
| CAGAGTTCTTGAAGTGGTGGCCTAACTACGGCTACACTAGAAGAACAGTATTTGGTATCTGCGC |
| TCTGCTGAAGCCAGTTACCTTCGGAAAAAGAGTTGGTAGCTCTTGATCCGGCAAACAAACCACC |
| GCTGGTAGCGGTTTTTTTGTTTGCAAGCAGCAGATTACGCGCAGAAAAAAAGGATCTCAAGAAG |
| ATCCTTTGATCTTTTCTACGGGGTCTGACGCTCAGTGGAACGAAAACTCACGTTAAGGGATTTTG |
| GTCATGAGATTATCAAAAAGGATCTTCACCTAGATCCTTTTAAATTAAAAATGAAGTTTTAAATC |
| AATCTAAAGTATATATGAGTAAACTTGGTCTGACAGTTACCAATGCTTAATCAGTGAGGCACCT |
| ATCTCAGCGATCTGTCTATTTCGTTCATCCATAGTTGCCTGACTCCCCGTCGTGTAGATAACTAC |
| GATACGGGAGGGCTTACCATCTGGCCCCAGTGCTGCAATGATACCGCGAGACCCACGCTCACCG |
| GCTCCAGATTTATCAGCAATAAACCAGCCAGCCGGAAGGGCCGAGCGCAGAAGTGGTCCTGCA |
| ACTTTATCCGCCTCCATCCAGTCTATTAATTGTTGCCGGGAAGCTAGAGTAAGTAGTTCGCCAGT |
| TAATAGTTTGCGCAACGTTGTTGCCATTGCTACAGGCATCGTGGTGTCACGCTCGTCGTTTGGTA |
| TGGCTTCATTCAGCTCCGGTTCCCAACGATCAAGGCGAGTTACATGATCCCCCATGTTGTGCAAA |
| AAAGCGGTTAGCTCCTTCGGTCCTCCGATCGTTGTCAGAAGTAAGTTGGCCGCAGTGTTATCACT |
| CATGGTTATGGCAGCACTGCATAATTCTCTTACTGTCATGCCATCCGTAAGATGCTTTTCTGTGA |
| CTGGTGAGTACTCAACCAAGTCATTCTGAGAATAGTGTATGCGGCGACCGAGTTGCTCTTGCCC |
| GGCGTCAATACGGGATAATACCGCGCCACATAGCAGAACTTTAAAAGTGCTCATCATTGGAAAA |
| CGTTCTTCGGGGCGAAAACTCTCAAGGATCTTACCGCTGTTGAGATCCAGTTCGATGTAACCCA |
| CTCGTGCACCCAACTGATCTTCAGCATCTTTTACTTTCACCAGCGTTTCTGGGTGAGCAAAAACA |
| GGAAGGCAAAATGCCGCAAAAAAGGGAATAAGGGCGACACGGAAATGTTGAATACTCATACTC |
| TTCCTTTTTCAATATTATTGAAGCATTTATCAGGGTTATTGTCTCATGAGCGGATACATATTTGA |
| ATGTATTTAGAAAAATAAACAAATAGGGGTTCCGCGCACATTTCCCCGAAAAGTGCCACCTGAC |
| GTC |
| SEQ ID NO: 8 |
| (RFP)<br>mCherry:<br>atggtgagcaagggcgaggaggataacatggccatcatcaaggagttcatgcgcttcaaggtgcacatggagggct |
| ccgtgaacggccacgagttcgagatcgagggcgagggcgagggccgcccctacgagggcacccagaccgccaagct |
| gaaggtgaccaagggtggccccctgcccttcgcctgggacatcctgtcccctcagttcatgtacggctccaaggcc |
| tacgtgaagcaccccgccgacatccccgactacttgaagctgtccttccccgagggcttcaagtgggagcgcgtga |
| tgaacttcgaggacggcggcgtggtgaccgtgacccaggactcctccctgcaggacggcgagttcatctacaaggt |
| gaagctgcgcggcaccaacttcccctccgacggccccgtaatgcagaagaagaccatgggctgggaggcctcctcc |
| gagcggatgtaccccgaggacggcgccctgaagggcgagatcaagcagaggctgaagctgaaggacggcggccact |
| acgacgctgaggtcaagaccacctacaaggccaagaagcccgtgcagctgcccggcgcctacaacgtcaacatcaa |
| gttggacatcacctcccacaacgaggactacaccatcgtggaacagtacgaacgcgccgagggccgccactccacc |
| ggcggcatggacgagctgtacaag |

-continued

| Sequence listing |
|---|

SEQ ID NO: 9

(riboswitch)
Aptazyme (Theophylline Dependent see Auslander 2010 Mol Biosys):
cugagaugcagguacauccagcugaugagucccaaauaggacgaaagccauaccagccgaaaggcccuuggcaggg uuccuggauuccacugcuauccac

SEQ ID NO: 10

(luciferase)
nLuc:
ATGGTCTTCACACTCGAAGATTTCGTTGGGGACTGGCGACAGACAGCCGGCTACAACCTGGACC

AAGTCCTTGAACAGGGAGGTGTGTCCAGTTTGTTTCAGAATCTCGGGGTGTCCGTAACTCCGAT

CCAAAGGATTGTCCTGAGCGGTGAAAATGGGCTGAAGATCGACATCCATGTCATCATCCCGTAT

GAAGGTCTGAGCGGCGACCAAATGGGCCAGATCGAAAAAATTTTTAAGGTGGTGTACCCTGTG

GATGATCATCACTTTAAGGTGATCCTGCACTATGGCACACTGGTAATCGACGGGGTTACGCCGA

ACATGATCGACTATTTCGGACGGCCGTATGAAGGCATCGCCGTGTTCGACGGCAAAAAGATCAC

TGTAACAGGGACCCTGTGGAACGGCAACAAAATTATCGACGAGCGCCTGATCAACCCCGACGG

CTCCCTGCTGTTCCGAGTAACCATCAACGGAGTGACCGGCTGGCGGCTGTGCGAACGCATTCTG

GCGTAA

Sequence ID 11

Kozak3XFLAG-EGF nostop (264 bps)
GGGAGCCACCATGGACTACAAGGACGACGACGACAAGATCATCGACTATAAAGACGACGACGA

TAAAGGTGGCGACTATAAGGACGACGACGACAAAGCCATTAATAGTGACTCTGAGTGTCCCCTG

TCCCACGACGGGTACTGCCTCCACGACGGTGTGTGCATGTATATTGAAGCATTGGACAAGTACG

CCTGCAACTGTGTTGTTGGCTACATCGGGGAGCGCTGTCAGTACCGAGACCTGAAGTGGTGGGA

ACTGCGCCT 5-13: Kozak sequence
14-262:3XFLAG-EGF

SEQ ID NO: 12

Kozak 3XFLAG-EGF stop (273 bps)
GGGAGCCACCATGGACTACAAGGACGACGACGACAAGATCATCGACTATAAAGACGACGACGA

TAAAGGTGGCGACTATAAGGACGACGACGACAAAGCCATTAATAGTGACTCTGAGTGTCCCCTG

TCCCACGACGGGTACTGCCTCCACGACGGTGTGTGCATGTATATTGAAGCATTGGACAAGTACG

CCTGCAACTGTGTTGTTGGCTACATCGGGGAGCGCTGTCAGTACCGAGACCTGAAGTGGTGGGA

ACTGCGCTGATAGTAACT 5-13: Kozak sequence
14-262: 3XFLAG-EGF
263-271: Triple stop codon

SEQ ID NO: 13

Kozak 3XFLAG-EGF P2A nostop (330 bps)
GGGAGCCACCATGGACTACAAGGACGACGACGACAAGATCATCGACTATAAAGACGACGACGA

TAAAGGTGGCGACTATAAGGACGACGACGACAAAGCCATTAATAGTGACTCTGAGTGTCCCCTG

TCCCACGACGGGTACTGCCTCCACGACGGTGTGTGCATGTATATTGAAGCATTGGACAAGTACG

CCTGCAACTGTGTTGTTGGCTACATCGGGGAGCGCTGTCAGTACCGAGACCTGAAGTGGTGGGA

ACTGCGCGGAAGCGGAGCTACTAACTTCAGCCTGCTGAAGCAGGCTGGAGACGTGGAGGAGAA

CCCTGGACCTCT

-continued

| Sequence listing |
| --- |

5-13: Kozak sequence
14-262: 3XFLAG-EGF
263-328: P2A

SEQ ID NO: 14

Splint for construct Kozak 3XFLAG-EGF nostop (264 bps)
GGTGGCTCCCAGGCGCAGTT

SEQ ID NO: 15

Splint for construct Kozak 3XFLAG-EGF stop (273 bps)
GCTTGGCTCCCAGTTACTATC

SEQ ID NO: 16

Splint for construct Kozak 3XFLAG-EGF P2A nostop (330 bps)
GGTGGCTCCCAGAGGTCCAG

SEQ ID NO: 17

Kozak 1XFLAG-EGF T2A 1XFLAG-Nluc P2A nostop (873 bps)
GGGAGCCACCATGGACTACAAGGACGACGACGACAAGATCATCAATAGTGACTCTGAGTGTCC

CCTGTCCCACGACGGGTACTGCCTCCACGACGGTGTGTGCATGTATATTGAAGCATTGGACAAG

TACGCCTGCAACTGTGTTGTTGGCTACATCGGGGAGCGCTGTCAGTACCGAGACCTGAAGTGGT

GGGAACTGCGCGGCTCCGGCGAGGGCAGGGGAAGTCTTCTAACATGCGGGGACGTGGAGGAAA

ATCCCGGCCCAGACTATAAGGACGACGACGACAAAATCATCGTCTTCACACTCGAAGATTTCGT

TGGGGACTGGCGACAGACAGCCGGCTACAACCTGGACCAAGTCCTTGAACAGGGAGGTGTGTC

CAGTTTGTTTCAGAATCTCGGGGTGTCCGTAACTCCGATCCAAAGGATTGTCCTGAGCGGTGAA

AATGGGCTGAAGATCGACATCCATGTCATCATCCCGTATGAAGGTCTGAGCGGCGACCAAATGG

GCCAGATCGAAAAAATTTTTAAGGTGGTGTACCCTGTGGATGATCATCACTTTAAGGTGATCCT

GCACTATGGCACACTGGTAATCGACGGGGTTACGCCGAACATGATCGACTATTTCGGACGGCCG

TATGAAGGCATCGCCGTGTTCGACGGCAAAAAGATCACTGTAACAGGGACCCTGTGGAACGGC

AACAAAATTATCGACGAGCGCCTGATCAACCCCGACGGCTCCCTGCTGTTCCGAGTAACCATCA

ACGGAGTGACCGGCTGGCGGCTGTGCGAACGCATTCTGGCGGGAAGCGGAGCTACTAACTTCA

GCCTGCTGAAGCAGGCTGGAGACGTGGAGGAGAACCCTGGACCTCT 5-13: Kozak sequence
14-202: 1XFLAG-EGF
203-265: T2A
266-805: 1XFLAG-Nluc
806-871: P2A

SEQ ID NO: 18

Kozak 1XFLAG-EGF stop 1XFLAG-Nluc stop (762 bps)
GGGAGCCACCATGGACTACAAGGACGACGACGACAAGATCATCAATAGTGACTCTGAGTGTCC

CCTGTCCCACGACGGGTACTGCCTCCACGACGGTGTGTGCATGTATATTGAAGCATTGGACAAG

TACGCCTGCAACTGTGTTGTTGGCTACATCGGGGAGCGCTGTCAGTACCGAGACCTGAAGTGGT

GGGAACTGCGCTGATAGTAAGACTATAAGGACGACGACGACAAAATCATCGTCTTCACACTCG

AAGATTTCGTTGGGGACTGGCGACAGACAGCCGGCTACAACCTGGACCAAGTCCTTGAACAGG

GAGGTGTGTCCAGTTTGTTTCAGAATCTCGGGGTGTCCGTAACTCCGATCCAAAGGATTGTCCTG

AGCGGTGAAAATGGGCTGAAGATCGACATCCATGTCATCATCCCGTATGAAGGTCTGAGCGGCG

ACCAAATGGGCCAGATCGAAAAAATTTTTAAGGTGGTGTACCCTGTGGATGATCATCACTTTAA

GGTGATCCTGCACTATGGCACACTGGTAATCGACGGGGTTACGCCGAACATGATCGACTATTTC

GGACGGCCGTATGAAGGCATCGCCGTGTTCGACGGCAAAAAGATCACTGTAACAGGGACCCTG

TGGAACGGCAACAAAATTATCGACGAGCGCCTGATCAACCCCGACGGCTCCCTGCTGTTCCGAG

TAACCATCAACGGAGTGACCGGCTGGCGGCTGTGCGAACGCATTCTGGCGTGATAGTAACT

Sequence listing 5-13: Kozak sequence
14-202: 1XFLAG-EGF
203-211: Triple stop codon
212-751: 1XFLAG-Nluc
752-760: Triple stop codon

SEQ ID NO: 19

Kozak 3XFLAG-EGF P2A nostop (330 bps)
GGGAGCCACCATGGACTACAAGGACGACGACGACAAGATCATCGACTATAAAGACGACGACGA

TAAAGGTGGCGACTATAAGGACGACGACGACAAAGCCATTAATAGTGACTCTGAGTGTCCCCTG

TCCCACGACGGGTACTGCCTCCACGACGGTGTGTGCATGTATATTGAAGCATTGGACAAGTACG

CCTGCAACTGTGTTGTTGGCTACATCGGGGAGCGCTGTCAGTACCGAGACCTGAAGTGGTGGGA

ACTGCGCGGAAGCGGAGCTACTAACTTCAGCCTGCTGAAGCAGGCTGGAGACGTGGAGGAGAA

CCCTGGACCTCT 5-13: Kozak sequence
14-262: 3XFLAG-EGF
263-328: P2A

SEQ ID NO: 20

Kozak 3XFLAG-EGF nostop (264 bps)
GGGAGCCACCATGGACTACAAGGACGACGACGACAAGATCATCGACTATAAAGACGACGACGA

TAAAGGTGGCGACTATAAGGACGACGACGACAAAGCCATTAATAGTGACTCTGAGTGTCCCCTG

TCCCACGACGGGTACTGCCTCCACGACGGTGTGTGCATGTATATTGAAGCATTGGACAAGTACG

CCTGCAACTGTGTTGTTGGCTACATCGGGGAGCGCTGTCAGTACCGAGACCTGAAGTGGTGGGA

ACTGCGCCT 5-13: Kozak sequence
14-262: 3XFLAG-EGF

SEQ ID NO: 21

Kozak 3XFLAG-EGFstop (273 bps)
GGGAGCCACCATGGACTACAAGGACGACGACGACAAGATCATCGACTATAAAGACGACGACGA

TAAAGGTGGCGACTATAAGGACGACGACGACAAAGCCATTAATAGTGACTCTGAGTGTCCCCTG

TCCCACGACGGGTACTGCCTCCACGACGGTGTGTGCATGTATATTGAAGCATTGGACAAGTACG

CCTGCAACTGTGTTGTTGGCTACATCGGGGAGCGCTGTCAGTACCGAGACCTGAAGTGGTGGGA

ACTGCGCTGATAGTAACT 5-13: Kozak sequence
14-262: 3XFLAG-EGF
263-271: Triple stop codon

SEQ ID NO: 22

EMCV IRES T2A 3XFLAG-EGF P2A nostop (954 bps)
GGGACCTAACGTTACTGGCCGAAGCCGCTTGGAACAAGGCCGGTGTGCGTTTGTCTATATGTTA

TTTTCCACCATATTGCCGTCTTTTGGCAATGTGAGGGCCCGGAAACCTGGCCCTGTCTTCTTGAC

GAGCATTCCTAGGGGTCTTTCCCCTCTCGCCAAAGGAATGCAAGGTCTGTTGAATGTCGTGAAG

GAAGCAGTTCCTCTGGAAGCTTCTTCAAGACAAACAACGTCTGTAGCGACCCTTTGCAGGCAGC

GGAACCCCCCACCTGGCGACAGGTGCCTCTGCGGCCAAAAGCCACGTGTATACGATACACCTGC

AAAGGCGGCACAACCCCAGTGCCACGTTGTGAGTTGGATAGTTGTGGAAAGAGTCAAATGGCT

CTCCTCAAGCGTATTCAACAAGGGGCTGAAGGATGCCCAGAAGGTACCCCATTGTATGGGATCT

GATCTGGGGCCTCGGTGCACATGCTTTACATGTGTTCAGTCGAGGTTAAAAAACGTCCAGGCCC

CCCGAACCACGGGGACGTGGTTTTCCTTTGAAAAACACGATGATAATATGGCCACAACCATGGG

CTCCGGCGAGGGCAGGGGAAGTCTTCTAACATGCGGGGACGTGGAGGAAAATCCCGGCCCAGA

CTACAAGGACGACGACGACAAGATCATCGACTATAAAGACGACGACGATAAAGGTGGCGACTA

TAAGGACGACGACGACAAAGCCATTAATAGTGACTCTGAGTGTCCCCTGTCCCACGACGGGTAC

Sequence listing

TGCCTCCACGACGGTGTGTGCATGTATATTGAAGCATTGGACAAGTACGCCTGCAACTGTGTTG

TTGGCTACATCGGGGAGCGCTGTCAGTACCGAGACCTGAAGTGGTGGGAACTGCGCGGAAGCG

GAGCTACTAACTTCAGCCTGCTGAAGCAGGCTGGAGACGTGGAGGAGAACCCTGGACCTCT 5-574: EMCV IRES
575-637: T2A
638-886: 3XFALG-EGF
887-952: P2A

SEQ ID NO: 23

EMCV T2A 3XFLAG Nluc P2A stop (1314 nts)
GGGACCTAACGTTACTGGCCGAAGCCGCTTGGAACAAGGCCGGTGTGCGTTTGTCTATATGTTA

TTTTCCACCATATTGCCGTCTTTTGGCAATGTGAGGGCCCGGAAACCTGGCCCTGTCTTCTTGAC

GAGCATTCCTAGGGGTCTTTCCCCTCTCGCCAAAGGAATGCAAGGTCTGTTGAATGTCGTGAAG

GAAGCAGTTCCTCTGGAAGCTTCTTCAAGACAAACAACGTCTGTAGCGACCCTTTGCAGGCAGC

GGAACCCCCCACCTGGCGACAGGTGCCTCTGCGGCCAAAAGCCACGTGTATACGATACACCTGC

AAAGGCGGCACAACCCCAGTGCCACGTTGTGAGTTGGATAGTTGTGGAAAGAGTCAAATGGCT

CTCCTCAAGCGTATTCAACAAGGGGCTGAAGGATGCCCAGAAGGTACCCCATTGTATGGGATCT

GATCTGGGGCCTCGGTGCACATGCTTTACATGTGTTCAGTCGAGGTTAAAAAACGTCCAGGCCC

CCCGAACCACGGGGACGTGGTTTTCCTTTGAAAAACACGATGATAATATGGCCACAACCATGGG

CTCCGGCGAGGGCAGGGGAAGTCTTCTAACATGCGGGGACGTGGAGGAAAATCCCGGCCCAGA

CTACAAGGACGACGACGACAAGATCATCGACTATAAAGACGACGACGATAAAGGTGGCGACTA

TAAGGACGACGACGACAAAGCCATTGTCTTCACACTCGAAGATTTCGTTGGGGACTGGCGACAG

ACAGCCGGCTACAACCTGGACCAAGTCCTTGAACAGGGAGGTGTGTCCAGTTTGTTTCAGAATC

TCGGGGTGTCCGTAACTCCGATCCAAAGGATTGTCCTGAGCGGTGAAAATGGGCTGAAGATCGA

CATCCATGTCATCATCCCGTATGAAGGTCTGAGCGGCGACCAAATGGGCCAGATCGAAAAAATT

TTTAAGGTGGTGTACCCTGTGGATGATCATCACTTTAAGGTGATCCTGCACTATGGCACACTGGT

AATCGACGGGGTTACGCCGAACATGATCGACTATTTCGGACGGCCGTATGAAGGCATCGCCGTG

TTCGACGGCAAAAAGATCACTGTAACAGGGACCCTGTGGAACGGCAACAAAATTATCGACGAG

CGCCTGATCAACCCCGACGGCTCCCTGCTGTTCCGAGTAACCATCAACGGAGTGACCGGCTGGC

GGCTGTGCGAACGCATTCTGGCGGGAAGCGGAGCTACTAACTTCAGCCTGCTGAAGCAGGCTGG

AGACGTGGAGGAGAACCCTGGACCTTGATAGTAACT 5-574: EMCV IRES
575-637: T2A
638-1237: 3XFLAG Nluc
1238-1303: P2A
1304-1312: Triple stop codon

SEQ ID NO: 24

EMCV T2A 3XFLAG Nluc P2A nostop (1305 nts)
GGGACCTAACGTTACTGGCCGAAGCCGCTTGGAACAAGGCCGGTGTGCGTTTGTCTATATGTTA

TTTTCCACCATATTGCCGTCTTTTGGCAATGTGAGGGCCCGGAAACCTGGCCCTGTCTTCTTGAC

GAGCATTCCTAGGGGTCTTTCCCCTCTCGCCAAAGGAATGCAAGGTCTGTTGAATGTCGTGAAG

GAAGCAGTTCCTCTGGAAGCTTCTTCAAGACAAACAACGTCTGTAGCGACCCTTTGCAGGCAGC

GGAACCCCCCACCTGGCGACAGGTGCCTCTGCGGCCAAAAGCCACGTGTATACGATACACCTGC

AAAGGCGGCACAACCCCAGTGCCACGTTGTGAGTTGGATAGTTGTGGAAAGAGTCAAATGGCT

CTCCTCAAGCGTATTCAACAAGGGGCTGAAGGATGCCCAGAAGGTACCCCATTGTATGGGATCT

GATCTGGGGCCTCGGTGCACATGCTTTACATGTGTTCAGTCGAGGTTAAAAAACGTCCAGGCCC

Sequence listing

CCCGAACCACGGGGACGTGGTTTTCCTTTGAAAAACACGATGATAATATGGCCACAACCATGGG

CTCCGGCGAGGGCAGGGGAAGTCTTCTAACATGCGGGGACGTGGAGGAAAATCCCGGCCCAGA

CTACAAGGACGACGACGACAAGATCATCGACTATAAAGACGACGACGATAAAGGTGGCGACTA

TAAGGACGACGACGACAAAGCCATTGTCTTCACACTCGAAGATTTCGTTGGGGACTGGCGACAG

ACAGCCGGCTACAACCTGGACCAAGTCCTTGAACAGGGAGGTGTGTCCAGTTTGTTTCAGAATC

TCGGGGTGTCCGTAACTCCGATCCAAAGGATTGTCCTGAGCGGTGAAAATGGGCTGAAGATCGA

CATCCATGTCATCATCCCGTATGAAGGTCTGAGCGGCGACCAAATGGGCCAGATCGAAAAAATT

TTTAAGGTGGTGTACCCTGTGGATGATCATCACTTTAAGGTGATCCTGCACTATGGCACACTGGT

AATCGACGGGGTTACGCCGAACATGATCGACTATTTCGGACGGCCGTATGAAGGCATCGCCGTG

TTCGACGGCAAAAAGATCACTGTAACAGGGACCCTGTGGAACGGCAACAAAATTATCGACGAG

CGCCTGATCAACCCCGACGGCTCCCTGCTGTTCCGAGTAACCATCAACGGAGTGACCGGCTGGC

GGCTGTGCGAACGCATTCTGGCGGGAAGCGGAGCTACTAACTTCAGCCTGCTGAAGCAGGCTGG

AGACGTGGAGGAGAACCCTGGACCTCT 5-574: EMCV IRES
575-637: T2A
638-1237: 3XFLAG Nluc
1238-1303: P2A

SEQ ID NO: 25

Kozak 1XFLAG-EGF T2A 1XFLAG-NLuc P2A stop (882 bps)
GGGAGCCACCATGGACTACAAGGACGACGACGACAAGATCATCAATAGTGACTCTGAGTGTCC

CCTGTCCCACGACGGGTACTGCCTCCACGACGGTGTGTGCATGTATATTGAAGCATTGGACAAG

TACGCCTGCAACTGTGTTGTTGGCTACATCGGGGAGCGCTGTCAGTACCGAGACCTGAAGTGGT

GGGAACTGCGCGGCTCCGGCGAGGGCAGGGGAAGTCTTCTAACATGCGGGGACGTGGAGGAAA

ATCCCGGCCCAGACTATAAGGACGACGACGACAAAATCATCGTCTTCACACTCGAAGATTTCGT

TGGGGACTGGCGACAGACAGCCGGCTACAACCTGGACCAAGTCCTTGAACAGGGAGGTGTGTC

CAGTTTGTTTCAGAATCTCGGGGTGTCCGTAACTCCGATCCAAAGGATTGTCCTGAGCGGTGAA

AATGGGCTGAAGATCGACATCCATGTCATCATCCCGTATGAAGGTCTGAGCGGCGACCAAATGG

GCCAGATCGAAAAAATTTTTAAGGTGGTGTACCCTGTGGATGATCATCACTTTAAGGTGATCCT

GCACTATGGCACACTGGTAATCGACGGGGTTACGCCGAACATGATCGACTATTTCGGACGGCCG

TATGAAGGCATCGCCGTGTTCGACGGCAAAAAGATCACTGTAACAGGGACCCTGTGGAACGGC

AACAAAATTATCGACGAGCGCCTGATCAACCCCGACGGCTCCCTGCTGTTCCGAGTAACCATCA

ACGGAGTGACCGGCTGGCGGCTGTGCGAACGCATTCTGGCGGGAAGCGGAGCTACTAACTTCA

GCCTGCTGAAGCAGGCTGGAGACGTGGAGGAGAACCCTGGACCTTGATAGTAACT 5-13: Kozak sequence
14-202: 1XFLAG-EGF
266-805: 1XFLAG-NLuc
806-871: P2A
872-880: Triple stop codon

SEQ ID NO: 26

Exemplary Repetitive Spacer Sequence
AAAAAACAAAAAACAAAACGGCTATTATGCGTTACCGGCGAGACGCTACGGACTTGGG

AAAATCCGTTGACCTTAAACGGTCGTGTGGGTTCAAGTCCCTCCACCCCCACGCCGGAAACGCA

ATAGCCGAAAAACAAAAACAAAAAAAACAAAAAAAAAACCAAAAAAACAAAACACA

-continued

| Sequence listing |
|---|

SEQ ID NO: 27
Forward primer used in Example 43 to amplify template from pCDNA3.1/CAT
CGCGGATCCTAATACGACTCACTATAGGGAGACCCAAGCTGGC SEQ ID NO: 28
Reverse primer used in Example 43 to amplify 0.5 kb template from pCDNA3.1/CAT
AATAGCCGTTTTGTTTTTTGGATTACCAGTGTGCCATAGTGCAGGATCACATCGTCGTGGTATTC

ACTCCAGAGCGATG

SEQ ID NO: 29
Reverse primer used in Example 43 to amplify 1 kb template from pCDNA3.1/CAT
AATAGCCGTTTTGTTTTTTGGATTACCAGTGTGCCATAGTGCAGGATCACACGGGGGAGGGGCA

AACAACAGATGG

SEQ ID NO: 30
Reverse primer used in Example 43 to amplify 2 kb template from pCDNA3.1/CAT
AATAGCCGTTTTGTTTTTTGGATTACCAGTGTGCCATAGTGCAGGATCACGCTTTTTGCAAAAGC

CTAGGCCTCCAAAAAAGCC

SEQ ID NO: 31
Reverse primer used in Example 43 to amplify 4 kb template from pCDNA3.1/CAT
AATAGCCGTTTTGTTTTTTGGATTACCAGTGTGCCATAGTGCAGGATCACTAGCACCGCCTACAT

ACCTCGCTCTGC

SEQ ID NO: 32
Reverse primer used in Example 43 to amplify 5 kb template from pCDNA3.1/CAT
AATAGCCGTTTTGTTTTTTGGATTACCAGTGTGCCATAGTGCAGGATCACCTATGTGGCGCGGTA

TTATCCCGTATTGAC

SEQ ID NO: 33
Reverse primer used in Example 43 to amplify 6.2 kb template from pCDNA3.1/CAT
AATAGCCGTTTTGTTTTTTGGATTACCAGTGTGCCATAGTGCAGGATCACATTTCGATAAGCCAG

TAAGCAGTGGGTTCTCTAG

SEQ ID NO: 34
Forward qPCR primer used in Example 43 to detect linear transcript from pCDNA3.1/CAT
ATTCTTGCCCGCCTGATGAA SEQ ID NO: 35
Reverse qPCR primer used in Example 43 to detect linear transcript from pCDNA3.1/CAT
TTGCTCATGGAAAACGGTGT SEQ ID NO: 36
Forward qPCR primer used in Example 43 to detect circular transcript from pCDNA3.1/CAT
TGATCCTGCACTATGGCACA SEQ ID NO: 37
Reverse qPCR primer used in Example 43 to detect circular transcript from pCDNA3.1/CAT
CTGGACTAGTGGATCCGAGC SEQ ID NO: 38
Forward primer sequence used in Example 44 to detect ACTIN
GACGAGGCCCAGAGCAAGAGAGG SEQ ID NO: 39
Reverse primer sequence used in Example 44 to detect ACTIN
GGTGTTGAAGGTCTCAAACATG SEQ ID NO: 40
Forward primer sequence used in Example 44 to detect RIG-I
TGTGGGCAATGTCATCAAAA Sequence listing SEQ ID NO: 41
Reverse primer sequence used in Example 44 to detect RIG-I
GAAGCACTTGCTACCTCTTGC SEQ ID NO: 42
Forward primer sequence used in Example 44 to detect MDA5
GGCACCATGGGAAGTGATT SEQ ID NO: 43
Reverse primer sequence used in Example 44 to detect MDA5
ATTTGGTAAGGCCTGAGCTG SEQ ID NO: 44
Forward primer sequence used in Example 44 to detect PKR
TCGCTGGTATCACTCGTCTG SEQ ID NO: 45
Reverse primer sequence used in Example 44 to detect PKR
GATTCTGAAGACCGCCAGAG SEQ ID NO: 46
Forward primer sequence used in Example 44 to detect IFN-beta
CTCTCCTGTTGTGCTTCTCC SEQ ID NO: 47
Reverse primer sequence used in Example 44 to detect IFN-beta
GTCAAAGTTCATCCTGTCCTTG.

SEQ ID NO: 48
EMCV T2A 3XFLAG-GFP F2A 3XFALG-Nluc P2A IS
GGGAATAGCCGAAAAACAAAAAACAAAAAAAACAAAAAAAAAACCAAAAAAACAAAACACA

ACGTTACTGGCCGAAGCCGCTTGGAACAAGGCCGGTGTGCGTTTGTCTATATGTTATTTTCCACC

ATATTGCCGTCTTTTGGCAATGTGAGGGCCCGGAAACCTGGCCCTGTCTTCTTGACGAGCATTCC

TAGGGGTCTTTCCCCTCTCGCCAAAGGAATGCAAGGTCTGTTGAATGTCGTGAAGGAAGCAGTT

CCTCTGGAAGCTTCTTGTAGACAAACAACGTCTGTAGCGACCCTTTGCAGGCAGCGGAACCCCC

CACCTGGCGACAGGTGCCTCTGCGGCCAAAAGCCACGTGTATACGATACACCTGCAAAGGCGG

CACAACCCCAGTGCCACGTTGTGAGTTGGATAGTTGTGGAAAGAGTCAAATGGCTCTCCTCAAG

CGTATTCAACAAGGGGCTGAAGGATGCCCAGAAGGTACCCCATTGTATGGGATCTGATCTGGGG

CCTCGGTGCACATGCTTTACATGTGTTCAGTCGAGGTTAAAAAACGTCCAGGCCCCCCGAACCA

CGGGGACGTGGTTTTCCTTTGAAAAACACGATGATAATATGGCCACAACCATGGGCTCCGGCGA

GGGCAGGGGAAGTCTTCTAACATGCGGGGACGTGGAGGAAAATCCCGGCCCAGACTACAAGGA

CGACGACGACAAGATCATCGACTATAAAGACGACGACGATAAAGGTGGCGACTATAAGGACGA

CGACGACAAAGCCATTGTGAGCAAGGGCGAGGAGCTGTTCACCGGGGTGGTGCCCATCCTGGT

CGAGCTGGACGGCGACGTAAACGGCCACAAGTTCAGCGTGTCCGGCGAGGGCGAGGGCGATGC

CACCTACGGCAAGCTGACCCTGAAGTTCATCTGCACCACCGGCAAGCTGCCCGTGCCCTGGCCC

ACCCTCGTGACCACCCTGACCTACGGCGTGCAGTGCTTCAGCCGCTACCCCGACCACATGAAGC

AGCACGACTTCTTCAAGTCCGCCATGCCCGAAGGCTACGTCCAGGAGCGCACCATCTTCTTCAA

GGACGACGGCAACTACAAGACCCGCGCCGAGGTGAAGTTCGAGGGCGACACCCTGGTGAACCG

CATCGAGCTGAAGGGCATCGACTTCAAGGAGGACGGCAACATCCTGGGGCACAAGCTGGAGTA

CAACTACAACAGCCACAACGTCTATATCATGGCCGACAAGCAGAAGAACGGCATCAAGGTGAA

CTTCAAGATCCGCCACAACATCGAGGACGGCAGCGTGCAGCTCGCCGACCACTACCAGCAGAA

CACCCCCATCGGCGACGGCCCCGTGCTGCTGCCCGACAACCACTACCTGAGCACCCAGTCCGCC

CTGAGCAAAGACCCCAACGAGAAGCGCGATCACATGGTCCTGCTGGAGTTCGTGACCGCCGCC

GGGATCACTCTCGGCATGGACGAGCTGTACAAGGGAAGCGGAGTGAAACAGACTTTGAATTTT

Sequence listing

GACCTTCTCAAGTTGGCGGGAGACGTGGAGTCCAACCCTGGACCTGACTACAAGGACGACGAC

GACAAGATCATCGACTATAAAGACGACGACGATAAAGGTGGCGACTATAAGGACGACGACGAC

AAAGCCATTATCATCGTCTTCACACTCGAAGATTTCGTTGGGGACTGGCGACAGACAGCCGGCT

ACAACCTGGACCAAGTCCTTGAACAGGGAGGTGTGTCCAGTTTGTTTCAGAATCTCGGGGTGTC

CGTAACTCCGATCCAAAGGATTGTCCTGAGCGGTGAAAATGGGCTGAAGATCGACATCCATGTC

ATCATCCCGTATGAAGGTCTGAGCGGCGACCAAATGGGCCAGATCGAAAAAATTTTTAAGGTGG

TGTACCCTGTGGATGATCATCACTTTAAGGTGATCCTGCACTATGGCACACTGGTAATCGACGG

GGTTACGCCGAACATGATCGACTATTTCGGACGGCCGTATGAAGGCATCGCCGTGTTCGACGGC

AAAAAGATCACTGTAACAGGGACCCTGTGGAACGGCAACAAAATTATCGACGAGCGCCTGATC

AACCCCGACGGCTCCCTGCTGTTCCGAGTAACCATCAACGGAGTGACCGGCTGGCGGCTGTGCG

AACGCATTCTGGCGGGAAGCGGAGCTACTAACTTCAGCCTGCTGAAGCAGGCTGGAGACGTGG

AGGAGAACCCTGGACCTTAAAAAAAACAAAAAACAAAACGGCTATT

SEQ ID NO: 49

EMCV T2A 3XFLAG-GFP F2A 3XFALG-Nluc P2A IS
GGGAATAGCCGAAAAACAAAAAACAAAAAAAACAAAAAAAAAACCAAAAAAACAAAACACA

ACGTTACTGGCCGAAGCCGCTTGGAACAAGGCCGGTGTGCGTTTGTCTATATGTTATTTTCCACC

ATATTGCCGTCTTTTGGCAATGTGAGGGCCCGGAAACCTGGCCCTGTCTTCTTGACGAGCATTCC

TAGGGGTCTTTCCCCTCTCGCCAAAGGAATGCAAGGTCTGTTGAATGTCGTGAAGGAAGCAGTT

CCTCTGGAAGCTTCTTGTAGACAAACAACGTCTGTAGCGACCCTTTGCAGGCAGCGGAACCCCC

CACCTGGCGACAGGTGCCTCTGCGGCCAAAAGCCACGTGTATACGATACACCTGCAAAGGCGG

CACAACCCCAGTGCCACGTTGTGAGTTGGATAGTTGTGGAAAGAGTCAAATGGCTCTCCTCAAG

CGTATTCAACAAGGGGCTGAAGGATGCCCAGAAGGTACCCCATTGTATGGGATCTGATCTGGGG

CCTCGGTGCACATGCTTTACATGTGTTCAGTCGAGGTTAAAAAACGTCCAGGCCCCCCGAACCA

CGGGGACGTGGTTTTCCTTTGAAAAACACGATGATAATATGGCCACAACCATGGGCTCCGGCGA

GGGCAGGGGAAGTCTTCTAACATGCGGGGACGTGGAGGAAAATCCCGGCCCAGACTACAAGGA

CGACGACGACAAGATCATCGACTATAAAGACGACGACGATAAAGGTGGCGACTATAAGGACGA

CGACGACAAAGCCATTGTGAGCAAGGGCGAGGAGCTGTTCACCGGGGTGGTGCCCATCCTGGT

CGAGCTGGACGGCGACGTAAACGGCCACAAGTTCAGCGTGTCCGGCGAGGGCGAGGGCGATGC

CACCTACGGCAAGCTGACCCTGAAGTTCATCTGCACCACCGGCAAGCTGCCCGTGCCCTGGCCC

ACCCTCGTGACCACCCTGACCTACGGCGTGCAGTGCTTCAGCCGCTACCCCGACCACATGAAGC

AGCACGACTTCTTCAAGTCCGCCATGCCCGAAGGCTACGTCCAGGAGCGCACCATCTTCTTCAA

GGACGACGGCAACTACAAGACCCGCGCCGAGGTGAAGTTCGAGGGCGACACCCTGGTGAACCG

CATCGAGCTGAAGGGCATCGACTTCAAGGAGGACGGCAACATCCTGGGGCACAAGCTGGAGTA

CAACTACAACAGCCACAACGTCTATATCATGGCCGACAAGCAGAAGAACGGCATCAAGGTGAA

CTTCAAGATCCGCCACAACATCGAGGACGGCAGCGTGCAGCTCGCCGACCACTACCAGCAGAA

CACCCCCATCGGCGACGGCCCCGTGCTGCTGCCCGACAACCACTACCTGAGCACCCAGTCCGCC

CTGAGCAAAGACCCCAACGAGAAGCGCGATCACATGGTCCTGCTGGAGTTCGTGACCGCCGCC

GGGATCACTCTCGGCATGGACGAGCTGTACAAGGGAAGCGGAGTGAAACAGACTTTGAATTTT

GACCTTCTCAAGTTGGCGGGAGACGTGGAGTCCAACCCTGGACCTTGATAGTAAGACTACAAGG

-continued

Sequence listing

ACGACGACGACAAGATCATCGACTATAAAGACGACGACGATAAAGGTGGCGACTATAAGGACG

ACGACGACAAAGCCATTATCATCGTCTTCACACTCGAAGATTTCGTTGGGGACTGGCGACAGAC

AGCCGGCTACAACCTGGACCAAGTCCTTGAACAGGGAGGTGTGTCCAGTTTGTTTCAGAATCTC

GGGGTGTCCGTAACTCCGATCCAAAGGATTGTCCTGAGCGGTGAAAATGGGCTGAAGATCGAC

ATCCATGTCATCATCCCGTATGAAGGTCTGAGCGGCGACCAAATGGGCCAGATCGAAAAAATTT

TTAAGGTGGTGTACCCTGTGGATGATCATCACTTTAAGGTGATCCTGCACTATGGCACACTGGTA

ATCGACGGGGTTACGCCGAACATGATCGACTATTTCGGACGGCCGTATGAAGGCATCGCCGTGT

TCGACGGCAAAAAGATCACTGTAACAGGGACCCTGTGGAACGGCAACAAAATTATCGACGAGC

GCCTGATCAACCCCGACGGCTCCCTGCTGTTCCGAGTAACCATCAACGGAGTGACCGGCTGGCG

GCTGTGCGAACGCATTCTGGCGGGAAGCGGAGCTACTAACTTCAGCCTGCTGAAGCAGGCTGGA

GACGTGGAGGAGAACCCTGGACCTTAAAAAAAACAAAAAACAAAACGGCTATT

SEQ ID NO: 50

URE
UCAUAAUCAAUUUAUUAUUUUCUUUUAUUUUAUUCACAUAAUUUUGUUUUU

SEQ ID NO: 51

CSE
AUUUUGUUUUUAACAUUUC

SEQ ID NO: 52

URE/CSE
UCAUAAUCAAUUUAUUAUUUUCUUUUAUUUUAUUCACAUAAUUUUGUUUUUAUUUUGUUUU

UAACAUUUC

SEQ ID NO: 53

CVB3-GLuc-STOP-URE
AAAAUCCGUUGACCUUAAACGGUCGUGUGGGUUCAAGUCCCUCCACCCCCACGCCGGAAACG

CAAUAGCCGAAAAACAAAAAACAAAAAAAACAAAAAAAAAACCAAAAAAACAAAACACAUU

AAAACAGCCUGUGGGUUGAUCCCACCCACAGGCCCAUUGGGCGCUAGCACUCUGGUAUCACG

GUACCUUUGUGCGCCUGUUUUAUACCCCCUCCCCCAACUGUAACUUAGAAGUAACACACACC

GAUCAACAGUCAGCGUGGCACACCAGCCACGUUUUGAUCAAGCACUUCUGUUACCCCGGACU

GAGUAUCAAUAGACUGCUCACGCGGUUGAAGGAGAAAGCGUUCGUUAUCCGGCCAACUACUU

CGAAAAACCUAGUAACACCGUGGAAGUUGCAGAGUGUUUCGCUCAGCACUACCCCAGUGUAG

AUCAGGUCGAUGAGUCACCGCAUUCCCCACGGGCGACCGUGGCGGUGGCUGCGUUGGCGGCC

UGCCCAUGGGGAAACCCAUGGGACGCUCUAAUACAGACAUGGUGCGAAGAGUCUAUUGAGCU

AGUUGGUAGUCCUCCGGCCCCUGAAUGCGGCUAAUCCUAACUGCGGAGCACACACCCUCAAG

CCAGAGGGCAGUGUGUCGUAACGGGCAACUCUGCAGCGGAACCGACUACUUUGGGUGUCCGU

GUUUCAUUUUAUUCCUAUACUGGCUGCUUAUGGUGACAAUUGAGAGAUCGUUACCAUAUAG

CUAUUGGAUUGGCCAUCCGGUGACUAAUAGAGCUAUUAUAUAUCCCUUUGUUGGGUUUAUA

CCACUUAGCUUGAAAGAGGUUAAAACAUUACAAUUCAUUGUUAAGUUGAAUACAGCAAAAU

GGGAGUCAAAGUUCUGUUUGCCCUGAUCUGCAUCGCUGUGGCCGAGGCCAAGCCCACCGAGA

ACAACGAAGACUUCAACAUCGUGGCCGUGGCCAGCAACUUCGCGACCACGGAUCUCGAUGCU

GACCGCGGGAAGUUGCCCGGCAAGAAGCUGCCGCUGGAGGUGCUCAAAGAGAUGGAAGCCAA

UGCCCGGAAAGCUGGCUGCACCAGGGGCUGUCUGAUCUGCCUGUCCCACAUCAAGUGCACGC

CCAAGAUGAAGAAGUUCAUCCCAGGACGCUGCCACACCUACGAAGGCGACAAAGAGUCCGCA

CAGGGCGGCAUAGGCGAGGCGAUCGUCGACAUUCCUGAGAUUCCUGGGUUCAAGGACUUGGA

-continued

| Sequence listing |
|---|

GCCCAUGGAGCAGUUCAUCGCACAGGUCGAUCUGUGUGUGGACUGCACAACUGGCUGCCUCA

AAGGGCUUGCCAACGUGCAGUGUUCUGACCUGCUCAAGAAGUGGCUGCCGCAACGCUGUGCG

ACCUUUGCCAGCAAGAUCCAGGGCCAGGUGGACAAGAUCAAGGGGGCCGGUGGUGACUAAUC

AUAAUCAAUUUAUUAUUUUCUUUUAUUUUAUUCACAUAAUUUUGUUUUUAUUUUGUUUUUA

ACAUUUCAAAAAACAAAAAACAAAACGGCUAUUAUGCGUUACCGGCGAGACGCUACGGACUU

SEQ ID NO: 54

CVB3-GLuc-STOP-URE/CSE
AAAAUCCGUUGACCUUAAACGGUCGUGUGGGUUCAAGUCCCUCCACCCCCACGCCGGAAACG

CAAUAGCCGAAAAACAAAAAACAAAAAAAACAAAAAAAAAACCAAAAAAACAAAACACAUU

AAAACAGCCUGUGGGUUGAUCCCACCCACAGGCCCAUUGGGCGCUAGCACUCUGGUAUCACG

GUACCUUUGUGCGCCUGUUUUAUACCCCCUCCCCCAACUGUAACUUAGAAGUAACACACACC

GAUCAACAGUCAGCGUGGCACACCAGCCACGUUUUGAUCAAGCACUUCUGUUACCCCGGACU

GAGUAUCAAUAGACUGCUCACGCGGUUGAAGGAGAAAGCGUUCGUUAUCCGGCCAACUACUU

CGAAAAACCUAGUAACACCGUGGAAGUUGCAGAGUGUUUCGCUCAGCACUACCCCAGUGUAG

AUCAGGUCGAUGAGUCACCGCAUUCCCCACGGGCGACCGUGGCGGUGGCUGCGUUGGCGGCC

UGCCCAUGGGGAAACCCAUGGGACGCUCUAAUACAGACAUGGUGCGAAGAGUCUAUUGAGCU

AGUUGGUAGUCCUCCGGCCCCUGAAUGCGGCUAAUCCUAACUGCGGAGCACACACCCUCAAG

CCAGAGGGCAGUGUGUCGUAACGGGCAACUCUGCAGCGGAACCGACUACUUUGGGUGUCCGU

GUUUCAUUUUAUUCCUAUACUGGCUGCUUAUGGUGACAAUUGAGAGAUCGUUACCAUAUAG

CUAUUGGAUUGGCCAUCCGGUGACUAAUAGAGCUAUUAUAUAUCCCUUUGUUGGGUUUAUA

CCACUUAGCUUGAAAGAGGUUAAAACAUUACAAUUCAUUGUUAAGUUGAAUACAGCAAAAU

GGGAGUCAAAGUUCUGUUUGCCCUGAUCUGCAUCGCUGUGGCCGAGGCCAAGCCCACCGAGA

ACAACGAAGACUUCAACAUCGUGGCCGUGGCCAGCAACUUCGCGACCACGGAUCUCGAUGCU

GACCGCGGGAAGUUGCCCGGCAAGAAGCUGCCGCUGGAGGUGCUCAAAGAGAUGGAAGCCAA

UGCCCGGAAAGCUGGCUGCACCAGGGGCUGUCUGAUCUGCCUGUCCCACAUCAAGUGCACGC

CCAAGAUGAAGAAGUUCAUCCCAGGACGCUGCCACACCUACGAAGGCGACAAAGAGUCCGCA

CAGGGCGGCAUAGGCGAGGCGAUCGUCGACAUUCCUGAGAUUCCUGGGUUCAAGGACUUGGA

GCCCAUGGAGCAGUUCAUCGCACAGGUCGAUCUGUGUGUGGACUGCACAACUGGCUGCCUCA

AAGGGCUUGCCAACGUGCAGUGUUCUGACCUGCUCAAGAAGUGGCUGCCGCAACGCUGUGCG

ACCUUUGCCAGCAAGAUCCAGGGCCAGGUGGACAAGAUCAAGGGGGCCGGUGGUGACUAAUC

AUAAUCAAUUUAUUAUUUUCUUUUAUUUUAUUCACAUAAUUUUGUUUUUAUUUUGUUUUUA

ACAUUUCAAAAAACAAAAAACAAAACGGCUAUUAUGCGUUACCGGCGAGACGCUACGGACUU

SEQ ID NO: 55

Complementary primer used for example 42
CACCGCTCAGGACAATCCTT

SEQ ID NO: 56

CVB3 IRES
TTAAAACAGCCTGTGGGTTGATCCCACCCACAGGCCCATTGGGCGCTAGCACTCTGGTATCACG

GTACCTTTGTGCGCCTGTTTTATACCCCCTCCCCCAACTGTAACTTAGAAGTAACACACACCGAT

CAACAGTCAGCGTGGCACACCAGCCACGTTTTGATCAAGCACTTCTGTTACCCCGGACTGAGTA

TCAATAGACTGCTCACGCGGTTGAAGGAGAAAGCGTTCGTTATCCGGCCAACTACTTCGAAAAA

-continued

| Sequence listing |
|---|

CCTAGTAACACCGTGGAAGTTGCAGAGTGTTTCGCTCAGCACTACCCCAGTGTAGATCAGGTCG

ATGAGTCACCGCATTCCCCACGGGCGACCGTGGCGGTGGCTGCGTTGGCGGCCTGCCCATGGGG

AAACCCATGGGACGCTCTAATACAGACATGGTGCGAAGAGTCTATTGAGCTAGTTGGTAGTCCT

CCGGCCCCTGAATGCGGCTAATCCTAACTGCGGAGCACACACCCTCAAGCCAGAGGGCAGTGTG

TCGTAACGGGCAACTCTGCAGCGGAACCGACTACTTTGGGTGTCCGTGTTTCATTTTATTCCTAT

ACTGGCTGCTTATGGTGACAATTGAGAGATCGTTACCATATAGCTATTGGATTGGCCATCCGGT

GACTAATAGAGCTATTATATATCCCTTTGTTGGGTTTATACCACTTAGCTTGAAAGAGGTTAAAA

CATTACAATTCATTGTTAAGTTGAATACAGCAAA

SEQ ID NO: 57

Gluc
ATGGGAGTCAAAGTTCTGTTTGCCCTGATCTGCATCGCTGTGGCCGAGGCCAAGCCCACCGAGA

ACAACGAAGACTTCAACATCGTGGCCGTGGCCAGCAACTTCGCGACCACGGATCTCGATGCTGA

CCGCGGGAAGTTGCCCGGCAAGAAGCTGCCGCTGGAGGTGCTCAAAGAGATGGAAGCCAATGC

CCGGAAAGCTGGCTGCACCAGGGGCTGTCTGATCTGCCTGTCCCACATCAAGTGCACGCCCAAG

ATGAAGAAGTTCATCCCAGGACGCTGCCACACCTACGAAGGCGACAAAGAGTCCGCACAGGGC

GGCATAGGCGAGGCGATCGTCGACATTCCTGAGATTCCTGGGTTCAAGGACTTGGAGCCCATGG

AGCAGTTCATCGCACAGGTCGATCTGTGTGTGGACTGCACAACTGGCTGCCTCAAAGGGCTTGC

CAACGTGCAGTGTTCTGACCTGCTCAAGAAGTGGCTGCCGCAACGCTGTGCGACCTTTGCCAGC

AAGATCCAGGGCCAGGTGGACAAGATCAAGGGGGCCGGTGGTGACTAA

SEQ ID NO: 58

EMCV IRES with stop mutations
ACGTTACTGGCCGAAGCCGCTTGGAACAAGGCCGGTGTGCGTTTGTCTATATGTTATTTTCCACC

ATATTGCCGTCTTTTGGCAATGTGAGGGCCCGGAAACCTGGCCCTGTCTTCTTGACGAGCATTCC

TAGGGGTCTTTCCCCTCTCGCCAAAGGAATGCAAGGTCTGTTGAATGTCGTGAAGGAAGCAGTT

CCTCTGGAAGCTTCTTCAAGACAAACAACGTCTGTAGCGACCCTTTGCAGGCAGCGGAACCCCC

CACCTGGCGACAGGTGCCTCTGCGGCCAAAAGCCACGTGTATACGATACACCTGCAAAGGCGG

CACAACCCCAGTGCCACGTTGTGAGTTGGATAGTTGTGGAAAGAGTCAAATGGCTCTCCTCAAG

CGTATTCAACAAGGGGCTGAAGGATGCCCAGAAGGTACCCCATTGTATGGGATCTGATCTGGGG

CCTCGGTGCACATGCTTTACATGTGTTCAGTCGAGGTTAAAAAACGTCCAGGCCCCCCGAACCA

CGGGGACGTGGTTTTCCTTTGAAAAACACGATGATAATATGGCCACAACCATG

SEQ ID NO: 59
(SEQ ID NO: 59)

SPACER 1
AAAAUCCGUUGACCUUAAACGGUCGUGUGGGUUCAAGUCCCUCCACCCCCACGCCGGAAACG

CAAUAGCCGAAAAACAAAAAACAAAAAAAACAAAAAAAAAACCAAAAAAACAAAACACA (SEQ ID NO: 135)

SPACER 2
AAAAAACAAAAAACAAAACGGCUAUUAUGCGUUACCGGCGAGACGCUACGGACUU

SEQ ID: 60

ATACCAGCCGAAAGGCCCTTGGCAGAGAGGTCTGAAAAGACCTCTGCTGACTATGTGATCTTAT

TAAAATTAGGTTAAATTTCGAGGTTAAAAATAGTTTTAATATTGCTATAGTCTTAGAGGTCTTGT

ATATTTATACTTACCACACAAGATGGACCGGAGCAGCCCTCCAATATCTAGTGTACCCTCGTGCT

CGCTCAAACATTAAGTGGTGTTGTGCGAAAAGAATCTCACTTCAAGAAAAAGAAACTAGT

EMBODIMENT PARAGRAPHS

[1] A method of in vivo expression of one or more expression sequences in a subject, comprising:

administering a circular polyribonucleotide to a cell of the subject wherein the circular polyribonucleotide comprises the one or more expression sequences; and expressing the one or more expression sequences from the circular polyribonucleotide in the cell, wherein the circular polyribonucleotide is configured such that expression of the one or more expression sequences in the cell at a later time point is equal to or higher than an earlier time point.

[2] A method of in vivo expression of one or more expression sequences in a subject, comprising:

administering a circular polyribonucleotide to a cell of the subject wherein the circular polyribonucleotide comprises the one or more expression sequences; and expressing the one or more expression sequences from the circular polyribonucleotide in the cell, wherein the circular polyribonucleotide is configured such that expression of the one or more expression sequences in the cell over a time period of at least 7, 8, 9, 10, 12, 14, or 16 days does not decrease by greater than about 40%.

[3] A method of in vivo expression of one or more expression sequences in a subject, comprising:

administering a circular polyribonucleotide to a cell of the subject wherein the circular polyribonucleotide comprises the one or more expression sequences; and expressing the one or more expression sequences from the circular polyribonucleotide in the cell, wherein the circular polyribonucleotide is configured such that expression of the one or more expression sequences in the cell is maintained at a level that does not vary by more than about 40% for at least 7, 8, 9, 10, 12, 14, or 16 days.

[4] The method of any one of paragraphs [1] to [3], wherein expression product of the one or more expression sequences comprises a therapeutic protein.

[5] The method of paragraph [4], wherein the therapeutic protein has antioxidant activity, binding, cargo receptor activity, catalytic activity, molecular carrier activity, molecular function regulator, molecular transducer activity, nutrient reservoir activity, protein tag, structural molecule activity, toxin activity, transcription regulator activity, translation regulator activity, or transporter activity.

[6] The method of any one of paragraphs [1] to[5], Expression product of the one or more expression sequences comprises a secretary protein.

[7] The method of paragraph [6], wherein the secretary protein comprises a secretary enzyme.

[8] The method of paragraph [6], wherein the secretary protein comprises a secretary antibody.

[9] The method of any one of paragraphs [1] to [8], wherein the circular polyribonucleotide is at least about 20 nucleotides, at least about 30 nucleotides, at least about 40 nucleotides, at least about 50 nucleotides, at least about 75 nucleotides, at least about 100 nucleotides, at least about 200 nucleotides, at least about 300 nucleotides, at least about 400 nucleotides, at least about 500 nucleotides, at least about 1,000 nucleotides, at least about 2,000 nucleotides, at least about 5,000 nucleotides, at least about 6,000 nucleotides, at least about 7,000 nucleotides, at least about 8,000 nucleotides, at least about 9,000 nucleotides, at least about 10,000 nucleotides, at least about 12,000 nucleotides, at least about 14,000 nucleotides, at least about 15,000 nucleotides, at least about 16,000 nucleotides, at least about 17,000 nucleotides, at least about 18,000 nucleotides, at least about 19,000 nucleotides, or at least about 20,000 nucleotides.

[10] The method of any one of paragraphs [1] to [9], wherein the circular polyribonucleotide has a persistence in the cell for at least about 1 hr, 2 hrs, 6 hrs, 12 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or longer or any time therebetween.

[11] The method of any one of paragraphs [1] to [10], wherein the circular polyribonucleotide has a persistence in the cell when the cell is dividing for at least about 1 hr, 2 hrs, 6 hrs, 12 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or longer or any time therebetween.

[12] The method of any one of paragraphs [1] to [11], wherein the circular polyribonucleotide has a persistence in the cell post division for at least about 1 hr, 2 hrs, 6 hrs, 12 hrs, 18 hrs, 24 hrs, 2 days, 3, days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or longer or any time therebetween.

[13] The method of any one of paragraphs [1] to [12], wherein the circular polyribonucleotide comprises at least one spacer sequence.

[14] The method of paragraph [13], wherein the spacer sequence is configured to provide conformational flexibility between elements of the circular polyribonucleotide on both sides of the spacer sequence.

[15] The method of paragraph [13] or [14], wherein a ratio of the spacer sequence to a non-spacer sequence of the circular polyribonucleotide, e.g., expression sequences, of about 0.05:1, about 0.06:1, about 0.07:1, about 0.08:1, about 0.09:1, about 0.1:1, about 0.12:1, about 0.125:1, about 0.15:1, about 0.175:1, about 0.2:1, about 0.225:1, about 0.25:1, about 0.3:1, about 0.35:1, about 0.4:1, about 0.45:1, about 0.5:1, about 0.55:1, about 0.6:1, about 0.65:1, about 0.7:1, about 0.75:1, about 0.8:1, about 0.85:1, about 0.9:1, about 0.95:1, about 0.98:1, about 1:1, about 1.02:1, about 1.05:1, about 1.1:1, about 1.15:1, about 1.2:1, about 1.25:1, about 1.3:1, about 1.35:1, about 1.4:1, about 1.45:1, about 1.5:1, about 1.55:1, about 1.6:1, about 1.65:1, about 1.7:1, about 1.75:1, about 1.8:1, about 1.85:1, about 1.9:1, about 1.95:1, about 1.975:1, about 1.98:1, or about 2:1.

[16] The method of any one of paragraphs [13] to [15], wherein the spacer sequence comprises at least 3 ribonucleotides, at least 4 ribonucleotides, at least 5 ribonucleotides, at least about 8 ribonucleotides, at least about 10 ribonucleotides, at least about 12 ribonucleotides, at least about 15 ribonucleotides, at least about 20 ribonucleotides, at least about 25 ribonucleotides, at least about 30 ribonucleotides, at least about 40 ribonucleotides, at least about 50 ribonucleotides, at least about 60 ribonucleotides, at least about 70 ribonucleotides, at least about 80 ribonucleotides, at least about 90 ribonucleotides, at least about 100 ribonucleotides, at least about 120 ribonucleotides, at least about 150 ribonucleotides, at least about 200 ribonucleotides, at least about 250 ribonucleotides, at least about 300 ribonucleotides, at least about 400 ribonucleotides, at least about 500 ribonucleotides, at least about 600 ribonucleotides, at least about 700 ribonucleotides, at least about 800 ribonucleotides, at least about 900 ribonucleotides, or at least about 100 ribonucleotides.

[17] The method of any one of paragraphs [13] to [16], wherein the spacer sequence comprises at least 95%, 90%, 85%, 80%, 75%, 70%, 65%, 60%, 55%, 50%, 55%, 50%, 45%, 40%, 35%, 30%, 20% or any percentage therebetween of adenine ribonucleotides.

[18] The method of any one of paragraphs [1] to [17], wherein the circular polyribonucleotide is competent for rolling translation.

[19] The method of paragraph [18], wherein each of the one or more expression sequences is separated from a succeeding expression sequence by a stagger element on the circular polyribonucleotide, wherein the rolling circle translation of the one or more expression sequences generates at least two polypeptide molecules.

[20] The method of paragraph [19], wherein the stagger element prevents generation of a single polypeptide (a) from two rounds of translation of a single expression sequence or (b) from one or more rounds of translation of two or more expression sequences.

[21] The method of paragraph [19] or [20], wherein the stagger element is a sequence separate from the one or more expression sequences.

[22] The method of paragraph [19] or [20], wherein the stagger element comprises a portion of an expression sequence of the one or more expression sequences.

[23] The method of any one of paragraphs [18] to [22], wherein the circular polyribonucleotide is configured such that at least 50%, at least 60%, at least 70%, at least 80%, at least 90%, at least 95%, at least 96%, at least 97%, at least 98%, at least 99%, or 100% of total polypeptides (molar/molar) generated during the rolling circle translation of the circular polyribonucleotide are discrete polypeptides, and wherein each of the discrete polypeptides is generated from a single round of translation or less than a single round of translation of the one or more expression sequences.

[24] The method of paragraph [23], wherein the circular polyribonucleotide is configured such that at least 50%, at least 60%, at least 70%, at least 80%, at least 90%, at least 95%, at least 96%, at least 97%, at least 98%, at least 99%, or 100% of total polypeptides (molar/molar) generated during the rolling circle translation of the circular polyribonucleotide are the discrete polypeptides, and wherein amount ratio of the discrete products over the total polypeptides is tested in an in vitro translation system.

[25] The method of paragraph [24], wherein the in vitro translation system comprises rabbit reticulocyte lysate.

[26] The method of any one of paragraphs [19] to [25], wherein the stagger element is at a 3' end of at least one of the one or more expression sequences, and wherein the stagger element is configured to stall a ribosome during rolling circle translation of the circular polyribonucleotide.

[27] The method of any one of paragraphs [19] to [26], wherein the stagger element encodes a peptide sequence selected from the group consisting of a 2A sequence and a 2A-like sequence.

[28] The method of any one of paragraphs [19] to [27], wherein the stagger element encodes a sequence with a C-terminal sequence that is GP.

[29] The method of any one of paragraphs [19] to [28], wherein the stagger element encodes a sequence with a C-terminal consensus sequence that is D(V/I)ExNPGP (SEQ ID NO: 61), where x=any amino acid.

[30] The method of any one of paragraphs [19] to [29], wherein the stagger element encodes a sequence selected from the group consisting of GDVESNPGP (SEQ ID NO: 62), GDIEENPGP (SEQ ID NO: 63), VEPNPGP (SEQ ID NO: 64), IETNPGP (SEQ ID NO: 65), GDIESNPGP (SEQ ID NO: 66), GDVELNPGP (SEQ ID NO: 67), GDIETNPGP (SEQ ID NO: 68), GDVENPGP (SEQ ID NO: 69), GDVEENPGP (SEQ ID NO: 70), GDVEQNPGP (SEQ ID NO: 71), IESNPGP (SEQ ID NO: 72), GDIELNPGP (SEQ ID NO: 73), HDIETNPGP (SEQ ID NO: 74), HDVETNPGP (SEQ ID NO: 75), HDVEMNPGP (SEQ ID NO: 76), GDMESNPGP (SEQ ID NO: 77), GDVETNPGP (SEQ ID NO: 78), GDIEQNPGP (SEQ ID NO: 79), and DSEFNPGP (SEQ ID NO: 80).

[31] The method of any one of paragraphs [19] to [30], wherein the stagger element is at 3' end of each of the one or more expression sequences.

[32] The method of any one of paragraphs [19] to [31], wherein the stagger element of a first expression sequence in the circular polyribonucleotide is upstream of (5' to) a first translation initiation sequence of an expression sequence succeeding the first expression sequence in the circular polyribonucleotide, and wherein a distance between the stagger element and the first translation initiation sequence enables continuous translation of the first expression sequence and the succeeding expression sequence.

[33] The method of any one of paragraphs [19] to [32], wherein the stagger element of a first expression sequence in the circular polyribonucleotide is upstream of (5' to) a first translation initiation sequence of an expression sequence succeeding the first expression in the circular polyribonucleotide, wherein the circular polyribonucleotide is continuously translated, wherein a corresponding circular polyribonucleotide comprising a second stagger element upstream of a second translation initiation sequence of a second expression sequence in the corresponding circular polyribonucleotide is not continuously translated, and wherein the second stagger element in the corresponding circular polyribonucleotide is at a greater distance from the second translation initiation sequence, e.g., at least 2×, 3×, 4×, 5×, 6×, 7×, 8×, 9×, 10×, than a distance between the stagger element and the first translation initiation in the circular polyribonucleotide.

[34] The method of any one of paragraphs [19] to [33], wherein the distance between the stagger element and the first translation initiation is at least 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, 40 nt, 45 nt, 50 nt, 55 nt, 60 nt, 65 nt, 70 nt, 75 nt, or greater.

[35] The method of any one of paragraphs [19] to [34], wherein the distance between the second stagger element and the second translation initiation is at least 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, 40 nt, 45 nt, 50 nt, 55 nt, 60 nt, 65 nt, 70 nt, 75 nt, or greater than the distance between the tagger element and the first translation initiation.

[36] The method of any one of paragraphs [19] to [35], wherein the expression sequence succeeding the first expression sequence on the circular polyribonucleotide is an expression sequence other than the first expression sequence.

[37] The method of any one of paragraphs [19] to [35], wherein the succeeding expression sequence of the first expression sequence on the circular polyribonucleotide is the first expression sequence.

[38] The method of any one of paragraphs [1] to [37], wherein the circular polyribonucleotide comprises at least one structural element selected from:

a) an encryptogen;
b) a stagger element;
c) a regulatory element;
d) a replication element; and
f) quasi-double-stranded secondary structure.

[39] The method of any one of paragraphs [1] to [38], wherein the circular polyribonucleotide comprises at least one functional characteristic selected from:

a) greater translation efficiency than a linear counterpart;
b) a stoichiometric translation efficiency of multiple translation products;
c) less immunogenicity than a counterpart lacking an encryptogen;
d) increased half-life over a linear counterpart; and
e) persistence during cell division.

[40] The method of any one of paragraphs [1] to [39], wherein the circular polyribonucleotide has a translation efficiency at least 5%, at least 10%, at least 15%, at least 20%, at least 30%, at least 40%, at least 50%, at least 60%, at least 70%, at least 80%, at least 90%, at least 100%, at least 150%, at least 2 fold, at least 3 fold, at least 4 fold, at least 5 fold, at least 6 fold, at least 7 fold, at least 8 fold, at least 9 fold, at least 10 fold, at least 20 fold, at least 50 fold, or at least 100 fold greater than a linear counterpart.

[41] The method of any one of paragraphs [1] to [40], wherein the circular polyribonucleotide has a translation efficiency at least 5 fold greater than a linear counterpart.

[42] The method of any one of paragraphs [1] to [41], wherein the circular polyribonucleotide lacks at least one of:

a) a 5'-UTR;
b) a 3'-UTR;
c) a poly-A sequence;
d) a 5'-cap;
e) a termination element;
f) an internal ribosomal entry site;
g) degradation susceptibility by exonucleases; and
h) binding to a cap-binding protein.

[43] The method of any one of [1] to [42], wherein the circular polyribonucleotide comprises an internal ribosomal entry site.

[44] The method of any one of [1] to [42], wherein the circular polyribonucleotide lacks an internal ribosomal entry site.

[45] The method of any one of [1] to [43], wherein the one or more expression sequences comprise a Kozak initiation sequence.

[46] The method of any one of [38] to [45], wherein the quasi-helical structure comprises at least one double-stranded RNA segment with at least one non-double-stranded segment.

[47] The method of paragraph [38] or [46], wherein the quasi-helical structure comprises a first sequence and a second sequence linked with a repetitive sequence, e.g., an A-rich sequence.

[48] The method of any one of paragraphs [38] to [47], wherein the encryptogen comprises a splicing element.

[49] The method of any one of paragraphs [38] to [48], wherein the circular polyribonucleotide comprises at least one modified ribonucleotide.

[50] The method of any one of paragraphs [38] to [49], wherein the circular polyribonucleotide comprises modified ribonucleotides in a portion of its entire length.

[51] The method of any one of paragraphs [38] to [50], wherein the encryptogen comprises at least one modified ribonucleotide, e.g., pseudo-uridine, N(6)methyladenosine (m6A).

[52] The method of any one of paragraphs [38] to [51], wherein the encryptogen comprises a protein binding site, e.g., ribonucleotide binding protein.

[53] The method of any one of paragraphs [38] to [52], wherein the encryptogen comprises an immunoprotein binding site, e.g., to evade Immune responses, e.g., CTL responses.

[54] The method of any one of paragraphs [38] to [53], wherein the circular polyribonucleotide has at least 2× less immunogenicity than a counterpart lacking the encryptogen, e.g., as assessed by expression or signaling or activation of at least one of RIG-I, TLR-3, TLR-7, TLR-8, MDA-5, LGP-2, OAS, OASL, PKR, IFN-beta.

[55] The method of any one of paragraphs [38] to [54], wherein the circular polyribonucleotide further comprises a riboswitch.

[56] The method of any one of paragraphs [38] to [55], wherein the circular polyribonucleotide further comprises an aptazyme.

[57] The method of any one of paragraphs [38] to [56], wherein the circular polyribonucleotide comprises a translation initiation sequence, e.g., GUG, CUG start codon, e.g., expression under stress conditions.

[58] The method of any one of paragraphs [38] to [57], wherein the circular polyribonucleotide comprises a stagger element, e.g., 2A.

[59] The method of any one of paragraphs [38] to [58], wherein the circular polyribonucleotide comprises a regulatory nucleic acid, e.g., a non-coding RNA.

[60] The method of any one of paragraphs [38] to [59], wherein the circular polyribonucleotide has a size in the range of about 20 bases to about 20 kb.

[61] The method of any one of paragraphs [38] to [60], wherein the circular polyribonucleotide is synthesized through circularization of a linear polynucleotide.

[62] The method of any one of paragraphs [38] to [61], wherein the circular polyribonucleotide comprises a plurality of expression sequences, either the same or different.

[63] The method of any one of paragraphs [38] to [62], wherein the circular polyribonucleotide is substantially resistant to degradation, e.g., exonuclease.

[64] The method of any one of paragraphs [38] to [63], wherein the circular polyribonucleotide lacks at least one of:

a) a 5'-UTR;

b) a 3'-UTR;

c) a poly-A sequence;

d) a 5'-cap;

e) a termination element;

f) an internal ribosomal entry site;

g) degradation susceptibility by exonucleases; and h) binding to a cap-binding protein.

[65] A pharmaceutical composition comprising a circular polyribonucleotide that comprises at least one structural element selected from:

a) an encryptogen;

b) a stagger element;

c) a regulatory element;

d) a replication element;

f) quasi-double-stranded secondary structure; and g) expression sequence;

and at least one functional characteristic selected from:

a) greater translation efficiency than a linear counterpart;

b) a stoichiometric translation efficiency of multiple translation products;

c) less immunogenicity than a counterpart lacking an encryptogen;

d) increased half-life over a linear counterpart; and e) persistence during cell division.

[66] The composition of paragraph [65], wherein the circular polyribonucleotide is translation competent.

[67] The composition of paragraph [65] or [66], wherein the quasi-helical structure comprises at least one double-stranded RNA segment with at least one non-double-stranded segment.

[68] The composition of any one of paragraphs [65] to [67], wherein the quasi-helical structure comprises a first sequence and a second sequence linked with a repetitive sequence, e.g., an A-rich sequence.

[69] The composition of any one of paragraphs [65] to [68], wherein the encryptogen comprises a splicing element.

[70] The composition of any one of paragraphs [65] to [69], wherein the circular polyribonucleotide comprises at least one modified ribonucleotide.

[71] The composition of any one of paragraphs [65] to [70], wherein the encryptogen comprises at least one modified ribonucleotide, e.g., pseudo-uridine, N(6) methyladenosine (m6A).

[72] The composition of any one of paragraphs [65] to [71], wherein the encryptogen comprises a protein binding site, e.g., ribonucleotide binding protein.

[73] The composition of any one of paragraphs [65] to [72], wherein the encryptogen comprises an immunoprotein binding site, e.g., to evade Immune responses, e.g., CTL responses.

[74] The composition of any one of paragraphs [65] to [73], wherein the circular polyribonucleotide has at least 2× less immunogenicity than a counterpart lacking the encryptogen, e.g., as assessed by expression or signaling or activation of at least one of RIG-I, TLR-3, TLR-7, TLR-8, MDA-5, LGP-2, OAS, OASL, PKR, IFN-beta.

[75] The composition of any one of paragraphs [65] to [74], wherein the circular polyribonucleotide further comprises a riboswitch.

[76] The composition of any one of paragraphs [65] to [75], wherein the circular polyribonucleotide further comprises an aptazyme.

[77] The composition of any one of paragraphs [65] to [76], wherein the circular polyribonucleotide comprises a translation initiation sequence, e.g., GUG, CUG start codon, e.g., expression under stress conditions.

[78] The composition of any one of paragraphs [65] to [77], wherein the circular polyribonucleotide comprises at least one expression sequence, e.g., encoding a polypeptide.

[79] The composition of paragraph [78], wherein the expression sequence encodes a peptide or polynucleotide.

[80] The composition of any one of paragraphs [65] to [79], wherein the circular polyribonucleotide comprises a stagger element, e.g., 2A.

[81] The composition of any one of paragraphs [65] to [80], wherein the circular polyribonucleotide comprises a regulatory nucleic acid, e.g., a non-coding RNA.

[82] The composition of any one of paragraphs [65] to [81], wherein the circular polyribonucleotide has a size in the range of about 20 bases to about 20 kb.

[83] The composition of any one of paragraphs [65] to [82], wherein the circular polyribonucleotide is synthesized through circularization of a linear polynucleotide.

[84] The composition of any one of paragraphs [65] to [83], wherein the circular polyribonucleotide comprises a plurality of expression sequences, either the same or different.

[85] The composition of any one of paragraphs [65] to [84], wherein the circular polyribonucleotide is substantially resistant to degradation, e.g., exonuclease.

[86] The composition of any one of paragraphs [65] to [85], wherein the circular polyribonucleotide lacks at least one of:

a) a 5'-UTR;

b) a 3'-UTR;

c) a poly-A sequence;

d) a 5'-cap;

e) a termination element;

f) an internal ribosomal entry site;

g) degradation susceptibility by exonucleases; and h) binding to a cap-binding protein.

[87] A method of producing the composition of any one of paragraphs [65] to [86] comprising combining the circular polyribonucleotide with a pharmaceutically acceptable carrier or excipient.

[88] A method of treatment comprising administering the composition of any one of paragraphs [65] to [86].

[89] A method for protein expression, comprising translating at least a region of the circular polyribonucleotide of any one of paragraphs [65] to [86].

[90] The method of paragraph [89], wherein the translation of the at least a region of the circular polyribonucleotide takes place in vitro.

[91] The method of paragraph [89], wherein the translation of the at least a region of the circular polyribonucleotide takes place in vivo.

[92] A polynucleotide encoding the circular polyribonucleotide of any one of paragraphs [65] to [86].

[93] A pharmaceutical composition comprising a pharmaceutically acceptable carrier or excipient and a circular polyribonucleotide that comprises one or more expression sequences, wherein the circular polyribonucleotide is competent for rolling circle translation.

[94] The composition of paragraph [93], wherein each of the one or more expression sequences is separated from a succeeding expression sequence by a stagger element on the circular polyribonucleotide, wherein the rolling circle translation of the one or more expression sequences generates at least two polypeptide molecules.

[95] The composition of paragraph [94], wherein the stagger element prevents generation of a single polypeptide (a) from two rounds of translation of a single expression sequence or (b) from one or more rounds of translation of two or more expression sequences.

[96] The composition of paragraph [94] or [95], wherein the stagger element is a sequence separate from the one or more expression sequences.

[97] The composition of paragraph [94] or [95], wherein the stagger element comprises a portion of an expression sequence of the one or more expression sequences.

[98] A pharmaceutical composition comprising a pharmaceutically acceptable carrier or excipient and a circular polyribonucleotide that comprises one or more expression sequences and is competent for rolling circle translation, wherein the circular polyribonucleotide is configured such that at least 50%, at least 60%, at least 70%, at least 80%, at least 90%, at least 95%, at least 96%, at least 97%, at least 98%, at least 99%, or 100% of total polypeptides (molar/molar) generated during the rolling circle translation of the circular polyribonucleotide are discrete polypeptides, and wherein each of the discrete polypeptides is generated from a single round of translation or less than a single round of translation of the one or more expression sequences.

[99] The composition of paragraph [98], wherein the circular polyribonucleotide is configured such that at least 50%, at least 60%, at least 70%, at least 80%, at least 90%, at least 95%, at least 96%, at least 97%, at least 98%, at least 99%, or 100% of total polypeptides (molar/molar) generated during the rolling circle translation of the circular polyribonucleotide are the discrete polypeptides, and wherein amount ratio of the discrete products over the total polypeptides is tested in an in vitro translation system.

[100] The composition of paragraph [99], wherein the in vitro translation system comprises rabbit reticulocyte lysate.

[101] The composition of any one of paragraphs [93] to [100], wherein the stagger element is at a 3' end of at least one of the one or more expression sequences, and wherein the stagger element is configured to stall a ribosome during rolling circle translation of the circular polyribonucleotide.

[102] A pharmaceutical composition comprising a pharmaceutically acceptable carrier or excipient and a circular polyribonucleotide that comprises one or more expression sequences and a stagger element at 3' end of at least one of the one or more expression sequences, wherein the stagger element is configured to stall a ribosome during rolling circle translation of the circular polyribonucleotide.

[103] The composition of paragraph [101] or [102], wherein the stagger element encodes a peptide sequence selected from the group consisting of a 2A sequence and a 2A-like sequence.

[104] The composition of any one of paragraph [101] to [103], wherein the stagger element encodes a sequence with a C-terminal sequence that is GP.

[105] The composition of any one of paragraph [101] to [104], wherein the stagger element encodes a sequence with a C-terminal consensus sequence that is D(V/I)ExNPGP (SEQ ID NO: 61), where x=any amino acid.

[106] The composition of any one of paragraph [101] to [105], wherein the stagger element encodes a sequence selected from the group consisting of GDVESNPGP (SEQ ID NO: 62), GDIEENPGP (SEQ ID NO: 63), VEPNPGP (SEQ ID NO: 64), IETNPGP (SEQ ID NO: 65), GDIESNPGP (SEQ ID NO: 66), GDVELNPGP (SEQ ID NO: 67), GDIETNPGP (SEQ ID NO: 68), GDVENPGP (SEQ ID NO: 69), GDVEENPGP (SEQ ID NO: 70), GDVEQNPGP (SEQ ID NO: 71), IESNPGP (SEQ ID NO: 72), GDIELNPGP (SEQ ID NO: 73), HDIETNPGP (SEQ ID NO: 74), HDVETNPGP (SEQ ID NO: 75), HDVEMNPGP (SEQ ID NO: 76), GDMESNPGP (SEQ ID NO: 77), GDVETNPGP (SEQ ID NO: 78), GDIEQNPGP (SEQ ID NO: 79), and DSEFNPGP (SEQ ID NO: 80).

[107] The composition of any one of paragraphs [101] to [106], wherein the stagger element is at 3' end of each of the one or more expression sequences.

[108] The composition of any one of paragraphs [93] to [107], wherein the stagger element of a first expression sequence in the circular polyribonucleotide is upstream of (5' to) a first translation initiation sequence of an expression sequence succeeding the first expression sequence in the circular polyribonucleotide, and wherein a distance between the stagger element and the first translation initiation sequence enables continuous translation of the first expression sequence and the succeeding expression sequence.

[109] The composition of any one of paragraphs [93] to [107], wherein the stagger element of a first expression sequence in the circular polyribonucleotide is upstream of (5' to) a first translation initiation sequence of an expression sequence succeeding the first expression in the circular polyribonucleotide, wherein the circular polyribonucleotide is continuously translated, wherein a corresponding circular polyribonucleotide comprising a second stagger element upstream of a second translation initiation sequence of a second expression sequence in the corresponding circular polyribonucleotide is not continuously translated, and wherein the second stagger element in the corresponding circular polyribonucleotide is at a greater distance from the second translation initiation sequence, e.g., at least 2×, 3×, 4×, 5×, 6×, 7×, 8×, 9×, 10×, than a distance between the stagger element and the first translation initiation in the circular polyribonucleotide.

[110] The composition of paragraph [108] or [109], wherein the distance between the stagger element and the first translation initiation is at least 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, 40 nt, 45 nt, 50 nt, 55 nt, 60 nt, 65 nt, 70 nt, 75 nt, or greater.

[111] The composition of paragraph [108] or [109], wherein the distance between the second stagger element and the second translation initiation is at least 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, 40 nt, 45 nt, 50 nt, 55 nt, 60 nt, 65 nt, 70 nt, 75 nt, or greater than the distance between the tagger element and the first translation initiation.

[112] The composition of any one of paragraphs [108] to [110], wherein the expression sequence succeeding the first expression sequence on the circular polyribonucleotide is an expression sequence other than the first expression sequence.

[113] The composition of any one of paragraphs [108] to [110], wherein the succeeding expression sequence of the first expression sequence on the circular polyribonucleotide is the first expression sequence.

[114] The composition of any one of paragraphs [93] to [113], wherein the circular polyribonucleotide comprises at least one structural element selected from:

a) an encryptogen;

b) a stagger element;

c) a regulatory element;

d) a replication element; and f) quasi-double-stranded secondary structure.

[115] The composition of any one of paragraphs [93] to [114], wherein the circular polyribonucleotide comprises at least one functional characteristic selected from:

a) greater translation efficiency than a linear counterpart;

b) a stoichiometric translation efficiency of multiple translation products;

c) less immunogenicity than a counterpart lacking an encryptogen;

d) increased half-life over a linear counterpart; and e) persistence during cell division.

[116] The composition of any one of paragraphs [93] to [115], wherein the circular polyribonucleotide has a translation efficiency at least 5%, at least 10%, at least 15%, at least 20%, at least 30%, at least 40%, at least 50%, at least 60%, at least 70%, at least 80%, at least 90%, at least 100%, at least 150%, at least 2 fold, at least 3 fold, at least 4 fold, at least 5 fold, at least 6 fold, at least 7 fold, at least 8 fold, at least 9 fold, at least 10 fold, at least 20 fold, at least 50 fold, or at least 100 fold greater than a linear counterpart.

[117] The composition of any one of paragraphs [93] to [115], wherein the circular polyribonucleotide has a translation efficiency at least 5 fold greater than a linear counterpart.

[118] The composition of any one of paragraphs [93] to [117], wherein the circular polyribonucleotide lacks at least one of:

a) a 5'-UTR;

b) a 3'-UTR;

c) a poly-A sequence;

d) a 5'-cap;

e) a termination element;

f) an internal ribosomal entry site;

g) degradation susceptibility by exonucleases; and h) binding to a cap-binding protein.

[119] The composition of any one of paragraphs[93] to [118], wherein the circular polyribonucleotide lacks an internal ribosomal entry site.

[120] The composition of any one of paragraphs [93] to [119], wherein the one or more expression sequences comprise a Kozak initiation sequence.

[121] The composition of any one of paragraphs [114] to [120], wherein the quasi-helical structure comprises at least one double-stranded RNA segment with at least one non-double-stranded segment.

[122] The composition of paragraph [121], wherein the quasi-helical structure comprises a first sequence and a second sequence linked with a repetitive sequence, e.g., an A-rich sequence.

[123] The composition of any one of paragraphs [114] to [122], wherein the encryptogen comprises a splicing element.

[124] The composition of any one of paragraphs [93] to [123], wherein the circular polyribonucleotide comprises at least one modified ribonucleotide.

[125] The composition of any one of paragraphs [93] to [124], wherein the encryptogen comprises at least one modified ribonucleotide, e.g., pseudo-uridine, N(6) methyladenosine (m6A).

[126] The composition of any one of paragraphs [93] to [125], wherein the encryptogen comprises a protein binding site, e.g., ribonucleotide binding protein.

[127] The composition of any one of paragraphs [93] to [126], wherein the encryptogen comprises an immunoprotein binding site, e.g., to evade immune responses, e.g., CTL responses.

[128] The composition of any one of paragraphs [93] to [127], wherein the circular polyribonucleotide has at least 2× less immunogenicity than a counterpart lacking the encryptogen, e.g., as assessed by expression or signaling or activation of at least one of RIG-I, TLR-3, TLR-7, TLR-8, MDA-5, LGP-2, OAS, OASL, PKR, IFN-beta.

[129] The composition of any one of paragraphs [93] to [128], wherein the circular polyribonucleotide further comprises a riboswitch.

[130] The composition of any one of paragraphs [93] to [129], wherein the circular polyribonucleotide further comprises an aptazyme.

[131] The composition of any one of paragraphs [93] to [130], wherein the circular polyribonucleotide comprises a non-canonical translation initiation sequence, e.g., GUG, CUG start codon, e.g., a translation initiation sequence that initiates expression under stress conditions.

[132] The composition of any one of paragraphs [93] to [131], wherein the one or more expression sequences encodes a peptide.

[133] The composition of any one of paragraphs [93] to [132], wherein the circular polyribonucleotide comprises a regulatory nucleic acid, e.g., a non-coding RNA.

[134] The composition of any one of paragraphs [93] to [133], wherein the circular polyribonucleotide has a size in the range of about 20 bases to about 20 kb.

[135] The composition of any one of paragraphs [93] to [134], wherein the circular polyribonucleotide is synthesized through circularization of a linear polyribonucleotide.

[136] The composition of any one of paragraphs [93] to [135], wherein the circular polyribonucleotide comprises a plurality of expression sequences having either a same nucleotide sequence or different nucleotide sequences.

[137] The composition of any one of paragraphs [93] to [136], wherein the circular polyribonucleotide is substantially resistant to degradation, e.g., exonuclease.

[138] The circular polyribonucleotide of any one of paragraphs [94] to [137].

[139] A method of producing the composition of any one of paragraphs [93] to [137], comprising combining the circular polyribonucleotide of any one of paragraphs

[93] to [137] and the pharmaceutically acceptable carrier or excipient of any one of paragraphs [93] to [137].

[140] A method of treatment, comprising administering the composition of any one of paragraphs [93] to [137].

[141] A method for protein expression, comprising translating at least a region of the circular polyribonucleotide of any one of paragraphs [93] to [137].

[142] The method of paragraph [141], wherein the translation of the at least a region of the circular polyribonucleotide takes place in vitro.

[143] The method of paragraph [141], wherein the translation of the at least a region of the circular polyribonucleotide takes place in vivo.

[144] A polynucleotide encoding the circular polyribonucleotide of any one of paragraphs [65] to [137].

[145] A method of producing the circular polyribonucleotide of any one of paragraphs [65] to [137].

[146] The method of paragraph [145], comprising splint ligation-mediated circularization of a linear polyribonucleotide.

[147] The method of paragraph [146], wherein the splint ligation-mediated circularization has an efficiency of at least 2%, at least 5%, at least 10%, at least 15%, at least 20%, at least 25%, at least 30%, at least 32%, at least 34%, at least 36%, at least 38%, at least 40%, at least 42%, at least 44%, at least 46%, at least 48%, or at least 50%.

[148] The method of paragraph [146], wherein the splint ligation-mediated circularization has an efficiency of about 40% to about 50% or more than 50%.

What is claimed is:

1. A pharmaceutical composition for expression of a first hormone and a second hormone comprising:
(a) a lipid nanoparticle carrier;
(b) a covalently closed polyribonucleotide that comprises, in the following order:
(i) a first internal ribosome entry site (IRES);
(ii) a first expression sequence that encodes the first hormone;
(iii) a second IRES; and
(iv) a second expression sequence that encodes the second hormone; and
(c) a pharmaceutically acceptable excipient.

2. The pharmaceutical composition of claim 1 wherein the covalently closed polyribonucleotide:
(a) lacks one or both of a 5' cap and a 3' poly A sequence;
(b) is detectable in-vivo for at least 7 days after administration of the composition to the human; or
(c) further comprises a miRNA target sequence, a miRNA binding site, or a protein binding site.

3. The pharmaceutical composition of claim 1, wherein the first IRES is an encephalomyocarditis virus (EMCV) IRES or a coxsackievirus B3 (CVB3) IRES.

4. The pharmaceutical composition of claim 1, wherein the second IRES is an EMCV IRES or a CVB3 IRES.

5. The pharmaceutical composition of claim 1, wherein the first hormone and the second hormone are the same.

6. The pharmaceutical composition of claim 1, wherein the first hormone and the second hormone are different.

7. The pharmaceutical composition of claim 1, wherein the first hormone or the second hormone is less than 300 amino acids in length.

8. The pharmaceutical composition of claim 1, wherein the covalently closed polyribonucleotide comprises, in the following order:
(i) a first spacer sequence;
(ii) the first IRES;
(iii) the first expression sequence that encodes the first hormone;
(iv) a second spacer;
(v) the second IRES; and
(vi) the second expression sequence that encodes the second hormone.

9. The pharmaceutical composition of claim 8, wherein the covalently closed polyribonucleotide comprises, in the following order:
(i) the first spacer sequence;
(ii) the first IRES;
(iii) the first expression sequence that encodes the first hormone;
(iv) the second spacer;
(v) the second IRES;
(vi) the second expression sequence that encodes the second hormone; and
(vii) a third spacer.

10. The pharmaceutical composition of claim 1, wherein the covalently closed polyribonucleotide comprises, in the following order:
(i) a first spacer sequence;
(ii) the first IRES;
(iii) the first expression sequence that encodes the first hormone;
(iv) the second IRES;
(v) the second expression sequence that encodes the second hormone; and
(vi) a second spacer.

11. A pharmaceutical composition for expression of a first hormone and a second hormone, comprising:
(a) a lipid nanoparticle carrier;
(b) a covalently closed polyribonucleotide comprising, in the following order:
(i) an IRES;
(ii) a first expression sequence that encodes the first hormone;
(iii) a stagger element; and
(iv) a second expression sequence that encodes the second hormone; and
(c) a pharmaceutically acceptable excipient.

12. The pharmaceutical composition of claim 11, wherein the covalently closed polyribonucleotide comprises, in the following order:
(i) the IRES;
(ii) a first translation initiation sequence;
(iii) the first expression sequence that encodes the first hormone;
(iv) the stagger element;
(v) a second translation initiation sequence; and
(vi) the second expression sequence that encodes the second hormone.

13. The pharmaceutical composition of claim 11, wherein the covalently closed polyribonucleotide comprises, in the following order:
(i) a first spacer sequence;
(ii) the IRES;
(iii) the first expression sequence that encodes the first hormone;
(iv) a second spacer;
(v) the stagger element; and
(vi) the second expression sequence that encodes the second hormone.

14. The pharmaceutical composition of claim 13, wherein the covalently closed polyribonucleotide comprises, in the following order:
(i) the first spacer sequence;
(ii) the IRES;
(iii) the first expression sequence that encodes the first hormone;
(iv) the second spacer;
(v) the stagger element;
(vi) the second expression sequence that encodes the second hormone; and
(vii) a third spacer.

* * * * *

SEQUENCE LISTING

```
Sequence total quantity: 136
SEQ ID NO: 1            moltype =   length =
SEQUENCE: 1
000

SEQ ID NO: 2            moltype = DNA  length = 717
FEATURE                 Location/Qualifiers
source                  1..717
                        mol_type = other DNA
                        organism = synthetic construct
                        note = Description of Artificial Sequence: Synthetic
                         polynucleotide
SEQUENCE: 2
atggtgagca agggcgagga gctgttcacc ggggtggtgc ccatcctggt cgagctggac  60
ggcgacgtaa acggccacaa gttcagcgtg tccggcgagg gcgagggcga tgccacctac  120
ggcaagctga ccctgaagtt catctgcacc accggcaagc tgcccgtgcc ctggcccacc  180
ctcgtgacca ccctgaccta cggcgtgcag tgcttcagcc gctaccccga ccacatgaag  240
cagcacgact tcttcaagtc cgccatgccc gaaggctacg tccaggagcg caccatcttc  300
ttcaaggacg acggcaacta caagacccgc gccgaggtga agttcgaggg cgacaccctg  360
gtgaaccgca tcgagctgaa gggcatcgac ttcaaggagg acggcaacat cctggggcac  420
aagctggagt acaactacaa cagccacaac gtctatatca tggccgacaa gcagaagaac  480
ggcatcaagg tgaacttcaa gatccgccac aacatcgagg acggcagcgt gcagctcgcc  540
gaccactacc agcagaacac ccccatcggc gacggccccg tgctgctgcc cgacaaccac  600
tacctgagca cccagtccgc cctgagcaaa gaccccaacg agaagcgcga tcacatggtc  660
ctgctggagt tcgtgaccgc cgccgggatc actctcggca tggacgagct gtacaag     717

SEQ ID NO: 3            moltype = DNA  length = 57
FEATURE                 Location/Qualifiers
source                  1..57
                        mol_type = other DNA
                        organism = synthetic construct
                        note = Description of Artificial Sequence: Synthetic
                         oligonucleotide
SEQUENCE: 3
gctactaact tcagcctgct gaagcaggct ggcgacgtgg aggagaaccc tggacct     57

SEQ ID NO: 4            moltype = DNA  length = 221
FEATURE                 Location/Qualifiers
source                  1..221
                        mol_type = other DNA
                        organism = synthetic construct
                        note = Description of Artificial Sequence: Synthetic
                         polynucleotide
SEQUENCE: 4
gtaaaaagag gtgaaaccta ttatgtgtga gcagggcaca gacgttgaaa ctggagccag  60
gagaagtatt ggcaggcttt aggttattag gtggttactc tgtcttaaaa atgttctggc  120
tttcttcctg catccactgg catactcatg gtctgttttt aaatatttta attcccattt  180
acaaagtgat ttacccacaa gcccaacctg tctgtcttca g                      221

SEQ ID NO: 5            moltype = DNA  length = 552
FEATURE                 Location/Qualifiers
source                  1..552
                        mol_type = other DNA
                        organism = synthetic construct
                        note = Description of Artificial Sequence: Synthetic
                         polynucleotide
SEQUENCE: 5
acgttactgg ccgaagccgc ttggaataag gccggtgtgc gtttgtctat atgttatttt  60
```

```
ccaccatatt gccgtctttt ggcaatgtga gggcccggaa acctggccct gtcttcttga  120
cgagcattcc taggggtctt tcccctctcg ccaaaggaat gcaaggtctg ttgaatgtcg  180
tgaaggaagc agttcctctg gaagcttctt gaagacaaac aacgtctgta gcgacccttt  240
gcaggcagcg gaacccccca cctggcgaca ggtgcctctg cggccaaaag ccacgtgtat  300
aagatacacc tgcaaaggcg gcacaacccc agtgccacgt tgtgagttgg atagttgtgg  360
aaagagtcaa atggctctcc tcaagcgtat tcaacaaggg gctgaaggat gcccagaagg  420
taccccattg tatgggatct gatctggggc ctcggtgcac atgctttaca tgtgtttagt  480
cgaggttaaa aaacgtctag gccccccgaa ccacggggac gtggttttcc tttgaaaaac  540
acgatgataa ta                                                      552

SEQ ID NO: 6            moltype = DNA  length = 6926
FEATURE                 Location/Qualifiers
source                  1..6926
                        mol_type = other DNA
                        organism = synthetic construct
                        note = Description of Artificial Sequence: Synthetic
                         polynucleotide
SEQUENCE: 6
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gtttaaactt aagcttggta ccgagctcgg atccactagt ccagtgtggt ggaattccat  960
tgagaaatga ctgagttccg gtgctctcaa gtcattgatc tttgtcgact tttatttggt  1020
ctctgtaata acgacttcaa aaacattaaa ttctgttgcg aagccagtaa gctacaaaaa  1080
gaaaaaaacaa gagagaatgc tatagtcgta tagtatagtt tcccgactat ctgataccca  1140
ttacttatct aggggggaatg cgaacccaaa attttatcag ttttctcgga tatcgataga  1200
tattggggaa taaatttaaa taaataaatt ttgggcgggt ttagggcgtg gcaaaaagtt  1260
ttttggcaaa tcgctagaaa tttacaagac ttataaaatt atgaaaaaat acaacaaaat  1320
tttaaacacg tgggcgtgac agttttgggc ggttttaggg cgttagagta ggcgaggaca  1380
gggttacatc gactaggctt tgatcctgat caagaatata tatactttat accgcttcct  1440
tctacatgtt acctattttt caacgaatct agtatacctt tttactgtac gatttatggg  1500
tataataata agctaaatcg agactaagtt ttattgttat atatattttt tttattttat  1560
gcagaaatta attaaaccgg tcctgcaggt gatcaggcgc gccggttacc ggccggcccc  1620
gcggagcgta agtattcaaa attccaaaat tttttactag aaatattcga ttttttaata  1680
ggcagtttct atactattgt atactattgt agattcgttg aaaagtatgt aacaggaaga  1740
ataaagcatt tccgaccatg taaagtatat atattcttaa taaggatcaa tagccgagtc  1800
gatctcgcca tgtccgtctg tcttattgtt ttattaccgc cgagacatca ggaactataa  1860
aagctagaag gatgagtttt agcatacaga ttctagagac aaggacgcag agcaagtttg  1920
ttgatccatg ctgccacgct ttaactttct caaattgccc aaaactgcca tgcccacatt  1980
tttgaactat tttcgaaatt ttttcataat tgtattactc gtgtaaattt ccatcaattt  2040
gccaaaaaac tttttgtcac gcgttaacgc cctaaagccg ccaatttggt cacgcccaca  2100
ctattgagca attatcaaat tttttctcat tttattcccc aatatctatc gatatccccg  2160
attatgaaat tattaaattt cgcgttcgca ttcacactag ctgagtaacg agtatctgat  2220
agttggggaa atcgacttat tttttatata caatgaaaat gaatttaatc atatgaatat  2280
cgattatagc tttttattta atatgaatat ttatttgggc ttaaggtgta acctcctcga  2340
cataagactc acatggcgca ggcacattga agacaaaaat actcattgtc gggtctcgca  2400
ccctccagca gcacctaaaa ttatgtcttc aattattgcc aacattggag acacaattag  2460
tctgtggcac ctcaggcggc cgctcgagtc tagagggccc gtttaaaccc gctgatcagc  2520
ctcgactgtg ccttctagtt gccagccatc tgttgtttgc ccctcccccg tgccttcctt  2580
gaccctggaa ggtgccactc ccactgtcct ttcctaataa aatgaggaaa ttgcatcgca  2640
ttgtctgagt aggtgtcatt ctattctggg gggtggggtg gggcaggaca gcaaggggga  2700
ggattgggaa gacaatagca ggcatgctgg ggatgcggtg ggctctatgg cttctgaggc  2760
ggaaagaacc agctggggct ctaggggggta tccccacgcg ccctgtagcg gcgcattaag  2820
cgcggcgggt gtggtggtta cgcgcagcgt gaccgctaca cttgccagcg ccctagcgcc  2880
cgctcctttc gctttcttcc cttcctttct cgccacgttc gccggctttc cccgtcaagc  2940
tctaaatcgg gggctccctt tagggttccg atttagtgct ttacggcacc tcgaccccaa  3000
aaaacttgat tagggtgatg gttcacgtag tgggccatcg ccctgataga cggtttttcg  3060
ccctttgacg ttggagtcca cgttctttaa tagtggactc ttgttccaaa ctggaacaac  3120
actcaaccct atctcggtct attcttttga tttataaggg attttgccga tttcggccta  3180
ttggttaaaa aatgagctga tttaacaaaa atttaacgcg aattaattct gtggaatgtg  3240
tgtcagttag ggtgtggaaa gtccccaggc tccccagcag gcagaagtat gcaaagcatg  3300
catctcaatt agtcagcaac caggtgtgga aagtccccag gctccccagc aggcagaagt  3360
atgcaaagca tgcatctcaa ttagtcagca accatagtcc cgcccctaac tccgcccatc  3420
ccgcccctaa ctccgcccag ttccgcccat tctccgcccc atggctgact aatttttttt  3480
atttatgcag aggccgaggc cgcctctgcc tctgagctat tccagaagta gtgaggaggc  3540
ttttttggag gcctaggctt ttgcaaaaag ctcccgggag cttgtatatc catttcgga  3600
tctgatcaag agacaggatg aggatcgttt cgcatgattg aacaagatgg attgcacgca  3660
```

```
ggttctccgg ccgcttgggt ggagaggcta ttcggctatg actgggcaca acagacaatc  3720
ggctgctctg atgccgccgt gttccggctg tcagcgcagg ggcgcccggt tctttttgtc  3780
aagaccgacc tgtccggtgc cctgaatgaa ctgcaggacg aggcagcgcg gctatcgtgg  3840
ctggccacga cgggcgttcc ttgcgcagct gtgctcgacg ttgtcactga agcgggaagg  3900
gactggctgc tattgggcga agtgccgggg caggatctcc tgtcatctca ccttgctcct  3960
gccgagaaag tatccatcat ggctgatgca atgcggcggc tgcatacgct tgatccggct  4020
acctgcccat tcgaccacca agcgaaacat cgcatcgagc gagcacgtac tcggatggaa  4080
gccggtcttg tcgatcagga tgatctggac gaagagcatc aggggctcgc gccagccgaa  4140
ctgttcgcca ggctcaaggc gcgcatgccc gacggcgagg atctcgtcgt gacccatggc  4200
gatgcctgct tgccgaatat catggtggaa aatggccgct tttctggatt catcgactgt  4260
ggccggctgg gtgtggcgga ccgctatcag gacatagcgt tggctacccg tgatattgct  4320
gaagagcttg gcggcgaatg ggctgaccgc ttcctcgtgc tttacggtat cgccgctccc  4380
gattcgcagc gcatcgcctt ctatcgcctt cttgacgagt tcttctgagc gggactctgg  4440
ggttcgaaat gaccgaccaa gcgacgccca acctgccatc acgagatttc gattccaccg  4500
ccgccttcta tgaaaggttg ggcttcggaa tcgttttccg ggacgccggc tggatgatcc  4560
tccagcgcgg ggatctcatg ctggagttct tcgcccaccc caacttgttt attgcagctt  4620
ataatggtta caaataaagc aatagcatca caaatttcac aaataaagca tttttttcac  4680
tgcattctag ttgtggtttg tccaaactca tcaatgtatc ttatcatgtc tgtataccgt  4740
cgacctctag ctagagcttg gcgtaatcat ggtcatagct gtttcctgtg tgaaattgtt  4800
atccgctcac aattccacac aacatacgag ccggaagcat aaagtgtaaa gcctggggtg  4860
cctaatgagt gagctaactc acattaattg cgttgcgctc actgcccgct ttccagtcgg  4920
gaaacctgtc gtgccagctg cattaatgaa tcggccaacg cgcggggaga ggcggtttgc  4980
gtattgggcg ctcttccgct tcctcgctca ctgactcgct gcgctcggtc gttcggctgc  5040
ggcgagcggt atcagctcac tcaaaggcgg taatacggtt atccacagaa tcaggggata  5100
acgcaggaaa gaacatgtga gcaaaaggcc agcaaaaggc caggaaccgt aaaaaggccg  5160
cgttgctggc gtttttccat aggctccgcc cccctgacga gcatcacaaa aatcgacgct  5220
caagtcagag gtggcgaaac ccgacaggac tataaagata ccaggcgttt ccccctggaa  5280
gctccctcgt gcgctctcct gttccgaccc tgccgcttac cggatacctg tccgcctttc  5340
tcccttcggg aagcgtggcg ctttctcata gctcacgctg taggtatctc agttcggtgt  5400
aggtcgttcg ctccaagctg ggctgtgtgc acgaaccccc cgttcagccc gaccgctgcg  5460
ccttatccgg taactatcgt cttgagtcca acccggtaag acacgactta tcgccactgg  5520
cagcagccac tggtaacagg attagcagag cgaggtatgt aggcggtgct acagagttct  5580
tgaagtggtg gcctaactac ggctacacta gaagaacagt atttggtatc tgcgctctgc  5640
tgaagccagt taccttcgga aaaagagttg gtagctcttg atccggcaaa caaaccaccg  5700
ctggtagcgg tttttttgtt tgcaagcagc agattacgcg cagaaaaaaa ggatctcaag  5760
aagatccttt gatcttttct acggggtctg acgctcagtg gaacgaaaac tcacgttaag  5820
ggattttggt catgagatta tcaaaaagga tcttcaccta gatcctttta aattaaaaat  5880
gaagttttaa atcaatctaa agtatatatg agtaaacttg gtctgacagt taccaatgct  5940
taatcagtga ggcacctatc tcagcgatct gtctatttcg ttcatccata gttgcctgac  6000
tccccgtcgt gtagataact acgatacggg agggcttacc atctggcccc agtgctgcaa  6060
tgataccgcg agacccacgc tcaccggctc cagatttatc agcaataaac cagccagccg  6120
gaagggccga gcgcagaagt ggtcctgcaa ctttatccgc ctccatccag tctattaatt  6180
gttgccggga agctagagta agtagttcgc cagttaatag tttgcgcaac gttgttgcca  6240
ttgctacagg catcgtggtg tcacgctcgt cgtttggtat ggcttcattc agctccggtt  6300
cccaacgatc aaggcgagtt acatgatccc ccatgttgtg caaaaaagcg gttagctcct  6360
tcggtcctcc gatcgttgtc agaagtaagt tggccgcagt gttatcactc atggttatgg  6420
cagcactgca taattctctt actgtcatgc catccgtaag atgcttttct gtgactggtg  6480
agtactcaac caagtcattc tgagaatagt gtatgcggcg accgagttgc tcttgcccgg  6540
cgtcaatacg ggataatacc gcgccacata gcagaacttt aaaagtgctc atcattggaa  6600
aacgttcttc ggggcgaaaa ctctcaagga tcttaccgct gttgagatcc agttcgatgt  6660
aacccactcg tgcacccaac tgatcttcag catcttttac tttcaccagc gtttctgggt  6720
gagcaaaaac aggaaggcaa aatgccgcaa aaaagggaat aagggcgaca cggaaatgtt  6780
gaatactcat actcttcctt tttcaatatt attgaagcat ttatcagggt tattgtctca  6840
tgagcggata catatttgaa tgtatttaga aaaataaaca aataggggtt ccgcgcacat  6900
ttccccgaaa agtgccacct gacgtc                                      6926

SEQ ID NO: 7           moltype =   length =
SEQUENCE: 7
000

SEQ ID NO: 8           moltype = DNA  length = 708
FEATURE                Location/Qualifiers
source                 1..708
                       mol_type = other DNA
                       organism = synthetic construct
                       note = Description of Artificial Sequence: Synthetic
                        polynucleotide
SEQUENCE: 8
atggtgagca agggcgagga ggataacatg gccatcatca aggagttcat gcgcttcaag  60
gtgcacatgg agggctccgt gaacggccac gagttcgaga tcgagggcga gggcgagggc  120
cgcccctacg agggcaccca gaccgccaag ctgaaggtga ccaagggtgg ccccctgccc  180
ttcgcctggg acatcctgtc ccctcagttc atgtacggct ccaaggccta cgtgaagcac  240
cccgccgaca tccccgacta cttgaagctg tccttccccg agggcttcaa gtgggagcgc  300
gtgatgaact tcgaggacgg cggcgtggtg accgtgaccc aggactcctc cctgcaggac  360
ggcgagttca tctacaaggt gaagctgcgc ggcaccaact tcccctccga cggccccgta  420
atgcagaaga agaccatggg ctgggaggcc tcctccgagc ggatgtaccc cgaggacggc  480
gccctgaagg gcgagatcaa gcagaggctg aagctgaagg acggcggcca ctacgacgct  540
gaggtcaaga ccacctacaa ggccaagaag cccgtgcagc tgcccggcgc ctacaacgtc  600
aacatcaagt tggacatcac ctcccacaac gaggactaca ccatcgtgga acagtacgaa  660
```

```
cgcgccgagg gccgccactc caccggcggc atggacgagc tgtacaag              708

SEQ ID NO: 9           moltype = RNA  length = 100
FEATURE                Location/Qualifiers
source                 1..100
                       mol_type = other RNA
                       organism = synthetic construct
                       note = Description of Artificial Sequence: Synthetic
                        polynucleotide
SEQUENCE: 9
ctgagatgca ggtacatcca gctgatgagt cccaaatagg acgaaagcca taccagccga  60
aaggcccttg gcagggttcc tggattccac tgctatccac                        100

SEQ ID NO: 10          moltype = DNA  length = 516
FEATURE                Location/Qualifiers
source                 1..516
                       mol_type = other DNA
                       organism = synthetic construct
                       note = Description of Artificial Sequence: Synthetic
                        polynucleotide
SEQUENCE: 10
atggtcttca cactcgaaga tttcgttggg gactggcgac agacagccgg ctacaacctg  60
gaccaagtcc ttgaacaggg aggtgtgtcc agtttgtttc agaatctcgg ggtgtccgta  120
actccgatcc aaaggattgt cctgagcggt gaaaatgggc tgaagatcga catccatgtc  180
atcatcccgt atgaaggtct gagcggcgac caaatgggcc agatcgaaaa aatttttaag  240
gtggtgtacc ctgtggatga tcatcacttt aaggtgatcc tgcactatgg cacactggta  300
atcgacgggg ttacgccgaa catgatcgac tatttcggac ggccgtatga aggcatcgcc  360
gtgttcgacg gcaaaaagat cactgtaaca gggaccctgt ggaacggcaa caaaattatc  420
gacgagcgcc tgatcaaccc cgacggctcc ctgctgttcc gagtaaccat caacggagtg  480
accggctggc ggctgtgcga acgcattctg gcgtaa                            516

SEQ ID NO: 11          moltype = DNA  length = 264
FEATURE                Location/Qualifiers
source                 1..264
                       mol_type = other DNA
                       organism = synthetic construct
                       note = Description of Artificial Sequence: Synthetic
                        polynucleotide
SEQUENCE: 11
gggagccacc atggactaca aggacgacga cgacaagatc atcgactata aagacgacga  60
cgataaaggt ggcgactata aggacgacga cgacaaagcc attaatagtg actctgagtg  120
tcccctgtcc cacgacgggt actgcctcca cgacggtgtg tgcatgtata ttgaagcatt  180
ggacaagtac gcctgcaact gtgttgttgg ctacatcggg gagcgctgtc agtaccgaga  240
cctgaagtgg tgggaactgc gcct                                         264

SEQ ID NO: 12          moltype = DNA  length = 273
FEATURE                Location/Qualifiers
source                 1..273
                       mol_type = other DNA
                       organism = synthetic construct
                       note = Description of Artificial Sequence: Synthetic
                        polynucleotide
SEQUENCE: 12
gggagccacc atggactaca aggacgacga cgacaagatc atcgactata aagacgacga  60
cgataaaggt ggcgactata aggacgacga cgacaaagcc attaatagtg actctgagtg  120
tcccctgtcc cacgacgggt actgcctcca cgacggtgtg tgcatgtata ttgaagcatt  180
ggacaagtac gcctgcaact gtgttgttgg ctacatcggg gagcgctgtc agtaccgaga  240
cctgaagtgg tgggaactgc gctgatagta act                               273

SEQ ID NO: 13          moltype = DNA  length = 330
FEATURE                Location/Qualifiers
source                 1..330
                       mol_type = other DNA
                       organism = synthetic construct
                       note = Description of Artificial Sequence: Synthetic
                        polynucleotide
SEQUENCE: 13
gggagccacc atggactaca aggacgacga cgacaagatc atcgactata aagacgacga  60
cgataaaggt ggcgactata aggacgacga cgacaaagcc attaatagtg actctgagtg  120
tcccctgtcc cacgacgggt actgcctcca cgacggtgtg tgcatgtata ttgaagcatt  180
ggacaagtac gcctgcaact gtgttgttgg ctacatcggg gagcgctgtc agtaccgaga  240
cctgaagtgg tgggaactgc gcggaagcgg agctactaac ttcagcctgc tgaagcaggc  300
tggagacgtg gaggagaacc ctggacctct                                   330

SEQ ID NO: 14          moltype = DNA  length = 20
FEATURE                Location/Qualifiers
source                 1..20
                       mol_type = other DNA
                       organism = synthetic construct
```

```
                         note = Description of Artificial Sequence: Synthetic
                          oligonucleotide
SEQUENCE: 14
ggtggctccc aggcgcagtt                                                20

SEQ ID NO: 15            moltype = DNA  length = 20
FEATURE                  Location/Qualifiers
source                   1..20
                         mol_type = other DNA
                         organism = synthetic construct
                         note = Description of Artificial Sequence: Synthetic
                          oligonucleotide
SEQUENCE: 15
ggtggctccc agttactatc                                                20

SEQ ID NO: 16            moltype = DNA  length = 20
FEATURE                  Location/Qualifiers
source                   1..20
                         mol_type = other DNA
                         organism = synthetic construct
                         note = Description of Artificial Sequence: Synthetic
                          oligonucleotide
SEQUENCE: 16
ggtggctccc agaggtccag                                                20

SEQ ID NO: 17            moltype = DNA  length = 873
FEATURE                  Location/Qualifiers
source                   1..873
                         mol_type = other DNA
                         organism = synthetic construct
                         note = Description of Artificial Sequence: Synthetic
                          polynucleotide
SEQUENCE: 17
gggagccacc atggactaca aggacgacga cgacaagatc atcaatagtg actctgagtg  60
tcccctgtcc cacgacgggt actgcctcca cgacggtgtg tgcatgtata ttgaagcatt  120
ggacaagtac gcctgcaact gtgttgttgg ctacatcggg gagcgctgtc agtaccgaga  180
cctgaagtgg tgggaactgc gcggctccgg cgagggcagg ggaagtcttc taacatgcgg  240
ggacgtggag gaaaatcccg gcccagacta taaggacgac gacgacaaaa tcatcgtctt  300
cacactcgaa gatttcgttg gggactggcg acagacagcc ggctacaacc tggaccaagt  360
ccttgaacag ggaggtgtgt ccagtttgtt tcagaatctc ggggtgtccg taactccgat  420
ccaaaggatt gtcctgagcg gtgaaaatgg gctgaagatc gacatccatg tcatcatccc  480
gtatgaaggt ctgagcggcg accaaatggg ccagatcgaa aaaattttta aggtggtgta  540
ccctgtggat gatcatcact ttaaggtgat cctgcactat ggcacactgg taatcgacgg  600
ggttacgccg aacatgatcg actatttcgg acggccgtat gaaggcatcg ccgtgttcga  660
cggcaaaaag atcactgtaa cagggaccct gtggaacggc aacaaaatta tcgacgagcg  720
cctgatcaac cccgacggct ccctgctgtt ccgagtaacc atcaacggag tgaccggctg  780
gcggctgtgc gaacgcattc tggcgggaag cggagctact aacttcagcc tgctgaagca  840
ggctggagac gtggaggaga accctggacc tct                                 873

SEQ ID NO: 18            moltype = DNA  length = 762
FEATURE                  Location/Qualifiers
source                   1..762
                         mol_type = other DNA
                         organism = synthetic construct
                         note = Description of Artificial Sequence: Synthetic
                          polynucleotide
SEQUENCE: 18
gggagccacc atggactaca aggacgacga cgacaagatc atcaatagtg actctgagtg  60
tcccctgtcc cacgacgggt actgcctcca cgacggtgtg tgcatgtata ttgaagcatt  120
ggacaagtac gcctgcaact gtgttgttgg ctacatcggg gagcgctgtc agtaccgaga  180
cctgaagtgg tgggaactgc gctgatagta agactataag gacgacgacg acaaaatcat  240
cgtcttcaca ctcgaagatt tcgttgggga ctggcgacag acagccggct acaacctgga  300
ccaagtcctt gaacagggag gtgtgtccag tttgtttcag aatctcgggg tgtccgtaac  360
tccgatccaa aggattgtcc tgagcggtga aaatgggctg aagatcgaca tccatgtcat  420
catcccgtat gaaggtctga gcggcgacca aatgggccag atcgaaaaaa tttttaaggt  480
ggtgtaccct gtggatgatc atcactttaa ggtgatcctg cactatggca cactggtaat  540
cgacggggtt acgccgaaca tgatcgacta tttcggacgg ccgtatgaag gcatcgccgt  600
gttcgacggc aaaaagatca ctgtaacagg gaccctgtgg aacggcaaca aaattatcga  660
cgagcgcctg atcaaccccg acggctccct gctgttccga gtaaccatca acggagtgac  720
cggctggcgg ctgtgcgaac gcattctggc gtgatagtaa ct                       762

SEQ ID NO: 19            moltype = DNA  length = 330
FEATURE                  Location/Qualifiers
source                   1..330
                         mol_type = other DNA
                         organism = synthetic construct
                         note = Description of Artificial Sequence: Synthetic
                          polynucleotide
SEQUENCE: 19
```

```
gggagccacc atggactaca aggacgacga cgacaagatc atcgactata aagacgacga  60
cgataaaggt ggcgactata aggacgacga cgacaaagcc attaatagtg actctgagtg  120
tcccctgtcc cacgacgggt actgcctcca cgacggtgtg tgcatgtata ttgaagcatt  180
ggacaagtac gcctgcaact gtgttgttgg ctacatcggg gagcgctgtc agtaccgaga  240
cctgaagtgg tgggaactgc gcggaagcgg agctactaac ttcagcctgc tgaagcaggc  300
tggagacgtg gaggagaacc ctggacctct                                    330

SEQ ID NO: 20          moltype = DNA  length = 264
FEATURE                Location/Qualifiers
source                 1..264
                       mol_type = other DNA
                       organism = synthetic construct
                       note = Description of Artificial Sequence: Synthetic
                        polynucleotide
SEQUENCE: 20
gggagccacc atggactaca aggacgacga cgacaagatc atcgactata aagacgacga  60
cgataaaggt ggcgactata aggacgacga cgacaaagcc attaatagtg actctgagtg  120
tcccctgtcc cacgacgggt actgcctcca cgacggtgtg tgcatgtata ttgaagcatt  180
ggacaagtac gcctgcaact gtgttgttgg ctacatcggg gagcgctgtc agtaccgaga  240
cctgaagtgg tgggaactgc gcct                                          264

SEQ ID NO: 21          moltype = DNA  length = 273
FEATURE                Location/Qualifiers
source                 1..273
                       mol_type = other DNA
                       organism = synthetic construct
                       note = Description of Artificial Sequence: Synthetic
                        polynucleotide
SEQUENCE: 21
gggagccacc atggactaca aggacgacga cgacaagatc atcgactata aagacgacga  60
cgataaaggt ggcgactata aggacgacga cgacaaagcc attaatagtg actctgagtg  120
tcccctgtcc cacgacgggt actgcctcca cgacggtgtg tgcatgtata ttgaagcatt  180
ggacaagtac gcctgcaact gtgttgttgg ctacatcggg gagcgctgtc agtaccgaga  240
cctgaagtgg tgggaactgc gctgatagta act                                273

SEQ ID NO: 22          moltype = DNA  length = 954
FEATURE                Location/Qualifiers
source                 1..954
                       mol_type = other DNA
                       organism = synthetic construct
                       note = Description of Artificial Sequence: Synthetic
                        polynucleotide
SEQUENCE: 22
gggacctaac gttactggcc gaagccgctt ggaacaaggc cggtgtgcgt ttgtctatat  60
gttattttcc accatattgc cgtcttttgg caatgtgagg gcccggaaac ctggccctgt  120
cttcttgacg agcattccta ggggtctttc ccctctcgcc aaaggaatgc aaggtctgtt  180
gaatgtcgtg aaggaagcag ttcctctgga agcttcttca agacaaacaa cgtctgtagc  240
gaccctttgc aggcagcgga acccccccacc tggcgacagg tgcctctgcg gccaaaagcc  300
acgtgtatac gatacacctg caaaggcggc acaaccccag tgccacgttg tgagttggat  360
agttgtggaa agagtcaaat ggctctcctc aagcgtattc aacaaggggc tgaaggatgc  420
ccagaaggta ccccattgta tgggatctga tctggggcct cggtgcacat gctttacatg  480
tgttcagtcg aggttaaaaa acgtccaggc cccccgaacc acggggacgt ggttttcctt  540
tgaaaaacac gatgataata tggccacaac catgggctcc ggcgagggca ggggaagtct  600
tctaacatgc ggggacgtgg aggaaaatcc cggcccagac tacaaggacg acgacgacaa  660
gatcatcgac tataaagacg acgacgataa aggtggcgac tataaggacg acgacgacaa  720
agccattaat agtgactctg agtgtcccct gtcccacgac gggtactgcc tccacgacgg  780
tgtgtgcatg tatattgaag cattggacaa gtacgcctgc aactgtgttg ttggctacat  840
cggggagcgc tgtcagtacc gagacctgaa gtggtgggaa ctgcgcggaa gcggagctac  900
taacttcagc ctgctgaagc aggctggaga cgtggaggag aaccctggac ctct        954

SEQ ID NO: 23          moltype = DNA  length = 1314
FEATURE                Location/Qualifiers
source                 1..1314
                       mol_type = other DNA
                       organism = synthetic construct
                       note = Description of Artificial Sequence: Synthetic
                        polynucleotide
SEQUENCE: 23
gggacctaac gttactggcc gaagccgctt ggaacaaggc cggtgtgcgt ttgtctatat  60
gttattttcc accatattgc cgtcttttgg caatgtgagg gcccggaaac ctggccctgt  120
cttcttgacg agcattccta ggggtctttc ccctctcgcc aaaggaatgc aaggtctgtt  180
gaatgtcgtg aaggaagcag ttcctctgga agcttcttca agacaaacaa cgtctgtagc  240
gaccctttgc aggcagcgga acccccccacc tggcgacagg tgcctctgcg gccaaaagcc  300
acgtgtatac gatacacctg caaaggcggc acaaccccag tgccacgttg tgagttggat  360
agttgtggaa agagtcaaat ggctctcctc aagcgtattc aacaaggggc tgaaggatgc  420
ccagaaggta ccccattgta tgggatctga tctggggcct cggtgcacat gctttacatg  480
tgttcagtcg aggttaaaaa acgtccaggc cccccgaacc acggggacgt ggttttcctt  540
tgaaaaacac gatgataata tggccacaac catgggctcc ggcgagggca ggggaagtct  600
tctaacatgc ggggacgtgg aggaaaatcc cggcccagac tacaaggacg acgacgacaa  660
```

```
gatcatcgac tataaagacg acgacgataa aggtggcgac tataaggacg acgacgacaa  720
agccattgtc ttcacactcg aagatttcgt tggggactgg cgacagacag ccggctacaa  780
cctggaccaa gtccttgaac agggaggtgt gtccagtttg tttcagaatc tcggggtgtc  840
cgtaactccg atccaaagga ttgtcctgag cggtgaaaat gggctgaaga tcgacatcca  900
tgtcatcatc ccgtatgaag gtctgagcgg cgaccaaatg ggccagatcg aaaaaatttt  960
taaggtggtg taccctgtgg atgatcatca ctttaaggtg atcctgcact atggcacact  1020
ggtaatcgac ggggttacgc cgaacatgat cgactatttc ggacggccgt atgaaggcat  1080
cgccgtgttc gacggcaaaa agatcactgt aacagggacc ctgtggaacg gcaacaaaat  1140
tatcgacgag cgcctgatca accccgacgg ctccctgctg ttccgagtaa ccatcaacgg  1200
agtgaccggc tggcggctgt gcgaacgcat tctggcggga agcggagcta ctaacttcag  1260
cctgctgaag caggctggag acgtggagga gaaccctgga ccttgatagt aact        1314

SEQ ID NO: 24          moltype = DNA  length = 1305
FEATURE                Location/Qualifiers
source                 1..1305
                       mol_type = other DNA
                       organism = synthetic construct
                       note = Description of Artificial Sequence: Synthetic
                        polynucleotide
SEQUENCE: 24
gggacctaac gttactggcc gaagccgctt ggaacaaggc cggtgtgcgt ttgtctatat  60
gttattttcc accatattgc cgtcttttgg caatgtgagg gcccggaaac ctggccctgt  120
cttcttgacg agcattccta ggggtctttc ccctctcgcc aaaggaatgc aaggtctgtt  180
gaatgtcgtg aaggaagcag ttcctctgga agcttcttca agacaaacaa cgtctgtagc  240
gaccctttgc aggcagcgga acccccacc tggcgacagg tgcctctgcg gccaaaagcc  300
acgtgtatac gatacacctg caaaggcggc acaaccccag tgccacgttg tgagttggat  360
agttgtggaa agagtcaaat ggctctcctc aagcgtattc aacaaggggc tgaaggatgc  420
ccagaaggta ccccattgta tggatctga tctggggcct cggtgcacat gctttacatg  480
tgttcagtcg aggttaaaaa acgtccaggc cccccgaacc acggggacgt ggttttcctt  540
tgaaaaacac gatgataata tggccacaac catgggctcc ggcgagggca ggggaagtct  600
tctaacatgc ggggacgtgg aggaaaatcc cggcccagac tacaaggacg acgacgacaa  660
gatcatcgac tataaagacg acgacgataa aggtggcgac tataaggacg acgacgacaa  720
agccattgtc ttcacactcg aagatttcgt tggggactgg cgacagacag ccggctacaa  780
cctggaccaa gtccttgaac agggaggtgt gtccagtttg tttcagaatc tcggggtgtc  840
cgtaactccg atccaaagga ttgtcctgag cggtgaaaat gggctgaaga tcgacatcca  900
tgtcatcatc ccgtatgaag gtctgagcgg cgaccaaatg ggccagatcg aaaaaatttt  960
taaggtggtg taccctgtgg atgatcatca ctttaaggtg atcctgcact atggcacact  1020
ggtaatcgac ggggttacgc cgaacatgat cgactatttc ggacggccgt atgaaggcat  1080
cgccgtgttc gacggcaaaa agatcactgt aacagggacc ctgtggaacg gcaacaaaat  1140
tatcgacgag cgcctgatca accccgacgg ctccctgctg ttccgagtaa ccatcaacgg  1200
agtgaccggc tggcggctgt gcgaacgcat tctggcggga agcggagcta ctaacttcag  1260
cctgctgaag caggctggag acgtggagga gaaccctgga cctct                  1305

SEQ ID NO: 25          moltype = DNA  length = 882
FEATURE                Location/Qualifiers
source                 1..882
                       mol_type = other DNA
                       organism = synthetic construct
                       note = Description of Artificial Sequence: Synthetic
                        polynucleotide
SEQUENCE: 25
gggagccacc atggactaca aggacgacga cgacaagatc atcaatagtg actctgagtg  60
tcccctgtcc cacgacgggt actgcctcca cgacggtgtg tgcatgtata ttgaagcatt  120
ggacaagtac gcctgcaact gtgttgttgg ctacatcggg gagcgctgtc agtaccgaga  180
cctgaagtgg tgggaactgc gcggctccgg cgagggcagg ggaagtcttc taacatgcgg  240
ggacgtggag gaaaatcccg gcccagacta taaggacgac gacgacaaaa tcatcgtctt  300
cacactcgaa gatttcgttg gggactggcg acagacagcc ggctacaacc tggaccaagt  360
ccttgaacag ggaggtgtgt ccagtttgtt tcagaatctc ggggtgtccg taactccgat  420
ccaaaggatt gtcctgagcg gtgaaaatgg gctgaagatc gacatccatg tcatcatccc  480
gtatgaaggt ctgagcggcg accaaatggg ccagatcgaa aaaattttta aggtggtgta  540
ccctgtggat gatcatcact ttaaggtgat cctgcactat ggcacactgg taatcgacgg  600
ggttacgccg aacatgatcg actatttcgg acggccgtat gaaggcatcg ccgtgttcga  660
cggcaaaaag atcactgtaa cagggaccct gtggaacggc aacaaaatta tcgacgagcg  720
cctgatcaac cccgacggct ccctgctgtt ccgagtaacc atcaacggag tgaccggctg  780
gcggctgtgc gaacgcattc tggcgggaag cggagctact aacttcagcc tgctgaagca  840
ggctggagac gtggaggaga accctggacc ttgatagtaa ct                     882

SEQ ID NO: 26          moltype = DNA  length = 179
FEATURE                Location/Qualifiers
source                 1..179
                       mol_type = other DNA
                       organism = synthetic construct
                       note = Description of Artificial Sequence: Synthetic
                        polynucleotide
SEQUENCE: 26
aaaaaacaaa aaacaaaacg gctattatgc gttaccggcg agacgctacg gacttgggaa  60
aatccgttga ccttaaacgg tcgtgtgggt tcaagtccct ccaccccac gccggaaacg  120
caatagccga aaaacaaaaa acaaaaaaaa caaaaaaaaa accaaaaaaa caaaacaca   179
```

```
SEQ ID NO: 27          moltype = DNA  length = 43
FEATURE                Location/Qualifiers
source                 1..43
                       mol_type = other DNA
                       organism = synthetic construct
                       note = Description of Artificial Sequence: Synthetic primer
SEQUENCE: 27
cgcggatcct aatacgactc actataggga gacccaagct ggc                   43

SEQ ID NO: 28          moltype = DNA  length = 79
FEATURE                Location/Qualifiers
source                 1..79
                       mol_type = other DNA
                       organism = synthetic construct
                       note = Description of Artificial Sequence: Synthetic primer
SEQUENCE: 28
aatagccgtt ttgtttttg gattaccagt gtgccatagt gcaggatcac atcgtcgtgg  60
tattcactcc agagcgatg                                              79

SEQ ID NO: 29          moltype = DNA  length = 76
FEATURE                Location/Qualifiers
source                 1..76
                       mol_type = other DNA
                       organism = synthetic construct
                       note = Description of Artificial Sequence: Synthetic primer
SEQUENCE: 29
aatagccgtt ttgtttttg gattaccagt gtgccatagt gcaggatcac acgggggagg  60
ggcaaacaac agatgg                                                 76

SEQ ID NO: 30          moltype = DNA  length = 84
FEATURE                Location/Qualifiers
source                 1..84
                       mol_type = other DNA
                       organism = synthetic construct
                       note = Description of Artificial Sequence: Synthetic primer
SEQUENCE: 30
aatagccgtt ttgtttttg gattaccagt gtgccatagt gcaggatcac gctttttgca  60
aaagcctagg cctccaaaaa agcc                                        84

SEQ ID NO: 31          moltype = DNA  length = 77
FEATURE                Location/Qualifiers
source                 1..77
                       mol_type = other DNA
                       organism = synthetic construct
                       note = Description of Artificial Sequence: Synthetic primer
SEQUENCE: 31
aatagccgtt ttgtttttg gattaccagt gtgccatagt gcaggatcac tagcaccgcc  60
tacatacctc gctctgc                                                77

SEQ ID NO: 32          moltype = DNA  length = 80
FEATURE                Location/Qualifiers
source                 1..80
                       mol_type = other DNA
                       organism = synthetic construct
                       note = Description of Artificial Sequence: Synthetic primer
SEQUENCE: 32
aatagccgtt ttgtttttg gattaccagt gtgccatagt gcaggatcac ctatgtggcg  60
cggtattatc ccgtattgac                                             80

SEQ ID NO: 33          moltype = DNA  length = 84
FEATURE                Location/Qualifiers
source                 1..84
                       mol_type = other DNA
                       organism = synthetic construct
                       note = Description of Artificial Sequence: Synthetic primer
SEQUENCE: 33
aatagccgtt ttgtttttg gattaccagt gtgccatagt gcaggatcac atttcgataa  60
gccagtaagc agtgggttct ctag                                        84

SEQ ID NO: 34          moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 34
attcttgccc gcctgatgaa                                             20

SEQ ID NO: 35          moltype = DNA  length = 20
```

```
FEATURE                Location/Qualifiers
source                 1..20
                       mol_type = other DNA
                       organism = synthetic construct
                       note = Description of Artificial Sequence: Synthetic primer
SEQUENCE: 35
ttgctcatgg aaaacggtgt                                             20

SEQ ID NO: 36          moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 36
tgatcctgca ctatggcaca                                             20

SEQ ID NO: 37          moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 37
ctggactagt ggatccgagc                                             20

SEQ ID NO: 38          moltype = DNA  length = 23
FEATURE                Location/Qualifiers
source                 1..23
                       mol_type = other DNA
                       organism = synthetic construct
                       note = Description of Artificial Sequence: Synthetic primer
SEQUENCE: 38
gacgaggccc agagcaagag agg                                         23

SEQ ID NO: 39          moltype = DNA  length = 22
FEATURE                Location/Qualifiers
source                 1..22
                       mol_type = other DNA
                       organism = synthetic construct
                       note = Description of Artificial Sequence: Synthetic primer
SEQUENCE: 39
ggtgttgaag gtctcaaaca tg                                          22

SEQ ID NO: 40          moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 40
tgtgggcaat gtcatcaaaa                                             20

SEQ ID NO: 41          moltype = DNA  length = 21
FEATURE                Location/Qualifiers
source                 1..21
                       mol_type = other DNA
                       organism = synthetic construct
                       note = Description of Artificial Sequence: Synthetic primer
SEQUENCE: 41
gaagcacttg ctacctcttg c                                           21

SEQ ID NO: 42          moltype = DNA  length = 19
FEATURE                Location/Qualifiers
source                 1..19
                       mol_type = other DNA
                       organism = synthetic construct
                       note = Description of Artificial Sequence: Synthetic primer
SEQUENCE: 42
ggcaccatgg gaagtgatt                                              19

SEQ ID NO: 43          moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 43
atttggtaag gcctgagctg                                             20
```

```
SEQ ID NO: 44          moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 44
tcgctggtat cactcgtctg                                              20

SEQ ID NO: 45          moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 45
gattctgaag accgccagag                                              20

SEQ ID NO: 46          moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 46
ctctcctgtt gtgcttctcc                                              20

SEQ ID NO: 47          moltype = DNA  length = 22
FEATURE                Location/Qualifiers
source                 1..22
                       mol_type = other DNA
                       organism = synthetic construct
                       note = Description of Artificial Sequence: Synthetic primer
SEQUENCE: 47
gtcaaagttc atcctgtcct tg                                           22

SEQ ID NO: 48          moltype = DNA  length = 2270
FEATURE                Location/Qualifiers
source                 1..2270
                       mol_type = other DNA
                       organism = synthetic construct
                       note = Description of Artificial Sequence: Synthetic
                        polynucleotide
SEQUENCE: 48
gggaatagcc gaaaaacaaa aaacaaaaaa aacaaaaaaa aaaccaaaaa aacaaaaacac  60
aacgttactg gccgaagccg cttggaacaa ggccggtgtg cgtttgtcta tatgttattt  120
tccaccatat tgccgtcttt tggcaatgtg agggcccgga aacctggccc tgtcttcttg  180
acgagcattc ctaggggtct ttcccctctc gccaaaggaa tgcaaggtct gttgaatgtc  240
gtgaaggaag cagttcctct ggaagcttct tgtagacaaa caacgtctgt agcgaccctt  300
tgcaggcagc ggaacccccc acctggcgac aggtgcctct gcggccaaaa gccacgtgta  360
tacgatacac ctgcaaaggc ggcacaaccc cagtgccacg ttgtgagttg gatagttgtg  420
gaaagagtca aatggctctc ctcaagcgta ttcaacaagg ggctgaagga tgcccagaag  480
gtaccccatt gtatgggatc tgatctgggg cctcggtgca catgctttac atgtgttcag  540
tcgaggttaa aaaacgtcca ggccccccga accacgggga cgtggttttc ctttgaaaaa  600
cacgatgata atatggccac aaccatgggc tccggcgagg gcaggggaag tcttctaaca  660
tgcggggacg tggaggaaaa tcccggccca gactacaagg acgacgacga caagatcatc  720
gactataaag acgacgacga taaaggtggc gactataagg acgacgacga caaagccatt  780
gtgagcaagg gcgaggagct gttcaccggg gtggtgccca tcctggtcga gctggacggc  840
gacgtaaacg gccacaagtt cagcgtgtcc ggcgagggcg agggcgatgc cacctacggc  900
aagctgaccc tgaagttcat ctgcaccacc ggcaagctgc ccgtgccctg gcccaccctc  960
gtgaccaccc tgacctacgg cgtgcagtgc ttcagccgct accccgacca catgaagcag  1020
cacgacttct tcaagtccgc catgcccgaa ggctacgtcc aggagcgcac catcttcttc  1080
aaggacgacg gcaactacaa gacccgcgcc gaggtgaagt tcgagggcga caccctggtg  1140
aaccgcatcg agctgaaggg catcgacttc aaggaggacg gcaacatcct ggggcacaag  1200
ctggagtaca actacaacag ccacaacgtc tatatcatgg ccgacaagca gaagaacggc  1260
atcaaggtga acttcaagat ccgccacaac atcgaggacg gcagcgtgca gctcgccgac  1320
cactaccagc agaacacccc catcggcgac ggccccgtgc tgctgcccga caaccactac  1380
ctgagcaccc agtccgccct gagcaaagac cccaacgaga agcgcgatca catggtcctg  1440
ctggagttcg tgaccgccgc cgggatcact ctcggcatgg acgagctgta caagggaagc  1500
ggagtgaaac agactttgaa ttttgacctt ctcaagttgg cgggagacgt ggagtccaac  1560
cctggacctg actacaagga cgacgacgac aagatcatcg actataaaga cgacgacgat  1620
aaaggtggcg actataagga cgacgacgac aaagccatta tcatcgtctt cacactcgaa  1680
gatttcgttg gggactggcg acagacagcc ggctacaacc tggaccaagt ccttgaacag  1740
ggaggtgtgt ccagtttgtt tcagaatctc ggggtgtccg taactccgat ccaaaggatt  1800
gtcctgagcg gtgaaaatgg gctgaagatc gacatccatg tcatcatccc gtatgaaggt  1860
ctgagcggcg accaaatggg ccagatcgaa aaaattttta aggtggtgta ccctgtggat  1920
gatcatcact ttaaggtgat cctgcactat ggcacactgg taatcgacgg ggttacgccg  1980
aacatgatcg actatttcgg acggccgtat gaaggcatcg ccgtgttcga cggcaaaaag  2040
```

-continued

```
atcactgtaa cagggaccct gtggaacggc aacaaaatta tcgacgagcg cctgatcaac  2100
cccgacggct ccctgctgtt ccgagtaacc atcaacggag tgaccggctg gcggctgtgc  2160
gaacgcattc tggcgggaag cggagctact aacttcagcc tgctgaagca ggctggagac  2220
gtggaggaga accctggacc ttaaaaaaaa caaaaaacaa aacggctatt             2270

SEQ ID NO: 49          moltype = DNA  length = 2279
FEATURE                Location/Qualifiers
source                 1..2279
                       mol_type = other DNA
                       organism = synthetic construct
                       note = Description of Artificial Sequence: Synthetic
                        polynucleotide
SEQUENCE: 49
gggaatagcc gaaaaacaaa aaacaaaaaa aacaaaaaaa aaaccaaaaa aacaaaacac  60
aacgttactg gccgaagccg cttggaacaa ggccggtgtg cgtttgtcta tatgttattt  120
tccaccatat tgccgtcttt tggcaatgtg agggcccgga aacctggccc tgtcttcttg  180
acgagcattc ctaggggtct ttcccctctc gccaaaggaa tgcaaggtct gttgaatgtc  240
gtgaaggaag cagttcctct ggaagcttct tgtagacaaa caacgtctgt agcgaccctt  300
tgcaggcagc ggaacccccc acctggcgac aggtgcctct gcggccaaaa gccacgtgta  360
tacgatacac ctgcaaaggc ggcacaaccc cagtgccacg ttgtgagttg gatagttgtg  420
gaaagagtca aatggctctc ctcaagcgta ttcaacaagg ggctgaagga tgcccagaag  480
gtaccccatt gtatgggatc tgatctgggg cctcggtgca catgctttac atgtgttcag  540
tcgaggttaa aaaacgtcca ggccccccga accacgggga cgtggttttc ctttgaaaaa  600
cacgatgata atatggccac aaccatgggc tccggcgagg gcaggggaag tcttctaaca  660
tgcggggacg tggaggaaaa tcccggccca gactacaagg acgacgacga caagatcatc  720
gactataaag acgacgacga taaaggtggc gactataagg acgacgacga caaagccatt  780
gtgagcaagg gcgaggagct gttcaccggg gtggtgccca tcctggtcga gctggacggc  840
gacgtaaacg gccacaagtt cagcgtgtcc ggcgagggcg agggcgatgc cacctacggc  900
aagctgaccc tgaagttcat ctgcaccacc ggcaagctgc ccgtgccctg gcccaccctc  960
gtgaccaccc tgacctacgg cgtgcagtgc ttcagccgct accccgacca catgaagcag  1020
cacgacttct tcaagtccgc catgcccgaa ggctacgtcc aggagcgcac catcttcttc  1080
aaggacgacg gcaactacaa gacccgcgcc gaggtgaagt tcgagggcga caccctggtg  1140
aaccgcatcg agctgaaggg catcgacttc aaggaggacg gcaacatcct ggggcacaag  1200
ctggagtaca actacaacag ccacaacgtc tatatcatgg ccgacaagca gaagaacggc  1260
atcaaggtga acttcaagat ccgccacaac atcgaggacg gcagcgtgca gctcgccgac  1320
cactaccagc agaacacccc catcggcgac ggccccgtgc tgctgcccga caaccactac  1380
ctgagcaccc agtccgccct gagcaaagac cccaacgaga agcgcgatca catggtcctg  1440
ctggagttcg tgaccgccgc cgggatcact ctcggcatgg acgagctgta caagggaagc  1500
ggagtgaaac agactttgaa ttttgacctt ctcaagttgg cgggagacgt ggagtccaac  1560
cctggacctt gatagtaaga ctacaaggac gacgacgaca agatcatcga ctataaagac  1620
gacgacgata aaggtggcga ctataaggac gacgacgaca aagccattat catcgtcttc  1680
acactcgaag atttcgttgg ggactggcga cagacagccg gctacaacct ggaccaagtc  1740
cttgaacagg gaggtgtgtc cagtttgttt cagaatctcg gggtgtccgt aactccgatc  1800
caaaggattg tcctgagcgg tgaaaatggg ctgaagatcg acatccatgt catcatcccg  1860
tatgaaggtc tgagcggcga ccaaatgggc cagatcgaaa aatttttaa ggtggtgtac  1920
cctgtggatg atcatcactt taaggtgatc ctgcactatg gcacactggt aatcgacggg  1980
gttacgccga acatgatcga ctatttcgga cggccgtatg aaggcatcgc cgtgttcgac  2040
ggcaaaaaga tcactgtaac agggaccctg tggaacggca acaaaattat cgacgagcgc  2100
ctgatcaacc ccgacggctc cctgctgttc cgagtaacca tcaacggagt gaccggctgg  2160
cggctgtgcg aacgcattct ggcgggaagc ggagctacta acttcagcct gctgaagcag  2220
gctggagacg tggaggagaa ccctggacct taaaaaaaac aaaaaacaaa acggctatt   2279

SEQ ID NO: 50          moltype = RNA  length = 51
FEATURE                Location/Qualifiers
source                 1..51
                       mol_type = other RNA
                       organism = synthetic construct
                       note = Description of Artificial Sequence: Synthetic
                        oligonucleotide
SEQUENCE: 50
tcataatcaa tttattattt tcttttattt tattcacata attttgtttt t           51

SEQ ID NO: 51          moltype = RNA  length = 19
FEATURE                Location/Qualifiers
source                 1..19
                       mol_type = other RNA
                       organism = synthetic construct
                       note = Description of Artificial Sequence: Synthetic
                        oligonucleotide
SEQUENCE: 51
attttgtttt taacatttc                                               19

SEQ ID NO: 52          moltype = RNA  length = 70
FEATURE                Location/Qualifiers
source                 1..70
                       mol_type = other RNA
                       organism = synthetic construct
                       note = Description of Artificial Sequence: Synthetic
                        oligonucleotide
```

```
SEQUENCE: 52
tcataatcaa tttattattt tcttttattt tattcacata attttgtttt tattttgttt  60
ttaacatttc                                                         70

SEQ ID NO: 53          moltype = RNA  length = 1545
FEATURE                Location/Qualifiers
source                 1..1545
                       mol_type = other RNA
                       organism = synthetic construct
                       note = Description of Artificial Sequence: Synthetic
                        polynucleotide
SEQUENCE: 53
aaaatccgtt gaccttaaac ggtcgtgtgg gttcaagtcc ctccaccccc acgccggaaa  60
cgcaatagcc gaaaaacaaa aaacaaaaaa aacaaaaaaa aaaccaaaaa aacaaaacac  120
attaaaacag cctgtgggtt gatcccaccc acaggcccat tgggcgctag cactctggta  180
tcacggtacc tttgtgcgcc tgttttatac ccccctcccc aactgtaact tagaagtaac  240
acacaccgat caacagtcag cgtggcacac cagccacgtt ttgatcaagc acttctgtta  300
ccccggactg agtatcaata gactgctcac gcggttgaag gagaaagcgt tcgttatccg  360
gccaactact tcgaaaaacc tagtaacacc gtggaagttg cagagtgttt cgctcagcac  420
taccccagtg tagatcaggt cgatgagtca ccgcattccc cacgggcgac cgtggcggtg  480
gctgcgttgg cggcctgccc atggggaaac ccatgggacg ctctaataca gacatggtgc  540
gaagagtcta ttgagctagt tggtagtcct ccggcccctg aatgcggcta atcctaactg  600
cggagcacac accctcaagc cagagggcag tgtgtcgtaa cgggcaactc tgcagcggaa  660
ccgactactt tgggtgtccg tgtttcattt tattcctata ctggctgctt atggtgacaa  720
ttgagagatc gttaccatat agctattgga ttggccatcc ggtgactaat agagctatta  780
tatatccctt tgttgggttt ataccactta gcttgaaaga ggttaaaaca ttacaattca  840
ttgttaagtt gaatacagca aaatgggagt caaagttctg tttgccctga tctgcatcgc  900
tgtggccgag gccaagccca ccgagaacaa cgaagacttc aacatcgtgg ccgtggccag  960
caacttcgcg accacggatc tcgatgctga ccgcgggaag ttgcccggca agaagctgcc  1020
gctggaggtg ctcaaagaga tggaagccaa tgcccggaaa gctggctgca ccaggggctg  1080
tctgatctgc ctgtcccaca tcaagtgcac gcccaagatg aagaagttca tcccaggacg  1140
ctgccacacc tacgaaggcg acaaagagtc cgcacagggc ggcataggcg aggcgatcgt  1200
cgacattcct gagattcctg ggttcaagga cttggagccc atggagcagt tcatcgcaca  1260
ggtcgatctg tgtgtggact gcacaactgg ctgcctcaaa gggcttgcca acgtgcagtg  1320
ttctgacctg ctcaagaagt ggctgccgca acgctgtgcg acctttgcca gcaagatcca  1380
gggccaggtg gacaagatca agggggccgg tggtgactaa tcataatcaa tttattattt  1440
tcttttattt tattcacata attttgtttt tattttgttt ttaacatttc aaaaaacaaa  1500
aaacaaaacg gctattatgc gttaccggcg agacgctacg gactt                 1545

SEQ ID NO: 54          moltype = RNA  length = 1545
FEATURE                Location/Qualifiers
source                 1..1545
                       mol_type = other RNA
                       organism = synthetic construct
                       note = Description of Artificial Sequence: Synthetic
                        polynucleotide
SEQUENCE: 54
aaaatccgtt gaccttaaac ggtcgtgtgg gttcaagtcc ctccaccccc acgccggaaa  60
cgcaatagcc gaaaaacaaa aaacaaaaaa aacaaaaaaa aaaccaaaaa aacaaaacac  120
attaaaacag cctgtgggtt gatcccaccc acaggcccat tgggcgctag cactctggta  180
tcacggtacc tttgtgcgcc tgttttatac ccccctcccc aactgtaact tagaagtaac  240
acacaccgat caacagtcag cgtggcacac cagccacgtt ttgatcaagc acttctgtta  300
ccccggactg agtatcaata gactgctcac gcggttgaag gagaaagcgt tcgttatccg  360
gccaactact tcgaaaaacc tagtaacacc gtggaagttg cagagtgttt cgctcagcac  420
taccccagtg tagatcaggt cgatgagtca ccgcattccc cacgggcgac cgtggcggtg  480
gctgcgttgg cggcctgccc atggggaaac ccatgggacg ctctaataca gacatggtgc  540
gaagagtcta ttgagctagt tggtagtcct ccggcccctg aatgcggcta atcctaactg  600
cggagcacac accctcaagc cagagggcag tgtgtcgtaa cgggcaactc tgcagcggaa  660
ccgactactt tgggtgtccg tgtttcattt tattcctata ctggctgctt atggtgacaa  720
ttgagagatc gttaccatat agctattgga ttggccatcc ggtgactaat agagctatta  780
tatatccctt tgttgggttt ataccactta gcttgaaaga ggttaaaaca ttacaattca  840
ttgttaagtt gaatacagca aaatgggagt caaagttctg tttgccctga tctgcatcgc  900
tgtggccgag gccaagccca ccgagaacaa cgaagacttc aacatcgtgg ccgtggccag  960
caacttcgcg accacggatc tcgatgctga ccgcgggaag ttgcccggca agaagctgcc  1020
gctggaggtg ctcaaagaga tggaagccaa tgcccggaaa gctggctgca ccaggggctg  1080
tctgatctgc ctgtcccaca tcaagtgcac gcccaagatg aagaagttca tcccaggacg  1140
ctgccacacc tacgaaggcg acaaagagtc cgcacagggc ggcataggcg aggcgatcgt  1200
cgacattcct gagattcctg ggttcaagga cttggagccc atggagcagt tcatcgcaca  1260
ggtcgatctg tgtgtggact gcacaactgg ctgcctcaaa gggcttgcca acgtgcagtg  1320
ttctgacctg ctcaagaagt ggctgccgca acgctgtgcg acctttgcca gcaagatcca  1380
gggccaggtg gacaagatca agggggccgg tggtgactaa tcataatcaa tttattattt  1440
tcttttattt tattcacata attttgtttt tattttgttt ttaacatttc aaaaaacaaa  1500
aaacaaaacg gctattatgc gttaccggcg agacgctacg gactt                 1545

SEQ ID NO: 55          moltype = DNA  length = 20
FEATURE                Location/Qualifiers
source                 1..20
                       mol_type = other DNA
                       organism = synthetic construct
```

```
                        note = Description of Artificial Sequence: Synthetic
                         oligonucleotide
SEQUENCE: 55
caccgctcag gacaatcctt                                            20

SEQ ID NO: 56           moltype = DNA  length = 741
FEATURE                 Location/Qualifiers
source                  1..741
                        mol_type = other DNA
                        organism = synthetic construct
                        note = Description of Artificial Sequence: Synthetic
                         polynucleotide
SEQUENCE: 56
ttaaaacagc ctgtgggttg atcccaccca caggcccatt gggcgctagc actctggtat  60
cacggtacct ttgtgcgcct gttttatacc ccctccccca actgtaactt agaagtaaca  120
cacaccgatc aacagtcagc gtggcacacc agccacgttt tgatcaagca cttctgttac  180
cccggactga gtatcaatag actgctcacg cggttgaagg agaaagcgtt cgttatccgg  240
ccaactactt cgaaaaacct agtaacaccg tggaagttgc agagtgtttc gctcagcact  300
accccagtgt agatcaggtc gatgagtcac cgcattcccc acgggcgacc gtggcggtgg  360
ctgcgttggc ggcctgccca tggggaaacc catgggacgc tctaatacag acatggtgcg  420
aagagtctat tgagctagtt ggtagtcctc cggcccctga atgcggctaa tcctaactgc  480
ggagcacaca ccctcaagcc agagggcagt gtgtcgtaac gggcaactct gcagcggaac  540
cgactacttt gggtgtccgt gtttcatttt attcctatac tggctgctta tggtgacaat  600
tgagagatcg ttaccatata gctattggat tggccatccg gtgactaata gagctattat  660
atatcccttt gttgggttta taccacttag cttgaaagag gttaaaacat tacaattcat  720
tgttaagttg aatacagcaa a                                           741

SEQ ID NO: 57           moltype = DNA  length = 558
FEATURE                 Location/Qualifiers
source                  1..558
                        mol_type = other DNA
                        organism = synthetic construct
                        note = Description of Artificial Sequence: Synthetic
                         polynucleotide
SEQUENCE: 57
atgggagtca aagttctgtt tgccctgatc tgcatcgctg tggccgaggc caagcccacc  60
gagaacaacg aagacttcaa catcgtggcc gtggccagca acttcgcgac cacggatctc  120
gatgctgacc gcgggaagtt gcccggcaag aagctgccgc tggaggtgct caaagagatg  180
gaagccaatg cccggaaagc tggctgcacc aggggctgtc tgatctgcct gtcccacatc  240
aagtgcacgc ccaagatgaa gaagttcatc ccaggacgct gccacaccta cgaaggcgac  300
aaagagtccg cacagggcgg cataggcgag gcgatcgtcg acattcctga gattcctggg  360
ttcaaggact tggagcccat ggagcagttc atcgcacagg tcgatctgtg tgtggactgc  420
acaactggct gcctcaaagg gcttgccaac gtgcagtgtt ctgacctgct caagaagtgg  480
ctgccgcaac gctgtgcgac ctttgccagc aagatccagg gccaggtgga caagatcaag  540
gggccggtg gtgactaa                                               558

SEQ ID NO: 58           moltype = DNA  length = 566
FEATURE                 Location/Qualifiers
source                  1..566
                        mol_type = other DNA
                        organism = synthetic construct
                        note = Description of Artificial Sequence: Synthetic
                         polynucleotide
SEQUENCE: 58
acgttactgg ccgaagccgc ttggaacaag gccggtgtgc gtttgtctat atgttatttt  60
ccaccatatt gccgtctttt ggcaatgtga gggcccggaa acctggccct gtcttcttga  120
cgagcattcc taggggtctt tcccctctcg ccaaaggaat gcaaggtctg ttgaatgtcg  180
tgaaggaagc agttcctctg gaagcttctt caagacaaac aacgtctgta gcgacccttt  240
gcaggcagcg gaacccccca cctggcgaca ggtgcctctg cggccaaaag ccacgtgtat  300
acgatacacc tgcaaaggcg gcacaacccc agtgccacgt tgtgagttgg atagttgtgg  360
aaagagtcaa atggctctcc tcaagcgtat tcaacaaggg gctgaaggat gcccagaagg  420
taccccattg tatgggatct gatctggggc ctcggtgcac atgctttaca tgtgttcagt  480
cgaggttaaa aaacgtccag gccccccgaa ccacggggac gtggttttcc tttgaaaaac  540
acgatgataa tatggccaca accatg                                     566

SEQ ID NO: 59           moltype = RNA  length = 121
FEATURE                 Location/Qualifiers
source                  1..121
                        mol_type = other RNA
                        organism = synthetic construct
                        note = Description of Artificial Sequence: Synthetic
                         polynucleotide
SEQUENCE: 59
aaaatccgtt gaccttaaac ggtcgtgtgg gttcaagtcc ctccaccccc acgccggaaa  60
cgcaatagcc gaaaaacaaa aaacaaaaaa aacaaaaaaa aaaccaaaaa aacaaaacac  120
a                                                                121

SEQ ID NO: 60           moltype = DNA  length = 254
FEATURE                 Location/Qualifiers
```

```
source                  1..254
                        mol_type = other DNA
                        organism = synthetic construct
                        note = Description of Artificial Sequence: Synthetic
                         polynucleotide
SEQUENCE: 60
ataccagccg aaaggccctt ggcagagagg tctgaaaaga cctctgctga ctatgtgatc  60
ttattaaaat taggttaaat ttcgaggtta aaaatagttt taatattgct atagtcttag  120
aggtcttgta tatttatact taccacacaa gatggaccgg agcagccctc caatatctag  180
tgtaccctcg tgctcgctca aacattaagt ggtgttgtgc gaaaagaatc tcacttcaag  240
aaaaagaaac tagt                                                    254

SEQ ID NO: 61           moltype = AA  length = 8
FEATURE                 Location/Qualifiers
source                  1..8
                        mol_type = protein
                        organism = synthetic construct
                        note = Description of Artificial Sequence: Synthetic peptide
VARIANT                 2
                        note = MOD_RES - Val or Ile
VARIANT                 4
                        note = MOD_RES - Any amino acid
SEQUENCE: 61
DXEXNPGP                                                           8

SEQ ID NO: 62           moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 62
GDVESNPGP                                                          9

SEQ ID NO: 63           moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 63
GDIEENPGP                                                          9

SEQ ID NO: 64           moltype = AA  length = 7
FEATURE                 Location/Qualifiers
source                  1..7
                        mol_type = protein
                        organism = synthetic construct
                        note = Description of Artificial Sequence: Synthetic peptide
SEQUENCE: 64
VEPNPGP                                                            7

SEQ ID NO: 65           moltype = AA  length = 7
FEATURE                 Location/Qualifiers
source                  1..7
                        mol_type = protein
                        organism = synthetic construct
                        note = Description of Artificial Sequence: Synthetic peptide
SEQUENCE: 65
IETNPGP                                                            7

SEQ ID NO: 66           moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 66
GDIESNPGP                                                          9

SEQ ID NO: 67           moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 67
GDVELNPGP                                                          9
```

```
SEQ ID NO: 68          moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 68
GDIETNPGP                                                                  9

SEQ ID NO: 69          moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 69
GDVENPGP                                                                   8

SEQ ID NO: 70          moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 70
GDVEENPGP                                                                  9

SEQ ID NO: 71          moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 71
GDVEQNPGP                                                                  9

SEQ ID NO: 72          moltype = AA  length = 7
FEATURE                Location/Qualifiers
source                 1..7
                       mol_type = protein
                       organism = synthetic construct
                       note = Description of Artificial Sequence: Synthetic peptide
SEQUENCE: 72
IESNPGP                                                                    7

SEQ ID NO: 73          moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 73
GDIELNPGP                                                                  9

SEQ ID NO: 74          moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 74
HDIETNPGP                                                                  9

SEQ ID NO: 75          moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 75
HDVETNPGP                                                                  9

SEQ ID NO: 76          moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 76
```

```
HDVEMNPGP                                                    9

SEQ ID NO: 77          moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 77
GDMESNPGP                                                    9

SEQ ID NO: 78          moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 78
GDVETNPGP                                                    9

SEQ ID NO: 79          moltype = AA  length = 9
FEATURE                Location/Qualifiers
source                 1..9
                       mol_type = protein
                       organism = synthetic construct
                       note = Description of Artificial Sequence: Synthetic peptide
SEQUENCE: 79
GDIEQNPGP                                                    9

SEQ ID NO: 80          moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 80
DSEFNPGP                                                     8

SEQ ID NO: 81          moltype = AA  length = 15
FEATURE                Location/Qualifiers
source                 1..15
                       mol_type = protein
                       organism = synthetic construct
                       note = Description of Artificial Sequence: Synthetic peptide
SEQUENCE: 81
GLNDIFEAQK IEWHE                                             15

SEQ ID NO: 82          moltype = AA  length = 26
FEATURE                Location/Qualifiers
source                 1..26
                       mol_type = protein
                       organism = synthetic construct
                       note = Description of Artificial Sequence: Synthetic peptide
SEQUENCE: 82
KRRWKKNFIA VSAANRFKKI SSSGAL                                 26

SEQ ID NO: 83          moltype = AA  length = 6
FEATURE                Location/Qualifiers
source                 1..6
                       mol_type = protein
                       organism = synthetic construct
                       note = Description of Artificial Sequence: Synthetic peptide
SEQUENCE: 83
EEEEEE                                                       6

SEQ ID NO: 84          moltype = AA  length = 13
FEATURE                Location/Qualifiers
source                 1..13
                       mol_type = protein
                       organism = synthetic construct
                       note = Description of Artificial Sequence: Synthetic peptide
SEQUENCE: 84
GAPVPYPDPL EPR                                               13

SEQ ID NO: 85          moltype = AA  length = 8
FEATURE                Location/Qualifiers
source                 1..8
                       mol_type = protein
                       organism = synthetic construct
```

```
                        note = Description of Artificial Sequence: Synthetic peptide
SEQUENCE: 85
DYKDDDDK                                                                 8

SEQ ID NO: 86           moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 86
YPYDVPDYA                                                                9

SEQ ID NO: 87           moltype = AA  length = 6
FEATURE                 Location/Qualifiers
source                  1..6
                        mol_type = protein
                        organism = synthetic construct
                        note = Description of Artificial Sequence: Synthetic 6xHis
                         tag
SEQUENCE: 87
HHHHHH                                                                   6

SEQ ID NO: 88           moltype = AA  length = 10
FEATURE                 Location/Qualifiers
source                  1..10
                        mol_type = protein
                        organism = synthetic construct
                        note = Description of Artificial Sequence: Synthetic peptide
SEQUENCE: 88
EQKLISEEDL                                                               10

SEQ ID NO: 89           moltype = AA  length = 18
FEATURE                 Location/Qualifiers
source                  1..18
                        mol_type = protein
                        organism = synthetic construct
                        note = Description of Artificial Sequence: Synthetic peptide
SEQUENCE: 89
TKENPRSNQE ESYDDNES                                                      18

SEQ ID NO: 90           moltype = AA  length = 15
FEATURE                 Location/Qualifiers
source                  1..15
                        mol_type = protein
                        organism = synthetic construct
                        note = Description of Artificial Sequence: Synthetic peptide
SEQUENCE: 90
KETAAAKFER QHMDS                                                         15

SEQ ID NO: 91           moltype = AA  length = 38
FEATURE                 Location/Qualifiers
source                  1..38
                        mol_type = protein
                        organism = synthetic construct
                        note = Description of Artificial Sequence: Synthetic
                         polypeptide
SEQUENCE: 91
MDEKTTGWRG GHVVEGLAGE LEQLRARLEH HPQGQREP                                38

SEQ ID NO: 92           moltype = AA  length = 13
FEATURE                 Location/Qualifiers
source                  1..13
                        mol_type = protein
                        organism = synthetic construct
                        note = Description of Artificial Sequence: Synthetic peptide
SEQUENCE: 92
SLAELLNAGL GGS                                                           13

SEQ ID NO: 93           moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 93
TQDPSRVG                                                                 8

SEQ ID NO: 94           moltype = AA  length = 12
```

```
FEATURE                Location/Qualifiers
source                 1..12
                       mol_type = protein
                       organism = synthetic construct
                       note = Description of Artificial Sequence: Synthetic peptide
SEQUENCE: 94
PDRVRAVSHW SS                                                         12

SEQ ID NO: 95          moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 95
WSHPQFEK                                                              8

SEQ ID NO: 96          moltype = AA  length = 6
FEATURE                Location/Qualifiers
source                 1..6
                       mol_type = protein
                       organism = synthetic construct
                       note = Description of Artificial Sequence: Synthetic peptide
SEQUENCE: 96
CCPGCC                                                                6

SEQ ID NO: 97          moltype = AA  length = 10
FEATURE                Location/Qualifiers
source                 1..10
                       mol_type = protein
                       organism = synthetic construct
                       note = Description of Artificial Sequence: Synthetic peptide
SEQUENCE: 97
EVHTNQDPLD                                                            10

SEQ ID NO: 98          moltype = AA  length = 14
FEATURE                Location/Qualifiers
source                 1..14
                       mol_type = protein
                       organism = synthetic construct
                       note = Description of Artificial Sequence: Synthetic peptide
SEQUENCE: 98
GKPIPNPLLG LDST                                                       14

SEQ ID NO: 99          moltype = AA  length = 11
FEATURE                Location/Qualifiers
source                 1..11
                       mol_type = protein
                       organism = synthetic construct
                       note = Description of Artificial Sequence: Synthetic peptide
SEQUENCE: 99
YTDIEMNRLG K                                                          11

SEQ ID NO: 100         moltype = AA  length = 8
FEATURE                Location/Qualifiers
source                 1..8
                       mol_type = protein
                       organism = synthetic construct
                       note = Description of Artificial Sequence: Synthetic peptide
SEQUENCE: 100
DLYDDDDK                                                              8

SEQ ID NO: 101         moltype = AA  length = 9
FEATURE                Location/Qualifiers
source                 1..9
                       mol_type = protein
                       organism = synthetic construct
                       note = Description of Artificial Sequence: Synthetic peptide
VARIANT                1
                       note = MOD_RES - Gly, His, or absent
VARIANT                2
                       note = MOD_RES - Asp, Gly, or absent
VARIANT                3
                       note = MOD_RES - Asp, Val, Ile, Ser, or Met
VARIANT                5
                       note = MOD_RES - Any amino acid
SEQUENCE: 101
XXXEXNPGP                                                             9
```

```
SEQ ID NO: 102         moltype = RNA  length = 96
FEATURE                Location/Qualifiers
source                 1..96
                       mol_type = unassigned RNA
                       organism = unidentified
                       note = Hepatitis delta virus
SEQUENCE: 102
ggctcatctc gacaagaggc ggcagtcctc agtactctta ctcttttctg taaagaggag  60
actgctggac tcgccgccca agttcgagca tgagcc                             96

SEQ ID NO: 103         moltype = RNA  length = 74
FEATURE                Location/Qualifiers
source                 1..74
                       mol_type = unassigned RNA
                       organism = unidentified
                       note = Hepatitis delta virus
SEQUENCE: 103
ggctagaggc ggcagtcctc agtactctta ctcttttctg taaagaggag actgctggac  60
tcgccgcccg agcc                                                     74

SEQ ID NO: 104         moltype = RNA  length = 90
FEATURE                Location/Qualifiers
source                 1..90
                       mol_type = unassigned RNA
                       organism = unidentified
                       note = Description of Unknown: Replication competent
                        circular RNA sense and/or antisense ribozyme
SEQUENCE: 104
cgggtcggca tggcatctcc acctcctcgc ggtccgacct gggcatccga aggaggacgc  60
acgtccactc ggatggctaa gggagagcca                                    90

SEQ ID NO: 105         moltype = RNA  length = 88
FEATURE                Location/Qualifiers
source                 1..88
                       mol_type = unassigned RNA
                       organism = unidentified
                       note = Description of Unknown: Replication competent
                        circular RNA sense and/or antisense ribozyme
SEQUENCE: 105
tggccggcat ggtcccagcc tcctcgctgg cgccggctgg gcaacattcc gaggggaccg  60
tcccctcggt aatggcgaat gggaccca                                      88

SEQ ID NO: 106         moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 106
acgacggtgt gtgcatgtat                                               20

SEQ ID NO: 107         moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 107
ttcccaccac ttcaggtctc                                               20

SEQ ID NO: 108         moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 108
tacgcctgca actgtgttgt                                               20

SEQ ID NO: 109         moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 109
tcgatgatct tgtcgtcgtc                                               20

SEQ ID NO: 110         moltype = DNA  length = 21
```

```
FEATURE                Location/Qualifiers
source                 1..21
                       mol_type = other DNA
                       organism = synthetic construct
                       note = Description of Artificial Sequence: Synthetic primer
SEQUENCE: 110
agggctgctt ttaactctgg t                                             21

SEQ ID NO: 111         moltype = DNA  length = 21
FEATURE                Location/Qualifiers
source                 1..21
                       mol_type = other DNA
                       organism = synthetic construct
                       note = Description of Artificial Sequence: Synthetic primer
SEQUENCE: 111
ccccacttga ttttggaggg a                                             21

SEQ ID NO: 112         moltype = RNA  length = 17
FEATURE                Location/Qualifiers
source                 1..17
                       mol_type = other RNA
                       organism = synthetic construct
                       note = Description of Artificial Sequence: Synthetic
                        oligonucleotide
SEQUENCE: 112
gaggtgctca aagagat                                                  17

SEQ ID NO: 113         moltype = DNA  length = 20
FEATURE                Location/Qualifiers
source                 1..20
                       mol_type = other DNA
                       organism = synthetic construct
                       note = Description of Artificial Sequence: Synthetic
                        oligonucleotide
SEQUENCE: 113
ggctattccc aatagccgtt                                               20

SEQ ID NO: 114         moltype = DNA  length = 35
FEATURE                Location/Qualifiers
source                 1..35
                       mol_type = other DNA
                       organism = synthetic construct
                       note = Description of Artificial Sequence: Synthetic
                        oligonucleotide
SEQUENCE: 114
ccgttgtggt ctcccagata aacagtattt tgtcc                              35

SEQ ID NO: 115         moltype = DNA  length = 74
FEATURE                Location/Qualifiers
source                 1..74
                       mol_type = other DNA
                       organism = synthetic construct
                       note = Description of Artificial Sequence: Synthetic primer
SEQUENCE: 115
ataccagccg aaaggccctt ggcagagagg tctgaaaaga cctctgctga ctatgtgatc  60
ttattaaaat tagg                                                     74

SEQ ID NO: 116         moltype = DNA  length = 74
FEATURE                Location/Qualifiers
source                 1..74
                       mol_type = other DNA
                       organism = synthetic construct
                       note = Description of Artificial Sequence: Synthetic primer
SEQUENCE: 116
gaaattaata cgactcacta tagggagacc acaacggttt ccctcctcta taccagccga  60
aaggcccttg gcag                                                     74

SEQ ID NO: 117         moltype = DNA  length = 79
FEATURE                Location/Qualifiers
source                 1..79
                       mol_type = other DNA
                       organism = synthetic construct
                       note = Description of Artificial Sequence: Synthetic primer
SEQUENCE: 117
acataccaga tttcgatctg gagaggtgaa gaatacgacc acctagaggt ctgaaaagac  60
ctctgctgac tatgtgatc                                                79

SEQ ID NO: 118         moltype = DNA  length = 70
FEATURE                Location/Qualifiers
```

```
source                  1..70
                        mol_type = other DNA
                        organism = synthetic construct
                        note = Description of Artificial Sequence: Synthetic primer
SEQUENCE: 118
gaaattaata cgactcacta tagggagacc acaacggttt ccctcctcta aaacatacca  60
gatttcgatc                                                         70

SEQ ID NO: 119          moltype = DNA  length = 1027
FEATURE                 Location/Qualifiers
source                  1..1027
                        mol_type = other DNA
                        organism = synthetic construct
                        note = Description of Artificial Sequence: Synthetic
                         polynucleotide
SEQUENCE: 119
gacacgcggc cttccaagca gttagggaaa ccgacttctt tgaagaagaa agctgactat  60
gtgatcttat taaaattagg ttaaatttcg aggttaaaaa tagttttaat attgctatag  120
tcttagaggt cttgtatatt tatacttacc acacaagatg gaccggagca gccctccaat  180
atctagtgta ccctcgtgct cgctcaaaca ttaagtggtg ttgtgcgaaa agaatctcac  240
ttcaagaaaa agaaactagt atggtcttca cactcgaaga tttcgttggg gactggcgac  300
agacagccgg ctacaacctg gaccaagtcc ttgaacaggg aggtgtgtcc agtttgtttc  360
agaatctcgg ggtgtccgta actccgatcc aaaggattgt cctgagcggt gaaaatgggc  420
tgaagatcga catccatgtc atcatcccgt atgaaggtct gagcggcgac caaatgggcc  480
agatcgaaaa aatttttaag gtggtgtacc ctgtggatga tcatcacttt aaggtgatcc  540
tgcactatgg cacactggta atcgacgggg ttacgccgaa catgatcgac tatttcggac  600
ggccgtatga aggcatcgcc gtgttcgacg gcaaaaagat cactgtaaca gggaccctgt  660
ggaacggcaa caaaattatc gacgagcgcc tgatcaaccc cgacggctcc ctgctgttcc  720
gagtaaccat caacggagtg accggctggc ggctgtgcga acgcattctg gcgtaactcg  780
agctcggtac ctgtccgcgg tcgcgacgta cgcgggcggc cgccataaat tggatccata  840
tatagggccc gggttataat tacctcaggt cgacgtccca tggttttgta tagaatttac  900
ggctagcgcc ggatgcgacg ccggtcgcgt cttatccggc cttcctatat caggcggtgt  960
ttaagacgcc gccgcttcgc ccaaatcctt atgccggttc gacgactgga caaaatactg  1020
tttatct                                                            1027

SEQ ID NO: 120          moltype = DNA  length = 1231
FEATURE                 Location/Qualifiers
source                  1..1231
                        mol_type = other DNA
                        organism = synthetic construct
                        note = Description of Artificial Sequence: Synthetic
                         polynucleotide
SEQUENCE: 120
gacacgcggc cttccaagca gttagggaaa ccgacttctt tgaagaagaa agctgactat  60
gtgatcttat taaaattagg ttaaatttcg aggttaaaaa tagttttaat attgctatag  120
tcttagaggt cttgtatatt tatacttacc acacaagatg gaccggagca gccctccaat  180
atctagtgta ccctcgtgct cgctcaaaca ttaagtggtg ttgtgcgaaa agaatctcac  240
ttcaagaaaa agaaactagt atggtgagca agggcgagga gctgttcacc ggggtggtgc  300
ccatcctggt cgagctggac ggcgacgtaa acggccacaa gttcagcgtg tccggcgagg  360
gcgagggcga tgccacctac ggcaagctga ccctgaagtt catctgcacc accggcaagc  420
tgcccgtgcc ctggcccacc ctcgtgacca ccctgaccta cggcgtgcag tgcttcagcc  480
gctaccccga ccacatgaag cagcacgact tcttcaagtc cgccatgccc gaaggctacg  540
tccaggagcg caccatcttc ttcaaggacg acggcaacta caagacccgc gccgaggtga  600
agttcgaggg cgacaccctg gtgaaccgca tcgagctgaa gggcatcgac ttcaaggagg  660
acggcaacat cctggggcac aagctggagt acaactacaa cagccacaac gtctatatca  720
tggccgacaa gcagaagaac ggcatcaagg tgaacttcaa gatccgccac aacatcgagg  780
acggcagcgt gcagctcgcc gaccactacc agcagaacac ccccatcggc gacggccccg  840
tgctgctgcc cgacaaccac tacctgagca cccagtccgc cctgagcaaa gaccccaacg  900
agaagcgcga tcacatggtc ctgctggagt tcgtgaccgc cgccgggatc actctcggca  960
tggacgagct gtacaagtaa ctcgagctcg gtacctgtcc gcggtcgcga cgtacgcggg  1020
cggccgccat aaattggatc catatatagg gcccgggtta taattacctc aggtcgacgt  1080
cccatggttt tgtatagaat ttacggctag cgccggatgc gacgccggtc gcgtcttatc  1140
cggccttcct atatcaggcg gtgtttaaga cgccgccgct tcgcccaaat ccttatgccg  1200
gttcgacgac tggacaaaat actgtttatc t                                 1231

SEQ ID NO: 121          moltype = DNA  length = 56
FEATURE                 Location/Qualifiers
source                  1..56
                        mol_type = other DNA
                        organism = synthetic construct
                        note = Description of Artificial Sequence: Synthetic primer
SEQUENCE: 121
gaaattaata cgactcacta tagggagacc acaacggttt ccctgactat gtgatc      56

SEQ ID NO: 122          moltype = DNA  length = 31
FEATURE                 Location/Qualifiers
source                  1..31
                        mol_type = other DNA
                        organism = synthetic construct
```

```
                      note = Description of Artificial Sequence: Synthetic primer
SEQUENCE: 122
agataaacag tattttgtcc agtcgtcgaa c                                  31

SEQ ID NO: 123         moltype = DNA  length = 35
FEATURE                Location/Qualifiers
source                 1..35
                       mol_type = other DNA
                       organism = synthetic construct
                       note = Description of Artificial Sequence: Synthetic
                        oligonucleotide
SEQUENCE: 123
ggacaaaata ctgtttatct gggagaccac aacgg                              35

SEQ ID NO: 124         moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 124
agatttcgtt ggggactggc                                               20

SEQ ID NO: 125         moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 125
caccgctcag gacaatcctt                                               20

SEQ ID NO: 126         moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 126
ctggagacgt ggaggagaac                                               20

SEQ ID NO: 127         moltype = DNA  length = 20
FEATURE                Location/Qualifiers
source                 1..20
                       mol_type = other DNA
                       organism = synthetic construct
                       note = Description of Artificial Sequence: Synthetic primer
SEQUENCE: 127
ccaaaagacg gcaatatggt                                               20

SEQ ID NO: 128         moltype = DNA  length = 32
FEATURE                Location/Qualifiers
source                 1..32
                       mol_type = other DNA
                       organism = synthetic construct
                       note = Description of Artificial Sequence: Synthetic
                        oligonucleotide
SEQUENCE: 128
gtcaacggat tttcccaagt ccgtagcgtc tc                                 32

SEQ ID NO: 129         moltype = RNA  length = 17
FEATURE                Location/Qualifiers
source                 1..17
                       mol_type = other RNA
                       organism = synthetic construct
                       note = Description of Artificial Sequence: Synthetic
                        oligonucleotide
SEQUENCE: 129
tagagaaact cgcggag                                                  17

SEQ ID NO: 130         moltype = DNA  length = 64
FEATURE                Location/Qualifiers
source                 1..64
                       mol_type = other DNA
                       organism = synthetic construct
                       note = Description of Artificial Sequence: Synthetic
                        oligonucleotide
SEQUENCE: 130
gaaagaaaga aagaaagaaa gaaagaaaga aagaaagaaa gaaagaaaga aagaaagaaa  60
```

```
gaaa                                                      64

SEQ ID NO: 131         moltype = AA  length = 5
FEATURE                Location/Qualifiers
source                 1..5
                       mol_type = protein
                       organism = unidentified
                       note = Description of Unknown: Thrombin-sensitive sequence
SEQUENCE: 131
CPRSC                                                     5

SEQ ID NO: 132         moltype = DNA  length = 54
FEATURE                Location/Qualifiers
source                 1..54
                       mol_type = other DNA
                       organism = synthetic construct
                       note = Description of Artificial Sequence: Synthetic
                        oligonucleotide
SEQUENCE: 132
gagggcaggg gaagtctact aacatgcggg gacgtggagg aaaatcccgg ccca        54

SEQ ID NO: 133         moltype = DNA  length = 60
FEATURE                Location/Qualifiers
source                 1..60
                       mol_type = other DNA
                       organism = synthetic construct
                       note = Description of Artificial Sequence: Synthetic
                        oligonucleotide
SEQUENCE: 133
cagtgtacta attatgctct cttgaaattg gctggagatg ttgagagcaa cccaggtccc  60

SEQ ID NO: 134         moltype = DNA  length = 796
FEATURE                Location/Qualifiers
source                 1..796
                       mol_type = other DNA
                       organism = synthetic construct
                       note = Description of Artificial Sequence: Synthetic
                        polynucleotide
SEQUENCE: 134
gtaagaagca aggtttcatt taggggaagg gaaatgattc aggacgagag tctttgtgct  60
gctgagtgcc tgtgatgaag aagcatgtta gtcctgggca acgtagcgag accccatctc  120
tacaaaaaat agaaaaatta gccaggtata gtggcgcaca cctgtgattc cagctacgca  180
ggaggctgag gtgggaggat tgcttgagcc caggaggttg aggctgcagt gagctgtaat  240
catgccacta ctccaacctg ggcaacacag caaggaccct gtctcaaaag ctacttacag  300
aaaagaatta ggctcggcac ggtagctcac acctgtaatc ccagcacttt gggaggctga  360
ggcgggcaga tcacttgagg tcaggagttt gagaccagcc tggccaacat ggtgaaacct  420
tgtctctact aaaaatatga aaattagcca ggcatggtgg cacattcctg taatcccagc  480
tactcgggag gctgaggcag gagaatcact tgaacccagg aggtggaggt tgcagtaagc  540
cgagatcgta ccactgtgct ctagccttgg tgacagagcg agactgtctt aaaaaaaaaa  600
aaaaaaaaaa aagaattaat taaaaattta aaaaaaaatg aaaaaaagct gcatgcttgt  660
tttttgtttt tagttattct acattgttgt cattattacc aaatattggg gaaaatacaa  720
cttacagacc aatctcagga gttaaatgtt actacgaagg caaatgaact atgcgtaatg  780
aacctggtag gcatta                                          796

SEQ ID NO: 135         moltype = RNA  length = 55
FEATURE                Location/Qualifiers
source                 1..55
                       mol_type = other RNA
                       organism = synthetic construct
                       note = Description of Artificial Sequence: Synthetic
                        oligonucleotide
SEQUENCE: 135
aaaaaacaaa aaacaaaacg gctattatgc gttaccggcg agacgctacg gactt       55

SEQ ID NO: 136         moltype = RNA  length = 120
FEATURE                Location/Qualifiers
source                 1..120
                       mol_type = other RNA
                       organism = synthetic construct
SEQUENCE: 136
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
```